(12) United States Patent
Raymond et al.

(10) Patent No.: US 11,999,949 B2
(45) Date of Patent: Jun. 4, 2024

(54) METHODS FOR TARGETED GENOMIC ANALYSIS

(71) Applicant: Resolution Bioscience, Inc., Kirkland, WA (US)

(72) Inventors: Christopher K. Raymond, Seattle, WA (US); Christopher D. Armour, Kirkland, WA (US); Lee P. Lim, Kirkland, WA (US)

(73) Assignee: Resolution Bioscience, Inc., Kirkland, WA (US)

( * ) Notice: Subject to any disclaimer, the term of this patent is extended or adjusted under 35 U.S.C. 154(b) by 626 days.

(21) Appl. No.: 17/141,510

(22) Filed: Jan. 5, 2021

(65) Prior Publication Data
US 2021/0198658 A1    Jul. 1, 2021

Related U.S. Application Data

(60) Continuation of application No. 15/873,510, filed on Jan. 17, 2018, now Pat. No. 10,907,149, which is a division of application No. 14/102,285, filed on Dec. 10, 2013, now Pat. No. 9,932,576.

(60) Provisional application No. 61/794,049, filed on Mar. 15, 2013, provisional application No. 61/735,417, filed on Dec. 10, 2012.

(51) Int. Cl.
| C12Q 1/68 | (2018.01) |
| C12N 15/10 | (2006.01) |
| C12Q 1/6806 | (2018.01) |
| C12Q 1/6827 | (2018.01) |
| C12Q 1/6874 | (2018.01) |
| C12Q 1/6888 | (2018.01) |

(52) U.S. Cl.
CPC ....... *C12N 15/1065* (2013.01); *C12Q 1/6806* (2013.01); *C12Q 1/6827* (2013.01); *C12Q 1/6874* (2013.01); *C12Q 1/6888* (2013.01)

(58) Field of Classification Search
CPC .............. C12N 15/1065; C12Q 1/6806; C12Q 1/6827; C12Q 1/6874; C12Q 1/6888
See application file for complete search history.

(56) References Cited

U.S. PATENT DOCUMENTS

| 5,185,243 A | 2/1993 | Ullman et al. |
| 5,512,445 A | 4/1996 | Yang et al. |

(Continued)

FOREIGN PATENT DOCUMENTS

| CN | 101932729 A | 12/2010 |
| CN | 102264914 A | 11/2011 |

(Continued)

OTHER PUBLICATIONS

Taton et al. (Science, 2000, vol. 289, p. 1757-1760) (Year: 2000).*

(Continued)

*Primary Examiner* — Stephanie K Mummert
(74) *Attorney, Agent, or Firm* — Casimir Jones, S.C.; Thomas A. Isenbarger

(57) ABSTRACT

The invention provides a method for genetic analysis in individuals that reveals both the genetic sequences and chromosomal copy number of targeted and specific genomic loci in a single assay. The present invention further provide methods for the sensitive and specific detection of target gene sequences and gene expression profiles.

28 Claims, 54 Drawing Sheets

Specification includes a Sequence Listing.

(56) References Cited

U.S. PATENT DOCUMENTS

| | | | |
|---|---|---|---|
| 5,514,551 A | 5/1996 | Yang et al. | |
| 5,591,582 A | 1/1997 | Bos et al. | |
| 6,025,133 A | 2/2000 | Stull et al. | |
| 6,025,139 A | 2/2000 | Yager et al. | |
| 6,087,133 A | 7/2000 | Dattagupta et al. | |
| 6,214,587 B1 | 4/2001 | Dattagupta et al. | |
| 6,480,791 B1 * | 11/2002 | Strathmann | C12N 15/1082 506/3 |
| 6,812,341 B1 | 11/2004 | Conrad | |
| 7,081,527 B2 | 7/2006 | Cunningham et al. | |
| 7,393,665 B2 | 7/2008 | Brenner | |
| 7,537,897 B2 | 5/2009 | Brenner et al. | |
| 7,585,631 B2 | 9/2009 | Cunningham et al. | |
| 8,148,068 B2 | 4/2012 | Brenner | |
| 8,168,385 B2 | 5/2012 | Brenner | |
| 8,318,433 B2 | 11/2012 | Brenner | |
| 8,383,338 B2 | 2/2013 | Kitzman et al. | |
| 8,470,996 B2 | 6/2013 | Brenner | |
| 8,476,018 B2 | 7/2013 | Brenner | |
| 8,828,688 B2 * | 9/2014 | Namsaraev | C12Q 1/6853 506/26 |
| 8,835,358 B2 | 9/2014 | Fodor et al. | |
| 8,865,410 B2 | 10/2014 | Shendure et al. | |
| 9,018,365 B2 | 4/2015 | Brenner | |
| 9,085,798 B2 | 7/2015 | Chee | |
| 9,121,069 B2 | 9/2015 | Lo et al. | |
| 9,290,808 B2 | 3/2016 | Fodor et al. | |
| 9,290,809 B2 | 3/2016 | Fodor et al. | |
| 9,315,857 B2 | 4/2016 | Fu et al. | |
| 9,340,830 B2 | 5/2016 | Lipson et al. | |
| 9,410,954 B2 | 8/2016 | Boshoff et al. | |
| 9,546,399 B2 | 1/2017 | Amorese et al. | |
| 9,598,731 B2 | 3/2017 | Talasaz | |
| 9,702,002 B2 | 7/2017 | Boutell | |
| 9,708,659 B2 | 7/2017 | Fodor et al. | |
| 9,783,847 B2 | 10/2017 | Chee | |
| 9,792,403 B2 | 10/2017 | Sun et al. | |
| 9,816,137 B2 | 11/2017 | Fodor et al. | |
| 9,834,822 B2 | 12/2017 | Talasaz | |
| 9,840,743 B2 | 12/2017 | Talasaz | |
| 9,850,523 B1 | 12/2017 | Chudova et al. | |
| 9,902,992 B2 | 2/2018 | Talasaz et al. | |
| 9,907,798 B2 | 3/2018 | Boshoff et al. | |
| 9,920,366 B2 | 3/2018 | Eltoukhy et al. | |
| 9,932,576 B2 | 4/2018 | Raymond et al. | |
| 9,965,585 B2 | 5/2018 | Lo et al. | |
| 10,000,800 B2 | 6/2018 | Chee | |
| 10,047,394 B2 | 8/2018 | Fodor et al. | |
| 10,059,991 B2 | 8/2018 | Fodor et al. | |
| 10,087,482 B2 | 10/2018 | Korfhage et al. | |
| 10,095,831 B2 | 10/2018 | Duenwald et al. | |
| 10,119,165 B2 | 11/2018 | Chee | |
| 10,202,646 B2 | 2/2019 | Fodor et al. | |
| 10,227,587 B2 | 3/2019 | Zhang et al. | |
| 10,240,209 B2 | 3/2019 | Lo et al. | |
| 10,266,883 B2 | 4/2019 | Chee | |
| 10,266,889 B2 | 4/2019 | Behlke et al. | |
| 10,287,630 B2 | 5/2019 | Xie et al. | |
| 10,297,342 B2 | 5/2019 | Lo et al. | |
| 10,378,064 B1 | 8/2019 | Schutz et al. | |
| 10,388,403 B2 | 8/2019 | Rava et al. | |
| 10,392,661 B2 | 8/2019 | Fodor et al. | |
| 10,453,556 B2 | 10/2019 | Lo et al. | |
| 10,494,678 B2 | 12/2019 | Talasaz | |
| 10,501,793 B2 | 12/2019 | Chee | |
| 10,501,810 B2 | 12/2019 | Talasaz | |
| 10,538,759 B2 | 1/2020 | Stuelpnagel et al. | |
| 10,577,601 B2 | 3/2020 | Shendure et al. | |
| 10,597,653 B2 | 3/2020 | Sabot et al. | |
| 10,597,708 B2 | 3/2020 | Zimmerman et al. | |
| 10,597,709 B2 | 3/2020 | Zimmerman et al. | |
| 10,619,203 B2 | 4/2020 | Fodor et al. | |
| 10,619,214 B2 | 4/2020 | Lo et al. | |
| 10,689,699 B2 | 6/2020 | Salk et al. | |
| 10,704,085 B2 | 7/2020 | Talasaz et al. | |
| 10,704,086 B2 | 7/2020 | Talasaz et al. | |
| 10,741,270 B2 | 8/2020 | Lo et al. | |
| 10,752,951 B2 | 8/2020 | Salk et al. | |
| 10,793,916 B2 | 10/2020 | Talasz | |
| 10,801,063 B2 | 10/2020 | Eltoukhy et al. | |
| 10,847,249 B2 | 11/2020 | Sun et al. | |
| 10,876,152 B2 | 12/2020 | Talasaz et al. | |
| 10,883,139 B2 | 1/2021 | Eltoukhy et al. | |
| 10,889,858 B2 | 1/2021 | Talasaz et al. | |
| 10,894,974 B2 | 1/2021 | Talasaz et al. | |
| 10,907,149 B2 | 2/2021 | Raymond et al. | |
| 11,319,594 B2 | 5/2022 | Raymond et al. | |
| 11,339,391 B2 | 5/2022 | Raymond et al. | |
| 2003/0148310 A1 | 8/2003 | Sorge | |
| 2004/0058328 A1 | 3/2004 | Chan et al. | |
| 2005/0032057 A1 | 2/2005 | Shoemaker | |
| 2007/0037139 A1 | 2/2007 | Tomono et al. | |
| 2007/0117089 A1 | 5/2007 | Croker et al. | |
| 2007/0117224 A1 | 5/2007 | Croker et al. | |
| 2007/0128624 A1 | 6/2007 | Gormley et al. | |
| 2007/0172873 A1 | 7/2007 | Brenner et al. | |
| 2008/0038782 A1 | 2/2008 | Borns | |
| 2009/0117573 A1 | 5/2009 | Fu et al. | |
| 2009/0143243 A1 | 6/2009 | Gunning et al. | |
| 2009/0191563 A1 | 7/2009 | Steemers et al. | |
| 2009/0264305 A1 | 10/2009 | Brandon et al. | |
| 2010/0093550 A1 | 4/2010 | Stuelpnagel et al. | |
| 2010/0273219 A1 | 10/2010 | May et al. | |
| 2011/0014657 A1 | 1/2011 | Rigatti et al. | |
| 2011/0160078 A1 | 6/2011 | Fodor et al. | |
| 2011/0294689 A1 | 12/2011 | Namsaraev | |
| 2011/0313145 A1 | 12/2011 | Sharon et al. | |
| 2012/0157322 A1 | 6/2012 | Myllykangas et al. | |
| 2013/0288915 A1 | 10/2013 | Seligmann et al. | |
| 2014/0100792 A1 | 4/2014 | Deciu et al. | |
| 2014/0242581 A1 | 8/2014 | Johnson | |
| 2014/0274731 A1 | 9/2014 | Raymond et al. | |
| 2014/0274740 A1 | 9/2014 | Srinivasan et al. | |
| 2015/0046180 A1 | 2/2015 | Futscher De et al. | |
| 2015/0072344 A1 | 3/2015 | Wiley | |
| 2015/0111757 A1 | 4/2015 | Boyden et al. | |
| 2015/0159222 A1 | 6/2015 | Gaulis et al. | |
| 2015/0275289 A1 | 10/2015 | Otwinowski et al. | |
| 2015/0376700 A1 | 12/2015 | Schnall-levin et al. | |
| 2016/0053253 A1 | 2/2016 | Salathia et al. | |
| 2016/0053301 A1 | 2/2016 | Raymond et al. | |
| 2017/0088887 A1 | 3/2017 | Makarov et al. | |
| 2017/0096706 A1 | 4/2017 | Behlke et al. | |
| 2017/0242960 A1 | 8/2017 | Rabinowitz et al. | |
| 2017/0283869 A1 | 10/2017 | Fang et al. | |
| 2017/0355984 A1 | 12/2017 | Evans et al. | |
| 2017/0356053 A1 | 12/2017 | Otto et al. | |
| 2018/0142234 A1 | 5/2018 | Raymond et al. | |
| 2018/0163272 A1 | 6/2018 | Raymond et al. | |
| 2018/0179578 A1 | 6/2018 | Raymond et al. | |
| 2018/0245072 A1 | 8/2018 | Raymond et al. | |
| 2018/0300449 A1 | 10/2018 | Kermani et al. | |
| 2018/0300456 A1 | 10/2018 | Eltoukhy et al. | |
| 2018/0363066 A1 | 12/2018 | Chalmers et al. | |
| 2019/0032118 A1 | 1/2019 | Lipson et al. | |
| 2019/0136301 A1 | 5/2019 | Lipson et al. | |
| 2019/0233897 A1 | 5/2019 | Lipson et al. | |
| 2020/0048703 A1 | 2/2020 | Chee et al. | |
| 2020/0299775 A1 | 9/2020 | Hawryluk et al. | |
| 2021/0198658 A1 | 7/2021 | Raymond et al. | |
| 2022/0073906 A1 | 3/2022 | Guo et al. | |
| 2022/0267763 A1 | 8/2022 | Raymond et al. | |
| 2022/0325353 A1 | 10/2022 | Raymond et al. | |

FOREIGN PATENT DOCUMENTS

| | | |
|---|---|---|
| CN | 102439177 A | 5/2012 |
| CN | 103103624 A | 5/2013 |
| CN | 103668471 A | 3/2014 |
| EP | 0709467 A2 | 5/1996 |
| EP | 0851033 A1 | 7/1998 |
| EP | 3192869 A1 | 7/2017 |
| EP | 3202915 A1 | 8/2017 |
| EP | 3329039 A1 | 6/2018 |

(56) References Cited

FOREIGN PATENT DOCUMENTS

| | | |
|---|---|---|
| EP | 3363904 A2 | 8/2018 |
| EP | 3421613 A1 | 1/2019 |
| EP | 3470533 A1 | 4/2019 |
| EP | 3502273 A1 | 6/2019 |
| EP | 3551769 A2 | 10/2019 |
| EP | 3567120 A1 | 11/2019 |
| EP | 3374525 B1 | 1/2021 |
| JP | 2013-536679 A | 9/2013 |
| JP | 2014-512817 A | 5/2014 |
| JP | 2017525371 A | 9/2017 |
| JP | 2019504618 A | 2/2019 |
| JP | 2019526257 A | 9/2019 |
| JP | 2020-516281 A | 6/2020 |
| WO | WO 1999/011819 A1 | 3/1999 |
| WO | WO-9923258 A1 | 5/1999 |
| WO | WO-0222890 A2 | 3/2002 |
| WO | WO 2004/053127 A1 | 6/2004 |
| WO | WO-2008070375 A2 | 6/2008 |
| WO | WO 2009/076238 A2 | 6/2009 |
| WO | WO 2009/091798 A1 | 7/2009 |
| WO | WO-2009099602 A1 | 8/2009 |
| WO | WO 2009/116863 | 9/2009 |
| WO | WO-2010048605 A1 | 4/2010 |
| WO | WO 2010/129937 A2 | 11/2010 |
| WO | WO 2011/156529 A2 | 12/2011 |
| WO | WO 2012/028746 A1 | 3/2012 |
| WO | WO 2012/040387 A1 | 3/2012 |
| WO | WO 2012/129363 A2 | 9/2012 |
| WO | WO 2012/142213 A2 | 10/2012 |
| WO | WO 2012/142334 A2 | 10/2012 |
| WO | WO-2012138365 A1 | 10/2012 |
| WO | WO 2012/148477 A1 | 11/2012 |
| WO | WO 2014/052487 A1 | 4/2014 |
| WO | WO 2014/055790 A2 | 4/2014 |
| WO | WO 2014/071295 A1 | 5/2014 |
| WO | WO 2014/093330 A1 | 6/2014 |
| WO | WO 2014/093825 A1 | 6/2014 |
| WO | WO 2014/122288 A1 | 8/2014 |
| WO | WO 2015/134552 A1 | 9/2014 |
| WO | WO 2015/117040 A1 | 8/2015 |
| WO | WO 2016/022833 A1 | 2/2016 |
| WO | WO 2016/028316 A1 | 2/2016 |
| WO | WO 2016/037389 A1 | 3/2016 |
| WO | WO 2016/040901 A1 | 3/2016 |
| WO | WO 2016/094853 A1 | 6/2016 |
| WO | WO 2016/109452 A1 | 7/2016 |
| WO | WO-2017019322 A1 | 2/2017 |
| WO | WO 2017/083562 A1 | 5/2017 |
| WO | WO 2018/039463 A1 | 3/2018 |
| WO | WO 2018/064629 A1 | 4/2018 |
| WO | WO 2018/094183 A1 | 5/2018 |
| WO | WO 2018/104908 A2 | 6/2018 |
| WO | WO 2020/106906 A1 | 5/2020 |
| WO | WO-2022212574 A1 | 10/2022 |

OTHER PUBLICATIONS

[Author Unknown] "TruSeq™ RNA and DNA Library Preparation Kits v2". Data Sheet: Illumina® Sequencing, © 2011, 2014 Illumina, Inc., Pub. No. 770-2009-039 Current as of Nov. 17, 2014, 4 pages.
Mamanova, et al., "Target-enrichment strategies for next-generation sequencing". Nature Methods. (Feb. 2010); 7(2): 111-118.
Atamaniuk et al., "Cell-free plasma DNA: a marker for apoptosis during hemodialysis." Clinical Chemistry (2006); 52.3: 523-526.
Blake, R. D., and Delcourt, S.G., "Thermodynamic effects of formamide on DNA stability." Nucleic Acids Research (1996); 24.11: 2095-2103.
Chan et al., "Cancer genome scanning in plasma: detection of tumor-associated copy number aberrations, single-nucleotide variants, and tumoral heterogeneity by massively parallel sequencing." Clinical Chemistry (2013); 59(1): 211-224.
Extended European Search Report in Application No. EP 13862440. 8, dated Oct. 11, 2016, 19 pages.
Extended European Search Report in Application No. EP 19153893. 3, dated Sep. 17, 2019, 9 pages.
Hoeijmakers et al., "Linear amplification for deep sequencing." Nature Protocols (2011); 6.7: 1026-1036.
KAPA Biosystems, "KAPA Library Quantification Kits Technical Data Sheet" (2011); 6 pages, www.kapabiosystems.com.
Leary et al. "Detection of chromosomal alterations in the circulation of cancer patients with whole-genome sequencing." Science Translational Medicine (2012); 4(162):162ra154.
Lin et al., "Exon array profiling detects EML4-ALK fusion in breast, colorectal, and non-small cell lung cancers." Molecular Cancer Research (2009); 7.9: 1466-1476.
Mano, H., "Non-solid oncogenes in solid tumors: EML4-ALK fusion genes in lung cancer." Cancer Science (2008); 99.12: 2349-2355.
McKernan et al., "Sequence and structural variation in a human genome uncovered by short-read, massively parallel ligation sequencing using two-base encoding." Genome Research (2009); 19.9: 1527-1541.
Melchior, W.B. and Hippel, P.H. "Alteration of the relative stability of dA· dT and dG· dC base pairs in DNA." Proceedings of the National Academy of Sciences USA (1973); 70.2: 298-302.
Meyer et al., "Targeted high-throughput sequencing of tagged nucleic acid samples." Nucleic Acids Research (2007); 35.15: e97, 5 pages.
Meyer et al., "From micrograms to picograms: quantitative PCR reduces the material demands of high-throughput sequencing" Nucleic Acids Research (2008); 36(1) :e5.
Partial Supplementary European Search Report in European Application No. 13862440.8 dated Jul. 4, 2016, 11 pages.
PCT/US2013/074102, International Preliminary Report on Patentability dated Jun. 16, 2015.
PCT/US2014/052317, International Preliminary Report on Patentability dated Feb. 28, 2017, 8 pages.
PCT/US2013/074102, International Search Report and Written Opinion dated Feb. 28, 2014.
PCT/US2014/052317, International Search Report and Written Opinion dated Jan. 13, 2015, 13 pages.
PCT/US2016/061395, International Search Report and Written Opinion dated Feb. 7, 2017, 14 pages.
PCT/US2017/048434, International Search Report and Written Opinion dated Dec. 26, 2017, 15 pages.
Samorodnitsky, et al., "Comparison of Custom Capture for Targeted Next-Generation DNA Sequencing." The Journal of Molecular Diagnostics (2015); 17(1): 64-75.
Shevelev and Hübscher, "The 3'5' exonucleases", *Nat Rev Mol Cell Biol.*, 3(5): 364-376 (2002).
Shiroguchi, et al., "Digital RNA sequencing minimizes sequence-dependent bias and amplification noise with optimized single-molecule barcodes." PNAS (2012); 109 (4): 1347-1352, Supporting Information, 14 pages.
Stellwagen, Earle, et al., "Monovalent cation size and DNA conformational stability." Biochemistry (2011); 50.15: 3084-3094.
Taton, T. Andrew, et al., "Scanometric DNA array detection with nanoparticle probes." Science (2000); 289.5485: 1757-1760.
Vogelstein et al., "Cancer genome landscapes." Science (2013); 339.6127: 1546-1558.
Yegnasubramanian et al., "Preparation of Fragment Libraries for Next-Generation Sequencing on the Applied Biosystems SOLiD Platform." Methods in Enzymology (2013); 529: 185-200.
Cheng Jie et al., "Construction of chlamys farreri Fosmid Library and analysis of Genomic Structure", Journal of Ocean University of China, Jan. 2008, vol. 38(01); 078-088 and English abstract, 11 pages.
Hess, et al., "Library preparation for next generation sequencing: A review of automation strategies". Biotechnol Adv. (Jul.-Aug. 2020); 41: 107537, 14 pages. Epub Mar. 19, 2020.
Hong and Shin, "Bisulfite-Converted DNA Quantity Evaluation: A Multiplex Quantitative Real-Time PCR System for Evaluation of Bisulfite Conversion". Front Genet. (Feb. 25, 2021); 12: 618955. eCollection 2021.

(56) References Cited

OTHER PUBLICATIONS

Ma, et al., "Pan-cancer genome and transcriptome analyses of 1,699 paediatric leukaemias and solid tumours". Nature (2018); 55: 371-376. Epub Feb. 28, 2018.

Malone, et al., "Molecular profiling for precision cancer therapies". Genome Med. (Jan. 14, 2020); 12(1): 8, 19 pages.

Manier, et al., "Whole-exome sequencing of cell-free DNA and circulating tumor cells in multiple myeloma". Nat Commun. (Apr. 27, 2018); 9(1): 1691, 11 pages.

Wang, et al., "Enzymatic approaches for profiling cytosine methylation and hydroxymethylation". Mol Metab. (Mar. 2022); 57: 101314. Epub Aug. 8, 2021.

Wang, et al., "Low-pass genome sequencing versus chromosomal microarray analysis: implementation in prenatal diagnosis". Genet Med. (Mar. 2020); 22(3): 500-510. Epub Aug. 26, 2019.

[Author Unknown] "An introduction to Next-Generation Sequencing Technology". Brochure, © 2017, Illumina, Inc., Pub. No. 770-2012-008-B, Retrieved online Aug. 7, 2022, https://www.illumina.com/content/dam/illumina-marketing/documents/products/illumina_sequencing_introduction.pdf, 16 pages.

Biswas, et al., "Sample quality control in agilent NGS solutions", Agilent (2018), 1-14, URL: https://www.agilent.com/cs/library/applications/application-ngs-electrophoresis-samplequalitycontrol-tapestation-5994-0127en-agilent.pdf.

International Search Report and Written Opinion for International Application No. PCT/US2022/022640, dated Jul. 25, 2022, 15 pages.

Jang, et al., "Quality control probes for spot-uniformity and quantitative analysis of oligonucleotide array", Journal of Microbiology and Biotechnology (2009); 19(7): 658-665.

Cunningham, et al., "Abstract 881. Rapid Detection of Mycoplasma pneumoniae from Clinical Specimens by Transcription-Mediated Amplification". ICAAC 40th Anniversary, Toronto, Sep. 17-20, 2000, 2 pages.

Diaz Jr. and Bardelli, "Liquid biopsies: genotyping circulating tumor DNA". J Clin Oncol. Feb. 20, 2014; 32(6): 579-586. Epub Jan. 21, 2014.

European Patent Application No. 19153893.3: Agilent Resolution ctDx First Technical Information, submitted with Response to Summons to Attend Oral Proceedings as "Annex B", on Mar. 17, 2023; 50 pages.

European Patent Application No. 19153893.3: Auxiliary Request 1, submitted with Response to Summons to Attend Oral Proceedings, on Mar. 17, 2023; 2 pages.

European Patent Application No. 19153893.3: Auxiliary Request 10, submitted with Response to Summons to Attend Oral Proceedings, on Apr. 17, 2023; 2 pages.

European Patent Application No. 19153893.3: Auxiliary Request 2, submitted with Response to Summons to Attend Oral Proceedings, on Mar. 17, 2023; 2 pages.

European Patent Application No. 19153893.3: Auxiliary Request 3, submitted with Response to Summons to Attend Oral Proceedings, on Mar. 17, 2023; 2 pages.

European Patent Application No. 19153893.3: Auxiliary Request 4, submitted with Response to Summons to Attend Oral Proceedings, on Mar. 17, 2023; 2 pages.

European Patent Application No. 19153893.3: Auxiliary Request 5, submitted with Response to Summons to Attend Oral Proceedings, on Mar. 17, 2023; 2 pages.

European Patent Application No. 19153893.3: Auxiliary Request 6, submitted with Response to Summons to Attend Oral Proceedings, on Mar. 17, 2023; 2 pages.

European Patent Application No. 19153893.3: Auxiliary Request 7, submitted with Response to Summons to Attend Oral Proceedings, on Mar. 17, 2023; 2 pages.

European Patent Application No. 19153893.3: Auxiliary Request 8, submitted with Response to Summons to Attend Oral Proceedings, on Apr. 17, 2023; 2 pages.

European Patent Application No. 19153893.3: Auxiliary Request 9, submitted with Response to Summons to Attend Oral Proceedings, on Apr. 17, 2023; 2 pages.

European Patent Application No. 19153893.3: Companion Diagnostics, submitted with Response to Summons to Attend Oral Proceedings as "Annex C", on Mar. 17, 2023; 2 pages.

European Patent Application No. 19153893.3: Declaration of Paul Stull with Exhibit B, signed Mar. 16, 2023, submitted with Response to Summons to Attend Oral Proceedings on Mar. 17, 2023; 8 total pages.

European Patent Application No. 19153893.3: Letter from Donna Roscoe, Ph.D. of Center for Devices and Radiological Health to Chris Pretzinger of Resolution Bioscience, Inc., signed Mar. 16, 2023, submitted with Response to Summons to Attend Oral Proceedings as "Annex A", on Mar. 17, 2023; 6 total pages.

European Patent Application No. 19153893.3: Main Request, submitted with Response to Summons to Attend Oral Proceedings, on Mar. 17, 2023; 2 pages.

European Patent Application No. 19153893.3: Response to Summons to Attend Oral Proceedings, dated Mar. 17, 2023; 31 pages.

Hocking, et al., "Liquid biopsies for liquid tumors: emerging potential of circulating free nucleic acid evaluation for the management of hematologic malignancies". Cancer Biol Med. Jun. 2016; 13(2): 215-225.

Jung, et al., "Cell-free DNA in the blood as a solid tumor biomarker—A critical appraisal of the literature". Clin Chim Acta. Nov. 11, 2010; 411(21-22): 1611-1624. Epub Aug. 2, 2010.

Kivioja, T., et al., "Counting absolute numbers of molecules using unique molecular identifiers", Nature Methods (Nov. 20, 2011); 9(1): 72-74.

PCT/US2021/049448, International Preliminary Report on Patentability dated Mar. 23, 2023, 7 pages.

Pollak, Julia, et al., "Analytical validation of the Agilent Resolution ctDx HRD plasma assay used to identify mCRPC patients with mutations, including homozygous deletions, in DNA repair genes as a companion diagnostic for niraparib". Poster Abstract# 52 RA# PR7000-3277, [publication date unknown], 1 page.

Stull and Blanchard, "Improvement in the Dispersion of Silica Nanoparticles". 241st ACS National Meeting, Mar. 28-31, 2011, Abstract, 2 pages.

Stull and Blanchard, "Surface coatings on anisotropic nanoparticles". 246th ACS National Meeting, Sep. 11-12, 2013, Abstract, 1 page.

[Author Unknown] "NGS Library Preparation for Whole Genome Bisulfite Sequencing (WGBS) on Illumina® Sequencing Platforms", Qiagen, Cat # 180495 ["retrieved date unknown"] https://www.qiagen.com/us/resources/resourcedetail?id=20735cc3-6bec-4865-9d97-8cb574840500&lang=en, Oct. 2016; pp. 1-10.

[Author Unknown] "QIAseq™ Methyl Library Handbook for DNA library construction for whole genome bisulfite sequencing on Illumina® sequencing platforms", Qiagen, Cat # 180502 ["retrieved date unknown"] https://www.qiagen.com/us/products/discovery-and-translational-research/next-generation-sequencing/dna-methylation-analysis/qiaseq-methyl-library-kit/, Nov. 2017; pp. 1-40.

[Author Unknown] "QIAseq® Targeted Methyl Panel Handbook Targeted next-generation sequencing of methylated DNA", Qiagen, Cat # 335501 ["retrieved date unknown"] https://www.qiagen.,com/us/products/discovery-and-translational-research/next-generation-sequencing/dna-methylation-analysis/qiaseq-targeted-methyl-panels/, Oct. 2019; pp. 1-60.

Porreca, G.J., et al., "Multiplex Amplification of Large Sets of Human Exons," Nature Methods, Oct. 14, 2007, vol. 4 (11), pp. 931-936.

[Author Unknown] "SureSelect$^{XT}$ Target Enrichment System for Illumina Paired-End Multiplexed Sequencing Library". Protocol, Version C3, Sep. 2019, Agilent Technologies, © Agilent Technologies, Inc. 2010-2019, 100 pages.

Wisegeek, "How many species of bacteria are there?" WiseGeek.com, accessed Jan. 21, 2014, 2 pages. (Year: 2014).

Wikipedia, "List of sequenced bacterial genomes" Wikipedia.com, accessed Jan. 24, 2014, 57 pages. (Year: 2014).

Begley, Sharon, "Psst, The Human Genome Was Never Completely Sequenced. Some Scientists Say it Should Be", STAT News, Jun.

(56) References Cited

OTHER PUBLICATIONS 20, 2017 (Year: 2017), downloaded Sep. 3, 2018 from https://www.statnews.com/2017/06/20/human-genome-not-fully-sequenced/, 8 pages.
Beltran, et al., "Circulating tumor DNA profile recognizes transformation to castration-resistant neuroendocrine prostate cancer". J Clin Invest (Apr. 1, 2020); 130(4): 1653-1668.
Cheng, et al., "Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology". J Mol Diagn. (May 2015); 17(3): 251-264. Epub Mar. 20, 2015.
Extended European Search Report in Application No. EP 16865029.9, dated Apr. 29, 2019, 11 pages.
Extended European Search Report in Application No. EP 17844424.6, dated Mar. 27, 2020, 8 pages.
Extended European Search Report in Application No. EP 21152311.3, dated Sep. 7, 2021, 14 pages.
Fakruddin, et al., "Nucleic acid amplification: Alternative methods of polymerase chain reaction". Journal of Pharmacy and Bioallied Sciences (Oct.-Dec. 2013); 5(4): 245-252.
Forster, et al., "A human gut bacterial genome and culture collection for improved metagenomic analyses". Nat Biotechnol. (Feb. 2019); 37(2): 186-192. Epub Feb. 4, 2019.
Horn, Susanne, "Target Enrichment via DNA Hybridization Capture" in Ancient DNA: Methods and Protocols, Methods in Molecular Biology (2012); 840: 177-188. Epub Dec. 8, 2011.
Jacobs, et al., "The thermal stability of oligonucleotide duplexes is sequence independent in tetraalkylammonium salt solutions: application to identifying recombinant DNA clones". Nucleic Acids Res. (May 25, 1988); 16(10): 4637-4650.
Miura, et al., "Highly efficient single-stranded DNA ligation technique improves low-input whole-genome bisulfite sequencing by post-bisulfite adaptor tagging." Nucleic Acids Research (Sep. 5, 2019); 47(15): e85-e85, p. 1-10. Epub May 22, 2019.
PCT/US2016/061395, International Preliminary Report on Patentability dated May 15, 2018, 10 pages.
PCT/US2017/048434, International Preliminary Report on Patentability dated Feb. 26, 2019, 10 pages.
PCT/US2021/049448, International Search Report and Written Opinion dated Dec. 28, 2021, 12 pages.
Piovesan, et al., "On the length, weight and GC content of the human genome". BMC Res Notes (Feb. 27, 2019); 12: 106, 7 pages.
Rittié and Perbal, "Enzymes used in molecular biology: a useful guide". J. Cell Commun. Signal. (Jun. 2008); 2 (1-2): 25-45. Epub Sep. 3, 2008.
Oxford Dictionary of Biochemistry and Molecular Biology, Definition of "base composition", general eds Attwood, et al. Revised Edition (2000), 3 pages.
Zhou, et al., "Systematic evaluation of library preparation methods and sequencing platforms for high-throughput whole genome bisulfite sequencing." Scientific Reports (2019); 9: 10383, 16 pages.

\* cited by examiner

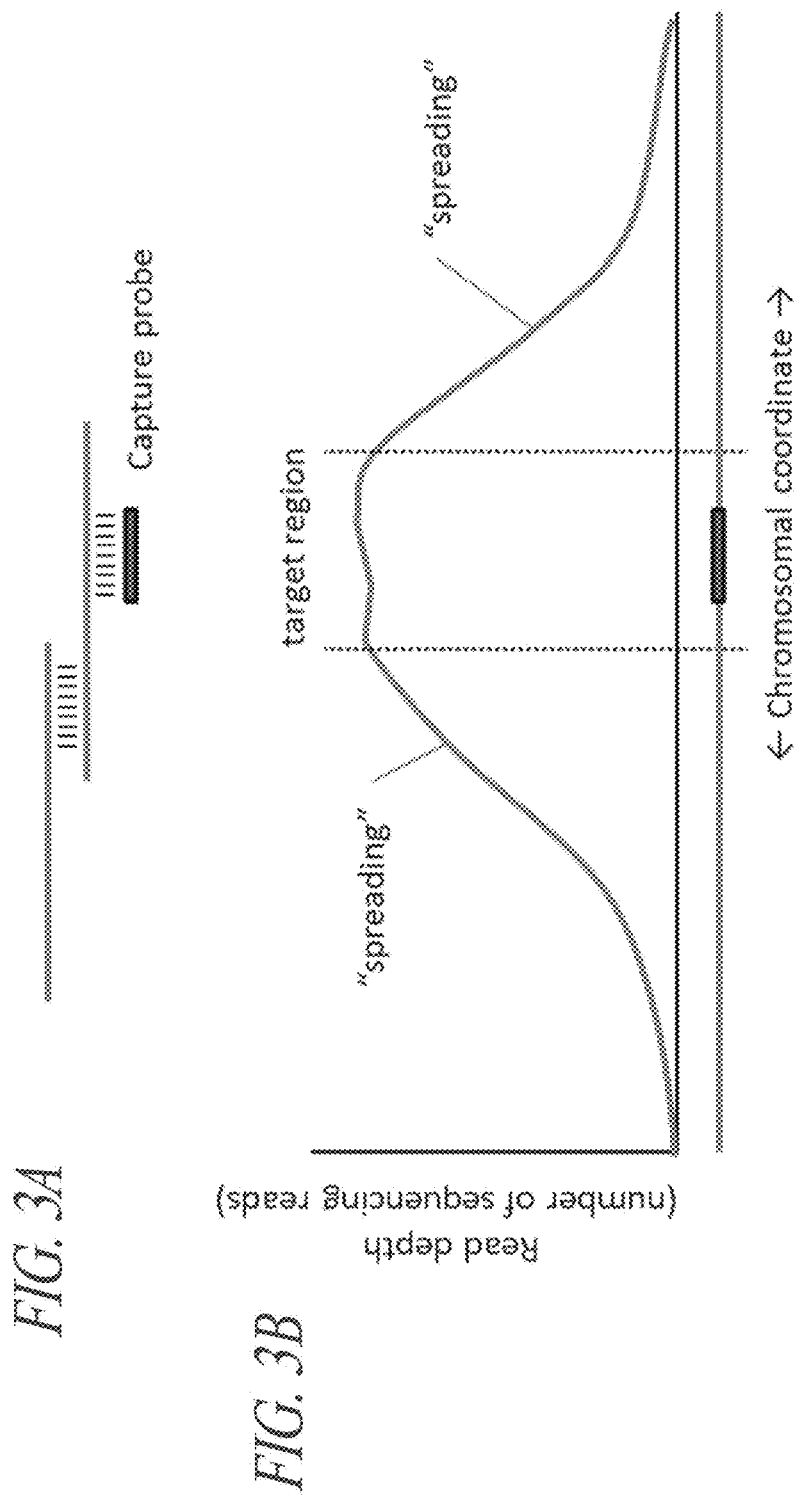

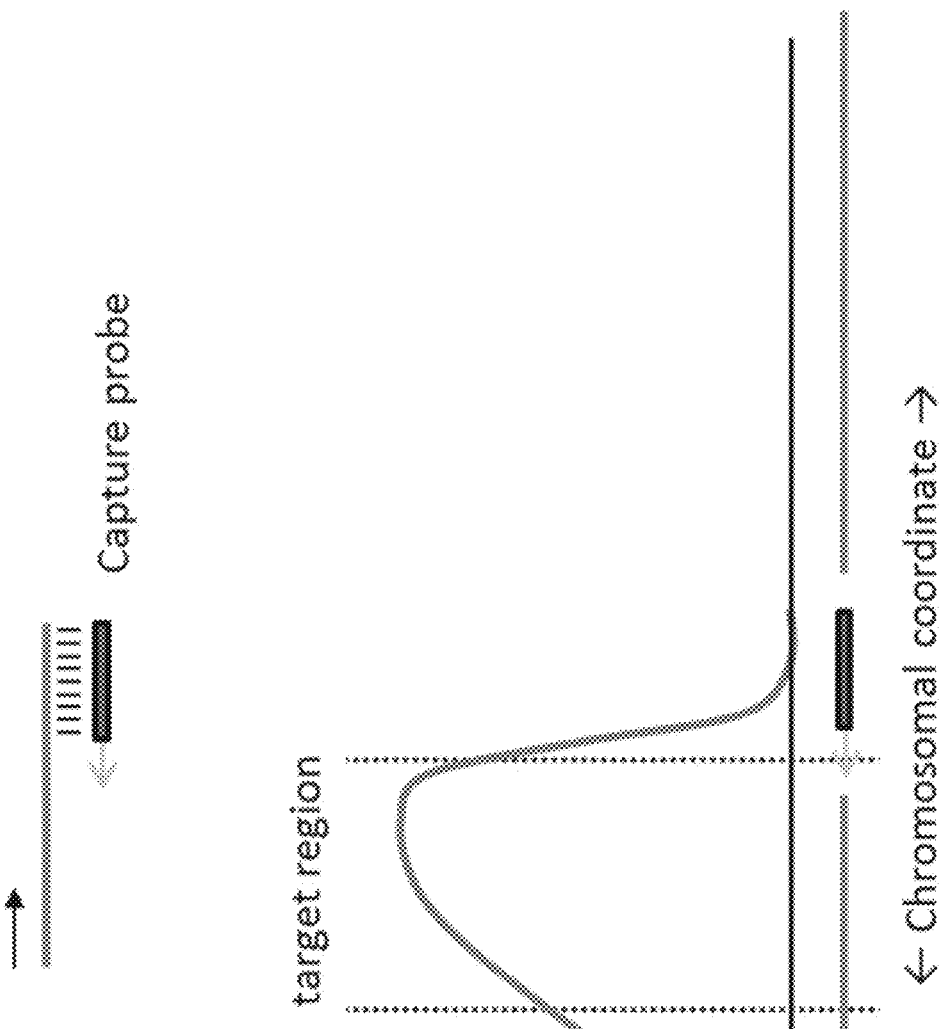

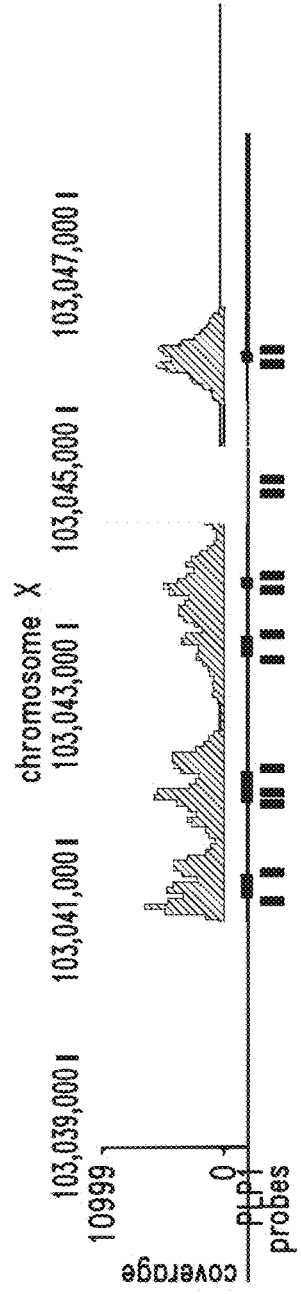
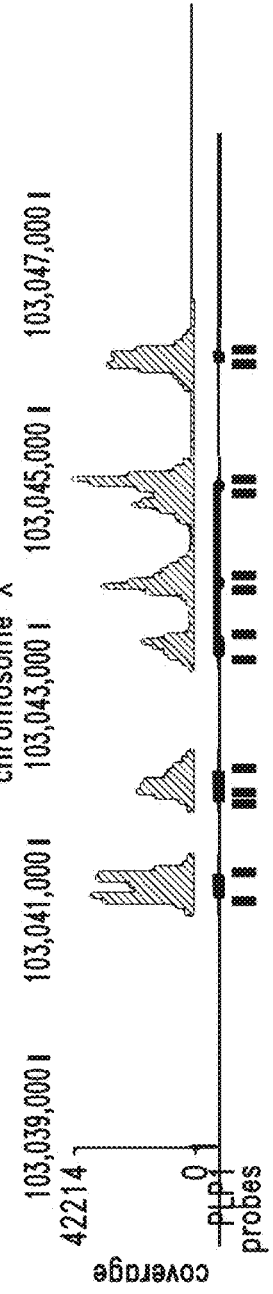
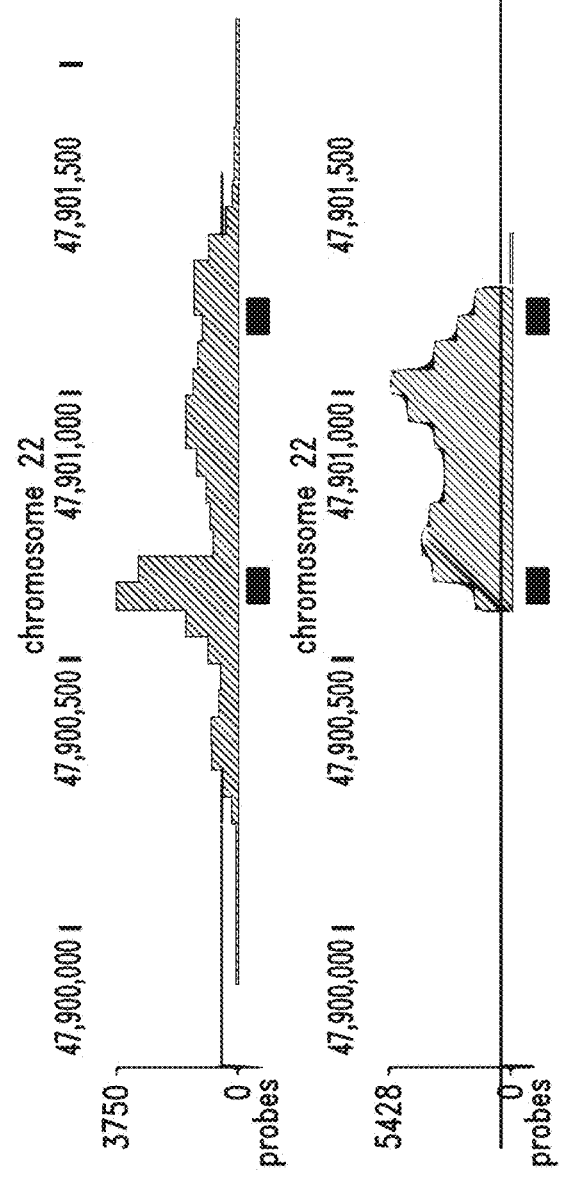
FIG. 18A
FIG. 18B
FIG. 18C
FIG. 18D

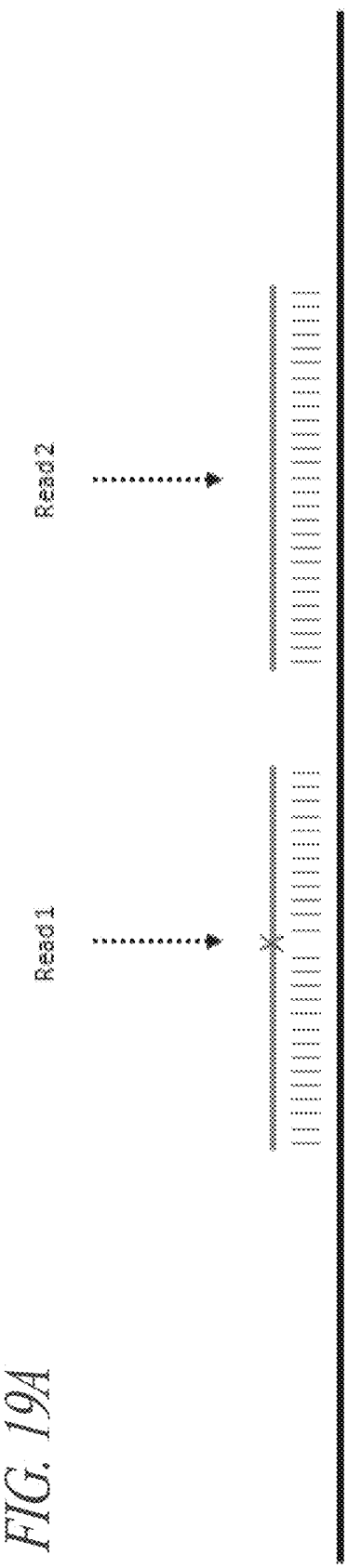
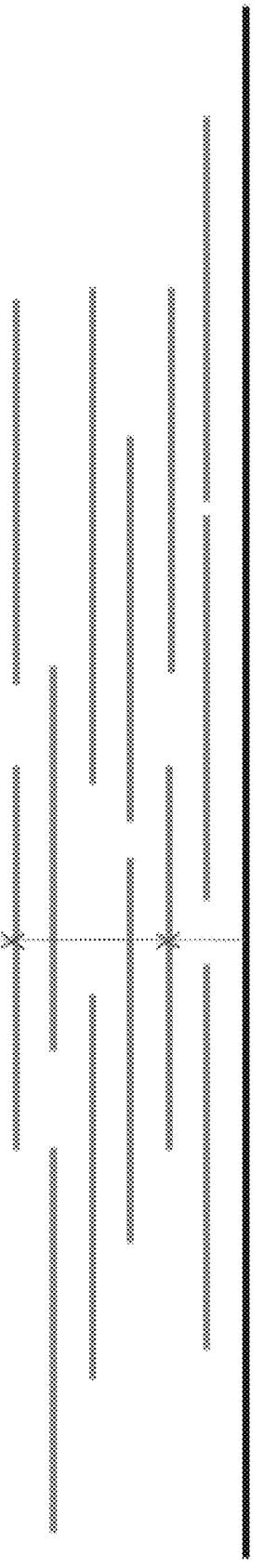
FIG. 19A
FIG. 19B

FIG. 23A
FIG. 23B
FIG. 23C

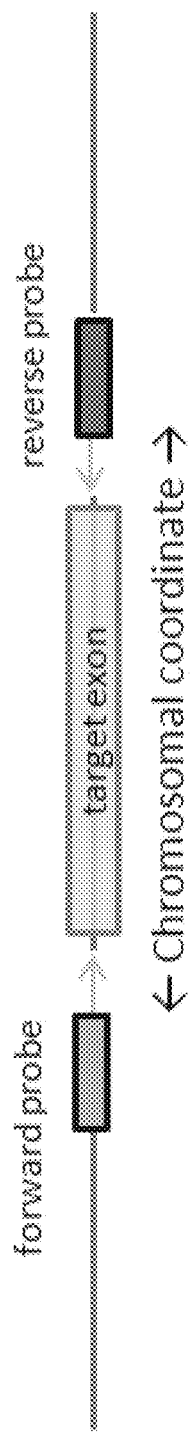
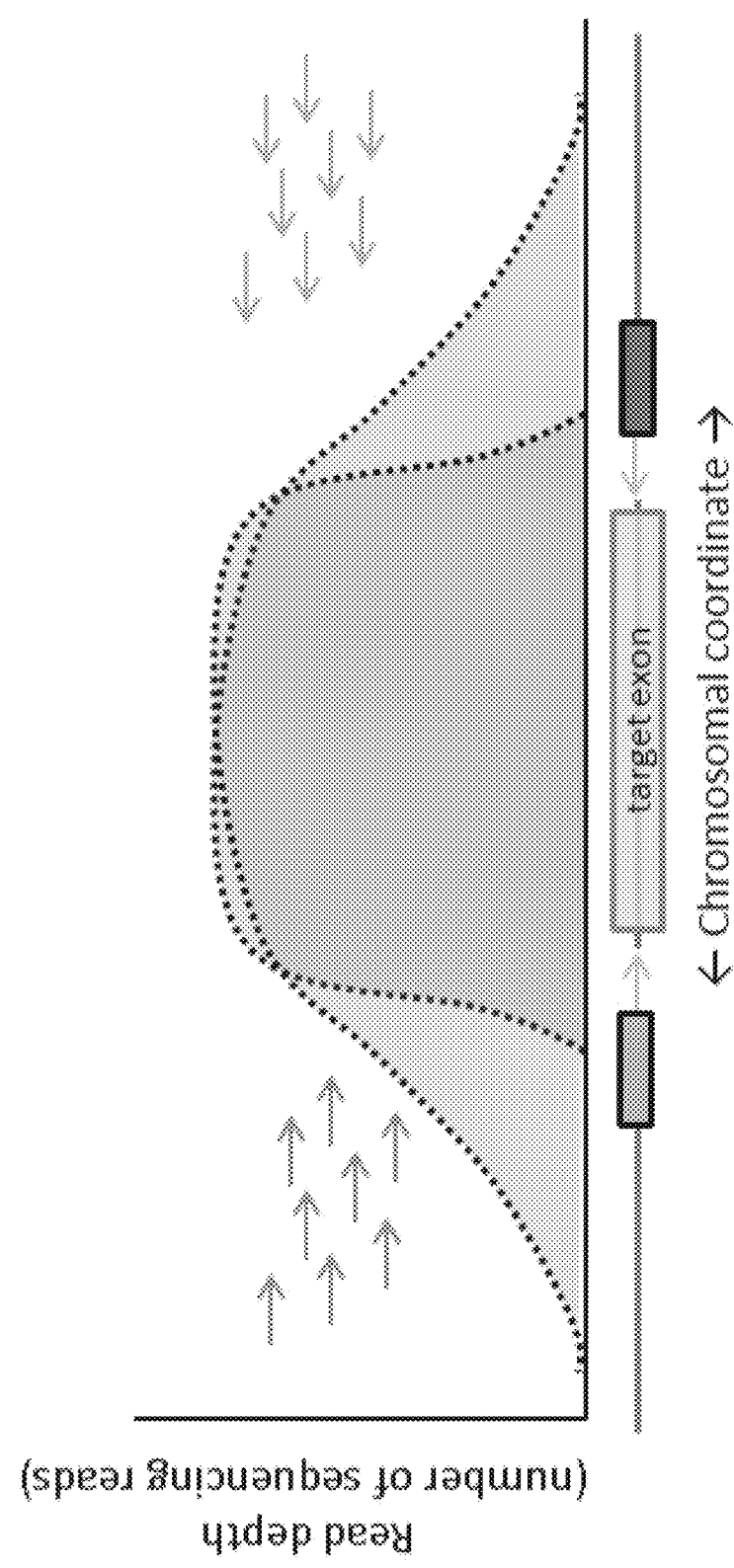
FIG. 26A
FIG. 26B

F S C L 11  13  15  16

1. Post capture RNA-seq C+P
2. Pippin prep lane 4
3. Pippin prep lane 5
4. ACA2-20 dT library
5. ACA2_FLFP + exome CAC3_FLRP dT library

FIG. 49

| | | | | Raw Ct value averages | | | | |
|---|---|---|---|---|---|---|---|---|
| plate 1 | 9 | 13 | 9 | 10 | 9 | 10 | 9 | 9 |
| | 10 | 9 | 9 | 9 | 9 | 9 | 9 | 9 |
| | 14 | 9 | 9 | 9 | 9 | 9 | 9 | 9 |

| | | | | | | | | |
|---|---|---|---|---|---|---|---|---|
| plate 2 | #DIV/0! | 9 | 13 | #DIV/0! | 9 | 9 | 9 | 9 |
| | 9 | 9 | 9 | 9 | 9 | 9 | 10 | 9 |
| | 9 | 9 | 10 | 9 | 9 | 9 | 9 | 9 |

| | | | | Converted to abs values | | | | |
|---|---|---|---|---|---|---|---|---|
| plate 1 | 1583 | 164 | 1984 | 1338 | 1739 | 970 | 2225 | 1756 |
| | 869 | 1729 | 1981 | 2142 | 1555 | 1751 | 2002 | 1688 |
| | | 1729 | 2346 | 1947 | 1817 | 1545 | 2337 | 1697 |

| | | | | | | | | |
|---|---|---|---|---|---|---|---|---|
| plate 2 | #DIV/0! | 1469 | 151 | #DIV/0! | 1843 | 2218 | 1495 | 1489 |
| | 2308 | 1622 | 1885 | 1439 | 1834 | 1500 | 852 | 1733 |
| | 1822 | 2061 | 1340 | 1812 | 2100 | 1689 | 1857 | 2168 |

| | | | | Normalized to pg/ul | | | | |
|---|---|---|---|---|---|---|---|---|
| plate 1 | 10 | 1 | 13 | 8 | 11 | 6 | 14 | 11 |
| | 5 | 11 | 13 | 14 | 10 | 11 | 13 | 11 |
| | | 11 | 15 | 12 | 11 | 10 | 15 | 11 |

| | | | | | | | | |
|---|---|---|---|---|---|---|---|---|
| plate 2 | #DIV/0! | 10 | 1 | #DIV/0! | 13 | 15 | 10 | 10 |
| | 16 | 11 | 13 | 10 | 12 | 10 | 6 | 12 |
| | 12 | 14 | 9 | 12 | 14 | 11 | 13 | 15 |

| | | | | Genomes per ul of ligation mix | | | | |
|---|---|---|---|---|---|---|---|---|
| plate 1 | | | | 4 | 2 | 3 | 2 | 4 | 3 |
| | 2 | 3 | 4 | 4 | 3 | 3 | 4 | 3 |
| | | 3 | 4 | 4 | 3 | 3 | 4 | 3 |

| | | | | | | | | |
|---|---|---|---|---|---|---|---|---|
| plate 2 | | | | | 4 | 4 | 3 | 3 |
| | 5 | 3 | 4 | 3 | 4 | 3 | 2 | 3 |
| | 4 | 4 | 3 | 4 | 4 | 3 | 4 | 4 |

FIG. 50

Library Concentrations (genomes/μL)

|   | 1 | 2 | 3 | 4 | 5 | 6 | 7 | 8 |
|---|---|---|---|---|---|---|---|---|
| A | 10 pg/ul STD | 1 pg/ul STD | F1 | F2 | F3 | F4 | F5 | F6 |
| B |  |  | 4 | 2 | 3 | 3 | 2 | 3 |
| C | F7 | F8 | F9 | F10 | F11 | F12 | F13 | F14 |
| D | 2 | 3 | 4 | 4 | 3 | 3 | 3 | 3 |
| E | F15 | F16 | M1 | M2 | M3 | M4 | M5 | M6 |
| F | 4 | 3 | 3 | 4 | 4 | 3 | 3 | 3 |

|   | 1 | 2 | 3 | 4 | 5 | 6 | 7 | 8 |
|---|---|---|---|---|---|---|---|---|
| A | 100 pg/ul STD | 10 pg/ul STD | 1 pg/ul STD | NTC | M1 | M2 | M3 | |
| B | 100 pg/ul STD | 10 pg/ul STD | 1 pg/ul STD | NTC |  | 4 | 3 | 3 |
| C | M1 | M2 | M3 | M4 | M5 | M6 | M7 | M8 |
| D | 5 | 3 | 4 | 3 | 4 | 3 | 2 | 3 |
| E | M9 | M10 | M11 | M12 | M13 | M14 | M15 | M16 |
| F | 4 | 4 | 4 | 4 | 4 | 3 | 4 | 4 |

FIG. 51

Calculation of the volume of each sample library needed for desired genome representation

| Sample | genomes/ul | # genomes needed | ul to get | H2O |
|---|---|---|---|---|
| F1 | 4 | 10.0 | 2.7 | 37.3 |
| F2 | 2 | 40.0 | 16.2 | 23.8 |
| F3 | 3 | C | | |
| F4 | 2 | 80.0 | 44.8 | -4.8 |
| F5 | 4 | 20.0 | 4.9 | 35.1 |
| F6 | 3 | 20.0 | 6.2 | 33.8 |
| F7 | 2 | 40.0 | 25.0 | 15.0 |
| F8 | 3 | | | |
| F9 | 4 | | | |
| F10 | 4 | 40.0 | 10.1 | 29.9 |
| F11 | 3 | | | |
| F12 | 3 | | | |
| F13 | 4 | | | |
| F14 | 3 | | | |
| F15 | 4 | | | |
| F16 | 3 | | | |

| Sample | genomes/ul | # genomes needed | ul to get | H2O |
|---|---|---|---|---|
| M1 | 4 ave | | | |
| M2 | 3 ave | | | |
| M3 | 3 ave C | 40.0 | 11.9 | 28.1 |
| M4 | 3 | | | |
| M5 | 4 | | | |
| M6 | 3 | | | |
| M7 | 2 | | | |
| M8 | 3 | 80.0 | 23.3 | 16.7 |
| M9 | 4 | | | |
| M10 | 4 | | | |
| M11 | 3 | 40.0 | 15.0 | 25.0 |
| M12 | 4 | 10.0 | 2.8 | 37.2 |
| M13 | 4 | 20.0 | 4.8 | 35.2 |
| M14 | 3 | | | |
| M15 | 4 | 40.0 | 10.9 | 29.1 |
| M16 | 4 | 20.0 | 4.6 | 35.4 |

FIG. 52 qPCR analysis of capture sensitivity and specificity

| Raw Cq | Assay 9 | Assay 10 | Assay 11 | Assay 12 | Assay 13 | Assay 14 | Assay 15 | Assay 16 |
|---|---|---|---|---|---|---|---|---|
| gDNA lib | 20 | 19 | 20 | 19 | 20 | 19 | 20 | 20 |
| 1st cap | 20 | 15 | 23 | 21 | 20 | 15 | 16 | 15 |
| cap + proc | 23 | 13 | 27 | 20 | 20 | 12 | 13 | 13 |

| Abs value | Assay 9 | Assay 10 | Assay 11 | Assay 12 | Assay 13 | Assay 14 | Assay 15 | Assay 16 |
|---|---|---|---|---|---|---|---|---|
| gDNA lib | 122 | 188 | 114 | 211 | 76 | 184 | 85 | 79 |
| 1st cap | 72 | 3240 | 15 | 59 | 85 | 2305 | 1231 | 2197 |
| cap + proc | 11 | 16518 | 1 | 69 | 97 | 19504 | 11189 | 13275 |

| Adj for dil | Assay 9 | Assay 10 | Assay 11 | Assay 12 | Assay 13 | Assay 14 | Assay 15 | Assay 16 |
|---|---|---|---|---|---|---|---|---|
| gDNA lib | 122 | 188 | 114 | 211 | 76 | 184 | 85 | 79 |
| 1st cap | 71606 | 3239810 | 14835 | 58862 | 84616 | 2304816 | 1230995 | 2196798 |
| cap + proc | 10793 | 16517508 | 713 | 69047 | 97429 | 19504350 | 11189209 | 13274986 |

| Fold enric | Assay 9 | Assay 10 | Assay 11 | Assay 12 | Assay 13 | Assay 14 | Assay 15 | Assay 16 |
|---|---|---|---|---|---|---|---|---|
| 1st cap | 585 | 17261 | 131 | 279 | 1108 | 12530 | 14513 | 27753 |
| cap + proc | 88 | 88000 | 6 | 328 | 1276 | 106034 | 131921 | 167709 |
| c+p/c | 0 | 5 | 0 | 1 | 1 | 8 | 9 | 6 |

FIG. 53

| Enrichment Protocol | No. of Reads Aligning to Genome (hg19) | No. of Reads Aligning to Target Regions | % of Aligned Reads within Target Regions |
|---|---|---|---|
| Capture Only | 4,122,637 | 1,031,370 | 25.0% |
| Capture + Processing | 6,949,695 | 5,433,442 | 78.2% |

FIG. 54

| EXPERIMENT: | 1 | 2 | 3 | 4 | 5 |
|---|---|---|---|---|---|
| T4 DNA polymerase | no | no | yes | yes | yes |
| T4 gene 32 protein | no | yes | no | yes | yes |
| T4 DNA ligase | no | yes | yes | no | yes |

FIG. 55

| hgnc_symbol | transcript | transcript_length | heart | liver | h/l | l/h |
|---|---|---|---|---|---|---|
| MYH7 | NM_000257 | 6030 | 2137.51 | 0.007 | 305358.6 | 0.0 |
| NEBL | NM_006393 | 9213 | 115.617 | 0.097 | 1191.9 | 0.0 |
| MGP | NM_000900 | 661 | 1059.49 | 11.155 | 95.0 | 0.0 |
| DKK3 | NM_013253 | 2746 | 118.464 | 1.136 | 104.3 | 0.0 |
| BVES | NM_147147 | 5505 | 11.27 | 0.11 | 102.5 | 0.0 |
| PDE4DIP | NM_001002812 | 4824 | 108.053 | 10.053 | 10.7 | 0.1 |
| HAND2 | NM_021973 | 2368 | 10.069 | 0.992 | 10.2 | 0.1 |
| RP9P | NR_003500 | 1297 | 1.279 | 0.125 | 10.2 | 0.1 |
| SOD2 | NM_000636 | 1593 | 492.028 | 500.782 | 1.0 | 1.0 |
| ATP5E | NM_006886 | 417 | 101.927 | 93.268 | 1.1 | 0.9 |
| TRAPPC1 | NM_021210 | 819 | 10.197 | 9.646 | 1.1 | 0.9 |
| TAF1A | NM_005681 | 1879 | 1.101 | 1.035 | 1.1 | 0.9 |
| MGST1 | NM_145764 | 910 | 43.368 | 429.307 | 0.1 | 9.9 |
| PDIA4 | NM_004911 | 2952 | 14.701 | 154.615 | 0.1 | 10.5 |
| STARD10 | NM_006645 | 1988 | 1.163 | 11.147 | 0.1 | 9.6 |
| TMEM14A | NM_014051 | 1014 | 0.11 | 1.119 | 0.1 | 10.2 |
| APOB | NM_000384 | 14121 | 5.822 | 765.522 | 0.0 | 131.5 |
| SERPINF2 | NM_001165921 | 2092 | 1.034 | 102.91 | 0.0 | 99.5 |
| TFR2 | NM_003227 | 2888 | 0.142 | 13.762 | 0.0 | 96.9 |
| FGL1 | NM_147203 | 1337 | 1.102 | 1305.36 | 0.0 | 1184.5 |
| FGA | NM_000508 | 3655 | 24.14 | 9012.08 | 0.0 | 373.3 |

FIG. 56

| HEART | Atlas | Total | Targeted | LIVER | Atlas | Total | Targeted |
|---|---|---|---|---|---|---|---|
| MYH7 | 50188 | 71792 | 40164 | MYH7 | 0 | 374 | 721 |
| NEBL | 2715 | 936 | 3460 | NEBL | 1 | 27 | 24 |
| MGP | 24876 | 1315 | 13162 | MGP | 90 | 42 | 393 |
| DKK3 | 2781 | 18092 | 20763 | DKK3 | 9 | 36 | 211 |
| BVES | 265 | 179 | 650 | BVES | 1 | 5 | 62 |
| PDE4DIP | 2537 | 860 | 5029 | PDE4DIP | 81 | 88 | 294 |
| HAND2 | 236 | 479 | 1052 | HAND2 | 8 | 42 | 279 |
| RP9P | 30 | 121 | 63 | RP9P | 1 | 20 | 12 |
| SOD2 | 11553 | 780 | 5437 | SOD2 | 4031 | 1503 | 8802 |
| ATP5E | 2393 | 1607 | 2363 | ATP5E | 751 | 451 | 2173 |
| TRAPPC1 | 239 | 536 | 1970 | TRAPPC1 | 78 | 80 | 397 |
| TAF1A | 26 | 22 | 34 | TAF1A | 8 | 7 | 48 |
| MGST1 | 1018 | 1312 | 2862 | MGST1 | 3455 | 5514 | 9281 |
| PDIA4 | 345 | 603 | 1310 | PDIA4 | 1244 | 1197 | 2144 |
| STARD10 | 27 | 908 | 1214 | STARD10 | 90 | 1857 | 3338 |
| TMEM14A | 3 | 74 | 57 | TMEM14A | 9 | 110 | 74 |
| APOB | 137 | 66 | 107 | APOB | 6162 | 5243 | 17030 |
| SERPINF2 | 24 | 119 | 89 | SERPINF2 | 828 | 7474 | 7795 |
| TFR2 | 3 | 20 | 11 | TFR2 | 111 | 3395 | 3489 |
| FGL1 | 26 | 50 | 44 | FGL1 | 10507 | 21763 | 11420 |
| FGA | 567 | 131 | 160 | FGA | 72538 | 50772 | 32014 |

SEQUENCE LISTING

<160> NUMBER OF SEQ ID NOS: 810

<210> SEQ ID NO 1
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 1
gaccagagaa ttcgaataca aaac                                              24

<210> SEQ ID NO 2
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 2
gaccagagaa ttcgaataca acac                                              24

<210> SEQ ID NO 3
<211> LENGTH: 24

```
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 3
gaccagagaa ttcgaataca agac                                          24

<210> SEQ ID NO 4
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 4
gaccagagaa ttcgaataca atac                                          24

<210> SEQ ID NO 5
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 5
gaccagagaa ttcgaataca caac                                          24

<210> SEQ ID NO 6
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 6
gaccagagaa ttcgaataca ccac                                          24

<210> SEQ ID NO 7
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 7
gaccagagaa ttcgaataca cgac                                          24

<210> SEQ ID NO 8
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 8
gaccagagaa ttcgaataca ctac                                          24

<210> SEQ ID NO 9
<211> LENGTH: 24
<212> TYPE: DNA
```

<213> ORGANISM: Artificial Sequence
<220> FEATURE:
<223> OTHER INFORMATION: Adaptor sequence - tag, sample code and
      universal amplification sequence

<400> SEQUENCE: 9
gaccagagaa ttcgaataca gaac                                              24

<210> SEQ ID NO 10
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 10
gaccagagaa ttcgaataca gcac                                              24

<210> SEQ ID NO 11
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 11
gaccagagaa ttcgaataca ggac                                              24

<210> SEQ ID NO 12
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 12
gaccagagaa ttcgaataca gtac                                              24

<210> SEQ ID NO 13
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 13
gaccagagaa ttcgaataca taac                                              24

<210> SEQ ID NO 14
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 14
gaccagagaa ttcgaataca tcac                                              24

<210> SEQ ID NO 15
<211> LENGTH: 24
<212> TYPE: DNA
<213> ORGANISM: Artificial Sequence

```
<220> FEATURE:
<223> OTHER INFORMATION: Adaptor sequence - tag, sample code and
      universal amplification sequence

<400> SEQUENCE: 15
gaccagagaa ttcgaataca tgac                                              24

<210> SEQ ID NO 16
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 16
gaccagagaa ttcgaataca ttac                                              24

<210> SEQ ID NO 17
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 17
gaccagagaa ttcgaataca aaga                                              24

<210> SEQ ID NO 18
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 18
gaccagagaa ttcgaataca acga                                              24

<210> SEQ ID NO 19
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 19
gaccagagaa ttcgaataca agga                                              24

<210> SEQ ID NO 20
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 20
gaccagagaa ttcgaataca atga                                              24

<210> SEQ ID NO 21
<211> LENGTH: 24
<212> TYPE: DNA
<213> ORGANISM: Artificial Sequence
<220> FEATURE:
```

```
<223> OTHER INFORMATION: Adaptor sequence - tag, sample code and
      universal amplification sequence

<400> SEQUENCE: 21
gaccagagaa ttcgaataca caga                                              24

<210> SEQ ID NO 22
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 22
gaccagagaa ttcgaataca ccga                                              24

<210> SEQ ID NO 23
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 23
gaccagagaa ttcgaataca cgga                                              24

<210> SEQ ID NO 24
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 24
gaccagagaa ttcgaataca ctga                                              24

<210> SEQ ID NO 25
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 25
gaccagagaa ttcgaataca gaga                                              24

<210> SEQ ID NO 26
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 26
gaccagagaa ttcgaataca gcga                                              24

<210> SEQ ID NO 27
<211> LENGTH: 24
<212> TYPE: DNA
<213> ORGANISM: Artificial Sequence
<220> FEATURE:
<223> OTHER INFORMATION: Adaptor sequence - tag, sample code and
``` universal amplification sequence

<400> SEQUENCE: 27
gaccagagaa ttcgaataca ggga                                          24

<210> SEQ ID NO 28
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 28
gaccagagaa ttcgaataca gtga                                          24

<210> SEQ ID NO 29
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 29
gaccagagaa ttcgaataca taga                                          24

<210> SEQ ID NO 30
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 30
gaccagagaa ttcgaataca tcga                                          24

<210> SEQ ID NO 31
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 31
gaccagagaa ttcgaataca tgga                                          24

<210> SEQ ID NO 32
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 32
gaccagagaa ttcgaataca ttga                                          24

<210> SEQ ID NO 33
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 33
gaccagagaa ttcgaataca aact                                              24

<210> SEQ ID NO 34
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 34
gaccagagaa ttcgaataca acct                                              24

<210> SEQ ID NO 35
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 35
gaccagagaa ttcgaataca agct                                              24

<210> SEQ ID NO 36
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 36
gaccagagaa ttcgaataca atct                                              24

<210> SEQ ID NO 37
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 37
gaccagagaa ttcgaataca cact                                              24

<210> SEQ ID NO 38
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 38
gaccagagaa ttcgaataca ccct                                              24

<210> SEQ ID NO 39
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

```
<400> SEQUENCE: 39
gaccagagaa ttcgaataca cgct                                          24

<210> SEQ ID NO 40
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 40
gaccagagaa ttcgaataca ctct                                          24

<210> SEQ ID NO 41
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 41
gaccagagaa ttcgaataca gact                                          24

<210> SEQ ID NO 42
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 42
gaccagagaa ttcgaataca gcct                                          24

<210> SEQ ID NO 43
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 43
gaccagagaa ttcgaataca ggct                                          24

<210> SEQ ID NO 44
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 44
gaccagagaa ttcgaataca gtct                                          24

<210> SEQ ID NO 45
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 45
```

```
gaccagagaa ttcgaataca tact                                          24
```

<210> SEQ ID NO 46
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 46

```
gaccagagaa ttcgaataca tcct                                          24
```

<210> SEQ ID NO 47
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 47

```
gaccagagaa ttcgaataca tgct                                          24
```

<210> SEQ ID NO 48
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 48

```
gaccagagaa ttcgaataca ttct                                          24
```

<210> SEQ ID NO 49
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 49

```
gaccagagaa ttcgaataca aatg                                          24
```

<210> SEQ ID NO 50
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 50

```
gaccagagaa ttcgaataca actg                                          24
```

<210> SEQ ID NO 51
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 51
gaccagagaa ttcgaataca agtg          24

<210> SEQ ID NO 52
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 52
gaccagagaa ttcgaataca attg          24

<210> SEQ ID NO 53
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 53
gaccagagaa ttcgaataca catg          24

<210> SEQ ID NO 54
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 54
gaccagagaa ttcgaataca cctg          24

<210> SEQ ID NO 55
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 55
gaccagagaa ttcgaataca cgtg          24

<210> SEQ ID NO 56
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 56
gaccagagaa ttcgaataca cttg          24

<210> SEQ ID NO 57
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 57
gaccagagaa ttcgaataca gatg          24

<210> SEQ ID NO 58
<211> LENGTH: 24
<212> TYPE: DNA
<213> ORGANISM: Artificial Sequence
<220> FEATURE:
<223> OTHER INFORMATION: Adaptor sequence - tag, sample code and universal amplification sequence

<400> SEQUENCE: 58
gaccagagaa ttcgaataca gctg                                              24

<210> SEQ ID NO 59
<211> LENGTH: 24
<212> TYPE: DNA
<213> ORGANISM: Artificial Sequence
<220> FEATURE:
<223> OTHER INFORMATION: Adaptor sequence - tag, sample code and universal amplification sequence

<400> SEQUENCE: 59
gaccagagaa ttcgaataca ggtg                                              24

<210> SEQ ID NO 60
<211> LENGTH: 24
<212> TYPE: DNA
<213> ORGANISM: Artificial Sequence
<220> FEATURE:
<223> OTHER INFORMATION: Adaptor sequence - tag, sample code and universal amplification sequence

<400> SEQUENCE: 60
gaccagagaa ttcgaataca gttg                                              24

<210> SEQ ID NO 61
<211> LENGTH: 24
<212> TYPE: DNA
<213> ORGANISM: Artificial Sequence
<220> FEATURE:
<223> OTHER INFORMATION: Adaptor sequence - tag, sample code and universal amplification sequence

<400> SEQUENCE: 61
gaccagagaa ttcgaataca tatg                                              24

<210> SEQ ID NO 62
<211> LENGTH: 24
<212> TYPE: DNA
<213> ORGANISM: Artificial Sequence
<220> FEATURE:
<223> OTHER INFORMATION: Adaptor sequence - tag, sample code and universal amplification sequence

<400> SEQUENCE: 62
gaccagagaa ttcgaataca tctg                                              24

<210> SEQ ID NO 63
<211> LENGTH: 24
<212> TYPE: DNA
<213> ORGANISM: Artificial Sequence
<220> FEATURE:
<223> OTHER INFORMATION: Adaptor sequence - tag, sample code and universal amplification sequence

<400> SEQUENCE: 63
gaccagagaa ttcgaataca tgtg                                              24

<210> SEQ ID NO 64
<211> LENGTH: 24
<212> TYPE: DNA
<213> ORGANISM: Artificial Sequence
<220> FEATURE:
<223> OTHER INFORMATION: Adaptor sequence - tag, sample code and
      universal amplification sequence

<400> SEQUENCE: 64
gaccagagaa ttcgaataca tttg                                          24

<210> SEQ ID NO 65
<211> LENGTH: 20
<212> TYPE: DNA
<213> ORGANISM: Artificial Sequence
<220> FEATURE:
<223> OTHER INFORMATION: Primer

<400> SEQUENCE: 65
aatgatacgg cgaccaccga                                               20

<210> SEQ ID NO 66
<211> LENGTH: 29
<212> TYPE: DNA
<213> ORGANISM: Artificial Sequence
<220> FEATURE:
<223> OTHER INFORMATION: Primer

<400> SEQUENCE: 66
aatgatacgg cgaccaccga gatctacac                                     29

<210> SEQ ID NO 67
<211> LENGTH: 25
<212> TYPE: DNA
<213> ORGANISM: Artificial Sequence
<220> FEATURE:
<223> OTHER INFORMATION: Primer

<400> SEQUENCE: 67
tgcaggacca gagaattcga ataca                                         25

<210> SEQ ID NO 68
<211> LENGTH: 33
<212> TYPE: DNA
<213> ORGANISM: Artificial Sequence
<220> FEATURE:
<223> OTHER INFORMATION: Primer

<400> SEQUENCE: 68
acacgtcatg caggaccaga gaattcgaat aca                                33

<210> SEQ ID NO 69
<211> LENGTH: 58
<212> TYPE: DNA
<213> ORGANISM: Artificial Sequence
<220> FEATURE:
<223> OTHER INFORMATION: Primer

<400> SEQUENCE: 69
aatgatacgg cgaccaccga gatctacacg tcatgcagga ccagagaatt cgaataca     58

<210> SEQ ID NO 70
<211> LENGTH: 20
<212> TYPE: DNA
<213> ORGANISM: Artificial Sequence
<220> FEATURE:

<223> OTHER INFORMATION: Primer

<400> SEQUENCE: 70
caagcagaag acggcatacg    20

<210> SEQ ID NO 71
<211> LENGTH: 24
<212> TYPE: DNA
<213> ORGANISM: Artificial Sequence
<220> FEATURE:
<223> OTHER INFORMATION: Primer

<400> SEQUENCE: 71
caagcagaag acggcatacg agat    24

<210> SEQ ID NO 72
<211> LENGTH: 25
<212> TYPE: DNA
<213> ORGANISM: Artificial Sequence
<220> FEATURE:
<223> OTHER INFORMATION: Primer

<400> SEQUENCE: 72
cacgggagtt gatcctggtt ttcac    25

<210> SEQ ID NO 73
<211> LENGTH: 33
<212> TYPE: DNA
<213> ORGANISM: Artificial Sequence
<220> FEATURE:
<223> OTHER INFORMATION: Primer

<400> SEQUENCE: 73
gtgactggca cgggagttga tcctggtttt cac    33

<210> SEQ ID NO 74
<211> LENGTH: 57
<212> TYPE: DNA
<213> ORGANISM: Artificial Sequence
<220> FEATURE:
<223> OTHER INFORMATION: Primer

<400> SEQUENCE: 74
caagcagaag acggcatacg agatgtgact ggcacgggag ttgatcctgg ttttcac    57

<210> SEQ ID NO 75
<211> LENGTH: 15
<212> TYPE: DNA
<213> ORGANISM: Artificial Sequence
<220> FEATURE:
<223> OTHER INFORMATION: Adapter sequence - partner strand for SEQ ID
    NO:23

<400> SEQUENCE: 75
tccgtgtatt cgaat    15

<210> SEQ ID NO 76
<211> LENGTH: 20
<212> TYPE: DNA
<213> ORGANISM: Artificial Sequence
<220> FEATURE:
<223> OTHER INFORMATION: Primer

<400> SEQUENCE: 76
gaccagagaa ttcgaataca    20

<210> SEQ ID NO 77
<211> LENGTH: 25
<212> TYPE: DNA
<213> ORGANISM: Artificial Sequence
<220> FEATURE:
<223> OTHER INFORMATION: Primer

<400> SEQUENCE: 77
tgcaggacca gagaattcga ataca                                25

<210> SEQ ID NO 78
<211> LENGTH: 57
<212> TYPE: DNA
<213> ORGANISM: Artificial Sequence
<220> FEATURE:
<223> OTHER INFORMATION: Primer

<400> SEQUENCE: 78
aatgatacgg cgaccaccga gatcacacgt catgcaggac cagagaattc gaataca    57

<210> SEQ ID NO 79
<211> LENGTH: 24
<212> TYPE: DNA
<213> ORGANISM: Artificial Sequence
<220> FEATURE:
<223> OTHER INFORMATION: Primer

<400> SEQUENCE: 79
ttagagtgct gtgcaagatg tctg                                 24

<210> SEQ ID NO 80
<211> LENGTH: 22
<212> TYPE: DNA
<213> ORGANISM: Artificial Sequence
<220> FEATURE:
<223> OTHER INFORMATION: Primer

<400> SEQUENCE: 80
accccaagaa acacaatcca gt                                   22

<210> SEQ ID NO 81
<211> LENGTH: 22
<212> TYPE: DNA
<213> ORGANISM: Artificial Sequence
<220> FEATURE:
<223> OTHER INFORMATION: Primer

<400> SEQUENCE: 81
gccactggat tgtgtttctt tg                                   22

<210> SEQ ID NO 82
<211> LENGTH: 24
<212> TYPE: DNA
<213> ORGANISM: Artificial Sequence
<220> FEATURE:
<223> OTHER INFORMATION: Primer

<400> SEQUENCE: 82
tcaattagct tttctgtgcc agtg                                 24

<210> SEQ ID NO 83
<211> LENGTH: 22
<212> TYPE: DNA
<213> ORGANISM: Artificial Sequence
<220> FEATURE:
<223> OTHER INFORMATION: Primer

<400> SEQUENCE: 83
actgttctgt ggctgtggac at                                    22

<210> SEQ ID NO 84
<211> LENGTH: 27
<212> TYPE: DNA
<213> ORGANISM: Artificial Sequence
<220> FEATURE:
<223> OTHER INFORMATION: Primer

<400> SEQUENCE: 84
tcttggtagt ttttggagaa ataggtc                               27

<210> SEQ ID NO 85
<211> LENGTH: 24
<212> TYPE: DNA
<213> ORGANISM: Artificial Sequence
<220> FEATURE:
<223> OTHER INFORMATION: Primer

<400> SEQUENCE: 85
ttcttcttcc ccaggcttgt taga                                  24

<210> SEQ ID NO 86
<211> LENGTH: 24
<212> TYPE: DNA
<213> ORGANISM: Artificial Sequence
<220> FEATURE:
<223> OTHER INFORMATION: Primer

<400> SEQUENCE: 86
caccccaaag aaacacaatc cagt                                  24

<210> SEQ ID NO 87
<211> LENGTH: 23
<212> TYPE: DNA
<213> ORGANISM: Artificial Sequence
<220> FEATURE:
<223> OTHER INFORMATION: Primer

<400> SEQUENCE: 87
ccctcatggc acagaaaagc taa                                   23

<210> SEQ ID NO 88
<211> LENGTH: 24
<212> TYPE: DNA
<213> ORGANISM: Artificial Sequence
<220> FEATURE:
<223> OTHER INFORMATION: Primer

<400> SEQUENCE: 88
tgggagggca ggtacttaca catt                                  24

<210> SEQ ID NO 89
<211> LENGTH: 25
<212> TYPE: DNA
<213> ORGANISM: Artificial Sequence
<220> FEATURE:
<223> OTHER INFORMATION: Primer

<400> SEQUENCE: 89
ccccttgttt tcttacacgt gttct                                 25

<210> SEQ ID NO 90

```
<211> LENGTH: 24
<212> TYPE: DNA
<213> ORGANISM: Artificial Sequence
<220> FEATURE:
<223> OTHER INFORMATION: Primer

<400> SEQUENCE: 90
cctcccttgg cttctccata ccta                                              24

<210> SEQ ID NO 91
<211> LENGTH: 24
<212> TYPE: DNA
<213> ORGANISM: Artificial Sequence
<220> FEATURE:
<223> OTHER INFORMATION: Primer

<400> SEQUENCE: 91
gtgtgtcatt gtttcccaaa atgg                                              24

<210> SEQ ID NO 92
<211> LENGTH: 24
<212> TYPE: DNA
<213> ORGANISM: Artificial Sequence
<220> FEATURE:
<223> OTHER INFORMATION: Primer

<400> SEQUENCE: 92
caccccttgt tattgccaca aaat                                              24

<210> SEQ ID NO 93
<211> LENGTH: 24
<212> TYPE: DNA
<213> ORGANISM: Artificial Sequence
<220> FEATURE:
<223> OTHER INFORMATION: Primer

<400> SEQUENCE: 93
taccagccaa gcccatacta gagg                                              24

<210> SEQ ID NO 94
<211> LENGTH: 24
<212> TYPE: DNA
<213> ORGANISM: Artificial Sequence
<220> FEATURE:
<223> OTHER INFORMATION: Primer

<400> SEQUENCE: 94
gggatcaaca gtggcataat tgaa                                              24

<210> SEQ ID NO 95
<211> LENGTH: 400
<212> TYPE: DNA
<213> ORGANISM: Homo sapiens

<400> SEQUENCE: 95
agtgcccact atctccgagc ctgtgagcac agggcctggc agaggggttt gagtggcatg       60
agctacctac tggatgtgcc tgactgtttc cccttcttct tccccaggct tgttagagtg      120
ctgtgcaaga tgtctggtag gggcccccctt tgcttccctg gtggccactg gattgtgttt     180
ctttggggtg gcactgttct gtggctgtgg acatgaagcc ctcactggca cagaaaagct      240
aattgagacc tatttctcca aaaactacca agactatgag tatctcatca atgtgtaagt      300
acctgccctc ccacacagac ccatctttt tttccctctc tccatcctgg agatagagaa       360
ctcttcagta ccttagtaac tagcagggga ctggggtgga                            400
```

<210> SEQ ID NO 96
<211> LENGTH: 399
<212> TYPE: DNA
<213> ORGANISM: Homo sapiens

<400> SEQUENCE: 96

```
tccaccccag tccctgcta gttactaagg tactgaagag ttctctatct ccaggatgga      60
gagagggaaa aaaagatgg gtctgtgtgg gagggcaggt acttacacat tgatgagata     120
ctcatagtct tggtagtttt tggagaaata ggtctcaatt agcttttctg tgccagtgag    180
ggcttcatgt ccacagccac agaacagtgc caccccaaag aaacacaatc cagtggccac    240
cagggaagca aaggggccc ctaccagaca tcttgcacag cactctaaca agcctgggga    300
agaagaaggg gaaacagtca ggcacatcca gtaggtagct catgccactc aaaccctct     360
gccaggccct gtgctcacag gctcggagat agtgggcac                            399
```

<210> SEQ ID NO 97
<211> LENGTH: 400
<212> TYPE: DNA
<213> ORGANISM: Homo sapiens

<400> SEQUENCE: 97

```
agtgcccact atctccgagc ctgtgagcac agggcctggc agaggggttt gagtggcatg      60
agctacctac tggatgtgcc tgactgtttc cccttcttct tccccaggct tgttagagtg    120
ctgtgcaaga tgtctggtag ggccccctt tgcttccctg gtggccactg gattgtgttt    180
ctttggggtg gcactgttct gtggctgtgg acatgaagcc ctcactggca cagaaaagct   240
aattgagacc tatttctcca aaaactacca agactatgag tatctcatca atgtgtaagt    300
acctgccctc ccacacagac ccatcttttt tttccctctc tccatcctgg agatagagaa    360
ctcttcagta ccttagtaac tagcagggga ctggggtgga                          400
```

<210> SEQ ID NO 98
<211> LENGTH: 400
<212> TYPE: DNA
<213> ORGANISM: Homo sapiens

<400> SEQUENCE: 98

```
agtgcccact atctccgagc ctgtgagcac agggcctggc agaggggttt gagtggcatg      60
agctacctac tggatgtgcc tgactgtttc cccttcttct tccccaggct tgttagagtg    120
ctgtgcaaga tgtctggtag ggccccctt tgcttccctg gtggccactg gattgtgttt    180
ctttggggtg gcactgttct gtggctgtgg acatgaagcc ctcactggca cagaaaagct   240
aattgagacc tatttctcca aaaactacca agactatgag tatctcatca atgtgtaagt    300
acctgccctc ccacacagac ccatcttttt tttccctctc tccatcctgg agatagagaa    360
ctcttcagta ccttagtaac tagcagggga ctggggtgga                          400
```

<210> SEQ ID NO 99
<211> LENGTH: 400
<212> TYPE: DNA
<213> ORGANISM: Homo sapiens

<400> SEQUENCE: 99

```
agtgcccact atctccgagc ctgtgagcac agggcctggc agaggggttt gagtggcatg      60
agctacctac tggatgtgcc tgactgtttc cccttcttct tccccaggct tgttagagtg    120
```

```
ctgtgcaaga tgtctggtag gggccccctt tgcttccctg gtggccactg gattgtgttt      180
ctttggggtg gcactgttct gtggctgtgg acatgaagcc ctcactggca cagaaaagct      240
aattgagacc tatttctcca aaaactacca agactatgag tatctcatca atgtgtaagt      300
acctgccctc ccacacagac ccatcttttt tttccctctc tccatcctgg agatagagaa      360
ctcttcagta ccttagtaac tagcagggga ctggggtgga                            400

<210> SEQ ID NO 100
<211> LENGTH: 400
<212> TYPE: DNA
<213> ORGANISM: Homo sapiens

<400> SEQUENCE: 100
agtgcccact atctccgagc ctgtgagcac agggcctggc agaggggttt gagtggcatg       60
agctacctac tggatgtgcc tgactgtttc cccttcttct tccccaggct tgttagagtg      120
ctgtgcaaga tgtctggtag gggccccctt tgcttccctg gtggccactg gattgtgttt      180
ctttggggtg gcactgttct gtggctgtgg acatgaagcc ctcactggca cagaaaagct      240
aattgagacc tatttctcca aaaactacca agactatgag tatctcatca atgtgtaagt      300
acctgccctc ccacacagac ccatcttttt tttccctctc tccatcctgg agatagagaa      360
ctcttcagta ccttagtaac tagcagggga ctggggtgga                            400

<210> SEQ ID NO 101
<211> LENGTH: 400
<212> TYPE: DNA
<213> ORGANISM: Homo sapiens

<400> SEQUENCE: 101
agtgcccact atctccgagc ctgtgagcac agggcctggc agaggggttt gagtggcatg       60
agctacctac tggatgtgcc tgactgtttc cccttcttct tccccaggct tgttagagtg      120
ctgtgcaaga tgtctggtag gggccccctt tgcttccctg gtggccactg gattgtgttt      180
ctttggggtg gcactgttct gtggctgtgg acatgaagcc ctcactggca cagaaaagct      240
aattgagacc tatttctcca aaaactacca agactatgag tatctcatca atgtgtaagt      300
acctgccctc ccacacagac ccatcttttt tttccctctc tccatcctgg agatagagaa      360
ctcttcagta ccttagtaac tagcagggga ctggggtgga                            400

<210> SEQ ID NO 102
<211> LENGTH: 100
<212> TYPE: DNA
<213> ORGANISM: Homo sapiens

<400> SEQUENCE: 102 cccccttgttt tcttacacgt gttctgactt ctgctaggtg tggttcatat tgcccaagtt      60
ggagcctcca gcgtagtagg tatggagaag ccaagggagg                            100

<210> SEQ ID NO 103
<211> LENGTH: 81
<212> TYPE: DNA
<213> ORGANISM: Homo sapiens

<400> SEQUENCE: 103
gtgtgtcatt gttttgggaaa atggctagga catcccgaca aggtgatcat cctcaggatt       60
ttgtggcaat aacaagggggt g                                                 81
```

```
<210> SEQ ID NO 104
<211> LENGTH: 96
<212> TYPE: DNA
<213> ORGANISM: Homo sapiens

<400> SEQUENCE: 104
taccagccaa gcccatacta gaggctgtcc ccagatgcta gcaaccatct gattgaataa    60
ccatctgtat cattcaatta tgccactgtt gatccc                              96

<210> SEQ ID NO 105
<211> LENGTH: 34
<212> TYPE: DNA
<213> ORGANISM: Artificial Sequence
<220> FEATURE:
<223> OTHER INFORMATION: 34 nt binding site of universal oligonucleotide
<220> FEATURE:
<221> NAME/KEY: modified_base
<222> LOCATION: (34)..(34)
<223> OTHER INFORMATION: dideoxycytosine
<220> FEATURE:
<221> NAME/KEY: misc_feature
<222> LOCATION: (34)..(34)
<223> OTHER INFORMATION: n is a, c, g, or t

<400> SEQUENCE: 105
cactggacta tgtagtacct cactcagcaa tacn                                34

<210> SEQ ID NO 106
<211> LENGTH: 34
<212> TYPE: DNA
<213> ORGANISM: Artificial Sequence
<220> FEATURE:
<223> OTHER INFORMATION: 34 nt binding site of universal oligonucleotide
<220> FEATURE:
<221> NAME/KEY: modified_base
<222> LOCATION: (34)..(34)
<223> OTHER INFORMATION: dideoxycytosine
<220> FEATURE:
<221> NAME/KEY: misc_feature
<222> LOCATION: (34)..(34)
<223> OTHER INFORMATION: n is a, c, g, or t

<400> SEQUENCE: 106
ggcaacgaac ggactggaat ctacggtcac caan                                34

<210> SEQ ID NO 107
<211> LENGTH: 400
<212> TYPE: DNA
<213> ORGANISM: Homo sapiens

<400> SEQUENCE: 107
agtgcccact atctccgagc ctgtgagcac agggcctggc agaggggttt gagtggcatg    60
agctacctac tggatgtgcc tgactgtttc cccttcttct tccccaggct tgttagagtg   120
ctgtgcaaga tgtctggtag gggccccctt tgcttccctg gtggccactg gattgtgttt   180
ctttggggtg gcactgttct gtggctgtgg acatgaagcc ctcactggca cagaaaagct   240
aattgagacc tatttctcca aaaactacca agactatgag tatctcatca atgtgtaagt   300
acctgccctc ccacacagac ccatcttttt tttccctctc tccatcctgg agatagagaa   360
ctcttcagta ccttagtaac tagcagggga ctggggtgga                         400

<210> SEQ ID NO 108
<211> LENGTH: 114
<212> TYPE: DNA
<213> ORGANISM: Artificial Sequence
<220> FEATURE:
```

<223> OTHER INFORMATION: Ultramer targeted to PLP1 exon 2

<400> SEQUENCE: 108

```
gagttgatcc tggttttcac tttgagtggc atgagctacc tactggatgt gcctgactgt      60
ttccccttct tcttccccag ggtattgctg agtgaggtac tacatagtcc agtg            114
```

<210> SEQ ID NO 109
<211> LENGTH: 114
<212> TYPE: DNA
<213> ORGANISM: Artificial Sequence
<220> FEATURE:
<223> OTHER INFORMATION: Ultramer targeted to PLP1 exon 2

<400> SEQUENCE: 109

```
gagttgatcc tggttttcac atgtctggta ggggcccct tgcttccct ggtggccact        60 ggattgtgtt tctttggggt ggtattgctg agtgaggtac tacatagtcc agtg            114
```

<210> SEQ ID NO 110
<211> LENGTH: 114
<212> TYPE: DNA
<213> ORGANISM: Artificial Sequence
<220> FEATURE:
<223> OTHER INFORMATION: Ultramer targeted to PLP1 exon 2

<400> SEQUENCE: 110

```
gagttgatcc tggttttcac cttggtagtt tttggagaaa taggtctcaa ttagcttttc      60
tgtgccagtg agggcttcat ggtattgctg agtgaggtac tacatagtcc agtg            114
```

<210> SEQ ID NO 111
<211> LENGTH: 114
<212> TYPE: DNA
<213> ORGANISM: Artificial Sequence
<220> FEATURE:
<223> OTHER INFORMATION: Ultramer targeted to PLP1 exon 2

<400> SEQUENCE: 111

```
gagttgatcc tggttttcac atctccagga tggagagagg gaaaaaaaag atgggtctgt      60
gtgggagggc aggtacttac ggtattgctg agtgaggtac tacatagtcc agtg            114
```

<210> SEQ ID NO 112
<211> LENGTH: 114
<212> TYPE: DNA
<213> ORGANISM: Artificial Sequence
<220> FEATURE:
<223> OTHER INFORMATION: Ultramer targeted to PLP1 exon 2

<400> SEQUENCE: 112

```
gagttgatcc tggttttcac tttgagtggc atgagctacc tactggatgt gcctgactgt      60
ttccccttct tcttccccag gttggtgacc gtagattcca gtccgttcgt tgcc            114
```

<210> SEQ ID NO 113
<211> LENGTH: 114
<212> TYPE: DNA
<213> ORGANISM: Artificial Sequence
<220> FEATURE:
<223> OTHER INFORMATION: Ultramer targeted to PLP1 exon 2

<400> SEQUENCE: 113

```
gagttgatcc tggttttcac atgtctggta ggggcccct tgcttccct ggtggccact        60 ggattgtgtt tctttggggt gttggtgacc gtagattcca gtccgttcgt tgcc            114
```

<210> SEQ ID NO 114
<211> LENGTH: 114
<212> TYPE: DNA
<213> ORGANISM: Artificial Sequence
<220> FEATURE:
<223> OTHER INFORMATION: Ultramer targeted to PLP1 exon 2

<400> SEQUENCE: 114
gagttgatcc tggttttcac cttggtagtt tttggagaaa taggtctcaa ttagcttttc    60
tgtgccagtg agggcttcat gttggtgacc gtagattcca gtccgttcgt tgcc         114

<210> SEQ ID NO 115
<211> LENGTH: 114
<212> TYPE: DNA
<213> ORGANISM: Artificial Sequence
<220> FEATURE:
<223> OTHER INFORMATION: Ultramer targeted to PLP1 exon 2

<400> SEQUENCE: 115
gagttgatcc tggttttcac atctccagga tggagagagg gaaaaaaaag atgggtctgt    60
gtgggagggc aggtacttac gttggtgacc gtagattcca gtccgttcgt tgcc         114

<210> SEQ ID NO 116
<211> LENGTH: 400
<212> TYPE: DNA
<213> ORGANISM: Homo sapiens

<400> SEQUENCE: 116
agtgcccact atctccgagc ctgtgagcac agggcctggc agaggggttt gagtggcatg    60
agctacctac tggatgtgcc tgactgtttc cccttcttct tccccaggct tgttagagtg   120
ctgtgcaaga tgtctggtag gggccccctt tgcttccctg gtggccactg gattgtgttt   180
ctttggggtg gcactgttct gtggctgtgg acatgaagcc ctcactggca cagaaaagct   240
aattgagacc tatttctcca aaaactacca agactatgag tatctcatca atgtgtaagt   300
acctgccctc ccacacagac ccatcttttt tttccctctc tccatcctgg agatagagaa   360
ctcttcagta ccttagtaac tagcagggga ctggggtgga                        400

<210> SEQ ID NO 117
<211> LENGTH: 400
<212> TYPE: DNA
<213> ORGANISM: Homo sapiens

<400> SEQUENCE: 117
agtgcccact atctccgagc ctgtgagcac agggcctggc agaggggttt gagtggcatg    60
agctacctac tggatgtgcc tgactgtttc cccttcttct tccccaggct tgttagagtg   120
ctgtgcaaga tgtctggtag gggccccctt tgcttccctg gtggccactg gattgtgttt   180
ctttggggtg gcactgttct gtggctgtgg acatgaagcc ctcactggca cagaaaagct   240
aattgagacc tatttctcca aaaactacca agactatgag tatctcatca atgtgtaagt   300
acctgccctc ccacacagac ccatcttttt tttccctctc tccatcctgg agatagagaa   360
ctcttcagta ccttagtaac tagcagggga ctggggtgga                        400

<210> SEQ ID NO 118
<211> LENGTH: 400
<212> TYPE: DNA
<213> ORGANISM: Homo sapiens

<400> SEQUENCE: 118

```
agtgcccact atctccgagc ctgtgagcac agggcctggc agaggggttt gagtggcatg    60
agctacctac tggatgtgcc tgactgtttc cccttcttct tccccaggct tgttagagtg   120
ctgtgcaaga tgtctggtag gggccccctt tgcttccctg gtggccactg gattgtgttt   180 cttggggtg gcactgttct gtggctgtgg acatgaagcc ctcactggca cagaaaagct    240
aattgagacc tatttctcca aaaactacca agactatgag tatctcatca atgtgtaagt   300
acctgccctc ccacacagac ccatcttttt tttccctctc tccatcctgg agatagagaa   360
ctcttcagta ccttagtaac tagcaggggagg ctggggtgga                       400
```

<210> SEQ ID NO 119
<211> LENGTH: 400
<212> TYPE: DNA
<213> ORGANISM: Homo sapiens

<400> SEQUENCE: 119

```
agtgcccact atctccgagc ctgtgagcac agggcctggc agaggggttt gagtggcatg    60
agctacctac tggatgtgcc tgactgtttc cccttcttct tccccaggct tgttagagtg   120
ctgtgcaaga tgtctggtag gggccccctt tgcttccctg gtggccactg gattgtgttt   180 cttggggtg gcactgttct gtggctgtgg acatgaagcc ctcactggca cagaaaagct    240
aattgagacc tatttctcca aaaactacca agactatgag tatctcatca atgtgtaagt   300
acctgccctc ccacacagac ccatcttttt tttccctctc tccatcctgg agatagagaa   360
ctcttcagta ccttagtaac tagcagggga ctggggtgga                         400
```

<210> SEQ ID NO 120
<211> LENGTH: 400
<212> TYPE: DNA
<213> ORGANISM: Homo sapiens

<400> SEQUENCE: 120

```
agtgcccact atctccgagc ctgtgagcac agggcctggc agaggggttt gagtggcatg    60
agctacctac tggatgtgcc tgactgtttc cccttcttct tccccaggct tgttagagtg   120
ctgtgcaaga tgtctggtag gggccccctt tgcttccctg gtggccactg gattgtgttt   180 cttggggtg gcactgttct gtggctgtgg acatgaagcc ctcactggca cagaaaagct    240
aattgagacc tatttctcca aaaactacca agactatgag tatctcatca atgtgtaagt   300
acctgccctc ccacacagac ccatcttttt tttccctctc tccatcctgg agatagagaa   360
ctcttcagta ccttagtaac tagcagggga ctggggtgga                         400
```

<210> SEQ ID NO 121
<211> LENGTH: 400
<212> TYPE: DNA
<213> ORGANISM: Homo sapiens

<400> SEQUENCE: 121

```
agtgcccact atctccgagc ctgtgagcac agggcctggc agaggggttt gagtggcatg    60
agctacctac tggatgtgcc tgactgtttc cccttcttct tccccaggct tgttagagtg   120
ctgtgcaaga tgtctggtag gggccccctt tgcttccctg gtggccactg gattgtgttt   180 cttggggtg gcactgttct gtggctgtgg acatgaagcc ctcactggca cagaaaagct    240
aattgagacc tatttctcca aaaactacca agactatgag tatctcatca atgtgtaagt   300
acctgccctc ccacacagac ccatcttttt tttccctctc tccatcctgg agatagagaa   360
ctcttcagta ccttagtaac tagcagggga ctggggtgga                         400
```

<210> SEQ ID NO 122
<211> LENGTH: 21
<212> TYPE: DNA
<213> ORGANISM: Artificial Sequence
<220> FEATURE:
<223> OTHER INFORMATION: Primer

<400> SEQUENCE: 122
ggcttcgact gaacgtctcc a                                    21

<210> SEQ ID NO 123
<211> LENGTH: 22
<212> TYPE: DNA
<213> ORGANISM: Artificial Sequence
<220> FEATURE:
<223> OTHER INFORMATION: Primer

<400> SEQUENCE: 123
agtgctccat ggctgctcag tt                                   22

<210> SEQ ID NO 124
<211> LENGTH: 25
<212> TYPE: DNA
<213> ORGANISM: Artificial Sequence
<220> FEATURE:
<223> OTHER INFORMATION: Primer

<400> SEQUENCE: 124
gaaccagagg aacgctgtgg taact                                25

<210> SEQ ID NO 125
<211> LENGTH: 23
<212> TYPE: DNA
<213> ORGANISM: Artificial Sequence
<220> FEATURE:
<223> OTHER INFORMATION: Primer

<400> SEQUENCE: 125
gacgtgtgcc tagatgcgtt ttc                                  23

<210> SEQ ID NO 126
<211> LENGTH: 25
<212> TYPE: DNA
<213> ORGANISM: Artificial Sequence
<220> FEATURE:
<223> OTHER INFORMATION: Primer

<400> SEQUENCE: 126
tggctgaaaa gtctccttga aactg                                25

<210> SEQ ID NO 127
<211> LENGTH: 25
<212> TYPE: DNA
<213> ORGANISM: Artificial Sequence
<220> FEATURE:
<223> OTHER INFORMATION: Primer

<400> SEQUENCE: 127
ctcagtgggt ctccttgaga gaggt                                25

<210> SEQ ID NO 128
<211> LENGTH: 25
<212> TYPE: DNA
<213> ORGANISM: Artificial Sequence
<220> FEATURE:

<223> OTHER INFORMATION: Primer

<400> SEQUENCE: 128
ctttcctcca gtcacaagcc atcta                                    25

<210> SEQ ID NO 129
<211> LENGTH: 25
<212> TYPE: DNA
<213> ORGANISM: Artificial Sequence
<220> FEATURE:
<223> OTHER INFORMATION: Primer

<400> SEQUENCE: 129
catgctgata gaaagtcccc tggta                                    25

<210> SEQ ID NO 130
<211> LENGTH: 25
<212> TYPE: DNA
<213> ORGANISM: Artificial Sequence
<220> FEATURE:
<223> OTHER INFORMATION: Primer

<400> SEQUENCE: 130
ttttcacaca gccaggagtc ttttc                                    25

<210> SEQ ID NO 131
<211> LENGTH: 25
<212> TYPE: DNA
<213> ORGANISM: Artificial Sequence
<220> FEATURE:
<223> OTHER INFORMATION: Primer

<400> SEQUENCE: 131
gggagatccg acaatacaga ttgaa                                    25

<210> SEQ ID NO 132
<211> LENGTH: 25
<212> TYPE: DNA
<213> ORGANISM: Artificial Sequence
<220> FEATURE:
<223> OTHER INFORMATION: Primer

<400> SEQUENCE: 132
cctgtcttgt ctttgctgat gtttc                                    25

<210> SEQ ID NO 133
<211> LENGTH: 25
<212> TYPE: DNA
<213> ORGANISM: Artificial Sequence
<220> FEATURE:
<223> OTHER INFORMATION: Primer

<400> SEQUENCE: 133
acaaaacagg ctcaggactt agcaa                                    25

<210> SEQ ID NO 134
<211> LENGTH: 25
<212> TYPE: DNA
<213> ORGANISM: Artificial Sequence
<220> FEATURE:
<223> OTHER INFORMATION: Primer

<400> SEQUENCE: 134
caacgttagc ttcaccaaca ggaac                                    25

```
<210> SEQ ID NO 135
<211> LENGTH: 25
<212> TYPE: DNA
<213> ORGANISM: Artificial Sequence
<220> FEATURE:
<223> OTHER INFORMATION: Primer

<400> SEQUENCE: 135
gctggtagaa gttctcctcc tcgtc                                         25

<210> SEQ ID NO 136
<211> LENGTH: 23
<212> TYPE: DNA
<213> ORGANISM: Artificial Sequence
<220> FEATURE:
<223> OTHER INFORMATION: Primer

<400> SEQUENCE: 136
gtctgctcca cctccagctt gta                                           23

<210> SEQ ID NO 137
<211> LENGTH: 24
<212> TYPE: DNA
<213> ORGANISM: Artificial Sequence
<220> FEATURE:
<223> OTHER INFORMATION: Primer

<400> SEQUENCE: 137
gttgagaggg tagggaaga ccac                                           24

<210> SEQ ID NO 138
<211> LENGTH: 25
<212> TYPE: DNA
<213> ORGANISM: Artificial Sequence
<220> FEATURE:
<223> OTHER INFORMATION: Primer

<400> SEQUENCE: 138
gaaccagagg aacgctgtgg taact                                         25

<210> SEQ ID NO 139
<211> LENGTH: 23
<212> TYPE: DNA
<213> ORGANISM: Artificial Sequence
<220> FEATURE:
<223> OTHER INFORMATION: Primer

<400> SEQUENCE: 139
gacgtgtgcc tagatgcgtt ttc                                           23

<210> SEQ ID NO 140
<211> LENGTH: 25
<212> TYPE: DNA
<213> ORGANISM: Artificial Sequence
<220> FEATURE:
<223> OTHER INFORMATION: Primer

<400> SEQUENCE: 140
cctgtcttgt ctttgctgat gtttc                                         25

<210> SEQ ID NO 141
<211> LENGTH: 25
<212> TYPE: DNA
<213> ORGANISM: Artificial Sequence
<220> FEATURE:
<223> OTHER INFORMATION: Primer
```

```
<400> SEQUENCE: 141
acaaaacagg ctcaggactt agcaa                                              25

<210> SEQ ID NO 142
<211> LENGTH: 25
<212> TYPE: DNA
<213> ORGANISM: Artificial Sequence
<220> FEATURE:
<223> OTHER INFORMATION: Primer

<400> SEQUENCE: 142
caacgttagc ttcaccaaca ggaac                                              25

<210> SEQ ID NO 143
<211> LENGTH: 25
<212> TYPE: DNA
<213> ORGANISM: Artificial Sequence
<220> FEATURE:
<223> OTHER INFORMATION: Primer

<400> SEQUENCE: 143
gctggtagaa gttctcctcc tcgtc                                              25

<210> SEQ ID NO 144
<211> LENGTH: 23
<212> TYPE: DNA
<213> ORGANISM: Artificial Sequence
<220> FEATURE:
<223> OTHER INFORMATION: Primer

<400> SEQUENCE: 144
gtctgctcca cctccagctt gta                                                23

<210> SEQ ID NO 145
<211> LENGTH: 24
<212> TYPE: DNA
<213> ORGANISM: Artificial Sequence
<220> FEATURE:
<223> OTHER INFORMATION: Primer

<400> SEQUENCE: 145
gttgagaggg taggggaaga ccac                                               24

<210> SEQ ID NO 146
<211> LENGTH: 60
<212> TYPE: DNA
<213> ORGANISM: Homo sapiens

<400> SEQUENCE: 146
agaattcatt gccagctata aatctgtgga aacgctgcca cacaatctta gcacacaaga        60

<210> SEQ ID NO 147
<211> LENGTH: 60
<212> TYPE: DNA
<213> ORGANISM: Homo sapiens

<400> SEQUENCE: 147
taaatgacat aacagttatg attttgcaga aaacagatct gtatttattt cagtgttact        60

<210> SEQ ID NO 148
<211> LENGTH: 60
<212> TYPE: DNA
<213> ORGANISM: Homo sapiens

<400> SEQUENCE: 148
```

```
aggtttccgc accaagaccc ctttaactca agactgcctc ccgctttgtg tgccccgctc    60
```

<210> SEQ ID NO 149
<211> LENGTH: 60
<212> TYPE: DNA
<213> ORGANISM: Homo sapiens

<400> SEQUENCE: 149

```
agagcagaga atccgaggac ggagagaagg cgctggagtc ttgcgaggcg caggacttgg    60
```

<210> SEQ ID NO 150
<211> LENGTH: 95
<212> TYPE: DNA
<213> ORGANISM: Homo sapiens

<400> SEQUENCE: 150

```
atgtgactgg cacgggagtt gatcctggtt ttcacaagca cctagcccca ttcctgctga    60
gcaggaggtg gcaggtaccc cagactggga ggtaa                               95
```

<210> SEQ ID NO 151
<211> LENGTH: 95
<212> TYPE: DNA
<213> ORGANISM: Homo sapiens

<400> SEQUENCE: 151

```
atgtgactgg cacgggagtt gatcctggtt ttcacagtcg gtggggccag gatgaggccc    60
agtctgttca cacatggctg ctgcctctca gctct                               95
```

<210> SEQ ID NO 152
<211> LENGTH: 95
<212> TYPE: DNA
<213> ORGANISM: Homo sapiens

<400> SEQUENCE: 152

```
atgtgactgg cacgggagtt gatcctggtt ttcacacctg agtagcatca ttgtagttct    60
cgatatctcc acttccagtt ttacatttac catca                               95
```

<210> SEQ ID NO 153
<211> LENGTH: 95
<212> TYPE: DNA
<213> ORGANISM: Homo sapiens

<400> SEQUENCE: 153

```
atgtgactgg cacgggagtt gatcctggtt ttcaccctgg ccctcagcca gtacagaaag    60
tcatttgtca aggccttcag ttggcagacg tgctc                               95
```

<210> SEQ ID NO 154
<211> LENGTH: 95
<212> TYPE: DNA
<213> ORGANISM: Homo sapiens

<400> SEQUENCE: 154

```
atgtgactgg cacgggagtt gatcctggtt ttcacagaat tcattgccag ctataaatct    60
gtggaaacgc tgccacacaa tcttagcaca caaga                               95
```

<210> SEQ ID NO 155
<211> LENGTH: 95
<212> TYPE: DNA
<213> ORGANISM: Homo sapiens

<400> SEQUENCE: 155
atgtgactgg cacgggagtt gatcctggtt ttcacgactt caaagaaatt acaagttgac    60
atcttggact ctacccctcg tactttatct cctat    95

<210> SEQ ID NO 156
<211> LENGTH: 95
<212> TYPE: DNA
<213> ORGANISM: Homo sapiens

<400> SEQUENCE: 156
atgtgactgg cacgggagtt gatcctggtt ttcactctct ttggggtcaa gaaagaatcc    60
ctagtggatt tgggattcta gaggaggtgt tataa    95

<210> SEQ ID NO 157
<211> LENGTH: 95
<212> TYPE: DNA
<213> ORGANISM: Homo sapiens

<400> SEQUENCE: 157
atgtgactgg cacgggagtt gatcctggtt ttcactgcga taccatgctg aagatgagct    60
aacccaacca gccaagcagg cagggctgcg aagga    95

<210> SEQ ID NO 158
<211> LENGTH: 95
<212> TYPE: DNA
<213> ORGANISM: Homo sapiens

<400> SEQUENCE: 158
atgtgactgg cacgggagtt gatcctggtt ttcacggggt aggtggaaaa cccaagtaat    60
gtgattttgt aacatccact gctgcatttg tttgc    95

<210> SEQ ID NO 159
<211> LENGTH: 95
<212> TYPE: DNA
<213> ORGANISM: Homo sapiens

<400> SEQUENCE: 159
atgtgactgg cacgggagtt gatcctggtt ttcacttact tccctccagt tttgttgctt    60
gcaaaacaac agaatcttct ctccatgaaa tcatg    95

<210> SEQ ID NO 160
<211> LENGTH: 95
<212> TYPE: DNA
<213> ORGANISM: Homo sapiens

<400> SEQUENCE: 160
atgtgactgg cacgggagtt gatcctggtt ttcaccaggg gtatctatta tccccatttt    60
ctcacaaagg aaaccaagat aaaaggttta aatgg    95

<210> SEQ ID NO 161
<211> LENGTH: 95
<212> TYPE: DNA
<213> ORGANISM: Homo sapiens

<400> SEQUENCE: 161
atgtgactgg cacgggagtt gatcctggtt ttcacgaaat tctcttgtga attcctgtgt    60
cctcttgaat cttcaatgct aaagtttttg aaact    95

```
<210> SEQ ID NO 162
<211> LENGTH: 95
<212> TYPE: DNA
<213> ORGANISM: Homo sapiens

<400> SEQUENCE: 162
atgtgactgg cacgggagtt gatcctggtt ttcacgggtt tgagtggcat gagctaccta      60
ctggatgtgc ctgactgttt cccttcttc ttccc                                  95

<210> SEQ ID NO 163
<211> LENGTH: 95
<212> TYPE: DNA
<213> ORGANISM: Homo sapiens

<400> SEQUENCE: 163
atgtgactgg cacgggagtt gatcctggtt ttcacctatc tccaggatgg agagagggaa      60
aaaaaagatg ggtctgtgtg ggagggcagg tactt                                 95

<210> SEQ ID NO 164
<211> LENGTH: 95
<212> TYPE: DNA
<213> ORGANISM: Homo sapiens

<400> SEQUENCE: 164
atgtgactgg cacgggagtt gatcctggtt ttcacgaaag aagccaggtc ttcaattaat      60
aagattccct ggtctcgttt gtctacctgt taatg                                 95

<210> SEQ ID NO 165
<211> LENGTH: 95
<212> TYPE: DNA
<213> ORGANISM: Homo sapiens

<400> SEQUENCE: 165
atgtgactgg cacgggagtt gatcctggtt ttcaccagac tcgcgcccaa ttttccccca      60
ccccttgtta ttgccacaaa atcctgagga tgatc                                 95

<210> SEQ ID NO 166
<211> LENGTH: 95
<212> TYPE: DNA
<213> ORGANISM: Homo sapiens

<400> SEQUENCE: 166
atgtgactgg cacgggagtt gatcctggtt ttcactcttt cttcttcctt tatggggccc      60
tcctgctggc tgagggcttc tacaccaccg gcgca                                 95

<210> SEQ ID NO 167
<211> LENGTH: 95
<212> TYPE: DNA
<213> ORGANISM: Homo sapiens

<400> SEQUENCE: 167
atgtgactgg cacgggagtt gatcctggtt ttcacgtttg tgtttctaca tctgcaggct      60
gatgctgatt tctaaccacc ccatgtcaat cattt                                 95

<210> SEQ ID NO 168
<211> LENGTH: 95
<212> TYPE: DNA
<213> ORGANISM: Homo sapiens

<400> SEQUENCE: 168
```

```
atgtgactgg cacgggagtt gatcctggtt ttcacaacca aatatatagt gcttccatag    60
tgggtaggag agccaaagca cccgtaccct aactc                                95

<210> SEQ ID NO 169
<211> LENGTH: 95
<212> TYPE: DNA
<213> ORGANISM: Homo sapiens

<400> SEQUENCE: 169
atgtgactgg cacgggagtt gatcctggtt ttcacagtct ccatgtggcc ccgtaactcc    60
ataaagctta ccctgcttgc tttttgtgtc ttact                                95

<210> SEQ ID NO 170
<211> LENGTH: 95
<212> TYPE: DNA
<213> ORGANISM: Homo sapiens

<400> SEQUENCE: 170
atgtgactgg cacgggagtt gatcctggtt ttcacccatg ggtgtaattt gtatggtatt    60
agctactccc ttgtaaaata acccaaataa cccac                                95

<210> SEQ ID NO 171
<211> LENGTH: 95
<212> TYPE: DNA
<213> ORGANISM: Homo sapiens

<400> SEQUENCE: 171
atgtgactgg cacgggagtt gatcctggtt ttcactttac agtggagcat attactgctg    60
ttgcaagaaa cagttcttcc tctttcattt tcctg                                95

<210> SEQ ID NO 172
<211> LENGTH: 95
<212> TYPE: DNA
<213> ORGANISM: Homo sapiens

<400> SEQUENCE: 172
atgtgactgg cacgggagtt gatcctggtt ttcacatagc tgtacccaca ctatctcagg    60
cctatttact tgccaagatc attcaaagtc aactc                                95

<210> SEQ ID NO 173
<211> LENGTH: 95
<212> TYPE: DNA
<213> ORGANISM: Homo sapiens

<400> SEQUENCE: 173
atgtgactgg cacgggagtt gatcctggtt ttcacgattt gaggagggag tgctttcttt    60
tctactctca ttcacattct ctcttctgtt cccta                                95

<210> SEQ ID NO 174
<211> LENGTH: 95
<212> TYPE: DNA
<213> ORGANISM: Homo sapiens

<400> SEQUENCE: 174
atgtgactgg cacgggagtt gatcctggtt ttcaccagca ttgtaggctg tgtggttaga    60
gcctcgctat tagagaaagg gggatttcta cggggg                               95

<210> SEQ ID NO 175
<211> LENGTH: 95
```

<212> TYPE: DNA
<213> ORGANISM: Homo sapiens

<400> SEQUENCE: 175
atgtgactgg cacgggagtt gatcctggtt ttcactgtta cctttaaaag acatctgctt    60
tctgccaaaa ttaatgtgct gaacttaaac ttacc                              95

<210> SEQ ID NO 176
<211> LENGTH: 95
<212> TYPE: DNA
<213> ORGANISM: Homo sapiens

<400> SEQUENCE: 176
atgtgactgg cacgggagtt gatcctggtt ttcacttccc agtaaattac tcttaccaat    60
gcaacagact ttaaagaagt tgtgttttac aatgc                              95

<210> SEQ ID NO 177
<211> LENGTH: 95
<212> TYPE: DNA
<213> ORGANISM: Homo sapiens

<400> SEQUENCE: 177
atgtgactgg cacgggagtt gatcctggtt ttcactaaat gacataacag ttatgatttt    60
gcagaaaaca gatctgtatt tatttcagtg ttact                              95

<210> SEQ ID NO 178
<211> LENGTH: 95
<212> TYPE: DNA
<213> ORGANISM: Homo sapiens

<400> SEQUENCE: 178
atgtgactgg cacgggagtt gatcctggtt ttcacgacag gttttgaaag atatttgtgt    60
tactaatgac tgtgctataa ctttttttc tttcc                               95

<210> SEQ ID NO 179
<211> LENGTH: 95
<212> TYPE: DNA
<213> ORGANISM: Homo sapiens

<400> SEQUENCE: 179
atgtgactgg cacgggagtt gatcctggtt ttcacactca aaaataaaa actataatta     60
ctccttaatg tcagcttatt atattcaatt taaac                              95

<210> SEQ ID NO 180
<211> LENGTH: 95
<212> TYPE: DNA
<213> ORGANISM: Homo sapiens

<400> SEQUENCE: 180
atgtgactgg cacgggagtt gatcctggtt ttcacaacac cttttttgaa gtaaaggtg     60
cactgtaata atccagactg tgtttctccc ttctc                              95

<210> SEQ ID NO 181
<211> LENGTH: 95
<212> TYPE: DNA
<213> ORGANISM: Homo sapiens

<400> SEQUENCE: 181
atgtgactgg cacgggagtt gatcctggtt ttcacgaaac ctttatctgt atcaaagaat    60
ggtcctgcac cagtaatatg catattaaaa caaga 95

<210> SEQ ID NO 182
<211> LENGTH: 95
<212> TYPE: DNA
<213> ORGANISM: Homo sapiens

<400> SEQUENCE: 182
atgtgactgg cacgggagtt gatcctggtt ttcacgtgta ttaaccttat gtgtgacatg 60
ttctaatata gtcacatttt cattatttt attat 95

<210> SEQ ID NO 183
<211> LENGTH: 95
<212> TYPE: DNA
<213> ORGANISM: Homo sapiens

<400> SEQUENCE: 183
atgtgactgg cacgggagtt gatcctggtt ttcaccccca gccagcggtc cgcaaccctt 60
gccgcatcca cgaaactttg cccatagcag cgggc 95

<210> SEQ ID NO 184
<211> LENGTH: 95
<212> TYPE: DNA
<213> ORGANISM: Homo sapiens

<400> SEQUENCE: 184
atgtgactgg cacgggagtt gatcctggtt ttcaccgact catctcagca ttaaagtgat 60
aaaaaaataa attaaaaggc aagtggactt cggtg 95

<210> SEQ ID NO 185
<211> LENGTH: 95
<212> TYPE: DNA
<213> ORGANISM: Homo sapiens

<400> SEQUENCE: 185
atgtgactgg cacgggagtt gatcctggtt ttcacctgtg gcgcgcactg cgcgctgcgc 60
caggtttccg caccaagacc cctttaactc aagac 95

<210> SEQ ID NO 186
<211> LENGTH: 95
<212> TYPE: DNA
<213> ORGANISM: Homo sapiens

<400> SEQUENCE: 186
atgtgactgg cacgggagtt gatcctggtt ttcacttcta ctgcgacgag gaggagaact 60
tctaccagca gcagcagcag agcgagctgc agccc 95

<210> SEQ ID NO 187
<211> LENGTH: 95
<212> TYPE: DNA
<213> ORGANISM: Homo sapiens

<400> SEQUENCE: 187
atgtgactgg cacgggagtt gatcctggtt ttcacaccga gctgctggga ggagacatgg 60
tgaaccagag tttcatctgc gacccggacg acgag 95

<210> SEQ ID NO 188
<211> LENGTH: 95
<212> TYPE: DNA
<213> ORGANISM: Homo sapiens

```
<400> SEQUENCE: 188
atgtgactgg cacgggagtt gatcctggtt ttcacgccgc cgcctcagag tgcatcgacc      60
cctcggtggt cttcccctac cctctcaacg acagc                                 95

<210> SEQ ID NO 189
<211> LENGTH: 95
<212> TYPE: DNA
<213> ORGANISM: Homo sapiens

<400> SEQUENCE: 189
atgtgactgg cacgggagtt gatcctggtt ttcacggcgg ctaggggaca ggggcggggt      60
gggcagcagc tcgaatttct tccagatatc ctcgc                                 95

<210> SEQ ID NO 190
<211> LENGTH: 95
<212> TYPE: DNA
<213> ORGANISM: Homo sapiens

<400> SEQUENCE: 190
atgtgactgg cacgggagtt gatcctggtt ttcacagacg agcttggcgg cggccgagaa      60
gccgctccac atacagtcct ggatgatgat gtttt                                 95

<210> SEQ ID NO 191
<211> LENGTH: 95
<212> TYPE: DNA
<213> ORGANISM: Homo sapiens

<400> SEQUENCE: 191
atgtgactgg cacgggagtt gatcctggtt ttcacaggag agcagagaat ccgaggacgg      60
agagaaggcg ctggagtctt gcgaggcgca ggact                                 95

<210> SEQ ID NO 192
<211> LENGTH: 95
<212> TYPE: DNA
<213> ORGANISM: Homo sapiens

<400> SEQUENCE: 192
atgtgactgg cacgggagtt gatcctggtt ttcactaaga gtggcccgtt aaataagctg      60
ccaatgaaaa tgggaaaggt atccagccgc ccact                                 95

<210> SEQ ID NO 193
<211> LENGTH: 95
<212> TYPE: DNA
<213> ORGANISM: Homo sapiens

<400> SEQUENCE: 193
atgtgactgg cacgggagtt gatcctggtt ttcacttgta tttgtacagc attaatctgg      60
taattgatta ttttaatgta accttgctaa aggag                                 95

<210> SEQ ID NO 194
<211> LENGTH: 95
<212> TYPE: DNA
<213> ORGANISM: Homo sapiens

<400> SEQUENCE: 194
atgtgactgg cacgggagtt gatcctggtt ttcacgaggc cacagcaaac ctcctcacag      60
cccactggtc ctcaagaggt gccacgtctc cacac                                 95
```

<210> SEQ ID NO 195
<211> LENGTH: 95
<212> TYPE: DNA
<213> ORGANISM: Homo sapiens

<400> SEQUENCE: 195
atgtgactgg cacgggagtt gatcctggtt ttcacagagg aggaacgagc taaaacggag    60
cttttttgcc ctgcgtgacc agatcccgga gttgg                               95

<210> SEQ ID NO 196
<211> LENGTH: 95
<212> TYPE: DNA
<213> ORGANISM: Homo sapiens

<400> SEQUENCE: 196
atgtgactgg cacgggagtt gatcctggtt ttcactccaa cttgaccctc ttggcagcag    60
gatagtcctt ccgagtggag ggaggcgctg cgtag                               95

<210> SEQ ID NO 197
<211> LENGTH: 95
<212> TYPE: DNA
<213> ORGANISM: Homo sapiens

<400> SEQUENCE: 197
atgtgactgg cacgggagtt gatcctggtt ttcacgcttg gacggacagg atgtatgctg    60
tggctttttt aaggataact accttggggg ccttt                               95

<210> SEQ ID NO 198
<211> LENGTH: 95
<212> TYPE: DNA
<213> ORGANISM: Homo sapiens

<400> SEQUENCE: 198
atgtgactgg cacgggagtt gatcctggtt ttcacgcatt tgatcatgca tttgaaacaa    60
gttcataggt gattgctcag gacatttctg ttaga                               95

<210> SEQ ID NO 199
<211> LENGTH: 46
<212> TYPE: DNA
<213> ORGANISM: Artificial Sequence
<220> FEATURE:
<223> OTHER INFORMATION: Primer

<400> SEQUENCE: 199
aatgatacgg cgaccaccga gatctacacg tcatgcagga ccagag                   46

<210> SEQ ID NO 200
<211> LENGTH: 57
<212> TYPE: DNA
<213> ORGANISM: Artificial Sequence
<220> FEATURE:
<223> OTHER INFORMATION: Primer

<400> SEQUENCE: 200
caagcagaag acggcatacg agatgtgact ggcacgggag ttgagaattc gaataca       57

<210> SEQ ID NO 201
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 201
aagcacctag ccccattcct gctgagcagg aggtggcagg taccccagac tgggaggtaa        60

<210> SEQ ID NO 202
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 202
agtcggtggg gccaggatga ggcccagtct gttcacacat ggctgctgcc tctcagctct        60

<210> SEQ ID NO 203
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 203
acctgagtag catcattgta gttctcgata tctccacttc cagttttaca tttaccatca        60

<210> SEQ ID NO 204
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 204
cctggccctc agccagtaca gaaagtcatt tgtcaaggcc ttcagttggc agacgtgctc        60

<210> SEQ ID NO 205
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 205
agaattcatt gccagctata aatctgtgga aacgctgcca cacaatctta gcacacaaga        60

<210> SEQ ID NO 206
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 206
gacttcaaag aaattacaag ttgacatctt ggactctacc cctcgtactt tatctcctat        60

<210> SEQ ID NO 207
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 207
tctctttggg gtcaagaaag aatccctagt ggatttggga ttctagagga ggtgttataa        60

<210> SEQ ID NO 208

```
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 208
tgcgatacca tgctgaagat gagctaaccc aaccagccaa gcaggcaggg ctgcgaagga    60

<210> SEQ ID NO 209
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 209
ggggtaggtg aaaacccaa gtaatgtgat tttgtaacat ccactgctgc atttgtttgc    60

<210> SEQ ID NO 210
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 210
ttacttccct ccagttttgt tgcttgcaaa acaacagaat cttctctcca tgaaatcatg    60

<210> SEQ ID NO 211
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 211
caggggtatc tattatcccc attttctcac aaaggaaacc aagataaaag gtttaaatgg    60

<210> SEQ ID NO 212
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 212
gaaattctct tgtgaattcc tgtgtcctct tgaatcttca atgctaaagt ttttgaaact    60

<210> SEQ ID NO 213
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 213
gggtttgagt ggcatgagct acctactgga tgtgcctgac tgtttcccct tcttcttccc    60

<210> SEQ ID NO 214
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 214
```
ctatctccag gatggagaga gggaaaaaaa agatgggtct gtgtgggagg gcaggtactt    60

<210> SEQ ID NO 215
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 215
gaaagaagcc aggtcttcaa ttaataagat tccctggtct cgtttgtcta cctgttaatg    60

<210> SEQ ID NO 216
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 216
cagactcgcg cccaattttc ccccacccct tgttattgcc acaaaatcct gaggatgatc    60

<210> SEQ ID NO 217
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 217
tctttcttct tcctttatgg ggccctcctg ctggctgagg gcttctacac caccggcgca    60

<210> SEQ ID NO 218
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 218
gtttgtgttt ctacatctgc aggctgatgc tgatttctaa ccaccccatg tcaatcattt    60

<210> SEQ ID NO 219
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 219
aaccaaatat atagtgcttc catagtgggt aggagagcca aagcacccgt accctaactc    60

<210> SEQ ID NO 220
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 220
agtctccatg tggccccgta actccataaa gcttaccctg cttgcttttt gtgtcttact    60

<210> SEQ ID NO 221
<211> LENGTH: 60
<212> TYPE: DNA

```
<213> ORGANISM: Artificial Sequence
<220> FEATURE:
<223> OTHER INFORMATION: Oligonucleotide probe

<400> SEQUENCE: 221
ccatgggtgt aatttgtatg gtattagcta ctcccttgta aaataaccca aataacccac      60

<210> SEQ ID NO 222
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 222
tttacagtgg agcatattac tgctgttgca agaaacagtt cttcctcttt cattttcctg      60

<210> SEQ ID NO 223
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 223
atagctgtac ccacactatc tcaggcctat ttacttgcca agatcattca aagtcaactc      60

<210> SEQ ID NO 224
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 224
gatttgagga gggagtgctt tcttttctac tctcattcac attctctctt ctgttcccta      60

<210> SEQ ID NO 225
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 225
cagcattgta ggctgtgtgg ttagagcctc gctattagag aaaggggat ttctacgggg      60

<210> SEQ ID NO 226
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 226
tgttaccttt aaaagacatc tgctttctgc caaaattaat gtgctgaact taaacttacc      60

<210> SEQ ID NO 227
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 227
ttcccagtaa attactctta ccaatgcaac agactttaaa gaagttgtgt tttacaatgc      60
```

<210> SEQ ID NO 228
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 228
taaatgacat aacagttatg attttgcaga aaacagatct gtatttattt cagtgttact    60

<210> SEQ ID NO 229
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 229
gacaggtttt gaaagatatt tgtgttacta atgactgtgc tataactttt ttttctttcc    60

<210> SEQ ID NO 230
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 230
actcaaaaaa taaaaactat aattactcct taatgtcagc ttattatatt caatttaaac    60

<210> SEQ ID NO 231
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 231
aacaccttTt ttgaagtaaa aggtgcactg taataatcca gactgtgttt ctcccttctc    60

<210> SEQ ID NO 232
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 232
gaaacctTta tctgtatcaa agaatggtcc tgcaccagta atatgcatat taaaacaaga    60

<210> SEQ ID NO 233
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 233
gtgtattaac cttatgtgtg acatgttcta atatagtcac attttcatta tttttattat    60

<210> SEQ ID NO 234
<211> LENGTH: 60
<212> TYPE: DNA
<213> ORGANISM: Artificial Sequence
<220> FEATURE:

<223> OTHER INFORMATION: Oligonucleotide probe

<400> SEQUENCE: 234
ccccagccag cggtccgcaa cccttgccgc atccacgaaa ctttgcccat agcagcgggc    60

<210> SEQ ID NO 235
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 235
cgactcatct cagcattaaa gtgataaaaa aataaattaa aaggcaagtg gacttcggtg    60

<210> SEQ ID NO 236
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 236
ctgtggcgcg cactgcgcgc tgcgccaggt ttccgcacca agacccctttt aactcaagac   60

<210> SEQ ID NO 237
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 237
ttctactgcg acgaggagga gaacttctac cagcagcagc agcagagcga gctgcagccc    60

<210> SEQ ID NO 238
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 238
accgagctgc tgggaggaga catggtgaac cagagtttca tctgcgaccc ggacgacgag    60

<210> SEQ ID NO 239
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 239
gccgccgcct cagagtgcat cgaccctcg gtggtcttcc cctaccctct caacgacagc    60

<210> SEQ ID NO 240
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 240
ggcggctagg ggacaggggc ggggtgggca gcagctcgaa tttcttccag atatcctcgc    60

```
<210> SEQ ID NO 241
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 241
agacgagctt ggcggcggcc gagaagccgc tccacataca gtcctggatg atgatgtttt    60

<210> SEQ ID NO 242
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 242
aggagagcag agaatccgag gacggagaga aggcgctgga gtcttgcgag gcgcaggact    60

<210> SEQ ID NO 243
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 243
taagagtggc ccgttaaata agctgccaat gaaaatggga aaggtatcca gccgcccact    60

<210> SEQ ID NO 244
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 244
ttgtatttgt acagcattaa tctggtaatt gattatttta atgtaacctt gctaaaggag    60

<210> SEQ ID NO 245
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 245
gaggccacag caaacctcct cacagcccac tggtcctcaa gaggtgccac gtctccacac    60

<210> SEQ ID NO 246
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 246
agaggaggaa cgagctaaaa cggagctttt ttgccctgcg tgaccagatc ccggagttgg    60

<210> SEQ ID NO 247
<211> LENGTH: 60
<212> TYPE: DNA
<213> ORGANISM: Artificial Sequence
<220> FEATURE:
<223> OTHER INFORMATION: Oligonucleotide probe
```

```
<400> SEQUENCE: 247
tccaacttga ccctcttggc agcaggatag tccttccgag tggagggagg cgctgcgtag    60

<210> SEQ ID NO 248
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 248
gcttggacgg acaggatgta tgctgtggct tttttaagga taactacctt gggggccttt    60

<210> SEQ ID NO 249
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 249
gcatttgatc atgcatttga aacaagttca taggtgattg ctcaggacat ttctgttaga    60

<210> SEQ ID NO 250
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 250
catcattgtt gaaaacaatg aatcctctgt ttcctctccc aaaagccact tggttgctcc    60

<210> SEQ ID NO 251
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 251
tttatctcca gaaatgacat cacagtatgt gccagcagga agaccagttt gcaaagttaa    60

<210> SEQ ID NO 252
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 252
ctattagagg acatgtctaa atacatattc tcaccttatt tggcgccatc gatgttcaca    60

<210> SEQ ID NO 253
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 253
tctgagcaag agaaggggag gcggggtaag ggaagtaggt ggaagattca gccaagctca    60

<210> SEQ ID NO 254
<211> LENGTH: 60
```

```
<212> TYPE: DNA
<213> ORGANISM: Artificial Sequence
<220> FEATURE:
<223> OTHER INFORMATION: Oligonucleotide probe

<400> SEQUENCE: 254
ccagaacaca gagtgactct gccctgggcc gaaaggcgac atttctggaa ggaaaaactt    60

<210> SEQ ID NO 255
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 255
cttcacttgc ctatttctgc cattcagtga catgtgttgc attggttttt tgtgtctttc    60

<210> SEQ ID NO 256
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 256
gtgtctctct ctggaaggta aaggagaaag ggaaagagaa gtgcatgtgc aagaccenttt    60

<210> SEQ ID NO 257
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 257
ccgaagaaag agactctgga aactcattat caggtctatc aactcttgta tttgttctcc    60

<210> SEQ ID NO 258
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 258
actagaaaat gagggagaag ggggagagag gaaggaggag gaagagaaag aaaagtatct    60

<210> SEQ ID NO 259
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 259
gtagttgcat tgtgtgtttt tgaccactga tgataaattc aagtctctct tccttcccaa    60

<210> SEQ ID NO 260
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 260
```
cataggagcg ttcactaaat atgatccccc ttatctcatg ctcccacttc ccttttcctt    60

<210> SEQ ID NO 261
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 261
ctcagactta gctcaacccg tcagtaccca gactgaccac tgcctctgcc tcttcttctc    60

<210> SEQ ID NO 262
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 262
caccaaccag gtctggccaa gctgctgtat tttagtgagg tctgggcccc aggagcactt    60

<210> SEQ ID NO 263
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 263
ggaagataca gttgttgaga aaggaaatt gagagaaaac acaattagta agagtaactc    60

<210> SEQ ID NO 264
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 264
ttttagattt atattggcct catatgtata tggatatttc ataggcattg tgtttctttt    60

<210> SEQ ID NO 265
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 265
tgtaggggcc aataattata ttcgaggtta ctgttaaatt atttacaaag tataggtgat    60

<210> SEQ ID NO 266
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 266
tttgagtaaa gatttttaaa ttctaacatt gttagtttgt aataaaatgt attgtttcta    60

<210> SEQ ID NO 267
<211> LENGTH: 60
<212> TYPE: DNA
<213> ORGANISM: Artificial Sequence

```
<220> FEATURE:
<223> OTHER INFORMATION: Oligonucleotide probe

<400> SEQUENCE: 267
catatcaagt tcatttgtag agatgaggac tacagcccat atcaagctat accttctact    60

<210> SEQ ID NO 268
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 268
atgtcagcaa gatttcttct tgcaaagata acatcatacc ataatatttg tttcaatttt    60

<210> SEQ ID NO 269
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 269
caaccacaga ttcataccaa atgcattact tttagattat taacatattc ttttacataa    60

<210> SEQ ID NO 270
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 270
aagaaaggta gtaattccaa attattaaca tctgttttg gtttatgtt tcttcttttt      60

<210> SEQ ID NO 271
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 271
ggcctatgtg tggccacccc agtccagctc cgggtgttcc gcgagttcca cctgcacctc    60

<210> SEQ ID NO 272
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 272
aggcgtggcc tccctcttga ggcttcctcg aggctgtggg gagcaaacca tgatctactt    60

<210> SEQ ID NO 273
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 273
cctagcttgg ccagaaggta gcagacagac agacggatct aacctctctt ggatcctcca    60
```

```
<210> SEQ ID NO 274
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 274
tgaatcgggt cccgatgcca gccctgcccc aatccaagca cccagcatcc cgcctccagg      60

<210> SEQ ID NO 275
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 275
agggagagca ggggtggagg tgtcagagcg aagtctgact gctgatcctg tctgttctcc      60

<210> SEQ ID NO 276
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 276
tgacacttac aagacagatg ggaacagggc aggaggcccc cacaagcagc aggagggcat      60

<210> SEQ ID NO 277
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 277 ccttttggt cagctgtctc ttgctctgtg acccgctccc tctccctctc cctctcctga      60

<210> SEQ ID NO 278
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 278
caaactcatc ctgagagggc tcggaggggg ttaaaggttg aggccctggg gctgagactc      60

<210> SEQ ID NO 279
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 279
agtttgaccc accctcccct tgcacatgga cccctgctca cctctctcct cctccactcc      60

<210> SEQ ID NO 280
<211> LENGTH: 60
<212> TYPE: DNA
<213> ORGANISM: Artificial Sequence
<220> FEATURE:
<223> OTHER INFORMATION: Oligonucleotide probe
```

<400> SEQUENCE: 280 aagggagaa gtgctcacag gcaggaggtc acatcagtgg ccaggatcag gaaggccaga    60

<210> SEQ ID NO 281
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 281
gttctgaagc ttctgagttc tgcagcctca cctctgagaa aacctctttg ccaccaatac    60

<210> SEQ ID NO 282
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 282
ggcagtgttg atctcaccct ggcctttcct ttcagtgggc tcagaccctc ccaccgcctg    60

<210> SEQ ID NO 283
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 283
accacagctg gctgggagca gaggctgctg gtctcatagt aatctaccac aaagttgcga    60

<210> SEQ ID NO 284
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 284
tcaggtgacc ttccctgaag acttcctgtc tctgagcagc tcagttcagt tccaggtcat    60

<210> SEQ ID NO 285
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 285
ggagcatata gtgggcctag gtgattggcc actttatcca tcaaagaggc acacacactt    60

<210> SEQ ID NO 286
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 286
cctttcaaag tattttactt tacaatgatc tcttgtaaca ttgtacctct agggatatac    60

<210> SEQ ID NO 287

```
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 287
atggggagga tggaaaacag actagcagag cttctcgggc agagcttggc ccatccacat      60

<210> SEQ ID NO 288
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 288
gatctggcca cccctgaaat gtttccaaga atgtcagtag agaggagagc agtccagaaa      60

<210> SEQ ID NO 289
<211> LENGTH: 62
<212> TYPE: DNA
<213> ORGANISM: Artificial Sequence
<220> FEATURE:
<223> OTHER INFORMATION: Oligonucleotide probe

<400> SEQUENCE: 289
agcaaccaga gcttggcata ttgtatctat acctttatta aatgctttta atttaataaa      60
tt                                                                    62

<210> SEQ ID NO 290
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 290
caaaactagt caatgaatca caaatacgca agcagtcaca taactaagct tttgttaaca      60

<210> SEQ ID NO 291
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 291
aaggagcata tagtggacct aggtgattgg tcaatttatc catcaaagag gcacacaccg      60

<210> SEQ ID NO 292
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 292
agcctttcaa agtattttac tttaccatta cctcttgtaa catgtacctc tagggataca      60

<210> SEQ ID NO 293
<211> LENGTH: 60
<212> TYPE: DNA
<213> ORGANISM: Artificial Sequence
<220> FEATURE:
<223> OTHER INFORMATION: Oligonucleotide probe
```

<400> SEQUENCE: 293
ggggaggatg gaaacagag acttacagag ctcctcgggc agagcttggc ccatccacat    60

<210> SEQ ID NO 294
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 294
gatatggcca cccctgaaat gtttccaaga atgtcagtag agaagatagt agtccagtaa    60

<210> SEQ ID NO 295
<211> LENGTH: 62
<212> TYPE: DNA
<213> ORGANISM: Artificial Sequence
<220> FEATURE:
<223> OTHER INFORMATION: Oligonucleotide probe

<400> SEQUENCE: 295
ctcaaccaga gcttggtata tggtatgtat gcttttatta aaatctttta atttaataaa    60
tt    62

<210> SEQ ID NO 296
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 296
cagaactagt caacaaatca caaattcaca agcagtcaca taactaagct tttgtttaca    60

<210> SEQ ID NO 297
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 297
ggaagtcccc caaacctgct tccccttctc agcctggctt ctggtccagc ctgtggtttc    60

<210> SEQ ID NO 298
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 298
gcctggtggg gtggggtgc caggtgtgtc cagaggagcc catttggtag tgaggcaggt    60

<210> SEQ ID NO 299
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 299
gcccagctcg gactacggtc atcacccacc cgggtcccac ggaaatctgt ctctgtcccc    60

<210> SEQ ID NO 300
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 300
aataggacta ggacctgtag tctgggggga tcctggcttg acaagaggcc ctgaccctcc    60

<210> SEQ ID NO 301
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 301
aagttcatgg gcccccgcct gtaccttcc tccctcggcc cctgcactgt ttcccagatg    60

<210> SEQ ID NO 302
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 302
gggctgacag gtgcagaatt ggaggtcatt tgggggctac cccgttctgt cccgagtatg    60

<210> SEQ ID NO 303
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 303
cattgcttta ttgtacatta gagcctctgg ctagggagca ggctggggac taggtacccc    60

<210> SEQ ID NO 304
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 304
tggagtcttg cagggtatc acccaggagc caggctcact gacgcccctc ccctcccac    60

<210> SEQ ID NO 305
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 305
agtgcatgtg tgtgagtgct gccgctgccc gcgacccctg gccccgaagg tgttggctga    60

<210> SEQ ID NO 306
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 306
aatgagaagg gaagtggggt acggaagggg gtgcgacgag aagaaaggaa agagccactt    60

<210> SEQ ID NO 307
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 307
ggaatctaag cctgagattt atttgaatac atgaacatat ttccctgtgc tctcttgttc    60

<210> SEQ ID NO 308
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 308
aagatggcat tcatctggcc ttgggaatgg atgaaaggaa gcagcaactt tcaaatgggt    60

<210> SEQ ID NO 309
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 309
ggtaaagtcc ctcatctggc ttgtggtgtc tggaatgaag tatgttttgt atcagcagag    60

<210> SEQ ID NO 310
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 310
tttattggcg attattgtgc tttatttgga agacttattc ttccttcttt gttttctcc    60

<210> SEQ ID NO 311
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 311
gaaaaaaatt gtttttcaac ttattccaga gaatatcatt ctgaaggcaa caaagagcat    60

<210> SEQ ID NO 312
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 312
atatatcatt tatctttgca atgttttca tatatcatat gatactgtgt tttcccctca    60

<210> SEQ ID NO 313

```
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 313
attagagaaa tataaatagc agcatatacc atacaaaagt cactttaca aaaaagtctt        60

<210> SEQ ID NO 314
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 314
atactccatc tcccgtaaaa atagtgagac ttgagtaatg tttgatgtca cttgtctttc        60

<210> SEQ ID NO 315
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 315
cagtcaccac tatattattc taggtatccc agaaaagtta aagtcaaatc tgaaacacat        60

<210> SEQ ID NO 316
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 316
ttcttactgt tctagcttgt ccttaaggcc tctgtgcttt ttaacaaatg gtttcttttg        60

<210> SEQ ID NO 317
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 317
tccgcatgca ctccctggac atgtggacac atggaccatg gtccacacct ggccaagctt        60

<210> SEQ ID NO 318
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 318
cttggcttgg gctgtgttgt gtgaacggaa cagttcaccc cagtatggcc ttcttgccga        60

<210> SEQ ID NO 319
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 319
```

```
gctgtgcata atcactggac aacaaactaa ttagcacttt tcaaaataat gcagttactt    60

<210> SEQ ID NO 320
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 320
gaacagcagt cagattgctc atctctatca cttttctca ttgtgtccct tttctctcct    60

<210> SEQ ID NO 321
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 321
agagaatgaa agggaaaaag aaaagccaaa gcgtactgac tattcaaggg gatcgtactt    60

<210> SEQ ID NO 322
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 322
tattgcaagt tttcatttgg ttaaggtttg gggttaattt tggaattggc tctgctcttc    60

<210> SEQ ID NO 323
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 323
aaaacttgtt aatattcacg ataaagaaaa attccagaga aagtaacaac gttaagactt    60

<210> SEQ ID NO 324
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 324
gcagaagaag ccccgccacc agcagcttct gccatctctc tcctcctttt tcttcagcca    60

<210> SEQ ID NO 325
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 325
ctactcccac gttctaagag agtgacagaa aggtaaagag gagcagccgc agaaatggat    60

<210> SEQ ID NO 326
<211> LENGTH: 60
<212> TYPE: DNA
```

```
<213> ORGANISM: Artificial Sequence
<220> FEATURE:
<223> OTHER INFORMATION: Oligonucleotide probe

<400> SEQUENCE: 326
agtattcttt tagtttgatt gctgcatatt tcagatattt ctttccttaa ctaaagtact    60

<210> SEQ ID NO 327
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 327
aatgaaaaca caacatgaat ataaacatca atatttgaaa tagaaaatca aagcattctt    60

<210> SEQ ID NO 328
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 328
gtaatttcaa atgttagctc attttgtta atggtggctt tttgtttgtt tgttttgttt    60

<210> SEQ ID NO 329
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 329
ctttcactta atagttgttt tagaagatat ttgcaagcat acaataaga aacatactt    60

<210> SEQ ID NO 330
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 330
gtactttttt ttcttcctaa gtgcaaaaga taactttata tcacttttaa acttttcttt    60

<210> SEQ ID NO 331
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 331
acagtaagat acagtctatc gggtttaagt tatacaacat agtacagtac attcatacct    60

<210> SEQ ID NO 332
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 332
tacttgttaa ttaaaaattc aagagttttt ttttcttatt ctgaggttat cttttacca    60
```

<210> SEQ ID NO 333
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 333
ccaaaatctg ttttccaata aattctcaga tccaggaaga ggaaaggaaa aacatcaaaa    60

<210> SEQ ID NO 334
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 334
tcaagtaggt gttggagaga ggggtgatgc ctggtgctgg tggaacccct gcacagagac    60

<210> SEQ ID NO 335
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 335
cctgtccttt cggggtccat tccctctatg acccagaagt gatccagcca ccatcccaat    60

<210> SEQ ID NO 336
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 336
aacccctcga ggctcagacc tttggagcag gagtgtgatt ctggccaacc accctctctg    60

<210> SEQ ID NO 337
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 337
cataaatatg tgtgctagtc ctgttagacc caagtgctgc ccaagggcag cgccctgctc    60

<210> SEQ ID NO 338
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 338
ttgcagcaag atggtgttct ctctctacct tgcttccttt acccacacgc tatttctttg    60

<210> SEQ ID NO 339
<211> LENGTH: 60
<212> TYPE: DNA
<213> ORGANISM: Artificial Sequence
<220> FEATURE:

<223> OTHER INFORMATION: Oligonucleotide probe

<400> SEQUENCE: 339
gagatcaagc caaaatcagt atgtgggttc atctgcaata aaaatgtttg ttttgctttt    60

<210> SEQ ID NO 340
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 340
gcaacagtga gaggaagttg tcttgttttt gaacaggcct tgttttcctt ggatgctttt    60

<210> SEQ ID NO 341
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 341
ctgccatttc attacaggca aagctgagca aaagtagata ttacaagacc agcatgtact    60

<210> SEQ ID NO 342
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 342
aaggtaaaag aaatcattga gtcccccgcc ttcagaagag ggtgcatttt caggaggaag    60

<210> SEQ ID NO 343
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 343
gcggatctcc cccggcctcg ccggcctccg cctgtcctcc caccaccctc tccgggccag    60

<210> SEQ ID NO 344
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 344
ctggtaggag ctgtttgcag ggtcctaact caatcggctt gttgtgatgc gtatccccgt    60

<210> SEQ ID NO 345
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 345
ttttgaaatg tgggtttgtt gccatgaaac gtgtttcaag catagttttg acagataacg    60

```
<210> SEQ ID NO 346
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 346
tgccctaaaa gtgtatgtat aacatccctg atgtctgcat ttgtcctttg actggtgttt     60

<210> SEQ ID NO 347
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 347
gtataccagc ctggagggtg taccagcctg gagggtgtac cagccccaag tggatgcact     60

<210> SEQ ID NO 348
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 348
ttcaacagat atgttcaggc caccaacctc attctgtttt gttctctatc gtgtccccac     60

<210> SEQ ID NO 349
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 349
aggatgtgtc tgggtggtgc ttggggacag aggcaccttc ccgacacccg cctgcccctc     60

<210> SEQ ID NO 350
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 350
cctcagccag tgccaccccc acagcccaca gggaggaggc acagaaagcg actcacacgt     60

<210> SEQ ID NO 351
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 351
ctggtgtgga gctgccgggc acttccatga ctttgtttct gtctctgctt cctcctcagt     60

<210> SEQ ID NO 352
<211> LENGTH: 60
<212> TYPE: DNA
<213> ORGANISM: Artificial Sequence
<220> FEATURE:
<223> OTHER INFORMATION: Oligonucleotide probe
```

```
<400> SEQUENCE: 352
ctggtgcagg ctgtgctcac tgcccgtgcc ctggacctcc cagcaccact cgccccgctc    60

<210> SEQ ID NO 353
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 353
gtcatggtga ggggtgtgct gggaccggct gggcagtgac cccgagccgc ctccggcccc    60

<210> SEQ ID NO 354
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 354
ccggggccca cggcggctcc acgcccaccg tgctgcgtgc ctcagtctcc ccacccgcat    60

<210> SEQ ID NO 355
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 355
ctgtaagtta tcgtaaaaag gagcatctag gtaggtcttt gtagccaatg ttacccgatt    60

<210> SEQ ID NO 356
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 356
agtaaaataa gtttcgaact ctggcacctt tcaattttgt cgcactctcc ttgttttga    60

<210> SEQ ID NO 357
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 357
gaagcaaact gcaattcttc ggcagcatct tcgccttccg acgaggtcga tacttataat    60

<210> SEQ ID NO 358
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 358
aatggccatt cttccaggag gcacagaaat tacaggccat gcacagagag aaatacccga    60

<210> SEQ ID NO 359
<211> LENGTH: 60
```

<212> TYPE: DNA
<213> ORGANISM: Artificial Sequence
<220> FEATURE:
<223> OTHER INFORMATION: Oligonucleotide probe

<400> SEQUENCE: 359
cttgcgcctc tgatcgcgag accacacgat gaatgcgttc atgggtcgct tcactctatc    60

<210> SEQ ID NO 360
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 360
gaaagctgta actctaagta tcagtgtgaa acgggagaaa acagtaaagg caacgtccag    60

<210> SEQ ID NO 361
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 361
agttcctctg ctggagttca tcctgctagc tgggttcccg agctgccggt ctgagcctga    60

<210> SEQ ID NO 362
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 362
tctgtgggag gccctggggt cagaactggg atctgcgagc agacggagag gaggctcggg    60

<210> SEQ ID NO 363
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 363
caagcctggc agagcccaca gggcagccag ggcatctccc aatgcctgtc ctgaccccct    60

<210> SEQ ID NO 364
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 364
tgtctggggc agaaggggc aagagtgtct gccctcggcc cacagagctg gcccgccaaa    60

<210> SEQ ID NO 365
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 365
tgatgggtgg gctcccgaag gggcctcccg cagacttgcg aagttcccac tctctgggcg      60

<210> SEQ ID NO 366
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 366
cagggtgcgg gggcatccag gctgcccaag cggaggctgg gccggctgtg ctggcctctt      60

<210> SEQ ID NO 367
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 367
ctccaccttc tttatctctg aaagtgaact ccctgctacc tttgtggact gacagctttt      60

<210> SEQ ID NO 368
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 368
tcgatccaaa gtaatacatc tgaaagaata tacgcatgta aaagtcccac tccaatacac      60

<210> SEQ ID NO 369
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 369
ctgcagcaga ggggacatga aatagttgtc ctagcacctg acgcctcgtt gtacatcaga      60

<210> SEQ ID NO 370
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 370
actctttcac atcctcccett tggaatggca cagggtacgt cttcaaggtg taaaatgctc      60

<210> SEQ ID NO 371
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 371
gcgtgtgatc aaaacataca agaaaataaa aaaggactct gctatgcttt tgtctggctg      60

<210> SEQ ID NO 372
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 372
acatcaaagc tgctttctgc cagggaggcc atgagctcct tgttgtgcag taagtgggaa    60

<210> SEQ ID NO 373
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 373
ctctgcccac tgtattcttc ttgcatgcac tgccatgcag cctggaattt gaggctaccc    60

<210> SEQ ID NO 374
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 374
tcatgtgatc tgaatgagag gagagaggcc tgggcacgta ggagaatggg ttggggcact    60

<210> SEQ ID NO 375
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 375
tgcgacgtgg tttattcccc gtatgcaacc cttgcctcag aattccttca gagagaggtg    60

<210> SEQ ID NO 376
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 376
cttcacaaag tcacttctaa acagccagac agatgcagag ctcaataggt cctggacagt    60

<210> SEQ ID NO 377
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 377
actgtatgta gtcatcaaag aatatgagaa aaaattaact gaaaattttt cttctggctc    60

<210> SEQ ID NO 378
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 378
attaatctgg aagctggaag tctgggatta gcgctcctgt gaaaatagat atgaggccat    60

<210> SEQ ID NO 379
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 379
cagatttgtt ttctaatcat attatgttct ttctttacgt tctgctcttt ttgccctcc    60

<210> SEQ ID NO 380
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 380
gcttaagcca ttttcttaat ttgaccctgg tttgacctat acatccaatc cgcccaacat    60

<210> SEQ ID NO 381
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 381
tgtgtccagc tgtgaaactc agagatgtaa ctgctgacat cctccctatt ttgcatctca    60

<210> SEQ ID NO 382
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 382
atttgaaaca attttatcat gaatgccatg accaaagtat tcttctgtat cttctttctt    60

<210> SEQ ID NO 383
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 383
ataaagagag gattgttcat accacaggtg ttccaggcat aacgaaactg tctttgtgtt    60

<210> SEQ ID NO 384
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 384
ttttcaagtt tggaaatgac tagggaatgg ttcaaaattt taccttattt cccacccact    60

<210> SEQ ID NO 385
<211> LENGTH: 60
<212> TYPE: DNA
<213> ORGANISM: Artificial Sequence
<220> FEATURE:
<223> OTHER INFORMATION: Oligonucleotide probe

```
<400> SEQUENCE: 385
cgccccgcgt ccgacccgcg gatcccgcgg cgtccggccc gggtggtctg gatcgcggag      60

<210> SEQ ID NO 386
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 386
tagaggggct tcagaccgtg ctatcgtccc tgctgggtcg ggcctaagcg ccgggcccgt      60

<210> SEQ ID NO 387
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 387
ggcgccgagg aggagatgga ggccgggcgg ccgcggcccg tgctgcgctc ggtgaactcg      60

<210> SEQ ID NO 388
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 388
ccatacgggc agcacgacgc gcggactgcg attgcagaag atgacctggg agggctcgcg      60

<210> SEQ ID NO 389
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 389
ggtgtgggcc accgtgccca gccaccggtg tggctcttta caaacctttg cttgtcccga      60

<210> SEQ ID NO 390
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 390
aagtggtcta tcctgtactt accacaacaa ccttatcttt ttaaaaagta aaacgtcagt      60

<210> SEQ ID NO 391
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 391
cttgttcgtt ccttgtactg agaccctagt ctgccactga ggatttggtt tttgcccttc      60

<210> SEQ ID NO 392
```

```
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 392
atcaagactc atcagtacca tcaaaagctg agatgaaaca gtgtaagttt caacagaaat    60

<210> SEQ ID NO 393
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 393
aagcacctag                                                           10

<210> SEQ ID NO 394
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 394
agtcggtggg                                                           10

<210> SEQ ID NO 395
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 395
acctgagtag                                                           10

<210> SEQ ID NO 396
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 396
cctggccctc                                                           10

<210> SEQ ID NO 397
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 397
agaattcatt                                                           10

<210> SEQ ID NO 398
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 398
```
gacttcaaag                                                          10

<210> SEQ ID NO 399
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 399
tctctttggg                                                          10

<210> SEQ ID NO 400
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 400
tgcgatacca                                                          10

<210> SEQ ID NO 401
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 401
ggggtaggtg                                                          10

<210> SEQ ID NO 402
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 402
ttacttccct                                                          10

<210> SEQ ID NO 403
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 403
cagggtatc                                                           10

<210> SEQ ID NO 404
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 404
gaaattctct                                                          10

<210> SEQ ID NO 405
<211> LENGTH: 10
<212> TYPE: DNA

```
<213> ORGANISM: Artificial Sequence
<220> FEATURE:
<223> OTHER INFORMATION: 10 nt read_2 sequence

<400> SEQUENCE: 405
gggtttgagt                                                              10

<210> SEQ ID NO 406
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 406
ctatctccag                                                              10

<210> SEQ ID NO 407
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 407
gaaagaagcc                                                              10

<210> SEQ ID NO 408
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 408
cagactcgcg                                                              10

<210> SEQ ID NO 409
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 409
tctttcttct                                                              10

<210> SEQ ID NO 410
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 410
gtttgtgttt                                                              10

<210> SEQ ID NO 411
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 411
aaccaaatat                                                              10
```

```
<210> SEQ ID NO 412
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 412
agtctccatg                                                          10

<210> SEQ ID NO 413
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 413
ccatgggtgt                                                          10

<210> SEQ ID NO 414
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 414
tttacagtgg                                                          10

<210> SEQ ID NO 415
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 415
atagctgtac                                                          10

<210> SEQ ID NO 416
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 416
gatttgagga                                                          10

<210> SEQ ID NO 417
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 417
cagcattgta                                                          10

<210> SEQ ID NO 418
<211> LENGTH: 10
<212> TYPE: DNA
<213> ORGANISM: Artificial Sequence
<220> FEATURE:
```

<223> OTHER INFORMATION: 10 nt read_2 sequence

<400> SEQUENCE: 418
tgttaccttt                                                                10

<210> SEQ ID NO 419
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 419
ttcccagtaa                                                                10

<210> SEQ ID NO 420
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 420
taaatgacat                                                                10

<210> SEQ ID NO 421
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 421
gacaggtttt                                                                10

<210> SEQ ID NO 422
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 422
actcaaaaaa                                                                10

<210> SEQ ID NO 423
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 423
aacaccttt                                                                 10

<210> SEQ ID NO 424
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 424
gaaaccttta                                                                10

```
<210> SEQ ID NO 425
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 425
gtgtattaac                                                          10

<210> SEQ ID NO 426
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 426
ccccagccag                                                          10

<210> SEQ ID NO 427
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 427
cgactcatct                                                          10

<210> SEQ ID NO 428
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 428
ctgtggcgcg                                                          10

<210> SEQ ID NO 429
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 429
ttctactgcg                                                          10

<210> SEQ ID NO 430
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 430
accgagctgc                                                          10

<210> SEQ ID NO 431
<211> LENGTH: 10
<212> TYPE: DNA
<213> ORGANISM: Artificial Sequence
<220> FEATURE:
<223> OTHER INFORMATION: 10 nt read_2 sequence
```

```
<400> SEQUENCE: 431
gccgccgcct                                                          10

<210> SEQ ID NO 432
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 432
ggcggctagg                                                          10

<210> SEQ ID NO 433
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 433
agacgagctt                                                          10

<210> SEQ ID NO 434
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 434
aggagagcag                                                          10

<210> SEQ ID NO 435
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 435
taagagtggc                                                          10

<210> SEQ ID NO 436
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 436
ttgtatttgt                                                          10

<210> SEQ ID NO 437
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 437
gaggccacag                                                          10

<210> SEQ ID NO 438
<211> LENGTH: 10
```

-continued

```
<212> TYPE: DNA
<213> ORGANISM: Artificial Sequence
<220> FEATURE:
<223> OTHER INFORMATION: 10 nt read_2 sequence

<400> SEQUENCE: 438
agaggaggaa                                                          10

<210> SEQ ID NO 439
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 439
tccaacttga                                                          10

<210> SEQ ID NO 440
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 440
gcttggacgg                                                          10

<210> SEQ ID NO 441
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 441
gcatttgatc                                                          10

<210> SEQ ID NO 442
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 442
catcattgtt                                                          10

<210> SEQ ID NO 443
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 443
tttatctcca                                                          10

<210> SEQ ID NO 444
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 444
```
ctattagagg                                                          10

<210> SEQ ID NO 445
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 445
tctgagcaag                                                          10

<210> SEQ ID NO 446
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 446
ccagaacaca                                                          10

<210> SEQ ID NO 447
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 447
cttcacttgc                                                          10

<210> SEQ ID NO 448
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 448
gtgtctctct                                                          10

<210> SEQ ID NO 449
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 449
ccgaagaaag                                                          10

<210> SEQ ID NO 450
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 450
actagaaaat                                                          10

<210> SEQ ID NO 451
<211> LENGTH: 10
<212> TYPE: DNA
<213> ORGANISM: Artificial Sequence

```
<220> FEATURE:
<223> OTHER INFORMATION: 10 nt read_2 sequence

<400> SEQUENCE: 451
gtagttgcat                                                              10

<210> SEQ ID NO 452
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 452
cataggagcg                                                              10

<210> SEQ ID NO 453
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 453
ctcagactta                                                              10

<210> SEQ ID NO 454
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 454
caccaaccag                                                              10

<210> SEQ ID NO 455
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 455
ggaagataca                                                              10

<210> SEQ ID NO 456
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 456
ttttagattt                                                              10

<210> SEQ ID NO 457
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 457
tgtaggggcc                                                              10
```

<210> SEQ ID NO 458
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 458
tttgagtaaa                                                                10

<210> SEQ ID NO 459
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 459
catatcaagt                                                                10

<210> SEQ ID NO 460
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 460
atgtcagcaa                                                                10

<210> SEQ ID NO 461
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 461
caaccacaga                                                                10

<210> SEQ ID NO 462
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 462
aagaaaggta                                                                10

<210> SEQ ID NO 463
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 463
ggcctatgtg                                                                10

<210> SEQ ID NO 464
<211> LENGTH: 10
<212> TYPE: DNA
<213> ORGANISM: Artificial Sequence
<220> FEATURE:
<223> OTHER INFORMATION: 10 nt read_2 sequence -continued

<400> SEQUENCE: 464
aggcgtggcc  10

<210> SEQ ID NO 465
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 465
cctagcttgg  10

<210> SEQ ID NO 466
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 466
tgaatcgggt  10

<210> SEQ ID NO 467
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 467
agggagagca  10

<210> SEQ ID NO 468
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 468
tgacacttac  10

<210> SEQ ID NO 469
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 469
ccttttggt  10

<210> SEQ ID NO 470
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 470
caaactcatc  10

<210> SEQ ID NO 471

<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 471
agtttgaccc                                                                 10

<210> SEQ ID NO 472
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 472
aaggggagaa                                                                 10

<210> SEQ ID NO 473
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 473
gttctgaagc                                                                 10

<210> SEQ ID NO 474
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 474
ggcagtgttg                                                                 10

<210> SEQ ID NO 475
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 475
accacagctg                                                                 10

<210> SEQ ID NO 476
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 476
tcaggtgacc                                                                 10

<210> SEQ ID NO 477
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 477

-continued ggagcatata                                                          10

<210> SEQ ID NO 478
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 478
cctttcaaag                                                          10

<210> SEQ ID NO 479
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 479
atggggagga                                                          10

<210> SEQ ID NO 480
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 480
gatctggcca                                                          10

<210> SEQ ID NO 481
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 481
agcaaccaga                                                          10

<210> SEQ ID NO 482
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 482
caaaactagt                                                          10

<210> SEQ ID NO 483
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 483
aaggagcata                                                          10

<210> SEQ ID NO 484
<211> LENGTH: 10
<212> TYPE: DNA

```
<213> ORGANISM: Artificial Sequence
<220> FEATURE:
<223> OTHER INFORMATION: 10 nt read_2 sequence

<400> SEQUENCE: 484
agcctttcaa                                                              10

<210> SEQ ID NO 485
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 485
ggggaggatg                                                              10

<210> SEQ ID NO 486
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 486
gatatggcca                                                              10

<210> SEQ ID NO 487
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 487
ctcaaccaga                                                              10

<210> SEQ ID NO 488
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 488
cagaactagt                                                              10

<210> SEQ ID NO 489
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 489
ggaagtcccc                                                              10

<210> SEQ ID NO 490
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 490
gcctggtggg                                                              10
```

<210> SEQ ID NO 491
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 491
gcccagctcg                                                          10

<210> SEQ ID NO 492
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 492
aataggacta                                                          10

<210> SEQ ID NO 493
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 493
aagttcatgg                                                          10

<210> SEQ ID NO 494
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 494
gggctgacag                                                          10

<210> SEQ ID NO 495
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 495
cattgcttta                                                          10

<210> SEQ ID NO 496
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 496
tggagtcttg                                                          10

<210> SEQ ID NO 497
<211> LENGTH: 10
<212> TYPE: DNA
<213> ORGANISM: Artificial Sequence
<220> FEATURE:

```
<223> OTHER INFORMATION: 10 nt read_2 sequence

<400> SEQUENCE: 497
agtgcatgtg                                                                   10

<210> SEQ ID NO 498
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 498
aatgagaagg                                                                   10

<210> SEQ ID NO 499
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 499
ggaatctaag                                                                   10

<210> SEQ ID NO 500
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 500
aagatggcat                                                                   10

<210> SEQ ID NO 501
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 501
ggtaaagtcc                                                                   10

<210> SEQ ID NO 502
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 502
tttattggcg                                                                   10

<210> SEQ ID NO 503
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 503
gaaaaaatt                                                                    10
```

```
<210> SEQ ID NO 504
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 504
atatatcatt                                                          10

<210> SEQ ID NO 505
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 505
attagagaaa                                                          10

<210> SEQ ID NO 506
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 506
atactccatc                                                          10

<210> SEQ ID NO 507
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 507
cagtcaccac                                                          10

<210> SEQ ID NO 508
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 508
ttcttactgt                                                          10

<210> SEQ ID NO 509
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 509
tccgcatgca                                                          10

<210> SEQ ID NO 510
<211> LENGTH: 10
<212> TYPE: DNA
<213> ORGANISM: Artificial Sequence
<220> FEATURE:
<223> OTHER INFORMATION: 10 nt read_2 sequence
```

```
<400> SEQUENCE: 510
cttggcttgg                                                              10

<210> SEQ ID NO 511
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 511
gctgtgcata                                                              10

<210> SEQ ID NO 512
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 512
gaacagcagt                                                              10

<210> SEQ ID NO 513
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 513
agagaatgaa                                                              10

<210> SEQ ID NO 514
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 514
tattgcaagt                                                              10

<210> SEQ ID NO 515
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 515
aaaacttgtt                                                              10

<210> SEQ ID NO 516
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 516
gcagaagaag                                                              10

<210> SEQ ID NO 517
<211> LENGTH: 10
```

```
<212> TYPE: DNA
<213> ORGANISM: Artificial Sequence
<220> FEATURE:
<223> OTHER INFORMATION: 10 nt read_2 sequence

<400> SEQUENCE: 517
ctactcccac                                                          10

<210> SEQ ID NO 518
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 518
agtattcttt                                                          10

<210> SEQ ID NO 519
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 519
aatgaaaaca                                                          10

<210> SEQ ID NO 520
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 520
gtaatttcaa                                                          10

<210> SEQ ID NO 521
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 521
ctttcactta                                                          10

<210> SEQ ID NO 522
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 522
gtacttttt                                                           10

<210> SEQ ID NO 523
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 523
```

-continued acagtaagat                                                                    10

<210> SEQ ID NO 524
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 524
tacttgttaa                                                                    10

<210> SEQ ID NO 525
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 525
ccaaaatctg                                                                    10

<210> SEQ ID NO 526
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 526
tcaagtaggt                                                                    10

<210> SEQ ID NO 527
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 527
cctgtccttt                                                                    10

<210> SEQ ID NO 528
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 528
aacccctcga                                                                    10

<210> SEQ ID NO 529
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 529
cataaatatg                                                                    10

<210> SEQ ID NO 530
<211> LENGTH: 10
<212> TYPE: DNA
<213> ORGANISM: Artificial Sequence

```
<220> FEATURE:
<223> OTHER INFORMATION: 10 nt read_2 sequence

<400> SEQUENCE: 530
ttgcagcaag                                                                 10

<210> SEQ ID NO 531
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 531
gagatcaagc                                                                 10

<210> SEQ ID NO 532
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 532
gcaacagtga                                                                 10

<210> SEQ ID NO 533
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 533
ctgccatttc                                                                 10

<210> SEQ ID NO 534
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 534
aaggtaaaag                                                                 10

<210> SEQ ID NO 535
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 535
gcggatctcc                                                                 10

<210> SEQ ID NO 536
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 536
ctggtaggag                                                                 10
```

<210> SEQ ID NO 537
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 537 ttttgaaatg					10

<210> SEQ ID NO 538
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 538 tgccctaaaa					10

<210> SEQ ID NO 539
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 539 gtataccagc					10

<210> SEQ ID NO 540
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 540 ttcaacagat					10

<210> SEQ ID NO 541
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 541 aggatgtgtc					10

<210> SEQ ID NO 542
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 542 cctcagccag					10

<210> SEQ ID NO 543
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 543
ctggtgtgga                                                              10

<210> SEQ ID NO 544
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 544
ctggtgcagg                                                              10

<210> SEQ ID NO 545
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 545
gtcatggtga                                                              10

<210> SEQ ID NO 546
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 546
ccggggccca                                                              10

<210> SEQ ID NO 547
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 547
ctgtaagtta                                                              10

<210> SEQ ID NO 548
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 548
agtaaaataa                                                              10

<210> SEQ ID NO 549
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 549
gaagcaaact                                                              10

<210> SEQ ID NO 550

```
<210> SEQ ID NO 550
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 550
aatggccatt                                                           10

<210> SEQ ID NO 551
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 551
cttgcgcctc                                                           10

<210> SEQ ID NO 552
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 552
gaaagctgta                                                           10

<210> SEQ ID NO 553
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 553
agttcctctg                                                           10

<210> SEQ ID NO 554
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 554
tctgtgggag                                                           10

<210> SEQ ID NO 555
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 555
caagcctggc                                                           10

<210> SEQ ID NO 556
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 556
```

```
tgtctggggc                                                           10

<210> SEQ ID NO 557
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 557
tgatgggtgg                                                           10

<210> SEQ ID NO 558
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 558
cagggtgcgg                                                           10

<210> SEQ ID NO 559
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 559
ctccaccttc                                                           10

<210> SEQ ID NO 560
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 560
tcgatccaaa                                                           10

<210> SEQ ID NO 561
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 561
ctgcagcaga                                                           10

<210> SEQ ID NO 562
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 562
actctttcac                                                           10

<210> SEQ ID NO 563
<211> LENGTH: 10
<212> TYPE: DNA
```

```
<213> ORGANISM: Artificial Sequence
<220> FEATURE:
<223> OTHER INFORMATION: 10 nt read_2 sequence

<400> SEQUENCE: 563
gcgtgtgatc                                                              10

<210> SEQ ID NO 564
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 564
acatcaaagc                                                              10

<210> SEQ ID NO 565
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 565
ctctgcccac                                                              10

<210> SEQ ID NO 566
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 566
tcatgtgatc                                                              10

<210> SEQ ID NO 567
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 567
tgcgacgtgg                                                              10

<210> SEQ ID NO 568
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 568
cttcacaaag                                                              10

<210> SEQ ID NO 569
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 569
actgtatgta                                                              10
```

```
<210> SEQ ID NO 570
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 570
attaatctgg                                                          10

<210> SEQ ID NO 571
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 571
cagatttgtt                                                          10

<210> SEQ ID NO 572
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 572
gcttaagcca                                                          10

<210> SEQ ID NO 573
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 573
tgtgtccagc                                                          10

<210> SEQ ID NO 574
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 574
atttgaaaca                                                          10

<210> SEQ ID NO 575
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 575
ataaagagag                                                          10

<210> SEQ ID NO 576
<211> LENGTH: 10
<212> TYPE: DNA
<213> ORGANISM: Artificial Sequence
<220> FEATURE:
```

<223> OTHER INFORMATION: 10 nt read_2 sequence

<400> SEQUENCE: 576
ttttcaagtt                                                          10

<210> SEQ ID NO 577
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 577
cgccccgcgt                                                          10

<210> SEQ ID NO 578
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 578
tagaggggct                                                          10

<210> SEQ ID NO 579
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 579
ggcgccgagg                                                          10

<210> SEQ ID NO 580
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 580
ccatacgggc                                                          10

<210> SEQ ID NO 581
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 581
ggtgtgggcc                                                          10

<210> SEQ ID NO 582
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 582
aagtggtcta                                                          10

```
<210> SEQ ID NO 583
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 583
cttgttcgtt                                                          10

<210> SEQ ID NO 584
<211> LENGTH: 10
<212> TYPE: DNA
<213> ORGANISM: Artificial Sequence
<220> FEATURE:
<223> OTHER INFORMATION: 10 nt read_2 sequence

<400> SEQUENCE: 584
atcaagactc                                                          10

<210> SEQ ID NO 585
<211> LENGTH: 24
<212> TYPE: DNA
<213> ORGANISM: Homo sapiens

<400> SEQUENCE: 585
ctggtgctcc attcttgagt gtgt                                          24

<210> SEQ ID NO 586
<211> LENGTH: 24
<212> TYPE: DNA
<213> ORGANISM: Homo sapiens

<400> SEQUENCE: 586
ggacaacagg ttgtacaggg atga                                          24

<210> SEQ ID NO 587
<211> LENGTH: 24
<212> TYPE: DNA
<213> ORGANISM: Homo sapiens

<400> SEQUENCE: 587
tacaggagac tggacatcgt cagg                                          24

<210> SEQ ID NO 588
<211> LENGTH: 24
<212> TYPE: DNA
<213> ORGANISM: Homo sapiens

<400> SEQUENCE: 588
ctttctgcac atttgggtgg tctt                                          24

<210> SEQ ID NO 589
<211> LENGTH: 24
<212> TYPE: DNA
<213> ORGANISM: Homo sapiens

<400> SEQUENCE: 589
ggtgatcaga tggacaatgc aaag                                          24

<210> SEQ ID NO 590
<211> LENGTH: 24
<212> TYPE: DNA
<213> ORGANISM: Homo sapiens
```

```
<400> SEQUENCE: 590
tcatttccag aacattcagg gtca                                          24

<210> SEQ ID NO 591
<211> LENGTH: 24
<212> TYPE: DNA
<213> ORGANISM: Homo sapiens

<400> SEQUENCE: 591
acctcaatgg cctaagcaag tgtc                                          24

<210> SEQ ID NO 592
<211> LENGTH: 24
<212> TYPE: DNA
<213> ORGANISM: Homo sapiens

<400> SEQUENCE: 592
gcctcttacc tgggtcacac attt                                          24

<210> SEQ ID NO 593
<211> LENGTH: 24
<212> TYPE: DNA
<213> ORGANISM: Homo sapiens

<400> SEQUENCE: 593
atcttgcaac ctggttcttc atgg                                          24

<210> SEQ ID NO 594
<211> LENGTH: 24
<212> TYPE: DNA
<213> ORGANISM: Homo sapiens

<400> SEQUENCE: 594
gctggcaatg atgaaaacta ctcg                                          24

<210> SEQ ID NO 595
<211> LENGTH: 24
<212> TYPE: DNA
<213> ORGANISM: Homo sapiens

<400> SEQUENCE: 595
ccaagtttca actctgctct gctg                                          24

<210> SEQ ID NO 596
<211> LENGTH: 24
<212> TYPE: DNA
<213> ORGANISM: Homo sapiens

<400> SEQUENCE: 596
gttgaacacg gcattcttcc tttc                                          24

<210> SEQ ID NO 597
<211> LENGTH: 24
<212> TYPE: DNA
<213> ORGANISM: Homo sapiens

<400> SEQUENCE: 597
ggaaagggac gaactggtgt aatg                                          24

<210> SEQ ID NO 598
<211> LENGTH: 24
<212> TYPE: DNA
<213> ORGANISM: Homo sapiens
```

-continued

```
<400> SEQUENCE: 598
aaatctaggg cctcttgtgc cttt                                              24

<210> SEQ ID NO 599
<211> LENGTH: 24
<212> TYPE: DNA
<213> ORGANISM: Homo sapiens

<400> SEQUENCE: 599
agccccatgg atctttctac catt                                              24

<210> SEQ ID NO 600
<211> LENGTH: 24
<212> TYPE: DNA
<213> ORGANISM: Homo sapiens

<400> SEQUENCE: 600
atactgccag ggctcctgat actg                                              24

<210> SEQ ID NO 601
<211> LENGTH: 100
<212> TYPE: DNA
<213> ORGANISM: Artificial Sequence
<220> FEATURE:
<223> OTHER INFORMATION: Oligonucleotide capture probe

<400> SEQUENCE: 601
aatcgggtaa cattggctac aaagacctac ctagatgctc cttttacga taacttacag        60 gtgaaaacca ggatcaactc ccgtgccagt cacatctcgt                            100

<210> SEQ ID NO 602
<211> LENGTH: 100
<212> TYPE: DNA
<213> ORGANISM: Artificial Sequence
<220> FEATURE:
<223> OTHER INFORMATION: Oligonucleotide capture probe

<400> SEQUENCE: 602
attataagta tcgacctcgt cggaaggcga agatgctgcc gaagaattgc agtttgcttc       60
gtgaaaacca ggatcaactc ccgtgccagt cacatctcgt                            100

<210> SEQ ID NO 603
<211> LENGTH: 24
<212> TYPE: DNA
<213> ORGANISM: Homo sapiens

<400> SEQUENCE: 603
ctggtgctcc attcttgagt gtgt                                              24

<210> SEQ ID NO 604
<211> LENGTH: 24
<212> TYPE: DNA
<213> ORGANISM: Homo sapiens

<400> SEQUENCE: 604
ggacaacagg ttgtacaggg atga                                              24

<210> SEQ ID NO 605
<211> LENGTH: 61
<212> TYPE: DNA
<213> ORGANISM: Artificial Sequence
<220> FEATURE:
```

```
<223> OTHER INFORMATION: qPCR Amplicon

<400> SEQUENCE: 605
ctggtgctcc attcttgagt gtgtggcttt cgtacagtca tccctgtaca acctgttgtc    60
c                                                                    61

<210> SEQ ID NO 606
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 606
ctgtaagtta tcgtaaaaag gagcatctag gtaggtcttt gtagccaatg ttacccgatt    60

<210> SEQ ID NO 607
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 607
gaagcaaact gcaattcttc ggcagcatct tcgccttccg acgaggtcga tacttataat    60

<210> SEQ ID NO 608
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 608
aatcgggtaa cattggctac aaagacctac ctagatgctc cttttacga taacttacag    60

<210> SEQ ID NO 609
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 609
attataagta tcgacctcgt cggaaggcga agatgctgcc gaagaattgc agtttgcttc    60

<210> SEQ ID NO 610
<211> LENGTH: 24
<212> TYPE: DNA
<213> ORGANISM: Homo sapiens

<400> SEQUENCE: 610
tacaggagac tggacatcgt cagg                                           24

<210> SEQ ID NO 611
<211> LENGTH: 24
<212> TYPE: DNA
<213> ORGANISM: Homo sapiens

<400> SEQUENCE: 611
ctttctgcac atttgggtgg tctt                                           24

<210> SEQ ID NO 612
<211> LENGTH: 67
```

```
<212> TYPE: DNA
<213> ORGANISM: Artificial Sequence
<220> FEATURE:
<223> OTHER INFORMATION: qPCR amplicon

<400> SEQUENCE: 612
tacaggagac tggacatcgt caggtcgctc tacgaagatc tggaagacca cccaaatgtg    60
cagaaag                                                              67

<210> SEQ ID NO 613
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 613
cttgttcgtt ccttgtactg agaccctagt ctgccactga ggatttggtt tttgcccttc    60

<210> SEQ ID NO 614
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 614
atcaagactc atcagtacca tcaaaagctg agatgaaaca gtgtaagttt caacagaaat    60

<210> SEQ ID NO 615
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 615
gaagggcaaa aaccaaatcc tcagtggcag actagggtct cagtacaagg aacgaacaag    60

<210> SEQ ID NO 616
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 616
atttctgttg aaacttacac tgtttcatct cagcttttga tggtactgat gagtcttgat    60

<210> SEQ ID NO 617
<211> LENGTH: 24
<212> TYPE: DNA
<213> ORGANISM: Homo sapiens

<400> SEQUENCE: 617
ggtgatcaga tggacaatgc aaag                                           24

<210> SEQ ID NO 618
<211> LENGTH: 24
<212> TYPE: DNA
<213> ORGANISM: Homo sapiens

<400> SEQUENCE: 618
tcatttccag aacattcagg gtca                                           24
```

<210> SEQ ID NO 619
<211> LENGTH: 73
<212> TYPE: DNA
<213> ORGANISM: Artificial Sequence
<220> FEATURE:
<223> OTHER INFORMATION: qPCR amplicon

<400> SEQUENCE: 619
ggtgatcaga tggacaatgc aaagcgcatg gagactaagg gagctggagt gaccctgaat    60
gttctggaaa tga    73

<210> SEQ ID NO 620
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 620
tgtgtccagc tgtgaaactc agagatgtaa ctgctgacat cctccctatt ttgcatctca    60

<210> SEQ ID NO 621
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 621
atttgaaaca attttatcat gaatgccatg accaaagtat tcttctgtat cttctttctt    60

<210> SEQ ID NO 622
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 622
tgagatgcaa aatagggagg atgtcagcag ttacatctct gagtttcaca gctggacaca    60

<210> SEQ ID NO 623
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 623
aagaaagaag atacagaaga atactttggt catggcattc atgataaaat gtttcaaat    60

<210> SEQ ID NO 624
<211> LENGTH: 24
<212> TYPE: DNA
<213> ORGANISM: Homo sapiens

<400> SEQUENCE: 624
acctcaatgg cctaagcaag tgtc    24

<210> SEQ ID NO 625
<211> LENGTH: 24
<212> TYPE: DNA
<213> ORGANISM: Homo sapiens

<400> SEQUENCE: 625

```
gcctcttacc tgggtcacac attt                                           24

<210> SEQ ID NO 626
<211> LENGTH: 57
<212> TYPE: DNA
<213> ORGANISM: Artificial Sequence
<220> FEATURE:
<223> OTHER INFORMATION: qPCR amplicon

<400> SEQUENCE: 626
acctcaatgg cctaagcaag tgtctgcagt gccaaatgtg tgacccaggt aagaggc      57

<210> SEQ ID NO 627
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 627
tgatgggtgg gctcccgaag gggcctcccg cagacttgcg aagttcccac tctctgggcg   60

<210> SEQ ID NO 628
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 628
cagggtgcgg gggcatccag gctgcccaag cggaggctgg gccggctgtg ctggcctctt   60

<210> SEQ ID NO 629
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 629
cgcccagaga gtgggaactt cgcaagtctg cgggaggccc cttcgggagc ccacccatca   60

<210> SEQ ID NO 630
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 630
aagaggccag cacagccggc ccagcctccg cttgggcagc ctggatgccc ccgcaccctg   60

<210> SEQ ID NO 631
<211> LENGTH: 24
<212> TYPE: DNA
<213> ORGANISM: Homo sapiens

<400> SEQUENCE: 631
atcttgcaac ctggttcttc atgg                                          24

<210> SEQ ID NO 632
<211> LENGTH: 24
<212> TYPE: DNA
<213> ORGANISM: Homo sapiens
```

<400> SEQUENCE: 632
gctggcaatg atgaaaacta ctcg                                           24

<210> SEQ ID NO 633
<211> LENGTH: 74
<212> TYPE: DNA
<213> ORGANISM: Artificial Sequence
<220> FEATURE:
<223> OTHER INFORMATION: qPCR amplicon

<400> SEQUENCE: 633
aatcttgcaa cctggttctt catggctgcg gtagcatttc tcagctcagc cgagtagttt    60
tcatcattgc cagc                                                      74

<210> SEQ ID NO 634
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 634
ttttgaaatg tgggtttgtt gccatgaaac gtgtttcaag catagttttg acagataacg    60

<210> SEQ ID NO 635
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 635
tgccctaaaa gtgtatgtat aacatccctg atgtctgcat tgtcctttg actggtgttt     60

<210> SEQ ID NO 636
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 636
cgttatctgt caaaactatg cttgaaacac gtttcatggc aacaaaccca catttcaaaa    60

<210> SEQ ID NO 637
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 637
aaacaccagt caaaggacaa atgcagacat cagggatgtt atacatacac ttttagggca    60

<210> SEQ ID NO 638
<211> LENGTH: 24
<212> TYPE: DNA
<213> ORGANISM: Homo sapiens

<400> SEQUENCE: 638
ccaagtttca actctgctct gctg                                           24

<210> SEQ ID NO 639
<211> LENGTH: 24

```
<212> TYPE: DNA
<213> ORGANISM: Homo sapiens

<400> SEQUENCE: 639
gttgaacacg gcattcttcc tttc                                           24

<210> SEQ ID NO 640
<211> LENGTH: 60
<212> TYPE: DNA
<213> ORGANISM: Artificial Sequence
<220> FEATURE:
<223> OTHER INFORMATION: qPCR amplicon

<400> SEQUENCE: 640
ccaagtttca actctgctct gctgagaagt ccaatcgaaa ggaagaatgc cgtgttcaac    60

<210> SEQ ID NO 641
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 641
aacccctcga ggctcagacc tttggagcag gagtgtgatt ctggccaacc accctctctg    60

<210> SEQ ID NO 642
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 642
cataaatatg tgtgctagtc ctgttagacc caagtgctgc ccaagggcag cgccctgctc    60

<210> SEQ ID NO 643
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 643
cagagagggt ggttggccag aatcacactc ctgctccaaa ggtctgagcc tcgagggatt    60

<210> SEQ ID NO 644
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 644
gagcagggcg ctgcccttgg gcagcacttg ggtctaacag gactagcaca catatttatg    60

<210> SEQ ID NO 645
<211> LENGTH: 24
<212> TYPE: DNA
<213> ORGANISM: Homo sapiens

<400> SEQUENCE: 645
ggaaagggac gaactggtgt aatg                                           24

<210> SEQ ID NO 646
```

-continued

```
<211> LENGTH: 24
<212> TYPE: DNA
<213> ORGANISM: Homo sapiens

<400> SEQUENCE: 646
aaatctaggg cctcttgtgc cttt                                              24

<210> SEQ ID NO 647
<211> LENGTH: 83
<212> TYPE: DNA
<213> ORGANISM: Artificial Sequence
<220> FEATURE:
<223> OTHER INFORMATION: qPCR amplicon

<400> SEQUENCE: 647
ggaaagggac gaactggtgt aatgatatgt gcatatttat tacatcgggg caaatttta       60 aaggcacaag aggccctaga ttt                                              83

<210> SEQ ID NO 648
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 648
tacttgttaa ttaaaaattc aagagttttt ttttcttatt ctgaggttat cttttacca        60

<210> SEQ ID NO 649
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 649
ccaaaatctg ttttccaata aattctcaga tccaggaaga ggaaaggaaa acatcaaaa        60

<210> SEQ ID NO 650
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 650
tggtaaaaag ataacctcag aataagaaaa aaaaactctt gaatttttaa ttaacaagta      60

<210> SEQ ID NO 651
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 651
ttttgatgtt tttcctttcc tcttcctgga tctgagaatt tattggaaaa cagattttgg      60

<210> SEQ ID NO 652
<211> LENGTH: 24
<212> TYPE: DNA
<213> ORGANISM: Homo sapiens

<400> SEQUENCE: 652
agccccatgg atctttctac catt                                             24
```

<210> SEQ ID NO 653
<211> LENGTH: 24
<212> TYPE: DNA
<213> ORGANISM: Homo sapiens

<400> SEQUENCE: 653
atactgccag ggctcctgat actg                                           24

<210> SEQ ID NO 654
<211> LENGTH: 69
<212> TYPE: DNA
<213> ORGANISM: Artificial Sequence
<220> FEATURE:
<223> OTHER INFORMATION: qPCR amplicon

<400> SEQUENCE: 654
agccccatgg atctttctac cattaagagg aagttagaca ctggacagta tcaggagccc     60
tggcagtat                                                            69

<210> SEQ ID NO 655
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 655
atactccatc tcccgtaaaa atagtgagac ttgagtaatg tttgatgtca cttgtctttc     60

<210> SEQ ID NO 656
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 656
cagtcaccac tatattattc taggtatccc agaaaagtta aagtcaaatc tgaaacacat     60

<210> SEQ ID NO 657
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 657
gaaagacaag tgacatcaaa cattactcaa gtctcactat ttttacggga gatggagtat     60

<210> SEQ ID NO 658
<211> LENGTH: 60
<212> TYPE: DNA
<213> ORGANISM: Artificial Sequence
<220> FEATURE:
<223> OTHER INFORMATION: Oligonucleotide probe

<400> SEQUENCE: 658
atgtgtttca gatttgactt taactttct gggataccta gaataatata gtggtgactg     60

<210> SEQ ID NO 659
<211> LENGTH: 40
<212> TYPE: DNA
<213> ORGANISM: Artificial Sequence
<220> FEATURE:

<223> OTHER INFORMATION: Oligonucleotide probe

<400> SEQUENCE: 659
gtgaaaacca ggatcaactc ccgtgccagt cacatctcgt                              40

<210> SEQ ID NO 660
<211> LENGTH: 40
<212> TYPE: DNA
<213> ORGANISM: Artificial Sequence
<220> FEATURE:
<223> OTHER INFORMATION: Oligonucleotide probe

<400> SEQUENCE: 660
acgagatgtg actggcacgg gagttgatcc tggttttcac                              40

<210> SEQ ID NO 661
<211> LENGTH: 58
<212> TYPE: DNA
<213> ORGANISM: Artificial Sequence
<220> FEATURE:
<223> OTHER INFORMATION: Primer

<400> SEQUENCE: 661
aatgatacgg cgaccaccga gatctacacg tcatgcagga ccagagaatt cgaataca         58

<210> SEQ ID NO 662
<211> LENGTH: 57
<212> TYPE: DNA
<213> ORGANISM: Artificial Sequence
<220> FEATURE:
<223> OTHER INFORMATION: Primer

<400> SEQUENCE: 662
caagcagaag acggcatacg agatgtgact ggcacgggag ttgatcctgg ttttcac          57

<210> SEQ ID NO 663
<211> LENGTH: 20
<212> TYPE: DNA
<213> ORGANISM: Artificial Sequence
<220> FEATURE:
<223> OTHER INFORMATION: Oligonucleotide probe
<220> FEATURE:
<221> NAME/KEY: modified_base
<222> LOCATION: (20)..(20)
<223> OTHER INFORMATION: dideoxycytosine
<220> FEATURE:
<221> NAME/KEY: misc_feature
<222> LOCATION: (20)..(20)
<223> OTHER INFORMATION: n is a, c, g, or t

<400> SEQUENCE: 663
agttgatcct ggttatacan                                                    20

<210> SEQ ID NO 664
<211> LENGTH: 31
<212> TYPE: DNA
<213> ORGANISM: Artificial Sequence
<220> FEATURE:
<223> OTHER INFORMATION: Adaptor ligation strand oligonucleotide

<400> SEQUENCE: 664
gtgtataacc aggatcaact cccgtgccag t                                       31

<210> SEQ ID NO 665
<211> LENGTH: 33
<212> TYPE: DNA
<213> ORGANISM: Artificial Sequence
<220> FEATURE:
<223> OTHER INFORMATION: Index 1 sequencing primer

<400> SEQUENCE: 665
gtgaaaacca ggatcaactc ccgtgccagt cac                          33

<210> SEQ ID NO 666
<211> LENGTH: 30
<212> TYPE: DNA
<213> ORGANISM: Artificial Sequence
<220> FEATURE:
<223> OTHER INFORMATION: Library-free Forward sequencing primer

<400> SEQUENCE: 666
gtcatgcagg agttgatcct ggttatacac                              30

<210> SEQ ID NO 667
<211> LENGTH: 25
<212> TYPE: DNA
<213> ORGANISM: Artificial Sequence
<220> FEATURE:
<223> OTHER INFORMATION: Post-processing amplification primer

<400> SEQUENCE: 667
actggcacgg gagttgatcc tggtt                                   25

<210> SEQ ID NO 668
<211> LENGTH: 59
<212> TYPE: DNA
<213> ORGANISM: Artificial Sequence
<220> FEATURE:
<223> OTHER INFORMATION: Library-free forward amplification primer

<400> SEQUENCE: 668
aatgatacgg cgaccaccga gatctacacg tcatgcagga gttgatcctg gttatacac   59

<210> SEQ ID NO 669
<211> LENGTH: 65
<212> TYPE: DNA
<213> ORGANISM: Artificial Sequence
<220> FEATURE:
<223> OTHER INFORMATION: Index N701 reverse primer

<400> SEQUENCE: 669
caagcagaag acggcatacg agattcgcct tagtgactgg cacgggagtt gatcctggtt   60
ttcac                                                         65

<210> SEQ ID NO 670
<211> LENGTH: 65
<212> TYPE: DNA
<213> ORGANISM: Artificial Sequence
<220> FEATURE:
<223> OTHER INFORMATION: Index N702 reverse primer

<400> SEQUENCE: 670
caagcagaag acggcatacg agatctagta cggtgactgg cacgggagtt gatcctggtt   60
ttcac                                                         65

<210> SEQ ID NO 671
<211> LENGTH: 65
<212> TYPE: DNA
<213> ORGANISM: Artificial Sequence
<220> FEATURE:
<223> OTHER INFORMATION: Index N703 reverse primer

```
<400> SEQUENCE: 671
caagcagaag acggcatacg agatttctgc ctgtgactgg cacgggagtt gatcctggtt    60
ttcac                                                                65

<210> SEQ ID NO 672
<211> LENGTH: 65
<212> TYPE: DNA
<213> ORGANISM: Artificial Sequence
<220> FEATURE:
<223> OTHER INFORMATION: Index N704 reverse primer

<400> SEQUENCE: 672
caagcagaag acggcatacg agatgctcag gagtgactgg cacgggagtt gatcctggtt    60
ttcac                                                                65

<210> SEQ ID NO 673
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: modified_base
<222> LOCATION: (36)..(41)
<223> OTHER INFORMATION: n = any nucleotide
<220> FEATURE:
<221> NAME/KEY: misc_feature
<222> LOCATION: (36)..(41)
<223> OTHER INFORMATION: n is a, c, g, or t

<400> SEQUENCE: 673
atgtgactgg cacgggagtt gatcctggtt ttcacnnnnn naagcaccta gccccattcc    60
tgctgagcag gaggtggcag gtaccccaga ctgggaggta a                       101

<210> SEQ ID NO 674
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 674
atgtgactgg cacgggagtt gatcctggtt ttcacnnnnn nagtcggtgg ggccaggatg    60
aggcccagtc tgttcacaca tggctgctgc ctctcagctc t                       101

<210> SEQ ID NO 675
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 675
atgtgactgg cacgggagtt gatcctggtt ttcacnnnnn nacctgagta gcatcattgt    60
agttctcgat atctccactt ccagttttac atttaccatc a                       101
```

```
<210> SEQ ID NO 676
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 676
atgtgactgg cacgggagtt gatcctggtt ttcacnnnnn ncctgccct cagccagtac      60 agaaagtcat ttgtcaaggc cttcagttgg cagacgtgct c                        101

<210> SEQ ID NO 677
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 677
atgtgactgg cacgggagtt gatcctggtt ttcacnnnnn nagaattcat tgccagctat      60
aaatctgtgg aaacgctgcc acacaatctt agcacacaag a                         101

<210> SEQ ID NO 678
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 678
atgtgactgg cacgggagtt gatcctggtt ttcacnnnnn ngacttcaaa gaaattacaa      60
gttgacatct tggactctac ccctcgtact ttatctccta t                         101

<210> SEQ ID NO 679
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 679
atgtgactgg cacgggagtt gatcctggtt ttcacnnnnn ntctctttgg ggtcaagaaa      60
gaatccctag tggatttggg attctagagg aggtgttata a                         101

<210> SEQ ID NO 680
<211> LENGTH: 101
<212> TYPE: DNA
<213> ORGANISM: Artificial Sequence
<220> FEATURE:
<223> OTHER INFORMATION: Oligonucleotide probe
<220> FEATURE:
```

<221> NAME/KEY: misc_feature
<222> LOCATION: (36)..(41)
<223> OTHER INFORMATION: n is a, c, g, or t

<400> SEQUENCE: 680
atgtgactgg cacgggagtt gatcctggtt ttcacnnnnn ntgcgatacc atgctgaaga    60
tgagctaacc caaccagcca agcaggcagg gctgcgaagg a    101

<210> SEQ ID NO 681
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 681
atgtgactgg cacgggagtt gatcctggtt ttcacnnnnn ngggtaggt ggaaaaccca    60 agtaatgtga ttttgtaaca tccactgctg catttgtttg c    101

<210> SEQ ID NO 682
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 682
atgtgactgg cacgggagtt gatcctggtt ttcacnnnnn nttacttccc tccagttttg    60
ttgcttgcaa aacaacagaa tcttctctcc atgaaatcat g    101

<210> SEQ ID NO 683
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 683
atgtgactgg cacgggagtt gatcctggtt ttcacnnnnn ncagggtat ctattatccc    60 cattttctca caaaggaaac caagataaaa ggtttaaatg g    101

<210> SEQ ID NO 684
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 684
atgtgactgg cacgggagtt gatcctggtt ttcacnnnnn ngaaattctc ttgtgaattc    60
ctgtgtcctc ttgaatcttc aatgctaaag tttttgaaac t       101

<210> SEQ ID NO 685
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 685
atgtgactgg cacgggagtt gatcctggtt ttcacnnnnn ngggtttgag tggcatgagc       60
tacctactgg atgtgcctga ctgtttcccc ttcttcttcc c       101

<210> SEQ ID NO 686
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 686
atgtgactgg cacgggagtt gatcctggtt ttcacnnnnn nctatctcca ggatggagag       60
agggaaaaaa aagatgggtc tgtgtgggag ggcaggtact t       101

<210> SEQ ID NO 687
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 687
atgtgactgg cacgggagtt gatcctggtt ttcacnnnnn ngaaagaagc caggtcttca       60
attaataaga ttccctggtc tcgtttgtct acctgttaat g       101

<210> SEQ ID NO 688
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 688
atgtgactgg cacgggagtt gatcctggtt ttcacnnnnn ncagactcgc gcccaatttt       60
cccccacccc ttgttattgc cacaaaatcc tgaggatgat c       101

<210> SEQ ID NO 689
<211> LENGTH: 101
<212> TYPE: DNA

<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 689
atgtgactgg cacgggagtt gatcctggtt ttcacnnnnn ntctttcttc ttcctttatg    60
gggccctcct gctggctgag ggcttctaca ccaccggcgc a                      101

<210> SEQ ID NO 690
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 690
atgtgactgg cacgggagtt gatcctggtt ttcacnnnnn ngtttgtgtt tctacatctg    60
caggctgatg ctgatttcta accaccccat gtcaatcatt t                      101

<210> SEQ ID NO 691
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 691
atgtgactgg cacgggagtt gatcctggtt ttcacnnnnn naaccaaata tatagtgctt    60
ccatagtggg taggagagcc aaagcacccg taccctaact c                      101

<210> SEQ ID NO 692
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 692
atgtgactgg cacgggagtt gatcctggtt ttcacnnnnn nagtctccat gtggccccgt    60
aactccataa agcttaccct gcttgctttt tgtgtcttac t                      101

<210> SEQ ID NO 693
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 693
atgtgactgg cacgggagtt gatcctggtt ttcacnnnnn nccatgggtg taatttgtat    60
ggtattagct actcccttgt aaaataaccc aaataaccca c    101

<210> SEQ ID NO 694
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 694
atgtgactgg cacgggagtt gatcctggtt ttcacnnnnn ntttacagtg gagcatatta    60
ctgctgttgc aagaaacagt tcttcctctt tcattttcct g    101

<210> SEQ ID NO 695
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 695
atgtgactgg cacgggagtt gatcctggtt ttcacnnnnn natagctgta cccacactat    60
ctcaggccta tttacttgcc aagatcattc aaagtcaact c    101

<210> SEQ ID NO 696
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 696
atgtgactgg cacgggagtt gatcctggtt ttcacnnnnn ngatttgagg agggagtgct    60
ttcttttcta ctctcattca cattctctct tctgttccct a    101

<210> SEQ ID NO 697
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 697
atgtgactgg cacgggagtt gatcctggtt ttcacnnnnn ncagcattgt aggctgtgtg    60
gttagagcct cgctattaga gaaaggggga tttctacggg g    101

-continued

```
<210> SEQ ID NO 698
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 698
atgtgactgg cacgggagtt gatcctggtt ttcacnnnnn ntgttacctt taaaagacat      60
ctgctttctg ccaaaattaa tgtgctgaac ttaaacttac c                        101

<210> SEQ ID NO 699
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 699
atgtgactgg cacgggagtt gatcctggtt ttcacnnnnn nttcccagta aattactctt      60
accaatgcaa cagactttaa agaagttgtg ttttacaatg c                        101

<210> SEQ ID NO 700
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 700
atgtgactgg cacgggagtt gatcctggtt ttcacnnnnn ntaaatgaca taacagttat      60
gattttgcag aaaacagatc tgtatttatt tcagtgttac t                        101

<210> SEQ ID NO 701
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 701
atgtgactgg cacgggagtt gatcctggtt ttcacnnnnn ngacaggttt tgaaagatat      60
ttgtgttact aatgactgtg ctataacttt tttttctttc c                        101

<210> SEQ ID NO 702
<211> LENGTH: 101
<212> TYPE: DNA
<213> ORGANISM: Artificial Sequence
<220> FEATURE:
<223> OTHER INFORMATION: Oligonucleotide probe
```

<220> FEATURE:
<221> NAME/KEY: misc_feature
<222> LOCATION: (36)..(41)
<223> OTHER INFORMATION: n is a, c, g, or t

<400> SEQUENCE: 702
atgtgactgg cacgggagtt gatcctggtt ttcacnnnnn nactcaaaaa ataaaaacta      60
taattactcc ttaatgtcag cttattatat tcaatttaaa c                        101

<210> SEQ ID NO 703
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 703
atgtgactgg cacgggagtt gatcctggtt ttcacnnnnn naacaccttt tttgaagtaa      60
aaggtgcact gtaataatcc agactgtgtt tctcccttct c                        101

<210> SEQ ID NO 704
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 704
atgtgactgg cacgggagtt gatcctggtt ttcacnnnnn ngaaaccttt atctgtatca      60
aagaatggtc ctgcaccagt aatatgcata ttaaaacaag a                        101

<210> SEQ ID NO 705
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 705
atgtgactgg cacgggagtt gatcctggtt ttcacnnnnn ngtgtattaa ccttatgtgt      60
gacatgttct aatatagtca cattttcatt atttttatta t                        101

<210> SEQ ID NO 706
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 706
atgtgactgg cacgggagtt gatcctggtt ttcacnnnnn ncccagcca gcggtccgca    60 acccttgccg catccacgaa actttgccca tagcagcggg c    101

<210> SEQ ID NO 707
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 707
atgtgactgg cacgggagtt gatcctggtt ttcacnnnnn ncgactcatc tcagcattaa    60
agtgataaaa aaataaatta aaaggcaagt ggacttcggt g    101

<210> SEQ ID NO 708
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 708
atgtgactgg cacgggagtt gatcctggtt ttcacnnnnn nctgtggcgc gcactgcgcg    60
ctgcgccagg tttccgcacc aagacccctt taactcaaga c    101

<210> SEQ ID NO 709
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 709
atgtgactgg cacgggagtt gatcctggtt ttcacnnnnn nttctactgc gacgaggagg    60
agaacttcta ccagcagcag cagcagagcg agctgcagcc c    101

<210> SEQ ID NO 710
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 710
atgtgactgg cacgggagtt gatcctggtt ttcacnnnnn naccgagctg ctgggaggag    60
acatggtgaa ccagagtttc atctgcgacc cggacgacga g    101

<210> SEQ ID NO 711
<211> LENGTH: 101

```
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 711
atgtgactgg cacgggagtt gatcctggtt ttcacnnnnn ngccgccgcc tcagagtgca      60
tcgacccctc ggtggtcttc ccctaccctc tcaacgacag c                        101

<210> SEQ ID NO 712
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 712
atgtgactgg cacgggagtt gatcctggtt ttcacnnnnn nggcggctag gggacagggg      60
cggggtgggc agcagctcga atttcttcca gatatcctcg c                        101

<210> SEQ ID NO 713
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 713
atgtgactgg cacgggagtt gatcctggtt ttcacnnnnn nagacgagct tggcggcggc      60
cgagaagccg ctccacatac agtcctggat gatgatgttt t                        101

<210> SEQ ID NO 714
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 714
atgtgactgg cacgggagtt gatcctggtt ttcacnnnnn naggagagca gagaatccga      60
ggacggagag aaggcgctgg agtcttgcga ggcgcaggac t                        101

<210> SEQ ID NO 715
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
```

<223> OTHER INFORMATION: n is a, c, g, or t

<400> SEQUENCE: 715
atgtgactgg cacgggagtt gatcctggtt ttcacnnnnn ntaagagtgg cccgttaaat    60
aagctgccaa tgaaaatggg aaaggtatcc agccgcccac t    101

<210> SEQ ID NO 716
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 716
atgtgactgg cacgggagtt gatcctggtt ttcacnnnnn nttgtatttg tacagcatta    60
atctggtaat tgattatttt aatgtaacct tgctaaagga g    101

<210> SEQ ID NO 717
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 717
atgtgactgg cacgggagtt gatcctggtt ttcacnnnnn ngaggccaca gcaaacctcc    60
tcacagccca ctggtcctca agaggtgcca cgtctccaca c    101

<210> SEQ ID NO 718
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 718
atgtgactgg cacgggagtt gatcctggtt ttcacnnnnn nagaggagga acgagctaaa    60
acggagcttt tttgccctgc gtgaccagat cccggagttg g    101

<210> SEQ ID NO 719
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 719
atgtgactgg cacgggagtt gatcctggtt ttcacnnnnn ntccaacttg accctcttgg    60
cagcaggata gtccttccga gtggagggag gcgctgcgta g    101

```
<210> SEQ ID NO 720
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 720
atgtgactgg cacgggagtt gatcctggtt ttcacnnnnn ngcttggacg gacaggatgt    60
atgctgtggc tttttaagg ataactacct tgggggcctt t                        101

<210> SEQ ID NO 721
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 721
atgtgactgg cacgggagtt gatcctggtt ttcacnnnnn ngcatttgat catgcatttg    60
aaacaagttc ataggtgatt gctcaggaca tttctgttag a                       101

<210> SEQ ID NO 722
<211> LENGTH: 20
<212> TYPE: DNA
<213> ORGANISM: Artificial Sequence
<220> FEATURE:
<223> OTHER INFORMATION: poly- dT primer
<220> FEATURE:
<221> NAME/KEY: modified_base
<222> LOCATION: (20)..(20)
<223> OTHER INFORMATION: n = any nucleotide
<220> FEATURE:
<221> NAME/KEY: misc_feature
<222> LOCATION: (20)..(20)
<223> OTHER INFORMATION: n is a, c, g, or t

<400> SEQUENCE: 722
tttttttttt tttttttvn                                                 20

<210> SEQ ID NO 723
<211> LENGTH: 45
<212> TYPE: DNA
<213> ORGANISM: Artificial Sequence
<220> FEATURE:
<223> OTHER INFORMATION: oligonucleotide aptamer
<220> FEATURE:
<221> NAME/KEY: misc_feature
<222> LOCATION: (26)..(33)
<223> OTHER INFORMATION: n is a, c, g, or t
<220> FEATURE:
<221> NAME/KEY: modified_base
<222> LOCATION: (36)..(43)
<223> OTHER INFORMATION: n = any nucleotide

<400> SEQUENCE: 723
tgcaggacca gagaattcga atacannnnn nnngactccg atccc                    45

<210> SEQ ID NO 724
```

```
<211> LENGTH: 12
<212> TYPE: DNA
<213> ORGANISM: Artificial Sequence
<220> FEATURE:
<223> OTHER INFORMATION: Oligonucleotide aptamer

<400> SEQUENCE: 724
gggatcggag tc                                                          12

<210> SEQ ID NO 725
<211> LENGTH: 45
<212> TYPE: DNA
<213> ORGANISM: Artificial Sequence
<220> FEATURE:
<223> OTHER INFORMATION: Oligonucleotide aptamer
<220> FEATURE:
<221> NAME/KEY: misc_feature
<222> LOCATION: (26)..(33)
<223> OTHER INFORMATION: n is a, c, g, or t
<220> FEATURE:
<221> NAME/KEY: modified_base
<222> LOCATION: (36)..(43)
<223> OTHER INFORMATION: n = any nucleotide

<400> SEQUENCE: 725
tgcaggacca gagaattcga atacannnnn nnncggaact cggag                      45

<210> SEQ ID NO 726
<211> LENGTH: 12
<212> TYPE: DNA
<213> ORGANISM: Artificial Sequence
<220> FEATURE:
<223> OTHER INFORMATION: Oligonucleotide aptamer

<400> SEQUENCE: 726
ctccgagttc cg                                                          12

<210> SEQ ID NO 727
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 727
atgtgactgg cacgggagtt gatcctggtt ttcacnnnnn ngccgaagag gaaatgctgg      60
aaaatgtcag cctggtctgt ccaaaagatg cgacccgatt c                         101

<210> SEQ ID NO 728
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 728
atgtgactgg cacgggagtt gatcctggtt ttcacnnnnn ncagctgacc tcatcgagat      60
tggcttggaa ggaaaaggct ttgagccaac attggaagct                           100
```

```
<210> SEQ ID NO 729
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 729
atgtgactgg cacgggagtt gatcctggtt ttcacnnnnn ntactggaga caggctggac    60
tcagctacat ccgatactcc cagatctgtg caaaagcagt g                       101

<210> SEQ ID NO 730
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 730
atgtgactgg cacgggagtt gatcctggtt ttcacnnnnn nctgaagaca gaattcaaag    60
caaatgctga aagacttct ggcagcaacg taaaaattgt g                        101

<210> SEQ ID NO 731
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 731
atgtgactgg cacgggagtt gatcctggtt ttcacnnnnn nacagagtcc agcccattga    60
gagaatcaac tgccataggt tttacacctg agttagaaag t                       101

<210> SEQ ID NO 732
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 732
atgtgactgg cacgggagtt gatcctggtt ttcacnnnnn nagccagctc cagtgacagt    60
gacgacggct tgcaccagtt tcttcggggt acctccagca                         100

<210> SEQ ID NO 733
<211> LENGTH: 100
<212> TYPE: DNA
<213> ORGANISM: Artificial Sequence
<220> FEATURE:
<223> OTHER INFORMATION: Oligonucleotide probe
<220> FEATURE:
```

```
<221> NAME/KEY: misc_feature
<222> LOCATION: (36)..(41)
<223> OTHER INFORMATION: n is a, c, g, or t

<400> SEQUENCE: 733
atgtgactgg cacgggagtt gatcctggtt ttcacnnnnn ngacacgcag cacaaattgc      60
gcagcgcggt ggaagagatg gaggcagaag aagctgctgc                          100

<210> SEQ ID NO 734
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 734
atgtgactgg cacgggagtt gatcctggtt ttcacnnnnn ntggtgtatg tgtgcaagcc      60
gaccttcgtg gggagccgtg accaagatgg ggagatcctg                          100

<210> SEQ ID NO 735
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 735
atgtgactgg cacgggagtt gatcctggtt ttcacnnnnn natgaggatc gtctgcctgg      60
tcctaagtgt ggtgggcaca gcatggactg cagatagtgg t                        101

<210> SEQ ID NO 736
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 736
atgtgactgg cacgggagtt gatcctggtt ttcacnnnnn nattttttct gtttattgcg      60
atcaagagac cagtttggga ggatggcttt tgatccagca                          100

<210> SEQ ID NO 737
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 737
atgtgactgg cacgggagtt gatcctggtt ttcacnnnnn ngtgttcagt ttcatccttg      60
```

```
ttaccaccgc tctgacaatg ggcagggaaa tttcggcgct c          101
```

<210> SEQ ID NO 738
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 738

```
atgtgactgg cacgggagtt gatcctggtt ttcacnnnnn ntgcaaacct gaatggtgta   60
tactacagcg gccctacac ggctaaaaca gacaatggga                         100
```

<210> SEQ ID NO 739
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 739

```
atgtgactgg cacgggagtt gatcctggtt ttcacnnnnn ncatcccaa cgtacccgcc   60 gacaccaaac tctccaaaat caagaccctg cgcctggcca                        100
```

<210> SEQ ID NO 740
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 740

```
atgtgactgg cacgggagtt gatcctggtt ttcacnnnnn ncgaccagaa tggcgaggcg   60
gaggccttca aggcagagat caagaagacc gacgtgaaag                        100
```

<210> SEQ ID NO 741
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 741

```
atgtgactgg cacgggagtt gatcctggtt ttcacnnnnn nctgatcctt cttgccatcc   60
tggccgcctt agcggtagta actttgtgtt atgaatcaca t                      101
```

<210> SEQ ID NO 742
<211> LENGTH: 100
<212> TYPE: DNA

<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 742

```
atgtgactgg cacgggagtt gatcctggtt ttcacnnnnn ncgagctcaa tagggaagcc    60
tgtgatgact acagactttg cgaacgctac gccatggttt                         100
```

<210> SEQ ID NO 743
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 743

```
atgtgactgg cacgggagtt gatcctggtt ttcacnnnnn naagaagtat cttcgaacag    60
atgacagagt agaacgtgta cgcagagccc acctgaatga                         100
```

<210> SEQ ID NO 744
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 744

```
atgtgactgg cacgggagtt gatcctggtt ttcacnnnnn ntattccttg agtggtcccg    60
accccctctac agccatcctg cacttcagac tatttgtcgg                        100
```

<210> SEQ ID NO 745
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 745

```
atgtgactgg cacgggagtt gatcctggtt ttcacnnnnn ncagaccagg cctttttgacc   60
tcaagaagga tgtcttcgtg cctgatgaca aacaggagtt t                       101
```

<210> SEQ ID NO 746
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 746
atgtgactgg cacgggagtt gatcctggtt ttcacnnnnn nagagctctt caaactcaag    60
aacgcctatg aggagtccct ggaacatctg gagaccttca                         100

<210> SEQ ID NO 747
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 747
atgtgactgg cacgggagtt gatcctggtt ttcacnnnnn ncaggtcttc tataagcctg    60
ttattgaaga cttaagcatg gaattggcca gaaaatgcac g                       101

<210> SEQ ID NO 748
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 748
atgtgactgg cacgggagtt gatcctggtt ttcacnnnnn naaagagcaa aactacaagg    60
ccactccggt aagcatgacc ccggagatag agagagtgag                         100

<210> SEQ ID NO 749
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 749
atgtgactgg cacgggagtt gatcctggtt ttcacnnnnn nggatatcgc actctgtccc    60
agcacctcaa tgacctgaag aaggagaact tcagcctcaa g                       101

<210> SEQ ID NO 750
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 750
atgtgactgg cacgggagtt gatcctggtt ttcacnnnnn ngaaagccaa gctgctgcag    60
agaagttggt gcaagcctta atggaaagaa attcagaatt                         100

<210> SEQ ID NO 751
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 751
atgtgactgg cacgggagtt gatcctggtt ttcacnnnnn nccggacgag gattcttcta       60
acagagaaaa tgccattgag gatgaagagg aggaggagga g                          101

<210> SEQ ID NO 752
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 752
atgtgactgg cacgggagtt gatcctggtt ttcacnnnnn ncgtcaaggt cgtggtggga       60
aagacctttg actccattgt gatggacccc aagaaggacg                            100

<210> SEQ ID NO 753
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 753
atgtgactgg cacgggagtt gatcctggtt ttcacnnnnn nagatcacga gttatgaaaa       60
acctcctcct gggcttatca aggttggcat tgcaaatggt                            100

<210> SEQ ID NO 754
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 754
atgtgactgg cacgggagtt gatcctggtt ttcacnnnnn naaagtttct tcatcgttgt       60
cctccctgct ggtcacatga gtttacgatt ccttagaagt g                          101

<210> SEQ ID NO 755
<211> LENGTH: 100
<212> TYPE: DNA
<213> ORGANISM: Artificial Sequence
<220> FEATURE:
<223> OTHER INFORMATION: Oligonucleotide probe

```
<220> FEATURE:
<221> NAME/KEY: misc_feature
<222> LOCATION: (36)..(41)
<223> OTHER INFORMATION: n is a, c, g, or t

<400> SEQUENCE: 755
atgtgactgg cacgggagtt gatcctggtt ttcacnnnnn ncccggcgcg ttccgactgg    60
ctgccaggat gtacctgcag aaaggatttc ccatcaaaga                         100

<210> SEQ ID NO 756
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 756
atgtgactgg cacgggagtt gatcctggtt ttcacnnnnn ngcctgaaag gcttcccccg    60
cggagacaag cttttcggcc ctgacttaaa acttgtgccc                         100

<210> SEQ ID NO 757
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 757
atgtgactgg cacgggagtt gatcctggtt ttcacnnnnn naacaacctg aacgtcaccg    60
aggagaagta ccaggaggcg ttggccaagg gagatgttac                         100

<210> SEQ ID NO 758
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 758
atgtgactgg cacgggagtt gatcctggtt ttcacnnnnn naggagaagc tgacggctgc    60
atctgttggt gtccaaggct caggttgggg ttggcttggt                         100

<210> SEQ ID NO 759
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 759
```
atgtgactgg cacgggagtt gatcctggtt ttcacnnnnn ngaccaagac tttcgcagct    60
tccggtcaga gtgtgaggct gaggtgggct ggaacctgac c                      101

<210> SEQ ID NO 760
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 760
atgtgactgg cacgggagtt gatcctggtt ttcacnnnnn nagatgtaca aggcgtgcct    60
caagtacccc gagtggaaac agaagcacct gcctcacttc a                      101

<210> SEQ ID NO 761
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 761
atgtgactgg cacgggagtt gatcctggtt ttcacnnnnn nttcagtgaa gaattaaaag    60
ggcctgtgac agatgatgaa gaagtggaaa catctgtgct c                      101

<210> SEQ ID NO 762
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 762
atgtgactgg cacgggagtt gatcctggtt ttcacnnnnn ngaaaccacc ttgcgtgggt    60
tcaagaagag tggaactcca ggaaaaactg gtggccaggc                        100

<210> SEQ ID NO 763
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 763
atgtgactgg cacgggagtt gatcctggtt ttcacnnnnn nctttggggt ctattccaga    60
gagcgcaaca actgtcccca agatcctctc agaccgtcta c                      101

<210> SEQ ID NO 764
<211> LENGTH: 100

```
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 764
atgtgactgg cacgggagtt gatcctggtt ttcacnnnnn naggcctacc cattcctgca      60
cacaaaggag gacacttatg agaacctgca taaggtgctg                          100

<210> SEQ ID NO 765
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 765
atgtgactgg cacgggagtt gatcctggtt ttcacnnnnn natcggtttt ggttatgcag      60
ccctcgtgac atttggaagc attttttggat ataagcggag a                       101

<210> SEQ ID NO 766
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 766
atgtgactgg cacgggagtt gatcctggtt ttcacnnnnn ngctttcttc ctggctacca      60
taatgggtgt gagatttaag aggtccaaga aaataatgcc                          100

<210> SEQ ID NO 767
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 767
atgtgactgg cacgggagtt gatcctggtt ttcacnnnnn ncacaacctg tacctgtttg      60
accggaatgg agtgtgtctg cactacagcg aatggcaccg c                        101

<210> SEQ ID NO 768
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
```

<223> OTHER INFORMATION: n is a, c, g, or t

<400> SEQUENCE: 768
atgtgactgg cacgggagtt gatcctggtt ttcacnnnnn natccgagat gtgctgcacc    60
acatctacag tgcgctgtat gtggagctgg tggtgaagaa                          100

<210> SEQ ID NO 769
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 769
atgtgactgg cacgggagtt gatcctggtt ttcacnnnnn ngccgaagag gaaatgctgg    60
aaaatgtcag cctggtctgt ccaaaagatg cgacccgatt c                        101

<210> SEQ ID NO 770
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 770
atgtgactgg cacgggagtt gatcctggtt ttcacnnnnn ncagctgacc tcatcgagat    60
tggcttggaa ggaaaaggct ttgagccaac attggaagct                          100

<210> SEQ ID NO 771
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 771
atgtgactgg cacgggagtt gatcctggtt ttcacnnnnn ntactggaga caggctggac    60
tcagctacat ccgatactcc cagatctgtg caaaagcagt g                        101

<210> SEQ ID NO 772
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 772
atgtgactgg cacgggagtt gatcctggtt ttcacnnnnn nctgaagaca gaattcaaag    60
caaatgctga gaagacttct ggcagcaacg taaaaattgt g                        101

<210> SEQ ID NO 773
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 773
atgtgactgg cacgggagtt gatcctggtt ttcacnnnnn nacagagtcc agcccattga    60
gagaatcaac tgccataggt tttacacctg agttagaaag t    101

<210> SEQ ID NO 774
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 774
atgtgactgg cacgggagtt gatcctggtt ttcacnnnnn nagccagctc cagtgacagt    60
gacgacggct tgcaccagtt tcttcggggt acctccagca    100

<210> SEQ ID NO 775
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 775
atgtgactgg cacgggagtt gatcctggtt ttcacnnnnn ngacacgcag cacaaattgc    60
gcagcgcggt ggaagagatg gaggcagaag aagctgctgc    100

<210> SEQ ID NO 776
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 776
atgtgactgg cacgggagtt gatcctggtt ttcacnnnnn ntggtgtatg tgtgcaagcc    60
gaccttcgtg gggagccgtg accaagatgg ggagatcctg    100

<210> SEQ ID NO 777
<211> LENGTH: 101
<212> TYPE: DNA
<213> ORGANISM: Artificial Sequence
<220> FEATURE:

<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 777
atgtgactgg cacgggagtt gatcctggtt ttcacnnnnn natgaggatc gtctgcctgg    60
tcctaagtgt ggtgggcaca gcatggactg cagatagtgg t    101

<210> SEQ ID NO 778
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 778
atgtgactgg cacgggagtt gatcctggtt ttcacnnnnn nattttttct gtttattgcg    60
atcaagagac cagtttggga ggatggcttt tgatccagca    100

<210> SEQ ID NO 779
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 779
atgtgactgg cacgggagtt gatcctggtt ttcacnnnnn ngtgttcagt ttcatccttg    60
ttaccaccgc tctgacaatg ggcagggaaa tttcggcgct c    101

<210> SEQ ID NO 780
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 780
atgtgactgg cacgggagtt gatcctggtt ttcacnnnnn ntgcaaacct gaatggtgta    60
tactacagcg gcccctacac ggctaaaaca gacaatggga    100

<210> SEQ ID NO 781
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 781

```
atgtgactgg cacgggagtt gatcctggtt ttcacnnnnn ncatcccaa cgtacccgcc    60 gacaccaaac tctccaaaat caagaccctg cgcctggcca                        100
```

<210> SEQ ID NO 782
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 782

```
atgtgactgg cacgggagtt gatcctggtt ttcacnnnnn ncgaccagaa tggcgaggcg    60
gaggccttca aggcagagat caagaagacc gacgtgaaag                         100
```

<210> SEQ ID NO 783
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 783

```
atgtgactgg cacgggagtt gatcctggtt ttcacnnnnn nctgatcctt cttgccatcc    60
tggccgcctt agcggtagta actttgtgtt atgaatcaca t                      101
```

<210> SEQ ID NO 784
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 784

```
atgtgactgg cacgggagtt gatcctggtt ttcacnnnnn ncgagctcaa tagggaagcc    60
tgtgatgact acagactttg cgaacgctac gccatggttt                        100
```

<210> SEQ ID NO 785
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 785

```
atgtgactgg cacgggagtt gatcctggtt ttcacnnnnn naagaagtat cttcgaacag    60
atgacagagt agaacgtgta cgcagagccc acctgaatga                        100
```

<210> SEQ ID NO 786

```
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 786
atgtgactgg cacgggagtt gatcctggtt ttcacnnnnn ntattccttg agtggtcccg    60
acccctctac agccatcctg cacttcagac tatttgtcgg                        100

<210> SEQ ID NO 787
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 787
atgtgactgg cacgggagtt gatcctggtt ttcacnnnnn ncagaccagg ccttttgacc    60
tcaagaagga tgtcttcgtg cctgatgaca aacaggagtt t                      101

<210> SEQ ID NO 788
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 788
atgtgactgg cacgggagtt gatcctggtt ttcacnnnnn nagagctctt caaactcaag    60
aacgcctatg aggagtccct ggaacatctg gagaccttca                        100

<210> SEQ ID NO 789
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 789
atgtgactgg cacgggagtt gatcctggtt ttcacnnnnn ncaggtcttc tataagcctg    60
ttattgaaga cttaagcatg gaattggcca gaaaatgcac g                      101

<210> SEQ ID NO 790
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
```

<222> LOCATION: (36)..(41)
<223> OTHER INFORMATION: n is a, c, g, or t

<400> SEQUENCE: 790
atgtgactgg cacgggagtt gatcctggtt ttcacnnnnn naaagagcaa aactacaagg    60
ccactccggt aagcatgacc ccggagatag agagagtgag                         100

<210> SEQ ID NO 791
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 791
atgtgactgg cacgggagtt gatcctggtt ttcacnnnnn nggatatcgc actctgtccc    60
agcacctcaa tgacctgaag aaggagaact tcagcctcaa g                       101

<210> SEQ ID NO 792
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 792
atgtgactgg cacgggagtt gatcctggtt ttcacnnnnn ngaaagccaa gctgctgcag    60
agaagttggt gcaagcctta atggaaagaa attcagaatt                         100

<210> SEQ ID NO 793
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 793
atgtgactgg cacgggagtt gatcctggtt ttcacnnnnn nccggacgag gattcttcta    60
acagagaaaa tgccattgag gatgaagagg aggaggagga g                       101

<210> SEQ ID NO 794
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 794
atgtgactgg cacgggagtt gatcctggtt ttcacnnnnn ncgtcaaggt cgtggtggga    60 aagaccttg actccattgt gatggacccc aagaaggacg                        100

<210> SEQ ID NO 795
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 795
atgtgactgg cacgggagtt gatcctggtt ttcacnnnnn nagatcacga gttatgaaaa      60
acctcctcct gggcttatca aggttggcat tgcaaatggt                        100

<210> SEQ ID NO 796
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 796
atgtgactgg cacgggagtt gatcctggtt ttcacnnnnn naaagtttct tcatcgttgt      60
cctccctgct ggtcacatga gtttacgatt ccttagaagt g                     101

<210> SEQ ID NO 797
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 797
atgtgactgg cacgggagtt gatcctggtt ttcacnnnnn ncccggcgcg ttccgactgg      60
ctgccaggat gtacctgcag aaaggatttc ccatcaaaga                        100

<210> SEQ ID NO 798
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 798
atgtgactgg cacgggagtt gatcctggtt ttcacnnnnn ngcctgaaag gcttccccg       60 cggagacaag cttttcggcc ctgacttaaa acttgtgccc                        100

<210> SEQ ID NO 799
<211> LENGTH: 100
<212> TYPE: DNA
<213> ORGANISM: Artificial Sequence

```
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 799
atgtgactgg cacgggagtt gatcctggtt ttcacnnnnn naacaacctg aacgtcaccg      60
aggagaagta ccaggaggcg ttggccaagg gagatgttac                          100

<210> SEQ ID NO 800
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 800
atgtgactgg cacgggagtt gatcctggtt ttcacnnnnn naggagaagc tgacggctgc      60
atctgttggt gtccaaggct caggttgggg ttggcttggt                          100

<210> SEQ ID NO 801
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 801
atgtgactgg cacgggagtt gatcctggtt ttcacnnnnn ngaccaagac tttcgcagct      60
tccggtcaga gtgtgaggct gaggtgggct ggaacctgac c                        101

<210> SEQ ID NO 802
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 802
atgtgactgg cacgggagtt gatcctggtt ttcacnnnnn nagatgtaca aggcgtgcct      60
caagtacccc gagtggaaac agaagcacct gcctcacttc a                        101

<210> SEQ ID NO 803
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t
```

<400> SEQUENCE: 803
atgtgactgg cacgggagtt gatcctggtt ttcacnnnnn nttcagtgaa gaattaaaag    60
ggcctgtgac agatgatgaa gaagtggaaa catctgtgct c    101

<210> SEQ ID NO 804
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 804
atgtgactgg cacgggagtt gatcctggtt ttcacnnnnn ngaaaccacc ttgcgtgggt    60
tcaagaagag tggaactcca ggaaaaactg gtggccaggc    100

<210> SEQ ID NO 805
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 805
atgtgactgg cacgggagtt gatcctggtt ttcacnnnnn nctttggggt ctattccaga    60
gagcgcaaca actgtcccca agatcctctc agaccgtcta c    101

<210> SEQ ID NO 806
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 806
atgtgactgg cacgggagtt gatcctggtt ttcacnnnnn naggcctacc cattcctgca    60
cacaaaggag gacacttatg agaacctgca taaggtgctg    100

<210> SEQ ID NO 807
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 807
atgtgactgg cacgggagtt gatcctggtt ttcacnnnnn natcggtttt ggttatgcag    60
ccctcgtgac atttggaagc attttttggat ataagcggag a    101

```
<210> SEQ ID NO 808
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 808
atgtgactgg cacgggagtt gatcctggtt ttcacnnnnn ngctttcttc ctggctacca      60
taatgggtgt gagatttaag aggtccaaga aaataatgcc                          100

<210> SEQ ID NO 809
<211> LENGTH: 101
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 809
atgtgactgg cacgggagtt gatcctggtt ttcacnnnnn ncacaacctg tacctgtttg      60
accggaatgg agtgtgtctg cactacagcg aatggcaccg c                        101

<210> SEQ ID NO 810
<211> LENGTH: 100
<212> TYPE: DNA
<213> ORGANISM: Artificial Sequence
<220> FEATURE:
<223> OTHER INFORMATION: Oligonucleotide probe
<220> FEATURE:
<221> NAME/KEY: misc_feature
<222> LOCATION: (36)..(41)
<223> OTHER INFORMATION: n is a, c, g, or t

<400> SEQUENCE: 810
atgtgactgg cacgggagtt gatcctggtt ttcacnnnnn natccgagat gtgctgcacc      60
acatctacag tgcgctgtat gtggagctgg tggtgaagaa                          100
```

METHODS FOR TARGETED GENOMIC ANALYSIS

CROSS-REFERENCE TO RELATED APPLICATIONS

This application is a continuation application of U.S. patent application Ser. No. 15/873,510, filed Jan. 17, 2018 (now U.S. Pat. No. 10,907,149, issued Feb. 2, 2021), which is a divisional application of U.S. patent application Ser. No. 14/102,285, filed Dec. 10, 2013 (now U.S. Pat. No. 9,932,576, issued Apr. 3, 2018), which claims the benefit under 35 U.S.C. § 119(e) of U.S. Provisional Application No. 61/794,049, filed Mar. 15, 2013, and U.S. Provisional Application No. 61/735,417, filed Dec. 10, 2012, which are incorporated by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is CLFK_001_04US_ST25.txt. The text file is about 188 KB, was created on Jan. 4, 2021, and is being submitted electronically via EFS-Web.

BACKGROUND OF INVENTION

Technical Field

The invention relates generally to a method for genetic analysis in individuals that reveals both the genetic sequences and chromosomal copy number of targeted and specific genomic loci in a single assay. In particular, the present invention relates to methods that provide sensitive and specific detection of target gene sequences or gene transcripts and methods that reveal both variant sequences and overall gene copy number in a single assay.

Description of the Related Art

Both complete human genome sequences of individual human subjects and partial genome resequencing studies have revealed the basic theme that all humans appear to possess less than perfect genomes. In particular, normal healthy human subjects are found to harbor hundreds if not thousands of genetic lesions within their genome sequences. Many of these lesions are known or predicted to eliminate the function of the gene in which they reside. The implication is that while normal diploid humans possess two functional copies of most genes, there are many instances in all humans where only one (or zero) functional gene copies are present. Similarly, instances where genes are overrepresented by gene duplication/amplification events are also encountered with significant frequency.

One of the key features in biological networks is functional redundancy. Normal, healthy individuals can tolerate the average load of genetic lesions because they possess, on average, two copies of every gene such that loss of one copy is inconsequential. Moreover, sets of genes often perform similar functions such that minor perturbations in specific gene functions are generally compensated for within a larger network of functional elements. While functional compensation in biological systems is a general theme, there are many instances in which specific gene loss can trigger acute disruptive events. By way of example, cancers appear to be the consequence of genetic disease in which the compound effect of multiple individual lesions is uncontrolled cell proliferation. Similarly, prescribed medicines are often specific chemical entities that are transported, metabolized and/or eliminated by very specific genes. Perturbations in these genes, while generally inconsequential under normal circumstances, can manifest as adverse events (e.g., side effects) during chemical therapy.

The central aim of "personalized medicine", increasingly referred to as "precision medicine," is to merge genetic information that is specific to the patient with treatment options that are compatible with the individual's genetic profile. However, the vast potential of personalized medicine has yet to be realized. To realize this goal, there must be clinically acceptable, robust genetic diagnostic tests that can reliably determine the genetic status of relevant genes.

BRIEF SUMMARY OF THE INVENTION

Particular embodiments contemplated herein provide a method for generating a tagged DNA library comprising treating fragmented DNA with end-repair enzymes to generate fragmented end-repaired DNA; and ligating a random nucleic acid tag sequence, and optionally a sample code sequence and/or a PCR primer sequence to the fragmented end-repaired DNA to generate the tagged DNA library.

In particular embodiments, the random nucleic acid tag sequence is from about 2 to about 100 nucleotides. In some embodiments, the present invention provides that the random nucleic acid tag sequence is from about 2 to about 8 nucleotides.

In certain embodiments, the fragmented end-repaired DNA contains blunt ends. In some embodiments, the blunt ends are further modified to contain a single base pair overhang.

In certain embodiments, the ligating comprises ligating a multifunctional adaptor module to the fragmented end-repaired DNA to generate the tagged DNA library, wherein the multifunctional adaptor molecule comprises: i) a first region comprising a random nucleic acid tag sequence; ii) a second region comprising a sample code sequence; and iii) a third region comprising a PCR primer sequence.

In additional embodiments, the method further comprises hybridizing a tagged DNA library with at least one multifunctional capture probe module to form a complex, wherein the multifunctional capture probe module hybridizes to a specific target region in the DNA library.

In further embodiments, the method further comprises isolating the tagged DNA library-multifunctional capture probe module complex.

In some embodiments, the method further comprises 3'-5' exonuclease enzymatic processing of the isolated tagged DNA library-multifunctional capture probe module complex to remove the single stranded 3' ends. In some embodiments, the enzyme for use in the 3'-5' exonuclease enzymatic processing is T4 polymerase.

In particular embodiments, the method further comprises 5'-3' DNA polymerase extension of the isolated tagged DNA library-multifunctional capture probe module complex from the 3' end of the multifunctional capture probe utilizing the isolated tagged DNA library fragments as template.

In certain embodiments, the method further comprises joining of the multifunctional capture probe and isolated tagged DNA library fragments through the concerted action of a 5' FLAP endonuclease, DNA polymerization and nick closure by a DNA ligase.

In further embodiments, the method further comprises performing PCR on the 3'-5' exonuclease enzymatically processed complex, wherein the tail portion of the multifunctional capture probe molecule is copied in order to generate a hybrid nucleic acid molecule, wherein the hybrid nucleic acid molecule comprises the genomic target region capable of hybridizing to the multifunctional capture probe module and the complement of the multifunctional capture probe module tail sequence.

In various embodiments, a method for targeted genetic analysis is provided comprising: a) hybridizing a tagged DNA library with a multifunctional capture probe module complex, wherein the multifunctional capture probe module selectively hybridizes to a specific target region in the DNA library; b) isolating the tagged DNA library-multifunctional capture probe module complex from a); c) performing 3'-5' exonuclease enzymatic processing on the isolated tagged DNA library-multifunctional capture probe module complex from b) using an enzyme with 3'-5' exonuclease activity to remove the single stranded 3' ends; d) performing PCR on the enzymatically processed complex from c) wherein the tail portion of the multifunctional capture probe molecule is copied in order to generate a hybrid nucleic acid molecule, wherein the hybrid nucleic acid molecule comprises the target region capable of hybridizing to the multifunctional capture probe module and the complement of the multifunctional capture probe module tail sequence; and e) performing targeted genetic analysis on the hybrid nucleic acid molecule from d).

In various particular embodiments, a method for targeted genetic analysis is provided comprising: a) hybridizing a tagged DNA library with a multifunctional capture probe module complex, wherein the multifunctional capture probe module selectively hybridizes to a specific target region in the DNA library; b) isolating the tagged genomic library-multifunctional capture probe module complex from a); c) performing 5'-3' DNA polymerase extension of multifunctional capture probe utilizing the isolated tagged DNA library fragments as template; d) performing PCR on the enzymatically processed complex from c) wherein the complement of the isolated target region is copied in order to generate a hybrid nucleic acid molecule, wherein the hybrid nucleic acid molecule comprises the complement of the DNA target region, the target-specific region of the multifunctional capture probe and the multifunctional capture probe module tail sequence; and e) performing targeted genetic analysis on the hybrid nucleic acid molecule from d).

In various certain embodiments, a method for targeted genetic analysis is provided comprising: a) hybridizing a tagged DNA library with a multifunctional capture probe module complex, wherein the multifunctional capture probe module selectively hybridizes to a specific target region in the DNA library; b) isolating the tagged DNA library-multifunctional capture probe module complex from a); c) performing the creation of a hybrid multifunctional capture probe-isolated tagged DNA target molecule through the concerted action of a 5' FLAP endonuclease, DNA polymerization and nick closure by a DNA ligase; d) performing PCR on the enzymatically processed complex from c) wherein the of the multifunctional capture probe molecule is joined to the isolated tagged DNA target clone in order to generate a hybrid nucleic acid molecule, wherein the hybrid nucleic acid molecule comprises the genomic target region capable of hybridizing to the multifunctional capture probe module and the complement of the multifunctional capture probe module; and e) performing targeted genetic analysis on the hybrid nucleic acid molecule from d).

In particular embodiments, a method for determining copy number of a specific target region is provided comprising: a) hybridizing a tagged DNA library with a multifunctional capture probe module complex, wherein the multifunctional capture probe module selectively hybridizes to a specific target region in the DNA library; b) isolating the tagged DNA library-multifunctional capture probe module complex from a); c) performing 3'-5' exonuclease enzymatic processing on the isolated tagged DNA library-multifunctional capture probe module complex from b) using an enzyme with 3'-5' exonuclease activity to remove the single stranded 3' ends; d) performing a PCR reaction on the enzymatically processed complex from c) wherein the tail portion of the multifunctional capture probe molecule is replicated in order to generate a hybrid nucleic acid molecule, wherein the hybrid nucleic acid molecule comprises the target region capable of hybridizing to the multifunctional capture probe module and the complement of the multifunctional capture probe module tail sequence; e) performing PCR amplification of the hybrid nucleic acid in d); and e) quantitating the PCR reaction in d), wherein the quantitation allows for a determination of copy number of the specific target region.

In certain embodiments, a method for determining copy number of a specific target region is provided comprising: a) hybridizing a tagged DNA library with a multifunctional capture probe module complex, wherein the multifunctional capture probe module selectively hybridizes to a specific target region in the DNA library; b) isolating the tagged DNA library-multifunctional capture probe module complex from a); c) performing 5'-3' DNA polymerase extension of multifunctional capture probe utilizing the isolated tagged DNA library fragments as template; d) performing a PCR reaction on the enzymatically processed complex from c) wherein the tail portion of the multifunctional capture probe molecule is replicated in order to generate a hybrid nucleic acid molecule, wherein the hybrid nucleic acid molecule comprises the target region capable of hybridizing to the multifunctional capture probe module and the complement of the multifunctional capture probe module tail sequence; e) performing PCR amplification of the hybrid nucleic acid in d); and e) quantitating the PCR reaction in d), wherein the quantitation allows for a determination of copy number of the specific target region.

In further embodiments, a method for determining copy number of a specific target region is provided comprising: a) hybridizing a tagged DNA library with a multifunctional capture probe module complex, wherein the multifunctional capture probe module selectively hybridizes to a specific target region in the DNA library; b) isolating the tagged DNA library-multifunctional capture probe module complex from a); c) performing the creation of a hybrid multifunctional capture probe-isolated tagged DNA target molecule through the concerted action of a 5' FLAP endonuclease, DNA polymerization and nick closure by a DNA ligase; d) performing a PCR reaction on the enzymatically processed complex from c) wherein the tail portion of the multifunctional capture probe molecule is replicated in order to generate a hybrid nucleic acid molecule, wherein the hybrid nucleic acid molecule comprises the target region capable of hybridizing to the multifunctional capture probe module and the complement of the multifunctional capture probe module tail sequence; e) performing PCR amplification of the hybrid nucleic acid in d); and e) quantitating the PCR reaction in d), wherein the quantitation allows for a determination of copy number of the specific target region.

In additional embodiments, a method for targeted genetic analysis is provided comprising: a) hybridizing a tagged DNA library with a multifunctional capture probe hybrid module complex, wherein the multifunctional capture probe hybrid module selectively hybridizes to a specific target region in the DNA library; b) isolating the tagged DNA library-multifunctional capture probe hybrid module complex from a); c) performing PCR on the complex from b) to replicate a region that is 3' relative to the sequence of the multifunctional capture probe in order to generate a hybrid nucleic acid molecule, wherein the hybrid nucleic acid molecule comprises the multifunctional capture probe hybrid module and the complement of a region of the tagged DNA library sequence that is located 3' relative to the multifunctional capture probe; and d) performing targeted genetic analysis on the hybrid nucleic acid molecule from c).

In particular embodiments, a method for targeted genetic analysis is provided comprising: a) hybridizing a tagged DNA library with a multifunctional capture probe hybrid module complex, wherein the multifunctional capture probe hybrid module selectively hybridizes to a specific target region in the genomic library; b) isolating the tagged DNA library-multifunctional capture probe hybrid module complex from a); c) performing 5'-3' DNA polymerase extension of multifunctional capture probe utilizing the isolated tagged DNA library fragments as template, wherein the hybrid nucleic acid molecule comprises the multifunctional capture probe hybrid module and the complement of a region of the tagged DNA library sequence that is located 3' relative to the multifunctional capture probe; and d) performing targeted genetic analysis on the hybrid nucleic acid molecule from c).

In certain embodiments, a method for targeted genetic analysis is provided comprising: a) hybridizing a tagged DNA library with a multifunctional capture probe hybrid module complex, wherein the multifunctional capture probe hybrid module selectively hybridizes to a specific target region in the DNA library; b) isolating the tagged DNA library-multifunctional capture probe hybrid module complex from a); c) performing the creation of a hybrid multifunctional capture probe-isolated tagged DNA target molecule through the concerted action of a 5' FLAP endonuclease, DNA polymerization and nick closure by a DNA ligase, wherein the hybrid nucleic acid molecule comprises the complement of the multifunctional capture probe hybrid module and a region of the tagged DNA library sequence that is located 5' relative to the multifunctional capture probe; and d) performing targeted genetic analysis on the hybrid nucleic acid molecule from c).

In particular embodiments, a method for determining copy number of a specific target region is provided comprising: a) hybridizing a tagged DNA library with a multifunctional capture probe hybrid module complex, wherein the multifunctional capture probe hybrid module selectively hybridizes to a specific target region in the DNA library; b) isolating the tagged DNA library-multifunctional capture probe hybrid module complex from a); c) performing PCR on the complex from b) to replicate a region that is 3' relative to sequence of the multifunctional capture probe in order to generate a hybrid nucleic acid molecule, wherein the hybrid nucleic acid molecule comprises the multifunctional capture probe hybrid module and the complement of a region of the tagged DNA library sequence that is located 3' relative to the multifunctional capture probe; d) performing PCR amplification of the hybrid nucleic acid in c); and e) quantitating the PCR reaction in d), wherein the quantitation allows for a determination of copy number of the specific target region.

In various embodiments, the targeted genetic analysis is sequence analysis.

In particular embodiments, the tagged DNA library is amplified by PCR to generate an amplified tagged DNA library.

In certain embodiments, the DNA is from a biological sample selected from the group consisting of blood, skin, hair, hair follicles, saliva, oral mucous, vaginal mucous, sweat, tears, epithelial tissues, urine, semen, seminal fluid, seminal plasma, prostatic fluid, pre-ejaculatory fluid (Cowper's fluid), excreta, biopsy, ascites, cerebrospinal fluid, lymph, and tissue extract sample or biopsy sample.

In further embodiments, a tagged DNA library comprises tagged DNA sequences, wherein each tagged DNA sequence comprises: i) fragmented end-repaired DNA; ii) a random nucleotide tag sequence; iii) a sample code sequence; and iv) a PCR primer sequence.

In additional embodiments, a hybrid tagged DNA library comprises hybrid tagged DNA sequences for use in targeted genetic analysis, wherein each hybrid tagged DNA sequence comprises: i) fragmented end-repaired DNA; ii) a random nucleotide tag sequence; iii) a sample code sequence; iv) a PCR primer sequence; and v) a multifunctional capture probe module tail sequence.

In further embodiments, a multifunctional adaptor module comprises: i) a first region comprising a random nucleotide tag sequence; ii) a second region comprising a sample code sequence; and iii) a third region comprising a PCR primer sequence.

In particular embodiments, a multifunctional capture probe module comprises: i) a first region capable of hybridizing to a partner oligonucleotide; ii) a second region capable of hybridizing to a specific target region; and iii) a third region comprising a tail sequence. In some embodiments, the first region of the capture probe module is bound to a partner oligonucleotide.

In some embodiments, the partner oligonucleotide is chemically modified.

In one embodiment, compositions comprise a tagged DNA library, a multifunctional adaptor module and a multifunctional capture probe module.

In particular embodiments, a composition comprises a hybrid tagged genomic library according to the methods of the present invention.

In certain embodiments, a composition comprises a reaction mixture for performing the methods contemplated herein.

In particular embodiments, a reaction mixture capable of generating a tagged DNA library comprises: a) fragmented DNA and b) DNA end-repair enzymes to generate fragmented end-repaired DNA.

In certain embodiments, a reaction mixture further comprises a multifunctional adaptor module.

In additional embodiments, a reaction mixture further comprises a multifunctional capture probe module.

In some embodiments, a reaction mixture further comprises an enzyme with 3'-5' exonuclease activity and PCR amplification activity.

In one embodiment, the reaction mixture comprises a FLAP endonuclease, a DNA polymerase, and DNA ligase.

In any of the foregoing embodiments, the DNA can be isolated genomic DNA or cDNA.

In various embodiments, a method for generating a tagged genomic library is provided comprising: treating fragmented genomic DNA with end-repair enzymes to generate fragmented end-repaired genomic DNA; and ligating a random nucleic acid tag sequence, and optionally a sample code sequence and/or a PCR primer sequence to the fragmented end-repaired genomic DNA to generate the tagged genomic library.

In particular embodiments, the random nucleic acid tag sequence is from about 2 to about 100 nucleotides.

In certain embodiments, the random nucleic acid tag sequence is from about 2 to about 8 nucleotides.

In additional embodiments, the fragmented end-repaired genomic DNA contains blunt ends.

In further embodiments, the blunt ends are further modified to contain a single base pair overhang.

In some embodiments, the ligating comprises ligating a multifunctional adaptor module to the fragmented end-repaired genomic DNA to generate the tagged genomic library, wherein the multifunctional adaptor molecule comprises: a first region comprising a random nucleic acid tag sequence; a second region comprising a sample code sequence; and a third region comprising a PCR primer sequence.

In particular embodiments, the methods contemplated herein comprise hybridizing a tagged genomic library with a multifunctional capture probe module to form a complex, wherein the multifunctional capture probe module hybridizes to a specific genomic target region in the genomic library.

In certain particular embodiments, the methods contemplated herein comprise isolating the tagged genomic library-multifunctional capture probe module complex.

In additional particular embodiments, the methods contemplated herein comprise 3'-5' exonuclease enzymatic processing of the isolated tagged genomic library-multifunctional capture probe module complex to remove the single stranded 3' ends.

In further particular embodiments, the enzyme for use in the 3'-5' exonuclease enzymatic processing is T4 DNA polymerase.

In some particular embodiments, the methods contemplated herein comprise performing PCR on the 3'-5' exonuclease enzymatically processed complex from the preceding claims, wherein the tail portion of the multifunctional capture probe molecule is copied in order to generate a hybrid nucleic acid molecule, wherein the hybrid nucleic acid molecule comprises the genomic target region capable of hybridizing to the multifunctional capture probe module and the complement of the multifunctional capture probe module tail sequence.

In various embodiments, a method for targeted genetic analysis is provided comprising: (a) hybridizing a tagged genomic library with a multifunctional capture probe module complex, wherein the multifunctional capture probe module selectively hybridizes to a specific genomic target region in the genomic library; (b) isolating the tagged genomic library-multifunctional capture probe module complex from a); (c) performing 3'-5' exonuclease enzymatic processing on the isolated tagged genomic library-multifunctional capture probe module complex from b) using an enzyme with 3'-5' exonuclease activity to remove the single stranded 3' ends; (d) performing PCR on the enzymatically processed complex from c) wherein the tail portion of the multifunctional capture probe molecule is copied in order to generate a hybrid nucleic acid molecule, wherein the hybrid nucleic acid molecule comprises the genomic target region capable of hybridizing to the multifunctional capture probe module and the complement of the multifunctional capture probe module tail sequence; and (e) performing targeted genetic analysis on the hybrid nucleic acid molecule from d).

In particular embodiments, steps a) through d) are repeated at least about twice and the targeted genetic analysis of e) comprises a sequence alignment of the hybrid nucleic acid molecule sequences obtained from the at least two d) steps.

In further embodiments, at least two different multifunctional capture probe modules are used in the at least two a) steps, wherein the at least two a) steps employ one multifunctional capture probe module each.

In some embodiments, at least one multifunctional capture probe module hybridizes downstream of the genomic target region and at least one multifunctional capture probe module hybridizes upstream of the genomic target region.

In various embodiments, a method for determining copy number of a specific genomic target region is provided comprising: (a) hybridizing a tagged genomic library with a multifunctional capture probe module complex, wherein the multifunctional capture probe module complex selectively hybridizes to a specific genomic target region in the genomic library; (b) isolating the tagged genomic library-multifunctional capture probe module complex from a); (c) performing 3'-5' exonuclease enzymatic processing on the isolated tagged genomic library-multifunctional capture probe module complex from b) using an enzyme with 3'-5' exonuclease activity to remove the single stranded 3' ends; (d) performing a PCR reaction on the enzymatically processed complex from c) wherein the tail portion of the multifunctional capture probe molecule is replicated in order to generate a hybrid nucleic acid molecule, wherein the hybrid nucleic acid molecule comprises the genomic target region capable of hybridizing to the multifunctional capture probe module and the complement of the multifunctional capture probe module tail sequence; (e) performing PCR amplification of the hybrid nucleic acid molecule in d); and (f) quantitating the PCR reaction in e), wherein the quantitation allows for a determination of copy number of the specific genomic target region.

In some embodiments, the methods contemplated herein comprise obtaining the sequences of the hybrid nucleic acid molecules from step e).

In further embodiments, steps a) through e) are repeated at least about twice and a sequence alignment is performed using the hybrid nucleic acid molecule sequences obtained from the at least two e) steps.

In additional embodiments, at least two different multifunctional capture probe modules are used in the at least two a) steps, wherein the at least two a) steps employ one multifunctional capture probe module each.

In certain embodiments, at least one multifunctional capture probe module hybridizes downstream of the genomic target region and at least one multifunctional capture probe module hybridizes upstream of the genomic target region.

In various embodiments, a method for determining copy number of a specific genomic target region is provided comprising: (a) hybridizing a tagged genomic library with a multifunctional capture probe module complex, wherein the multifunctional capture probe module complex selectively hybridizes to a specific genomic target region in the genomic library; (b) isolating the tagged genomic library-multifunctional capture probe module complex from a); (c) performing 3'-5' exonuclease enzymatic processing on the isolated tagged genomic library-multifunctional capture probe module complex from b) using an enzyme with 3'-5' exonuclease activity to remove the single stranded 3' ends; (d) performing a PCR reaction on the enzymatically processed complex from c) wherein the tail portion of the multifunctional capture probe molecule is replicated in order to generate a hybrid nucleic acid molecule, wherein the hybrid nucleic acid molecule comprises the genomic target region capable of hybridizing to the multifunctional capture probe module and the complement of the multifunctional capture probe module tail sequence; and (e) performing PCR amplification of the hybrid nucleic acid molecule in d).

In certain embodiments, the methods contemplated herein comprise obtaining the sequences of the hybrid nucleic acid molecules from step e).

In particular embodiments, steps a) through e) are repeated at least about twice and a sequence alignment is performed using the hybrid nucleic acid molecule sequences obtained from the at least two e) steps.

In some embodiments, at least two different multifunctional capture probe modules are used in the at least two a) steps, wherein the at least two a) steps employ one multifunctional capture probe module each.

In additional embodiments, at least one multifunctional capture probe module hybridizes downstream of the genomic target region and at least one multifunctional capture probe module hybridizes upstream of the genomic target region.

In various embodiments, a method for determining copy number of a specific genomic target region is provided comprising: (a) hybridizing a tagged genomic library with a multifunctional capture probe module complex, wherein the multifunctional capture probe module comprises selectively hybridizes to a specific genomic target region in the genomic library; (b) isolating the tagged genomic library-multifunctional capture probe module complex from a); (c) performing 3'-5' exonuclease enzymatic processing on the isolated tagged genomic library-multifunctional capture probe module complex from b) using an enzyme with 3'-5' exonuclease activity to remove the single stranded 3' ends; (d) performing a PCR reaction on the enzymatically processed complex from c) wherein the tail portion of the multifunctional capture probe molecule is replicated in order to generate a hybrid nucleic acid molecule, wherein the hybrid nucleic acid molecule comprises the genomic target region capable of hybridizing to the multifunctional capture probe module and the complement of the multifunctional capture probe module tail sequence; (e) performing PCR amplification of the hybrid nucleic acid molecule in d); and (f) performing targeted genetic analysis on the hybrid nucleic acid molecule from e).

In particular embodiments, steps a) through e) are repeated at least about twice and the targeted genetic analysis of f) comprises performing a sequence alignment of the hybrid nucleic acid molecule sequences from the at least two e) steps.

In certain embodiments, at least two different multifunctional capture probe modules are used in the at least two a) steps, wherein the at least two a) steps employ one multifunctional capture probe module each.

In additional embodiments, at least one multifunctional capture probe module hybridizes downstream of the genomic target region and at least one multifunctional capture probe module hybridizes upstream of the genomic target region.

In various embodiments, a method for targeted genetic analysis is provided comprising: (a) hybridizing a tagged genomic library with a multifunctional capture probe hybrid module complex, wherein the multifunctional capture probe hybrid module selectively hybridizes to a specific genomic target region in the genomic library; (b) isolating the tagged genomic library-multifunctional capture probe hybrid module complex from a); (c) performing 5' to 3' DNA polymerase extension of the multifunctional capture probe on the complex from b) to replicate a region of the captured, tagged genomic target region that is 3' of the multifunctional capture probe in order to generate a hybrid nucleic acid molecule, wherein the hybrid nucleic acid molecule comprises the multifunctional capture probe hybrid module and the complement of a region of the tagged genomic target region that is located in the 3' direction from the location where the multifunctional capture probe hybrid module hybridizes to the genomic target region; and (d) performing targeted genetic analysis on the hybrid nucleic acid molecule from c).

In further embodiments, steps a) through c) are repeated at least about twice and the targeted genetic analysis of d) comprises a sequence alignment of the hybrid nucleic acid molecule sequences obtained from the at least two d) steps.

In some embodiments, at least two different multifunctional capture probe modules are used in the at least two a) steps, wherein the at least two a) steps employ one multifunctional capture probe module each.

In particular embodiments, at least one multifunctional capture probe module hybridizes downstream of the genomic target region and at least one multifunctional capture probe module hybridizes upstream of the genomic target region.

In various embodiments, a method for determining copy number of a specific genomic target region is provided comprising: (a) hybridizing a tagged genomic library with a multifunctional capture probe hybrid module complex, wherein the multifunctional capture probe hybrid module selectively hybridizes to a specific genomic target region in the genomic library; (b) isolating the tagged genomic library-multifunctional capture probe hybrid module complex from a); (c) performing 5' to 3' DNA polymerase extension of the multifunctional capture probe on the complex from b) to replicate a region of the captured tagged genomic target region that is 3' of the multifunctional capture probe in order to generate a hybrid nucleic acid molecule, wherein the hybrid nucleic acid molecule comprises the multifunctional capture probe hybrid module and the complement of a region of the tagged genomic target region that is located in the 3' direction from the location where the multifunctional capture probe hybrid module hybridizes to the genomic target region; and (d) performing PCR amplification of the hybrid nucleic acid molecule in c); and (e) quantitating the PCR reaction in d), wherein the quantitation allows for a determination of copy number of the specific genomic target region.

In particular embodiments, the methods contemplated herein comprise obtaining the sequences of the hybrid nucleic acid molecules from step d).

In certain embodiments, steps a) through d) are repeated at least about twice and a sequence alignment of the hybrid nucleic acid molecules from the at least two d) steps.

In additional embodiments, at least two different multifunctional capture probe modules are used in the at least two a) steps, wherein the at least two a) steps employ one multifunctional capture probe module each.

In further embodiments, at least one multifunctional capture probe module hybridizes downstream of the genomic target region and at least one multifunctional capture probe module hybridizes upstream of the genomic target region.

In some embodiments, the targeted genetic analysis is sequence analysis.

In particular embodiments, the tagged genomic library is amplified by PCR to generate an amplified tagged genomic library.

In related particular embodiments, the genomic DNA is from a biological sample selected from the group consisting of blood, skin, hair, hair follicles, saliva, oral mucous, vaginal mucous, sweat, tears, epithelial tissues, urine, semen, seminal fluid, seminal plasma, prostatic fluid, pre-ejaculatory fluid (Cowper's fluid), excreta, biopsy, ascites, cerebrospinal fluid, lymph, and tissue extract sample or biopsy sample.

In various embodiments, a tagged genomic library is provided comprising tagged genomic sequences, wherein each tagged genomic sequence comprises: fragmented end-repaired genomic DNA; a random nucleotide tag sequence; a sample code sequence; and a PCR primer sequence.

In various related embodiments, a tagged cDNA library is provided comprising tagged cDNA sequences, wherein each tagged cDNA sequence comprises: fragmented end-repaired cDNA; a random nucleotide tag sequence; a sample code sequence; and a PCR primer sequence.

In various particular embodiments, a hybrid tagged genomic library is provided comprising hybrid tagged genomic sequences for use in targeted genetic analysis, wherein each hybrid tagged genomic sequence comprises: fragmented end-repaired genomic DNA; a random nucleotide tag sequence; a sample code sequence; a PCR primer sequence; a genomic target region; and a multifunctional capture probe module tail sequence.

In various certain embodiments, a hybrid tagged cDNA library is provided comprising hybrid tagged cDNA sequences for use in targeted genetic analysis, wherein each hybrid tagged cDNA sequence comprises: fragmented end-repaired cDNA; a random nucleotide tag sequence; a sample code sequence; a PCR primer sequence; a cDNA target region; and a multifunctional capture probe module tail sequence.

In various certain embodiments, a multifunctional adaptor module is provided comprising: a first region comprising a random nucleotide tag sequence; a second region comprising a sample code sequence; and a third region comprising a PCR primer sequence.

In various additional embodiments, a multifunctional capture probe module is provided comprising: a first region capable of hybridizing to a partner oligonucleotide; a second region capable of hybridizing to a specific genomic target region; and a third region comprising a tail sequence.

In particular embodiments, the first region is bound to a partner oligonucleotide.

In particular embodiments, a multifunctional adaptor probe hybrid module is provided comprising: a first region capable of hybridizing to a partner oligonucleotide and capable of functioning as a PCR primer and a second region capable of hybridizing to a specific genomic target region.

In certain embodiments, the first region is bound to a partner oligonucleotide.

In some embodiments, the partner oligonucleotide is chemically modified.

In further embodiments, a composition comprising a tagged genomic library, a multifunctional adaptor module and a multifunctional capture probe module is provided.

In additional embodiments, a composition comprising a hybrid tagged genomic or c DNA library according to any of the preceding embodiments is provided.

In various embodiments, a reaction mixture for performing a method of any one of the preceding embodiments is provided.

In particular embodiments, a reaction mixture capable of generating a tagged genomic library is provided comprising: fragmented genomic DNA; and DNA end-repair enzymes to generate fragmented end-repaired genomic DNA.

In particular embodiments, a reaction mixture capable of generating a tagged genomic library is provided comprising: fragmented cDNA; and DNA end-repair enzymes to generate fragmented end-repaired cDNA.

In particular embodiments, a reaction mixture comprises a multifunctional adaptor module.

In some embodiments, a reaction mixture comprises a multifunctional capture probe module.

In certain embodiments, a reaction mixture comprises an enzyme with 3'-5' exonuclease activity and PCR amplification activity.

In various embodiments, a method for DNA sequence analysis is provided comprising: obtaining one or more clones, each clone comprising a first DNA sequence and a second DNA sequence, wherein the first DNA sequence comprises targeted genomic DNA sequence and the second DNA sequence comprises a capture probe sequence; performing a paired end sequencing reaction on the one or more clones and obtaining one or more sequencing reads; and ordering or clustering the sequencing reads of the one or more clones according to the probe sequence of the sequencing reads.

In particular embodiments, a method for DNA sequence analysis is provided comprising: obtaining one or more clones, each clone comprising a first DNA sequence and a second DNA sequence, wherein the first DNA sequence comprises targeted genomic DNA sequence and the second DNA sequence comprises a capture probe sequence; performing a sequencing reaction on the one or more clones in which a single long sequencing read of greater than about 100 nucleotides is obtained, wherein the read is sufficient to identify both the first DNA sequence and the second DNA sequence; and ordering or clustering sequencing reads of the one or more clones according to the probe sequence of the sequencing reads.

In certain embodiments, the sequences of the one or more clones are compared to one or more human reference DNA sequences.

In additional embodiments, sequences that do not match the one or more human reference DNA sequences are identified.

In further embodiments, non-matching sequences are used to create a de novo assembly from the non-matching sequence data.

In some embodiments, the de novo assemblies are used to identify novel sequence rearrangements associated with the capture probe.

In various embodiments, a method for genomic copy number determination analysis is provided comprising: obtaining one or more clones, each clone comprising a first DNA sequence and a second DNA sequence, wherein the first DNA sequence comprises a random nucleotide tag sequence and a targeted genomic DNA sequence and the second DNA sequence comprises a capture probe sequence; performing a paired end sequencing reaction on the one or more clones and obtaining one or more sequencing reads; and ordering or clustering the sequencing reads of the one or more clones according to the probe sequence of the sequencing reads.

In some embodiments, a method for genomic copy number determination analysis is provided comprising: obtaining one or more clones, each clone comprising a first DNA sequence and a second DNA sequence, wherein the first DNA sequence comprises a random nucleotide tag sequence and a targeted genomic DNA sequence and the second DNA sequence comprises a capture probe sequence; performing a sequencing reaction on the one or more clones in which a single long sequencing read of greater than about 100 nucleotides is obtained, wherein the read is sufficient to identify both the first DNA sequence and the second DNA sequence; and ordering or clustering sequencing reads of the one or more clones according to the probe sequence of the sequencing reads.

In certain embodiments, the random nucleotide tag sequence is about 2 to about 50 nucleotides in length.

In further embodiments, the methods contemplated herein comprise analyzing all sequencing reads associated with a second read sequence by: determining the distributions of unique and redundant sequencing reads; counting the number of times a unique read is encountered; fitting a frequency distribution of the unique reads to a statistical distribution; inferring a total number of unique reads; and normalizing the total number of inferred unique read to an assumption that most human genetic loci are generally diploid.

In additional embodiments, an inferred copy number of one or more targeted loci are determined.

In some embodiments, the one or more target loci that deviate from an expected copy number value are determined.

In further embodiments, the one or more targeted loci of a gene are grouped together in a collection of loci and the copy number measurements from the collection of targeted loci are averaged and normalized.

In additional embodiments, the inferred copy number of a gene is represented by the normalized average of all the target loci representing that gene.

In certain embodiments, a method for generating a tagged RNA expression library is provided comprising: fragmenting a cDNA library; treating the fragmented cDNA library with end-repair enzymes to generate fragmented end-repaired cDNA; and ligating a multifunctional adapter molecule to the fragmented end-repaired c DNA to generate a tagged RNA expression library.

In particular embodiments, a method for generating a tagged RNA expression library is provided comprising: preparing a cDNA library from the total RNA of one or more cells; fragmenting the cDNA library; treating the fragmented cDNA with end-repair enzymes to generate fragmented end-repaired cDNA; and ligating a multifunctional adapter molecule to the fragmented end-repaired c DNA to generate a tagged RNA expression library.

In various embodiments, the cDNA library is an oligo-dT primed cDNA library.

In particular embodiments, the cDNA library is primed by random oligonucleotides comprising about 6 to about 20 random nucleotides.

In certain embodiments, the cDNA library is primed by random hexamers or random octamers.

In additional embodiments, the cDNA library is fragmented to a size of about 250 bp to about 750 bp.

In further embodiments, the cDNA library is fragmented to a size of about 500 bp.

In some embodiments, the multifunctional adaptor module comprises: a first region comprising a random nucleic acid tag sequence, and optionally; a second region comprising a sample code sequence, and optionally a third region comprising a PCR primer sequence.

In related embodiments, the multifunctional adaptor module comprises a first region comprising a random nucleic acid tag sequence, a second region comprising a sample code sequence, and a third region comprising a PCR primer sequence.

In various embodiments, the methods contemplated herein comprise hybridizing a tagged cDNA library with a multifunctional capture probe module to form a complex, wherein the multifunctional capture probe module hybridizes to a specific target region in the cDNA library.

In some embodiments, the methods contemplated herein comprise isolating the tagged cDNA library-multifunctional capture probe module complex.

In particular embodiments, the methods contemplated herein comprise 3'-5' exonuclease enzymatic processing of the isolated tagged cDNA library-multifunctional capture probe module complex to remove the single stranded 3' ends.

In some embodiments, the enzyme for use in the 3'-5' exonuclease enzymatic processing is T4 DNA polymerase.

In certain embodiments, the methods contemplated herein comprise performing PCR on the 3'-5' exonuclease enzymatically processed complex, wherein a tail portion of the multifunctional capture probe molecule is copied in order to generate a hybrid nucleic acid molecule, wherein the hybrid nucleic acid molecule comprises the cDNA target region capable of hybridizing to the multifunctional capture probe module and the complement of the multifunctional capture probe module tail sequence.

In further embodiments, a method for targeted gene expression analysis is provided comprising: (a) hybridizing a tagged RNA expression library with a multifunctional capture probe module complex, wherein the multifunctional capture probe module selectively hybridizes to a specific target region in the tagged RNA expression library; (b) isolating the tagged RNA expression library-multifunctional capture probe module complex from a); (c) performing 3'-5' exonuclease enzymatic processing on the isolated tagged RNA expression library-multifunctional capture probe module complex from b) using an enzyme with 3'-5' exonuclease activity to remove the single stranded 3' ends; (d) performing PCR on the enzymatically processed complex from c) wherein the tail portion of the multifunctional capture probe molecule is copied in order to generate a hybrid nucleic acid molecule, wherein the hybrid nucleic acid molecule comprises the target region capable of hybridizing to the multifunctional capture probe module and the complement of the multifunctional capture probe module tail sequence; and (e) performing targeted gene expression analysis on the hybrid nucleic acid molecule from d).

In additional embodiments, a method for targeted gene expression analysis is provided comprising: (a) hybridizing a tagged RNA expression library with a multifunctional capture probe hybrid module complex, wherein the multifunctional capture probe hybrid module selectively hybridizes to a specific target region in the RNA expression library; (b) isolating the tagged RNA expression library-multifunctional capture probe hybrid module complex from a); (c) performing 5' to 3' DNA polymerase extension of the multifunctional capture probe on the complex from b) to replicate a region of the captured, tagged target region that is 3' of the multifunctional capture probe in order to generate a hybrid nucleic acid molecule, wherein the hybrid nucleic acid molecule comprises the multifunctional capture probe hybrid module and the complement of the tagged target region that is located in the 3'direction from the location where the multifunctional capture probe hybrid module hybridizes to the target region; and (d) performing targeted genetic analysis on the hybrid nucleic acid molecule from c).

In various embodiments, a method for targeted gene expression analysis is provided comprising: (a) hybridizing a tagged cDNA library with a multifunctional capture probe hybrid module complex, wherein the multifunctional capture probe hybrid module selectively hybridizes to a specific target region in the cDNA library; (b) isolating the tagged cDNA library-multifunctional capture probe hybrid module complex from a); (c) performing 5' to 3' DNA polymerase extension of the multifunctional capture probe on the complex from b) to replicate a region of the captured, tagged target region in the cDNA library that is 3' of the multifunctional capture probe in order to generate a hybrid nucleic acid molecule, wherein the hybrid nucleic acid molecule comprises the multifunctional capture probe hybrid module and the complement of the tagged target region in the cDNA library that is located in the 3'direction from the location where the multifunctional capture probe hybrid module hybridizes to the target region; and (d) performing targeted genetic analysis on the hybrid nucleic acid molecule from c).

In particular embodiments, at least two different multifunctional capture probe modules are used in the at least two (a) steps, wherein the at least two a) steps employ one multifunctional capture probe module each.

In certain embodiments, at least one multifunctional capture probe module hybridizes downstream of the target region and at least one multifunctional capture probe module hybridizes upstream of the target region.

In additional embodiments, a method for cDNA sequence analysis is provided comprising: (a) obtaining one or more clones, each clone comprising a first cDNA sequence and a second cDNA sequence, wherein the first cDNA sequence comprises targeted genomic cDNA sequence and the second cDNA sequence comprises a capture probe sequence; (b) performing a paired end sequencing reaction on the one or more clones and obtaining one or more sequencing reads; and (c) ordering or clustering the sequencing reads of the one or more clones according to the probe sequence of the sequencing reads.

In various embodiments, a method for cDNA sequence analysis is provided comprising: (a) obtaining one or more clones, each clone comprising a first cDNA sequence and a second cDNA sequence, wherein the first cDNA sequence comprises targeted genomic DNA sequence and the second cDNA sequence comprises a capture probe sequence; (b) performing a sequencing reaction on the one or more clones in which a single long sequencing read of greater than about 100 nucleotides is obtained, wherein the read is sufficient to identify both the first cDNA sequence and the second cDNA sequence; and (c) ordering or clustering sequencing reads of the one or more clones according to the probe sequence of the sequencing reads.

In particular embodiments, the methods contemplated herein comprise analyzing all sequencing reads associated with a second read sequence by: determining the distributions of unique and redundant sequencing reads; counting the number of times a unique read is encountered; fitting a frequency distribution of the unique reads to a statistical distribution; inferring a total number of unique reads; and converting unique read counts into transcript abundance using normalization to the total reads collected within each cDNA library sample.

In certain embodiments, a method for targeted genetic analysis is provided comprising: (a) hybridizing a tagged DNA library with a multifunctional capture probe hybrid module complex, wherein the multifunctional capture probe hybrid module selectively hybridizes to a specific target region in the DNA library; (b) isolating the tagged DNA library-multifunctional capture probe hybrid module complex from a); (c) performing a concerted enzymatic processing of the tagged DNA library-multifunctional capture probe hybrid module complex from b) that includes 5' FLAP endonuclease activity, 5' to 3' DNA polymerase extension, and nick closure by a DNA ligase to join the complement of the multifunctional capture probe to the target region that is 5' of the multifunctional capture probe binding site in order to generate a hybrid nucleic acid molecule, wherein the hybrid nucleic acid molecule comprises the complement of the multifunctional capture probe hybrid module and a region of the tagged target region that is located 5' of the location where the multifunctional capture probe hybrid module hybridizes to the genomic target region; and (d) performing targeted genetic analysis on the hybrid nucleic acid molecule from c).

In various embodiments, steps a) through c) are repeated at least about twice and the targeted genetic analysis of d) comprises a sequence alignment of the hybrid nucleic acid molecule sequences obtained from the at least two d) steps.

In certain embodiments, at least two different multifunctional capture probe modules are used in the at least two a) steps, wherein the at least two a) steps employ one multifunctional capture probe module each.

In particular embodiments, at least one multifunctional capture probe module hybridizes downstream of the target region and at least one multifunctional capture probe module hybridizes upstream of the target region.

In additional embodiments, a method for determining copy number of a specific target region is provided comprising: (a) hybridizing a tagged DNA library with a multifunctional capture probe hybrid module complex, wherein the multifunctional capture probe hybrid module selectively hybridizes to a specific target region in the genomic library; (b) isolating the tagged DNA library-multifunctional capture probe hybrid module complex from a); (c) performing a concerted enzymatic processing of the tagged DNA library-multifunctional capture probe hybrid module complex from b) that includes 5' FLAP endonuclease activity, 5' to 3' DNA polymerase extension, and nick closure by a DNA ligase to join the complement of the multifunctional capture probe to the target region that is 5' of the multifunctional capture probe binding site in order to generate a hybrid nucleic acid molecule, wherein the hybrid nucleic acid molecule comprises the complement of the multifunctional capture probe hybrid module and a region of the tagged target region that is located 5' of the location where the multifunctional capture probe hybrid module hybridizes to the target region; and (d) performing PCR amplification of the hybrid nucleic acid molecule in c); and (e) quantitating the PCR reaction in d), wherein the quantitation allows for a determination of copy number of the specific target region.

In various embodiments, the methods contemplated herein comprise obtaining the sequences of the hybrid nucleic acid molecules from step d).

In particular embodiments, steps a) through d) are repeated at least about twice and a sequence alignment of the hybrid nucleic acid molecules from the at least two d) steps.

In particular embodiments, at least two different multifunctional capture probe modules are used in the at least two a) steps, wherein the at least two a) steps employ one multifunctional capture probe module each.

In certain embodiments, at least one multifunctional capture probe module hybridizes downstream of the genomic target region and at least one multifunctional capture probe module hybridizes upstream of the genomic target region.

In additional embodiments, the targeted genetic analysis is sequence analysis.

In further embodiments, the target region is a genomic target region and the DNA library is a genomic DNA library.

In some embodiments, the target region is a cDNA target region and the DNA library is a cDNA library.

BRIEF DESCRIPTION OF THE SEVERAL VIEWS OF THE DRAWINGS

(FIG. 2A) Structure of a prototypical 114 nt probe. Region 1 is a 34 nt sequence that shares perfect complementarity to a highly modified, 34 nt partner oligonucleotide. The partner oligonucleotide was modified on its 5' end with a biotin—TEG chemical entity that enabled capture on streptavidin-coated magnetic beads. B stands for the "Bio-TEG" modification. Region 2 is the 60 nt probe region designed to interact with genomic DNA targets. Region 3 is a 20 nt tail that introduced PCR amplification sequences into the captured genomic fragments. (FIG. 2B) An example of the highly modified partner strand that is complementary to region 1 of each individual probe.

FIG. 3A-FIG. 3B: Sequence "spreading" in conventional, hybridization-based capture experiments. (FIG. 3A) Flanking fragments can "hitch-hike" into capture libraries by way of legitimate hybridization triplexes involving probe-fragment-flanking fragment interactions. (FIG. 3B) The net result of cross-fragment hybridization is sequence "spreading", meaning sequences that are within proximity to the target region (dashed lines) but fall outside the boundaries of the desired target.

(FIG. 4A) The purified complex of fragment (light gray) and probe (black) prior to processing. B—biotin affinity modification. (FIG. 4B) DNA polymerase (e.g. T4 DNA polymerase) encoded 3'→5' exonuclease activity removes the 3' segment of the captured fragment. (FIG. 4C) Upon encountering the probe: fragment duplex region, the polymerase copies the probe tail segment onto the hybridized genomic fragment. (FIG. 4D) The final modified fragment in which the tail segment of the multifunctional capture probe hybrid module has been copied onto the target genomic fragment.

FIG. 5A-FIG. 5B: Enzymatic processing of capture complexes "focuses" sequencing reads on the target region. (FIG. 5A) Enzymatically processed fragment shown in relation to the capture probe. The orientation of the sequencing read is specified by the probe and is denoted by the thin black arrow. (FIG. 5B) Hypothetical trace of focused reads where "spreading" is minimized.

(FIG. 6A) Typical exons average 100-150 bp. Directional capture probes are positioned in intronic region flanking the target segment. (FIG. 6B) The sequence read distribution for each individual probe is shown by the dashed line. The additive coverage is shown by the solid line. The directional nature of coverage can be used, as shown in this example, to obtain sharp focus on query regions.

FIG. 18A-FIG. 18D: Enhanced focusing of target sequences by the alternative processing method. The sequence reads obtained in Example 13 were displayed in the UCSC Genome Browser to assess the coverage and distribution of captured fragments within specific target sites. The density of sequence reads corresponding to 'capture only' and 'processed' libraries are shown (black) for two target regions on the X chromosome, one corresponding to exons of the PLP1 gene (FIG. 18A and FIG. 18B) and the other an intronic segment of the ZNF630 gene (FIG. 18C and FIG. 18D). Reads from libraries generated by the alternative processing method (FIG. 18B and FIG. 18D) are more highly concentrated in target sites than libraries constructed by capture alone (FIG. 18A and FIG. 18C). Capture probe binding sites are shown in red. Each track is scaled to the maximal read density values (y-axis) observed for a given stretch of genomic coordinates (x-axis).

FIG. 19A-FIG. 19B: Diagram of vertical alignment. All next generation sequence (NGS) analysis starts with alignment to a reference genome. (FIG. 19A) Initial read alignment is based on configurable word string searches that can accommodate single nucleotide variants (SNVs) and, to a limited extent, insertions/deletions. (FIG. 19B) The collective set of aligned reads is analyzed for SNVs. In the example shown, the candidate SNV was observed twice, but the read coordinates for these two reads was identical. The vertical alignment paradigm generates a large number of SNVs and/or insertions/deletion hypotheses that require orthogonal validation.

FIG. 23A-FIG. 23C: Diagram of "high confidence" SNV calls. Candidate nucleotide variants can be actual events harbored in the individual from whom the sample was collected and processed, but they can also be artifacts introduced during processing and sequencing of samples. The methods described here were designed to differentiate between actual, "high confidence" variant calls and artifactual "low confidence" variant calls. Sequencing reads covering a target region are collected from multiple different clones in both possible sequencing orientations, and each read is annotated with tag information. The tags allow reads derived from distinct cloning events to be identified. Examples shown are (FIG. 23A) reads with the same start point but different sequence labels, (FIG. 23B) reads in the same orientation that have different start points and different labels and (FIG. 23C) reads in opposite orientations. In all these instances, the occurrence and detect of a variant in independent cloning events marks that variant with high confidence, and such variants are followed up with further, orthogonal validation methods.

FIG. 26A-FIG. 26B: Dual probe interrogation of target regions (e. g. exons). (FIG. 26A) Typical exons average 100-150 bp. Capture probes are positioned in the intronic region flanking the target segment. These probes have opposite sequence polarity (one queries the "+" stand, the other the "−" strand. (FIG. 26B) The sequence read distribution for each individual probe is indicated by the shaded areas and the read orientations are specified by arrows. Key aspects are that target regions are sequenced by multiple reads in both orientations. Moreover, each probe captures reads that sequence the adjacent probe binding sites. This arrangement is one element that increases the confidence of variant calls.

(FIG. 27A) A false-positive variant call is one in which a variant is identified among a collection of sibling sequences that all bear identical sequence tags. (FIG. 27B) A high confidence variant call is found among a collection of sequences that have different sequence tags.

(FIG. 31A) the initial capture complex comprises a "standard" tagged genomic library fragment, a tailed capture probe that targets a genomic "target region" that is 5' to the probe, and a biotinylated partner Oligonucleotide that is common to all probes. (FIG. 31B) Processing of the complex into a sequence-ready clone comprises 3 steps: (1) the 5' FLAP endonuclease of DNA polymerase holoenzyme (e.g., full length Bst polymerase) clips the 5' tail of the genomic clone; (2) the polymerase extends the partner oligo sequence by polymerization (can occur concurrently with step 1); and (3) Taq ligase repairs the nick between the partner oligo and the genomic fragment. These concerted steps create a sequence-ready clone.

FIG. 49 shows the Cq values of STDs and samples (the average of duplicate measurements described in Example 10 except (i) the experiment repeated on plate 2 and (ii) M1, M2 and M3 were measured in three sets of duplicates—average of the three measurements taken).

FIG. 50 shows the genomes per μl for each library that was made in Example 10.

FIG. 51 shows the conversion of designated samples in Example 10 into 10 copy, 20 copy, 40 copy, 80 copy, etc. libraries for downstream capture tests.

FIG. 52 shows the qPCR measurement of capture sensitivity and specificity described in Example 12.

FIG. 53 shows a summary of alignment statistics for each library pool described in Example 13.

FIG. 54 shows the design of an experiment for evaluating the enzymatic requirements for complex processing described in Example 20.

FIG. 55 shows the list of candidate transcripts and their reported RPKM values described in Example 21.

FIG. 56 shows the final read count of the data set described in Example 21.

DETAILED DESCRIPTION

A. Overview

Figure 1:
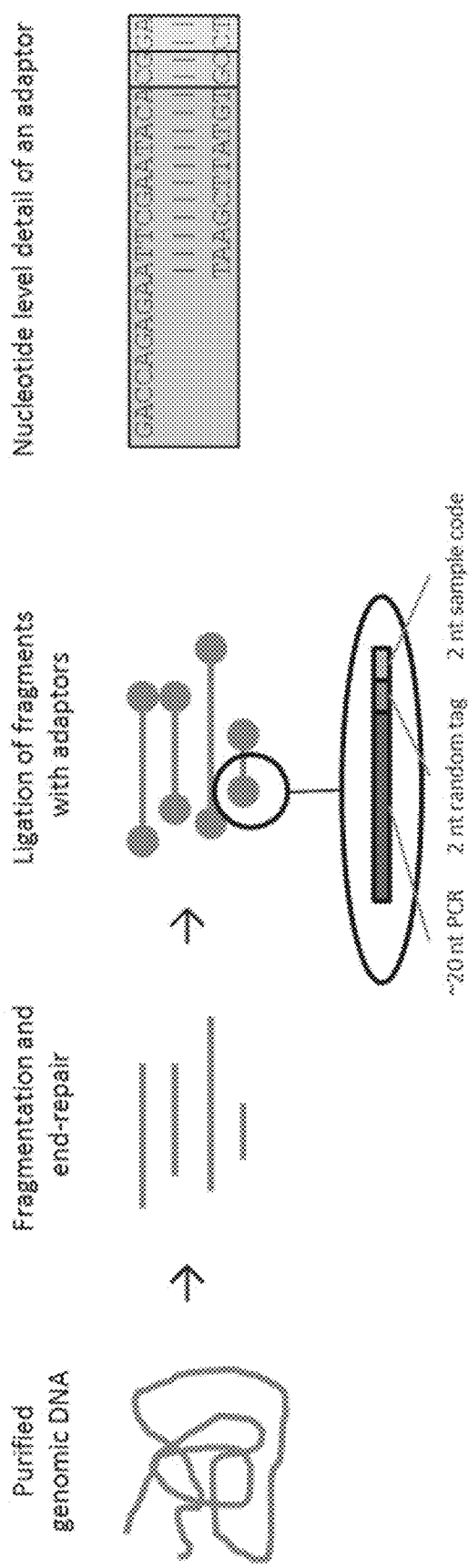
FIG. 1: Construction of an amplifiable, sample coded, tagged genomic DNA library. Purified genomic DNA was isolated from a source such as whole blood or a buccal cheek swab. The DNA was fragmented (e.g. by mechanical, enzymatic or chemical means) and the ends of the DNA were repaired, in this example, to blunt ends. The repaired DNA was ligated to a multifunctional adaptor module that contained a universal amplification sequence, a random nucleotide tag sequence and a sample code sequence. A specific example of a typical adaptor duplex molecule is shown by way of example.

The present invention is based at least in part, on the discovery that the coordinated utilization of several key molecular modules can be employed in performing targeted genetic analyses.

The practice of the invention will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); Transcription and Translation (B. Hames & S. Higgins, Eds., 1984); Perbal, *A Practical Guide to Molecular Cloning* (1984); and Harlow and Lane, Antibodies, (Cold Spring Harbor Laboratory Press, Cold Spring Harbor, N.Y., 1998).

All publications, patents and patent applications cited herein are hereby incorporated by reference in their entirety.

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred embodiments of compositions, methods and materials are described herein. For the purposes of the present invention, the following terms are defined below.

The articles "a," "an," and "the" are used herein to refer to one or to more than one (i.e. to at least one) of the grammatical object of the article. By way of example, "an element" means one element or more than one element.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. In particular embodiments, the terms "include," "has," "contains," and "comprise" are used synonymously.

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "isolated" means material that is substantially or essentially free from components that normally accompany it in its native state. In particular embodiments, the term "obtained" or "derived" is used synonymously with isolated.

As used herein, the term "DNA" refers to deoxyribonucleic acid. In various embodiments, the term DNA refers to genomic DNA, recombinant DNA, synthetic DNA, or cDNA. In one embodiment, DNA refers to genomic DNA or cDNA. In particular embodiments, the DNA comprises a "target region." DNA libraries contemplated herein include genomic DNA libraries and cDNA libraries constructed from RNA, e.g., an RNA expression library. In various embodiments, the DNA libraries comprise one or more additional DNA sequences and/or tags.

A "target region" refers to a region of interest within a DNA sequence. In various embodiments, targeted genetic analyses are performed on the target region. In particular embodiments, the target region is sequenced or the copy number of the target region is determined.

C. Exemplary Embodiments

The present invention contemplates, in part, a method for generating a tagged genomic library. In particular embodiments, the method comprises treating fragmented DNA, e.g., genomic DNA or cDNA, with end-repair enzymes to generate fragmented end-repaired DNA followed by ligating a random nucleic acid tag sequence to generate the tagged genomic library. In some embodiments, a sample code sequence and/or a PCR primer sequence are optionally ligated to the fragmented end-repaired DNA.

The present invention contemplates, in part, a method for generating a tagged DNA library. In particular embodiments, the method comprises treating fragmented DNA with end-repair enzymes to generate fragmented end-repaired DNA followed by ligating a random nucleic acid tag sequence to generate the tagged DNA library. In some embodiments, a sample code sequence and/or a PCR primer sequence are optionally ligated to the fragmented end-repaired DNA.

Illustrative methods for fragmenting DNA include, but are not limited to: shearing, sonication, enzymatic digestion; including restriction digests, as well as other methods. In particular embodiments, any method known in the art for fragmenting DNA can be employed with the present invention.

In some embodiments, the fragmented DNA is processed by end-repair enzymes to generate end-repaired DNA. In some embodiments, the end-repair enzymes can yield for example blunt ends, 5'-overhangs, and 3'-overhangs. In some embodiments, the end-repaired DNA contains blunt ends. In some embodiments, the end-repaired DNA is processed to contain blunt ends. In some embodiments, the blunt ends of the end-repaired DNA are further modified to contain a single base pair overhang. In some embodiments, end-repaired DNA containing blunt ends can be further processed to contain adenine (A)/thymine (T) overhang. In some embodiments, end-repaired DNA containing blunt ends can be further processed to contain adenine (A)/thymine (T) overhang as the single base pair overhang. In some embodiments, the end-repaired DNA has non-templated 3' overhangs. In some embodiments, the end-repaired DNA is processed to contain 3'-overhangs. In some embodiments, the end-repaired DNA is processed with terminal transferase (TdT) to contain 3'-overhangs. In some embodiments, a G-tail can be added by TdT. In some embodiments, the end-repaired DNA is processed to contain overhang ends using partial digestion with any known restriction enzymes (e.g., with the enzyme Sau3A, and the like.

In particular embodiments, DNA fragments are tagged using one or more "random nucleotide tags" or "random nucleic acid tags." As used herein, the terms "random nucleotide tag" or "random nucleic acid tag" refer to a polynucleotide of discrete length wherein the nucleotide sequence has been randomly generated or selected. In particular illustrative embodiments, the length of the random nucleic acid tag is from about 2 to about 100 nucleotides, from about 2 to about 75 nucleotides, about 2 to about 50 nucleotides, about 2 to about 25 nucleotides, about 2 to about 20 nucleotides, about 2 to about 15 nucleotides, about 2 to about 10 nucleotides, about 2 to about 8 nucleotides, or about 2 to about 6 nucleotides. In certain embodiments, the length of the random nucleotide tag is from about 2 to about 6 nucleotides (see, e.g., FIG. 1). In one embodiment, the random nucleotide tag sequence is about 2, about 3, about 4, about 5, about 6, about 7, about 8, about 9, or about 10 nucleotides.

In particular embodiments, methods known in the art can be employed to add the random nucleotide tags of the present invention to the fragmented DNA. In some embodiments, "tagmentation" can be employed. Tagmentation is a Nextera Technology that is commercially available (from Illumina and Epicenter, USA) and which can be used to load transposon protein complexes with the random nucleotide tags and/or the multifunctional adaptor modules of the invention. The loaded transposon complexes can then be used in creation of the tagged genomic library according to described methods.

DNA for use in the present methods can come from any source known to those of skill in the art. DNA can be collected from any source, synthesized from RNA as copy DNA (cDNA), and processed into pure or substantially pure DNA for use in the present methods. In some embodiments, the size of the fragmented DNA is in the range of about 2 to about 500 base pairs, about 2 to about 400 base pairs, about 2 to about 300 base pairs, about 2 to about 250 base pairs, about 2 to about 200 base pairs, about 2 to about 100 base pairs or about 2 to about 50 base pairs.

The combination of the introduced "random nucleic acid tag" or "random nucleic acid tags" with the DNA fragment end sequence constitutes a combination of two elements that will hereafter be referred to as "the genomic tag" or the "the cDNA tag." In some embodiments the uniqueness of "the genomic tag" or the "the cDNA tag" can be determined by the combinatorial product of the diversity within the attached random nucleotide tag pool multiplied by the diversity of the DNA fragment end sequence pool.

The present invention also contemplates, in part, a multifunctional adaptor module. As used herein, the term "multifunctional adaptor module" refers to a polynucleotide comprising: (i) a first region comprising a random nucleotide tag sequence; optionally (ii) a second region comprising a sample code sequence; and optionally (iii) a third region comprising a PCR primer sequence. In particular embodiments, a multifunctional adaptor module comprises a PCR primer sequence, a random nucleotide tag, and a sample code sequence. In certain embodiments, a multifunctional adaptor module comprises a PCR primer sequence and a random nucleotide tag or a sample code sequence. In some embodiments, the second region comprising the sample code is optional. In some embodiments, the multifunctional adaptor module does not include a second region, but instead only a first and third region. The multifunctional adaptor module of the present invention can include blunt or complementary ends appropriate for the ligation method employed, including those disclosed elsewhere herein, as well as any others known to those of skill in the art for ligating the multifunctional adaptor module to the fragmented DNA.

In various embodiments, a first region comprises a random nucleotide tag sequence. In particular embodiments, the first region comprises a random nucleotide tag sequence that is from about 2 to about 100 nucleotides, from about 2 to about 75 nucleotides, about 2 to about 50 nucleotides, about 2 to about 25 nucleotides, about 2 to about 20 nucleotides, about 2 to about 15 nucleotides, about 2 to about 10 nucleotides, about 2 to about 8 nucleotides, or about 2 to about 6 nucleotides, or any intervening number of nucleotides.

In particular embodiments, a second region, when optionally present, comprises a sample code sequence. As used herein, the term "sample code sequence" refers to a polynucleotide that is used to identify the sample. In particular embodiments, the second region comprises a sample code sequence that is from about 1 to about 100 nucleotides, from about 2 to about 75 nucleotides, about 2 to about 50 nucleotides, about 2 to about 25 nucleotides, about 2 to about 20 nucleotides, about 2 to about 15 nucleotides, about 2 to about 10 nucleotides, about 2 to about 8 nucleotides, or about 2 to about 6 nucleotides, or any intervening number of nucleotides.

In certain embodiments, a third region, when optionally present, comprises a PCR primer sequence. In particular embodiments, the third region comprises a PCR primer sequence that is from about 5 to about 200 nucleotides, from about 5 to about 150 nucleotides, from about 10 to about 100 nucleotides from about 10 to about 75 nucleotides, about 10 to about 50 nucleotides, about 10 to about 40 nucleotides, about 20 to about 40 nucleotides, or about 20 to about 30 nucleotides, or any intervening number of nucleotides.

In particular embodiments, a ligation step comprises ligating a multifunctional adaptor module to the fragmented end-repaired DNA. This ligation reaction can be used to generate the tagged DNA library, which comprises end-repaired DNA ligated to a multifunctional adaptor molecule and/or random nucleotide tag. In some embodiments, a single multifunctional adaptor module is employed. In some embodiments, more than one multifunctional adaptor module is employed. In some embodiments, a single multifunctional adaptor module of identical sequence is ligated to each end of the fragmented end-repaired DNA.

The present invention also provides a multifunctional capture probe module. As used herein, the term "multifunctional capture probe module" refers to a polynucleotide comprising: (i) a first region capable of hybridizing to a partner oligonucleotide; (ii) a second region capable of hybridizing to a specific target region; and optionally (iii) a third region comprising a tail sequence.

In one embodiment, a multifunctional capture probe module comprises a region capable of hybridizing to a partner oligonucleotide, a region capable of hybridizing to a DNA target sequence, and a tail sequence.

In one embodiment, a multifunctional capture probe module comprises a region capable of hybridizing to a partner oligonucleotide and a region capable of hybridizing to a genomic target sequence.

In particular embodiments, the multifunctional capture probe module optionally comprises a random nucleotide tag sequence.

In various embodiments, a first region comprises a region capable of hybridizing to a partner oligonucleotide. As used herein, the term "partner oligonucleotide" refers to an oligonucleotide that is complementary to a nucleotide sequence of the multifunctional capture probe module. In particular embodiments, the first region capable of hybridizing to a partner oligonucleotide is a sequence that is from about 20 to about 200 nucleotides, from about 20 to about 150 nucleotides, about 30 to about 100 nucleotides, about 30 to about 75 nucleotides, about 20 to about 50 nucleotides, about 30 to about 45 nucleotides, or about 35 to about 45 nucleotides. In certain embodiments, the region is about 30 to about 50 nucleotides, about 30 to about 40 nucleotides, about 30 to about 35 nucleotides or about 34 nucleotides, or any intervening number of nucleotides.

In particular embodiments, a second region, when optionally present, comprises a region capable of hybridizing to a specific DNA target region. As used herein, the term "DNA target region" refers to a region of the genome or cDNA selected for analyses using the compositions and methods contemplated herein. In particular embodiments, the second region comprises a region capable of hybridizing to a specific target region is a sequence from about 20 to about 200 nucleotides, from about 30 to about 150 nucleotides, about 50 to about 150 nucleotides, about 30 to about 100 nucleotides, about 50 to about 100 nucleotides, about 50 to about 90 nucleotides, about 50 to about 80 nucleotides, about 50 to about 70 nucleotides or about 50 to about 60 nucleotides. In certain embodiments, the second region is about 60 nucleotides, or any intervening number of nucleotides.

In certain embodiments, a third region, when optionally present, comprises a tail sequence. As used herein, the term "tail sequence" refers to a polynucleotide at the 5' end of the multifunctional capture probe module, which in particular embodiments can serve as a PCR primer binding site. In particular embodiments, the third region comprises a tail sequence that is from about 5 to about 100 nucleotides, about 10 to about 100 nucleotides, about 5 to about 75 nucleotides, about 5 to about 50 nucleotides, about 5 to about 25 nucleotides, or about 5 to about 20 nucleotides. In certain embodiments, the third region is from about 10 to about 50 nucleotides, about 15 to about 40 nucleotides, about 20 to about 30 nucleotides or about 20 nucleotides, or any intervening number of nucleotides.

In one embodiment, a multifunctional capture probe module comprises a region capable of hybridizing to a partner oligonucleotide and a region capable of hybridizing to a genomic target sequence. In particular embodiments, wherein the multifunctional capture probe module comprises a region capable of hybridizing to a partner oligonucleotide and a region capable of hybridizing to a genomic target sequence, the partner oligo may also function as a tail sequence or primer binding site.

In one embodiment, a multifunctional capture probe module comprises a tail region and a region capable of hybridizing to a genomic target sequence.

In various embodiments, the multifunctional capture probe comprises a specific member of a binding pair to enable isolation and/or purification of one or more captured fragments of a tagged DNA library that hybridizes to the multifunctional capture probe. In particular embodiments, the multifunctional capture probe is conjugate to biotin or another suitable hapten, e.g., dinitrophenol, digoxigenin.

The present invention further contemplates, in part, hybridizing a tagged DNA library with a multifunctional capture probe module to form a complex. In some embodiments, the multifunctional capture probe module substantially hybridizes to a specific genomic target region in the DNA library.

Hybridization or hybridizing conditions can include any reaction conditions where two nucleotide sequences form a stable complex; for example, the tagged DNA library and multifunctional capture probe module forming a stable tagged DNA library—multifunctional capture probe module complex. Such reaction conditions are well known in the art and those of skill in the art will appreciated that such conditions can be modified as appropriate and within the scope of the present invention. Substantial hybridization can occur when the second region of the multifunctional capture probe complex exhibits 100%, 99%, 98%, 97%, 96%, 95%, 94%, 93%, 92% 91%, 90%, 89%, 88%, 85%, 80%, 75%, or 70% sequence identity, homology or complementarity to a region of the tagged DNA library.

In particular embodiments, the first region of the multifunctional capture probe module does not substantially hybridize to the region of the tagged DNA library to which the second region does substantially hybridize. In some embodiments, the third region of the multifunctional capture probe module does not substantially hybridize to the region of the tagged DNA library to which the second region of the multifunctional capture probe module does substantially hybridize. In some embodiments, the first and third regions of the multifunctional capture probe module do not substantially hybridize to the region of the tagged DNA library to which the second region of the multifunctional capture probe module does substantially hybridize.

In certain embodiments, the methods contemplated herein comprise isolating a tagged DNA library—multifunctional capture probe module complex. In particular embodiments, methods for isolating DNA complexes are well known to those skilled in the art and any methods deemed appropriate by one of skill in the art can be employed with the methods of the present invention (Ausubel et al., *Current Protocols in Molecular Biology*, 2007-2012). In particular embodiments, the complexes are isolated using biotin-streptavidin isolation techniques. In some embodiments, the partner oligonucleotide capable of hybridizing to the first region of the multifunctional capture probe module is modified to contain a biotin at the 5'-end or 3'-end which is capable of interacting with streptavidin linked to a column, bead or other substrate for use in DNA complex isolation methods.

In particular embodiments, a first region of a multifunctional capture probe module is bound to a partner oligonucleotide. In some embodiments, the multifunctional capture probe module is bound to the partner oligonucleotide prior to formation of a tagged DNA library—multifunctional capture probe module complex. In some embodiments, the multifunctional capture probe module is bound to the partner oligonucleotide after the formation of a tagged DNA library—multifunctional capture probe module complex. In some embodiments, the multifunctional capture probe module is bound to the partner oligonucleotide simultaneously with the formation of a tagged DNA library—multifunctional capture probe module complex. In some embodiments, the partner oligonucleotide is chemically modified.

In particular embodiments, removal of the single stranded 3'-ends from the isolated tagged DNA library-multifunctional capture probe module complex is contemplated. In certain embodiments, the methods comprise 3'-5' exonuclease enzymatic processing of the isolated tagged DNA library-multifunctional capture probe module complex to remove the single stranded 3' ends.

In certain other embodiments, the methods comprise performing 5'-3' DNA polymerase extension of multifunctional capture probe utilizing the isolated tagged DNA library fragments as template.

In certain other embodiments, the methods comprise creating a hybrid multifunctional capture probe-isolated tagged DNA target molecule through the concerted action of a 5' FLAP endonuclease, DNA polymerization and nick closure by a DNA ligase.

A variety of enzymes can be employed for the 3'-5' exonuclease enzymatic processing of the isolated tagged DNA library-multifunctional capture probe module complex. Illustrative examples of suitable enzymes, which exhibit 3'-5' exonuclease enzymatic activity, that can be employed in particular embodiments include, but are not limited to: T4 or Exonucleases I, III, V (see also, Shevelev IV, Hübscher U., "The 3' 5' exonucleases," *Nat Rev Mol Cell Biol.* 3(5):364-76 (2002)). In particular embodiments, the enzyme comprising 3'-5' exonuclease activity is T4 polymerase. In particular embodiments, an enzyme which exhibits 3'-5' exonuclease enzymatic activity and is capable of primer template extension can be employed, including for example T4 or Exonucleases I, III, V. Id. 3'5'

In some embodiments, the methods contemplated herein comprise performing PCR on the 3'-5' exonuclease enzymatically processed complex discussed supra and elsewhere herein. In particular embodiments, a tail portion of a multifunctional capture probe molecule is copied in order to generate a hybrid nucleic acid molecule. In one embodiment, the hybrid nucleic acid molecule generated comprises the target region capable of hybridizing to the multifunctional capture probe module and the complement of the multifunctional capture probe module tail sequence.

In various embodiments, a method for targeted genetic analysis is also contemplated. In certain embodiments a method for targeted genetic analysis comprises: a) hybridizing a tagged DNA library with a multifunctional capture probe module complex, wherein the multifunctional capture probe module selectively hybridizes to a specific target region in the genomic library; b) isolating the tagged DNA library-multifunctional capture probe module complex from a); c) performing 3'-5' exonuclease enzymatic processing on the isolated tagged DNA library-multifunctional capture probe module complex from b) using an enzyme with 3'-5' exonuclease activity to remove the single stranded 3' ends; d) performing PCR on the enzymatically processed complex from c) wherein the tail portion of the multifunctional capture probe molecule is copied in order to generate a hybrid nucleic acid molecule, wherein the hybrid nucleic acid molecule comprises the target region capable of hybridizing to the multifunctional capture probe module and the complement of the multifunctional capture probe module tail sequence; and e) performing targeted genetic analysis on the hybrid nucleic acid molecule from d).

In various embodiments, methods for determining copy number of a specific target region are contemplated. In particular embodiments, a method for determining copy number of a specific target region comprises: a) hybridizing a tagged DNA library with a multifunctional capture probe module complex, wherein the multifunctional capture probe module comprises selectively hybridizes to a specific target region in the DNA library; b) isolating the tagged DNA library-multifunctional capture probe module complex from a); c) performing 3'-5' exonuclease enzymatic processing on the isolated tagged DNA library-multifunctional capture probe module complex from b) using an enzyme with 3'-5' exonuclease activity to remove the single stranded 3' ends; d) performing a PCR reaction on the enzymatically processed complex from c) wherein the tail portion of the multifunctional capture probe molecule is replicated in order to generate a hybrid nucleic acid molecule, wherein the hybrid nucleic acid molecule comprises the target region capable of hybridizing to the multifunctional capture probe module and the complement of the multifunctional capture probe module tail sequence; e) performing PCR amplification of the hybrid nucleic acid in d); and f) quantitating the PCR reaction in e), wherein the quantitation allows for a determination of copy number of the specific target region.

In various embodiments, a method for targeted genetic analysis is also contemplated. In certain embodiments a method for targeted genetic analysis comprises: a) hybridizing a tagged DNA library with a multifunctional capture probe module complex, wherein the multifunctional capture probe module selectively hybridizes to a specific target region in the genomic library; b) isolating the tagged DNA library-multifunctional capture probe module complex from a); c) performing 5'-3' DNA polymerase extension of multifunctional capture probe utilizing the isolated tagged DNA library fragments as template; d) performing PCR on the enzymatically processed complex from c) wherein the tail portion of the multifunctional capture probe molecule is copied in order to generate a hybrid nucleic acid molecule, wherein the hybrid nucleic acid molecule comprises the target region capable of hybridizing to the multifunctional capture probe module and the complement of the multifunctional capture probe module tail sequence; and e) performing targeted genetic analysis on the hybrid nucleic acid molecule from d).

In various embodiments, methods for determining copy number of a specific target region are contemplated. In particular embodiments, a method for determining copy number of a specific target region comprises: a) hybridizing a tagged DNA library with a multifunctional capture probe module complex, wherein the multifunctional capture probe module comprises selectively hybridizes to a specific target region in the DNA library; b) isolating the tagged DNA library-multifunctional capture probe module complex from a); c) performing 5'-3' DNA polymerase extension of multifunctional capture probe utilizing the isolated tagged DNA library fragments as template; d) performing a PCR reaction on the enzymatically processed complex from c) wherein the tail portion of the multifunctional capture probe molecule is replicated in order to generate a hybrid nucleic acid molecule, wherein the hybrid nucleic acid molecule comprises the target region capable of hybridizing to the multifunctional capture probe module and the complement of the multifunctional capture probe module tail sequence; e) performing PCR amplification of the hybrid nucleic acid in d); and f) quantitating the PCR reaction in e), wherein the quantitation allows for a determination of copy number of the specific target region.

In various embodiments, a method for targeted genetic analysis is also contemplated. In certain embodiments a method for targeted genetic analysis comprises: a) hybridizing a tagged DNA library with a multifunctional capture probe module complex, wherein the multifunctional capture probe module selectively hybridizes to a specific target region in the genomic library; b) isolating the tagged DNA library-multifunctional capture probe module complex from a); c) creating a hybrid multifunctional capture probe-isolated tagged DNA target molecule through the concerted action of a 5' FLAP endonuclease, DNA polymerization and nick closure by a DNA ligase; d) performing PCR on the enzymatically processed complex from c) wherein the tail portion of the multifunctional capture probe molecule is copied in order to generate a hybrid nucleic acid molecule, wherein the hybrid nucleic acid molecule comprises the target region capable of hybridizing to the multifunctional capture probe module and the complement of the multifunctional capture probe module tail sequence; and e) performing targeted genetic analysis on the hybrid nucleic acid molecule from d).

In various embodiments, methods for determining copy number of a specific target region are contemplated. In particular embodiments, a method for determining copy number of a specific target region comprises: a) hybridizing a tagged DNA library with a multifunctional capture probe module complex, wherein the multifunctional capture probe module comprises selectively hybridizes to a specific target region in the DNA library; b) isolating the tagged DNA library-multifunctional capture probe module complex from a); c) creating a hybrid multifunctional capture probe-isolated tagged DNA target molecule through the concerted action of a 5' FLAP endonuclease, DNA polymerization and nick closure by a DNA ligase; d) performing a PCR reaction on the enzymatically processed complex from c) wherein the tail portion of the multifunctional capture probe molecule is replicated in order to generate a hybrid nucleic acid molecule, wherein the hybrid nucleic acid molecule comprises the target region capable of hybridizing to the multifunctional capture probe module and the complement of the multifunctional capture probe module tail sequence; e) performing PCR amplification of the hybrid nucleic acid in d); and f) quantitating the PCR reaction in e), wherein the quantitation allows for a determination of copy number of the specific target region.

In particular embodiments, PCR can be performed using any standard PCR reaction conditions well known to those of skill in the art. In certain embodiments, the PCR reaction in e) employs two PCR primers. In one embodiment, the PCR reaction in e) employs a first PCR primer that hybridizes to the target region. In a particular embodiment, the PCR reaction in e) employs a second PCR primer hybridizes to the hybrid molecule at the target region/tail junction. In certain embodiments, the PCR reaction in e) employs a first PCR primer that hybridizes to the target region and a second PCR primer hybridizes to the hybrid molecule at the target genomic region/tail junction. In particular embodiments, the second primer hybridizes to the target region/tail junction such that at least one or more nucleotides of the primer hybridize to the target region and at least one or more nucleotides of the primer hybridize to the tail sequence. In certain embodiments, the hybrid nucleic acid molecules obtained from step e) are sequenced and the sequences aligned horizontally, i.e., aligned to one another but not aligned to a reference sequence. In particular embodiments, steps a) through e) are repeated one or more times with one or more multifunctional capture probe module complexes. The multifunctional capture probe complexes can be the same or different and designed to target either DNA strand of the target sequence. In some embodiments, when the multifunctional capture probe complexes are different, they hybridize near the same target region within the tagged DNA library. In one embodiment, one or more multifunctional capture probe hybridize within about 5, 10, 15, 20, 25, 30, 35, 40, 45, 50, 100, 200, 300, 400, 500, 600, 700, 800, 900, 1000, 1500, 2000, 2500, 3000, 3500, 4000, 4500, 5000, or more bp of the target region in a tagged DNA library, included all intervening distances from the target region In some embodiments, the method can be performed using two multifunctional capture probe modules per target region, wherein one hybridizes to the "Watson" strand (non-coding or template strand) upstream of the target region and one hybridizes to the "Crick" strand (coding or non-template strand) downstream of the target region.

In particular embodiments, the methods contemplated herein can further be performed multiple times with any number of multifunctional probe modules, for example 2, 3, 4, 5, 6, 7, 8, 9, or 10 or more multifunctional capture probe modules per target region any number of which hybridize to the Watson or Crick strand in any combination. In some embodiments, the sequences obtained can be aligned to one another in order to identify any of a number of differences.

In certain embodiments, a plurality of target regions are interrogated, e.g., 100, 200, 300, 400, 500, 600, 700, 800, 900, 1000, 1500, 2000, 2500, 3000, 3500, 4000, 4500, 5000, 10000, 50000, 100000, 500000 or more in a single reaction, using one or more multifunctional probe modules.

Copy number can provide useful information regarding unique reads and duplicative reads, as well as assisting with searching for variants of known reads. As used herein, the terms "read," "read sequence," or "sequencing read" are used synonymously and refer to a polynucleotide sequence obtained by sequencing a polynucleotide. In particular embodiments, DNA tags, e.g., a random nucleotide tag, can be used to determine copy number of a nucleic acid sequence being analyzed.

In one embodiment, a multifunctional capture probe hybrid module comprises: (i) a first region capable of hybridizing to a partner oligonucleotide and capable of functioning as a PCR primer and (ii) a second region capable of hybridizing to a specific genomic target region.

In various embodiments, a first region of a multifunctional capture probe hybrid module comprises a PCR primer sequence. In particular embodiments, this first region comprises a PCR primer sequence that is from about 5 to about 200 nucleotides, from about 5 to about 150 nucleotides, from about 10 to about 100 nucleotides from about 10 to about 75 nucleotides, about 10 to about 50 nucleotides, about 10 to about 40 nucleotides, about 20 to about 40 nucleotides, or about 20 to about 30 nucleotides, including any intervening number of nucleotides.

In particular embodiments, a first region of a multifunctional capture probe hybrid module is bound to a partner oligonucleotide. In certain embodiments, the multifunctional capture hybrid probe module is bound to the partner oligonucleotide prior to formation of a tagged DNA library—multifunctional capture probe hybrid module complex. In particular embodiments, the multifunctional capture probe hybrid module is bound to the partner oligonucleotide after the formation of a tagged DNA library—multifunctional capture probe hybrid module complex. In some embodiments, the multifunctional capture probe hybrid module is bound to the partner oligonucleotide simultaneously with the formation of a tagged DNA library—multifunctional capture hybrid probe module complex. In some embodiments, the partner oligonucleotide is chemically modified.

In various embodiments, the methods contemplated herein comprise performing PCR on the tagged DNA library—multifunctional capture probe hybrid module complex so as to copy the captured tagged DNA library sequence to generate a hybrid nucleic acid molecule comprising the multifunctional capture probe hybrid module complex and a sequence complementary to a region of the captured tagged DNA library sequence located 3' or 5' of the multifunctional capture probe sequence relative to where the hybrid module hybridizes to the genomic target. In particular embodiments, the copied target region is anywhere from 1 to 5000 nt from the, 3' or 5'-end of sequence where the multifunctional capture probe hybrid module hybridizes to the genomic target. In certain embodiments, the complementary sequence of the region that is 3' to the location where the multifunctional capture probe hybrid module hybridizes is copied in order to generate a hybrid nucleic acid molecule. The hybrid nucleic acid molecule generated comprises the multifunctional capture probe hybrid module and the complement of a region of captured tagged DNA library sequence that is located 3' or 5' from the location where the multifunctional capture probe hybrid module hybridizes to the target region.

In various embodiments, the methods contemplated herein comprise processing a tagged DNA library-multifunctional capture probe module complex to generate a hybrid nucleic acid molecule (i.e., a hybrid multifunctional capture probe-isolated tagged DNA target molecule). In particular embodiments, a hybrid nucleic acid molecule comprises the multifunctional capture probe hybrid module and the complement of a region of the tagged DNA library sequence that is located 3' relative to the location where the multifunctional capture probe hybrid module hybridizes to the target region. In one non-limiting embodiment, the hybrid nucleic acid molecule is generated by 3'-5' exonuclease enzymatic processing that removes single stranded 3'-ends from an isolated tagged DNA library-multifunctional capture probe module complex and/or 5'-3' DNA polymerase extension of the multifunctional capture probe.

In other particular embodiments, a hybrid nucleic acid molecule comprises the multifunctional capture probe hybrid module and the complement of a region of the tagged DNA library sequence that is located 5' relative to the location where the multifunctional capture probe hybrid module hybridizes to the target region. In one non-limiting embodiment, the hybrid nucleic acid molecule is generated by the concerted action of a 5' FLAP endonuclease, DNA polymerization and nick closure by a DNA ligase.

In various embodiments, a method for targeted genetic analysis is provided. In one embodiment, a method for targeted genetic analysis comprises: a) hybridizing a tagged DNA library with a multifunctional capture probe hybrid module complex, wherein the multifunctional capture probe hybrid module selectively hybridizes to a specific target region in the DNA library; b) isolating the tagged DNA library-multifunctional capture probe hybrid module complex from a); c) performing PCR on the complex from b) to form a hybrid nucleic acid molecule and d) performing targeted genetic analysis on the hybrid nucleic acid molecule from c). In particular embodiments, the hybrid nucleic acid molecules obtained from step c) are sequenced and the sequences aligned horizontally, i.e., aligned to one another but not aligned to a reference sequence. In certain embodiments, steps a) through c) are repeated one or more times with one or more multifunctional capture probe module.

The multifunctional capture probe modules can be the same or different and designed to hybridize against either strand of the genome. In some embodiments, when the multifunctional capture probe modules are different, they hybridize anywhere from 1 to 5000 nt of the same target region in the tagged DNA library.

In particular embodiments, the method can be performed twice, using two multifunctional capture probe modules, wherein one hybridizes upstream of the genomic target region (i.e., at the 5'-end; i.e., a forward multifunctional capture probe module or complex) and one hybridizes downstream of the genomic target region on the opposite genomic strand (i.e., at the 3'-end; i.e., a reverse multifunctional capture probe module or complex).

In one embodiment, one or more multifunctional capture probe hybridize within about 5, 10, 15, 20, 25, 30, 35, 40, 45, 50, 100, 200, 300, 400, 500, 600, 700, 800, 900, 1000, 1500, 2000, 2500, 3000, 3500, 4000, 4500, 5000, or more bp of the target region in a tagged DNA library, included all intervening distances from the target region.

In some embodiments, the method can further be performed multiple times with any number of multifunctional probe modules, for example 2, 3, 4, 5, 6, 7, 8, 9, 10 or more multifunctional capture probe modules per target region, any number of which hybridize to the Watson or Crick strand in any combination.

In certain embodiments, a plurality of target regions are interrogated, e.g., 100, 200, 300, 400, 500, 600, 700, 800, 900, 1000, 1500, 2000, 2500, 3000, 3500, 4000, 4500, 5000, 10000, 50000, 100000, 500000 or more in a single reaction, using one or more multifunctional probe modules.

In particular embodiments, the sequences obtained by the method can be aligned to one another in order to identify mutations and without being aligned to a reference sequence. In certain embodiments, the sequences obtained in can optionally be aligned to a reference sequence.

In various embodiments, methods for determining copy number of a specific target region are contemplated. In particular embodiments, a method for determining copy number of a specific target region comprises: a) hybridizing a tagged DNA library with a multifunctional capture probe hybrid module complex, wherein the multifunctional capture probe hybrid module comprises selectively hybridizes to a specific target region in the DNA library; b) isolating the tagged DNA library-multifunctional capture probe hybrid module complex from a); c) performing PCR on the complex from b) to form a hybrid nucleic acid molecule; d) performing PCR amplification of the hybrid nucleic acid in c); and e) quantitating the PCR reaction in d), wherein the quantitation allows for a determination of copy number of the specific target region. In particular embodiments, PCR can be performed using any standard PCR reaction conditions well known to those of skill in the art. In certain embodiments, the PCR reaction in d) employs two PCR primers. In particular embodiments, the PCR reaction in d) employs two PCR primers each of which hybridize to a region downstream to the location where the multifunctional capture probe hybrid module hybridizes to the tagged DNA library. In further embodiments, the region where the PCR primers hybridize is located in the region amplified in step c). In various embodiments, the hybrid nucleic acid molecules obtained from step c) are sequenced and the sequences aligned horizontally, i.e., aligned to one another but not aligned to a reference sequence. In particular embodiments, steps a) through c) are repeated one or more times with one or more multifunctional capture probe module. The multifunctional capture probe modules can be the same or different and designed to hybridize to either strand of the genome.

In one embodiment, one or more multifunctional capture probe hybridize within about 5, 10, 15, 20, 25, 30, 35, 40, 45, 50, 100, 200, 300, 400, 500, 600, 700, 800, 900, 1000, 1500, 2000, 2500, 3000, 3500, 4000, 4500, 5000, or more bp of the target region in a tagged DNA library, included all intervening distances from the target region.

In some embodiments, the method can further be performed multiple times with any number of multifunctional probe modules, for example 2, 3, 4, 5, 6, 7, 8, 9, 10 or more multifunctional capture probe modules per target region, any number of which hybridize to the Watson or Crick strand in any combination.

In certain embodiments, a plurality of target regions are interrogated, e.g., 100, 200, 300, 400, 500, 600, 700, 800, 900, 1000, 1500, 2000, 2500, 3000, 3500, 4000, 4500, 5000, 10000, 50000, 100000, 500000 or more in a single reaction, using one or more multifunctional probe modules.

In particular illustrative embodiments, a tagged DNA library is amplified, e.g., by PCR, to generate an amplified tagged DNA library.

All genomic target regions will have a 5'-end and a 3'-end. In particular embodiments, the methods described herein can be performed with two multifunctional capture probe complexes which provide for amplification of a targeted genomic region from both the 5' and 3' directions, respectively. In one embodiment, one or more multifunctional capture probe hybridize within about 5, 10, 15, 20, 25, 30, 35, 40, 45, 50, 100, 200, 300, 400, 500, 600, 700, 800, 900, 1000, 1500, 2000, 2500, 3000, 3500, 4000, 4500, 5000, or more bp of the target region in a tagged DNA library, included all intervening distances from the target region.

In some embodiments, the method can further be performed multiple times with any number of multifunctional probe modules, for example 2, 3, 4, 5, 6, 7, 8, 9, 10 or more multifunctional capture probe modules per target region, any number of which hybridize to the Watson or Crick strand in any combination.

In certain embodiments, a plurality of target regions are interrogated, e.g., 100, 200, 300, 400, 500, 600, 700, 800, 900, 1000, 1500, 2000, 2500, 3000, 3500, 4000, 4500, 5000, 10000, 50000, 100000, or more in a single reaction, using one or more multifunctional probe modules.

In particular embodiments, the targeted genetic analysis is a sequence analysis. In particular embodiments, sequence analysis comprises any analysis wherein one sequence is distinguished from a second sequence. In various embodiments, sequence analysis excludes any purely mental sequence analysis performed in the absence of a composition or method for sequencing. In certain embodiments, sequence analysis includes, but is not limited to: sequencing, single nucleotide polymorphism (SNP) analysis, gene copy number analysis, haplotype analysis, mutation analysis, methylation status analysis (as determined by example, but not limited to, bisulfate conversion of unmethylated cytosine residues), targeted resequencing of DNA sequences obtained in a chromatin-immunoprecipitation experiment (CHIP-seq), paternity testing in sequence captured fetal DNA collected from pregnant maternal plasma DNA, microbial presence and population assessment in samples captured with microbe-specific capture probes, and fetal genetic sequence analysis (for example, using fetal cells or extra-cellular fetal DNA in maternal samples).

Copy number analyses include, but are not limited to analyses that examine the number of copies of a particular gene or mutation that occurs in a given genomic DNA sample and can further include quantitative determination of the number of copies of a given gene or sequence differences in a given sample.

Figure 20:
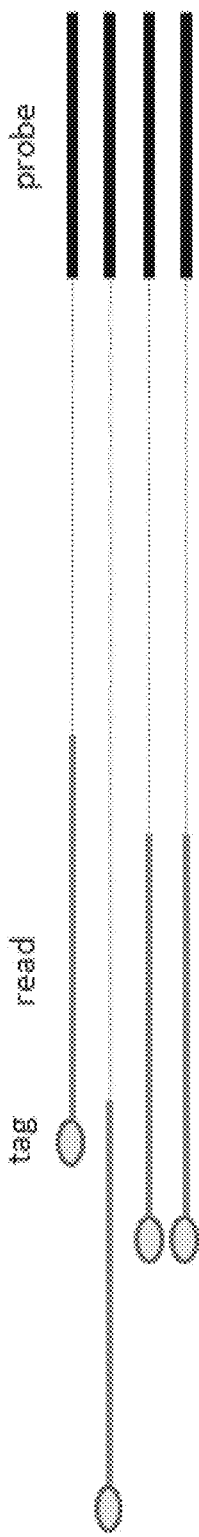
FIG. 20: Diagram of data analysis scheme. Step one is to match reads to probes. Step two will be to analyze the sequence information connected "horizontally" to each probe.

Also contemplated herein, are methods for sequence alignment analysis that can be performed without the need for alignment to a reference sequence, referred to herein as horizontal sequence analysis (exemplified in, for example, FIG. 20). Such analysis can be performed on any sequences generated by the methods contemplated herein or any other methods. In particular embodiments, the sequence analysis comprises performing sequence alignments on the hybrid nucleic acid molecules obtained by the methods contemplated herein. In one embodiment, one or more multifunctional capture probe hybridize within about 5, 10, 15, 20, 25, 30, 35, 40, 45, 50, 100, 200, 300, 400, 500, 600, 700, 800, 900, 1000, 1500, 2000, 2500, 3000, 3500, 4000, 4500, 5000, or more bp of the target region in a tagged DNA library, included all intervening distances from the target region.

In some embodiments, the method can further be performed multiple times with any number of multifunctional probe modules, for example 2, 3, 4, 5, 6, 7, 8, 9, 10 or more multifunctional capture probe modules per target region, any number of which hybridize to the Watson or Crick strand in any combination.

In certain embodiments, a plurality of target regions are interrogated, e.g., 100, 200, 300, 400, 500, 600, 700, 800, 900, 1000, 1500, 2000, 2500, 3000, 3500, 4000, 4500, 5000, 10000, 50000, 100000, or more in a single reaction, using one or more multifunctional probe modules.

In particular embodiments DNA can be isolated from any biological source. Illustrative sources for DNA include, but are not limited to: blood, skin, hair, hair follicles, saliva, oral mucous, vaginal mucous, sweat, tears, epithelial tissues, urine, semen, seminal fluid, seminal plasma, prostatic fluid, pre-ejaculatory fluid (Cowper's fluid), excreta, biopsy, ascites, cerebrospinal fluid, lymph, or tissue extract sample or biopsy sample.

In one embodiment, tagged DNA libraries for use with the methods contemplated herein are provided. In some embodiments, a tagged DNA library comprises tagged genomic sequences. In particular embodiments, each tagged DNA sequence includes: i) fragmented end-repaired DNA; ii) one or more random nucleotide tag sequences; iii) one or more sample code sequences; and iv) one or more PCR primer sequences.

In one embodiment, a hybrid tagged DNA library is contemplated. In particular embodiments, a hybrid tagged DNA library comprises hybrid tagged DNA sequences. In certain embodiments, each hybrid tagged DNA sequence includes: i) fragmented end-repaired DNA comprising a target region; ii) one or more random nucleotide tag sequences; iii) one or more sample code sequences; iv) one or more PCR primer sequences; and v) a multifunctional capture probe module tail sequence.

In various embodiments, kits and compositions of reagents used in the methods contemplated herein. In some embodiments, the composition includes a tagged DNA library, a multifunctional adaptor module and a multifunctional capture probe module. In particular embodiments, the composition includes a tagged genomic library. In certain embodiments, the composition includes a hybrid tagged genomic library.

In various embodiments, reaction mixtures for carrying out the methods contemplated herein are provided. In particular embodiments, the reaction mixture is a reaction mixture for performing any of the methods contemplated herein. In certain embodiments, the reaction mixture is capable generating a tagged DNA library. In some embodiments, the reaction mixture capable of generating a tagged DNA library includes: a) fragmented DNA and b) DNA end-repair enzymes to generate fragmented end-repaired DNA. In particular embodiments, the reaction mixture further comprises a multifunctional adaptor module. In various embodiments, the reaction mixture further comprises a multifunctional capture probe module. In certain embodiments, the reaction mixture further comprises an enzyme with 3'-5' exonuclease activity and PCR amplification activity.

In various embodiments, methods for DNA sequence analysis are provided for the sequence of one or more clones contemplated herein. In one embodiment, the method comprises obtaining one or more or a plurality of tagged DNA library clones, each clone comprising a first DNA sequence and a second DNA sequence, wherein the first DNA sequence comprises targeted DNA sequence and the second DNA sequence comprises a capture probe sequence; performing a paired end sequencing reaction on the one or more clones and obtaining one or more sequencing reads or performing a sequencing reaction on the one or more clones in which a single long sequencing read of greater than about 100, 200, 300, 400, 500 or more nucleotides is obtained, wherein the read is sufficient to identify both the first DNA sequence and the second DNA sequence; and ordering or clustering the sequencing reads of the one or more clones according to the probe sequences of the sequencing reads.

The sequence reads can be compared to one or more human reference DNA sequences. Sequence reads that do not match the reference sequence may be identified and used to create a de novo assembly from the non-matching sequence data. In particular embodiments, the de novo assemblies are used to identify novel sequence rearrangements associated with the capture probe.

In various embodiments, a method for copy number determination analysis is provided comprising obtaining one or more or a plurality of clones, each clone comprising a first DNA sequence and a second DNA sequence, wherein the first DNA sequence comprises a random nucleotide tag sequence and a targeted DNA sequence and the second DNA sequence comprises a capture probe sequence. In related embodiments, a paired end sequencing reaction on the one or more clones is performed and one or more sequencing reads are obtained. In another embodiment, a sequencing reaction on the one or more clones is performed in which a single long sequencing read of greater than about 100 nucleotides is obtained, wherein the read is sufficient to identify both the first DNA sequence and the second DNA sequence. The sequencing reads of the one or more clones can be ordered or clustered according to the probe sequence of the sequencing reads.

In particular embodiments, a method for determining the copy number is provided. In particular embodiments, the method comprises obtaining one or more or a plurality of clones, each clone comprising a first DNA sequence and a second DNA sequence, wherein the first DNA sequence comprises a random nucleotide tag sequence and a targeted DNA sequence and the second DNA sequence comprises a capture probe sequence; ordering or clustering sequencing reads of the one or more clones according to the probe sequence of the sequencing reads. In particular embodiments, the random nucleotide tag is about 2 to about 50 nucleotides in length.

The methods may further comprise analyzing all sequencing reads associated with a second read sequence by determining the distributions of unique and redundant sequencing reads; counting the number of times a unique read is encountered; fitting a frequency distribution of the unique reads to a statistical distribution; inferring a total number of unique reads; and normalizing the total number of inferred unique read to an assumption that humans are generally diploid.

In particular embodiments, the methods contemplated herein can be used to calculate an inferred copy number of one or more targeted loci and the deviation of that calculation, if any, from an expected copy number value. In certain embodiments, one or more targeted loci of a gene are grouped together in a collection of loci and the copy number measurements from the collection of targeted loci are averaged and normalized. In one embodiment, the inferred copy number of a gene can be represented by the normalized average of all the target loci representing that gene.

In various embodiments, the compositions and methods contemplated herein are also applicable to generating and analyzing RNA expression. Without wishing to be bound to any particular theory, it is contemplated that any of the methods and compositions that are used to make tagged gDNA libraries may also be used to create tagged cDNA libraries, and capture and process target regions corresponding to RNA sequences embodied in the cDNA for subsequent RNA expression analysis, including, without limitation, sequence analysis.

In various embodiments, a method for generating a tagged RNA expression library comprises first obtaining or preparing a cDNA library. Methods of cDNA library synthesis are known in the art and may be applicable to various embodiments. The cDNA library may be prepared from one or a plurality of the same or different cell types depending on the application. In one embodiment, the method comprises fragmenting a cDNA library; treating the fragmented cDNA library with end-repair enzymes to generate fragmented end-repaired cDNA; and ligating a multifunctional adapter molecule to the fragmented end-repaired cDNA to generate a tagged RNA expression library.

In a particular embodiment a tagged RNA expression library (cDNA library) is prepared by obtaining or preparing a cDNA library from the total RNA of one or more cells; fragmenting the cDNA library; treating the fragmented cDNA with end-repair enzymes to generate fragmented end-repaired cDNA; and ligating a multifunctional adapter molecule to the fragmented end-repaired cDNA to generate a tagged RNA expression library.

In certain embodiments, the cDNA library is an oligo-dT primed cDNA library.

In certain embodiments, the cDNA library is primed by random oligonucleotides comprising about 6 to about 20 random nucleotides. In particular preferred embodiments, the cDNA library is primed by random hexamers or random octamers.

The cDNA libraries may be sheared or fragmented using known methods in order to achieve a desired average library fragment size. In one embodiment, the cDNA library is fragmented to an average size of about 250 bp to about 750 bp. In a certain embodiment, the cDNA library is fragmented to an average size of about 500 bp.

In various embodiments, RNA expression libraries contemplated herein may be captured, processed, amplified, and sequenced, etc., using any of the methods contemplated herein for capturing, processing, and sequencing tagged genomic DNA libraries, without or without minor variations.

In one embodiment, a method for targeted gene expression analysis is provided comprising: hybridizing a tagged RNA expression library with a multifunctional capture probe module complex, wherein the multifunctional capture probe module selectively hybridizes to a specific target region in the tagged RNA expression library; isolating the tagged RNA expression library-multifunctional capture probe module complex; performing 3'-5' exonuclease enzymatic processing and/or 5'-3' DNA polymerase extension on the isolated tagged RNA expression library-multifunctional capture probe module complex; performing PCR on the enzymatically processed complex, wherein a tail portion (e.g., a PCR primer binding site) of the multifunctional capture probe molecule is copied in order to generate a hybrid nucleic acid molecule, wherein the hybrid nucleic acid molecule comprises the complement of the target region, the specific multifunctional capture probe sequence and the capture module tail sequence; and performing targeted gene expression analysis on the hybrid nucleic acid molecule.

In one embodiment, a method for targeted gene expression analysis comprises: hybridizing a tagged RNA expression library with a multifunctional capture probe hybrid module complex, wherein the multifunctional capture probe hybrid module selectively hybridizes to a specific target region in the RNA expression library; isolating the tagged RNA expression library-multifunctional capture probe hybrid module complex; performing PCR on the complex to form a hybrid nucleic acid molecule.

In particular embodiments, at least two different multifunctional capture probe modules are used in the at least two hybridization steps, wherein the at least two hybridization steps employ one multifunctional capture probe module each. In certain embodiments, at least one multifunctional capture probe module hybridizes 5' of the target region and at least one multifunctional capture probe module hybridizes 3' of the target region.

In one embodiment, one or more multifunctional capture probe hybridize within about 5, 10, 15, 20, 25, 30, 35, 40, 45, 50, 100, 200, 300, 400, 500, 600, 700, 800, 900, 1000, 1500, 2000, 2500, 3000, 3500, 4000, 4500, 5000, or more bp of the target region in a tagged RNA expression or cDNA library, included all intervening distances from the target region.

In some embodiments, the method can further be performed multiple times with any number of multifunctional probe modules, for example 2, 3, 4, 5, 6, 7, 8, 9, 10 or more multifunctional capture probe modules per target region, any number of which hybridize to the Watson or Crick strand in any combination.

In certain embodiments, a plurality of target regions are interrogated, e.g., 100, 200, 300, 400, 500, 600, 700, 800, 900, 1000, 1500, 2000, 2500, 3000, 3500, 4000, 4500, 5000, 10000, 50000, 100000, or more in a single reaction, using one or more multifunctional probe modules.

In a further embodiment, methods for cDNA sequence analysis are provided, which allow the skilled artisan to conduct gene expression analysis from the cDNA library. In particular embodiments, any of the sequencing methods contemplated herein may be adapted to sequence the cDNA libraries with little or no deviation from their application to sequencing tagged genomic clones. As described above, the statistical distribution of tagged cDNA sequencing reads of a target region of a cDNA in the RNA expression analyses contemplated herein, correlates to the level of gene expression of the target region in a cell from which the cDNA library was prepared or obtained.

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1: Preparation of Target Genomic Region for Genetic Analyses

Overview: In particular embodiments, the methods contemplated herein comprise the coordinated utilization of several key molecular modules. In the following section, each module is described separately. At the end of this section, the interconnection of modules is described.

Section 1: Tagging of Genomic DNA Fragments

Genomic DNA from an individual can be collected, processed into pure DNA, fragmented and random nucleotide sequences of one nucleotide or more, in some embodiments in the range of 2-100 nucleotides, or in the range of 2-6 nucleotides are attached to the random ends of genomic DNA fragments (FIG. 1). The combination of the introduced random nucleotide tag sequence together with the genomic fragment end sequence constitutes a unique combination of two elements that will hereafter be referred to as a the first region of the multifunctional adaptor module. The uniqueness of first region of the multifunctional adaptor module is determined by the combinatorial product of the diversity within the attached first region of the multifunctional adaptor module pool times the diversity of the genomic fragment end sequences.

Section 2: Addition of Sample-Specific Codes and Universal Amplification Sequences Multifunctional adapter molecules can further comprise sample-specific codes (referred to herein as the second region of the multifunctional adaptor module) and universal amplification sequences (referred to herein as the PCR primer sequence or the third region of the multifunctional adaptor module). In addition to the introduced random nucleotides from the first region of the multifunctional adaptor module, each segment that is attached to fragmented genomic DNA may include an additional set of nucleotides that is common to each sample but different between samples such that the DNA sequence of this region can be used to uniquely identify a given samples sequences in a set of sequences where multiple samples have been combined together (in other words, sample barcoding). In addition, the attached nucleotide sequence may contain a universal sequence that can be used to amplify (e.g., by PCR) the polynucleotides. The combined elements of the random nucleotide tag sequence, the sample code, and the universal amplification sequence constitute an "adaptor" (also refer to as a multifunctional adaptor module) that is most commonly attached to the fragmented genomic DNA by means of nucleotide ligation.

An illustrative example of a multifunctional adaptor module ligated to fragmented gDNA are illustrated in FIG. 1 and (while not wishing to be limited by example) an exemplary set of such sequences is shown in Table 1. Within Table 1, the sets of adaptor sequences are clustered into four sets of adaptor sequences. Within each column, all adaptors share the same two base code and all 16 possible random tags are represented. The 16 possible adaptors are mixed prior to ligation to fragment. Only the top, "ligation strand" of each adaptor is shown; this is the strand that becomes covalently attached to end-repaired DNA fragments. The bottom, partner strand that is eventually lost, while shown in FIG. 1, is not included in Table 1.

TABLE 1

5' to 3' DNA sequence of a set of 64 tagging and sample ID adapters

| Sample code AC | SEQ ID NO: | Sample code GA | SEQ ID NO: |
|---|---|---|---|
| GACCAGAGAATTCGAATACAAAAC | 1 | GACCAGAGAATTCGAATACAAAGA | 17 |
| GACCAGAGAATTCGAATACAACAC | 2 | GACCAGAGAATTCGAATACAACGA | 18 |
| GACCAGAGAATTCGAATACAAGAC | 3 | GACCAGAGAATTCGAATACAAGGA | 19 |
| GACCAGAGAATTCGAATACAATAC | 4 | GACCAGAGAATTCGAATACAATGA | 20 |
| GACCAGAGAATTCGAATACACAAC | 5 | GACCAGAGAATTCGAATACACAGA | 21 |
| GACCAGAGAATTCGAATACACCAC | 6 | GACCAGAGAATTCGAATACACCGA | 22 |
| GACCAGAGAATTCGAATACACGAC | 7 | GACCAGAGAATTCGAATACACGGA | 23 |
| GACCAGAGAATTCGAATACACTAC | 8 | GACCAGAGAATTCGAATACACTGA | 24 |
| GACCAGAGAATTCGAATACAGAAC | 9 | GACCAGAGAATTCGAATACAGAGA | 25 |
| GACCAGAGAATTCGAATACAGCAC | 10 | GACCAGAGAATTCGAATACAGCGA | 26 |
| GACCAGAGAATTCGAATACAGGAC | 11 | GACCAGAGAATTCGAATACAGGGA | 27 |
| GACCAGAGAATTCGAATACAGTAC | 12 | GACCAGAGAATTCGAATACAGTGA | 28 |
| GACCAGAGAATTCGAATACATAAC | 13 | GACCAGAGAATTCGAATACATAGA | 29 |

TABLE 1-continued

5' to 3' DNA sequence of a set of 64 tagging and sample ID adapters

| | | | |
|---|---|---|---|
| GACCAGAGAATTCGAATACATCAC | 14 | GACCAGAGAATTCGAATACATCGA | 30 |
| GACCAGAGAATTCGAATACATGAC | 15 | GACCAGAGAATTCGAATACATGGA | 31 |
| GACCAGAGAATTCGAATACATTAC | 16 | GACCAGAGAATTCGAATACATTGA | 32 |

| Sample code CT | SEQ ID NO: | Sample code TG | SEQ ID NO: |
|---|---|---|---|
| GACCAGAGAATTCGAATACAAACT | 33 | GACCAGAGAATTCGAATACAAATG | 49 |
| GACCAGAGAATTCGAATACAACCT | 34 | GACCAGAGAATTCGAATACAACTG | 50 |
| GACCAGAGAATTCGAATACAAGCT | 35 | GACCAGAGAATTCGAATACAAGTG | 51 |
| GACCAGAGAATTCGAATACAATCT | 36 | GACCAGAGAATTCGAATACAATTG | 52 |
| GACCAGAGAATTCGAATACACACT | 37 | GACCAGAGAATTCGAATACACATG | 53 |
| GACCAGAGAATTCGAATACACCCT | 38 | GACCAGAGAATTCGAATACACCTG | 54 |
| GACCAGAGAATTCGAATACACGCT | 39 | GACCAGAGAATTCGAATACACGTG | 55 |
| GACCAGAGAATTCGAATACACTCT | 40 | GACCAGAGAATTCGAATACACTTG | 56 |
| GACCAGAGAATTCGAATACAGACT | 41 | GACCAGAGAATTCGAATACAGATG | 57 |
| GACCAGAGAATTCGAATACAGCCT | 42 | GACCAGAGAATTCGAATACAGCTG | 58 |
| GACCAGAGAATTCGAATACAGGCT | 43 | GACCAGAGAATTCGAATACAGGTG | 59 |
| GACCAGAGAATTCGAATACAGTCT | 44 | GACCAGAGAATTCGAATACAGTTG | 60 |
| GACCAGAGAATTCGAATACATACT | 45 | GACCAGAGAATTCGAATACATATG | 61 |
| GACCAGAGAATTCGAATACATCCT | 46 | GACCAGAGAATTCGAATACATCTG | 62 |
| GACCAGAGAATTCGAATACATGCT | 47 | GACCAGAGAATTCGAATACATGTG | 63 |
| GACCAGAGAATTCGAATACATTCT | 48 | GACCAGAGAATTCGAATACATTTG | 64 |

The application of a single group of adaptors (i.e., a universal amplification sequence, a sample-specific code, and a set of random tags; also referred to as a multifunctional adaptor module) with a single amplification sequence on both ends of the genomic fragment has several significant advantages, including the fact that the same genomic fragment is tagged independently on its two ends. As described in the next few sections, the two strands of any given fragment are eventually separated from one another and will behave in the present invention as independent molecules. Therefore the presence of two different tags at the two ends of the same fragment becomes an advantage rather than a liability of the present invention. Additionally, there is the fact that adaptor-to-adaptor ligation events are a huge problem in next-generation library construction where the initial goal is to create amplicons with dissimilar ends. Using the methods of the present invention, the methods introduce this asymmetry later in the process and therefore identical ends are acceptable with the present invention. An unforeseen and surprising benefit of the present methods is that adaptor dimers are not observed in the library construction methods of the present invention. While not being bound by theory, present inventors contemplate that this may be because the rare adaptor dimer species that are formed rapidly form tight hairpin structures during the steps of denaturation and annealing that are necessary for PCR amplification and it is further contemplated that these hairpin structures are completely resistant to further primer-directed amplification.

The ability to make adaptor-dimer free libraries is a significant technical feature in extremely low input applications like single-to-few cell genomic analysis, circulating DNA analysis (as in fetal diagnostics, tissue transplantation rejection surveillance, or cancer screening applications) or single cell transcriptome analysis. As such, the present methods provide significant utility in such applications. An additional significant feature of single-primer amplicons is that it is possible to "turn on" amplification with a PCR primer of 25 nt and to "turn off" amplification with a longer 58 nt primer. This is described in more detail, and the significance to the present invention is highlighted, in section 6-5 below.

Overall

The adaptor strategy in which a single universal amplification sequence is used on both ends of target fragments eliminates issues with adaptor dimer. This is clearly demonstrated by way of example in Example 3: Construction of single-adaptor genomic library.

Section 3: Library Quantification

An additional aspect of the present methods for genomic analysis strategy is that the "coverage depth" is known, that is, the average number of genomic copies present in a library are known or can be determined. The cover depth is measured using purified ligation reactions prior to the bulk amplification of the library that is necessary for subsequent steps. By way of illustration, if 50 genomes worth of DNA is put into the library scheme of an embodiment of the present invention and there is 100% efficient ligation of adaptors to both ends of the fragments, then the coverage depth is 100 because each adaptor end acts independently of the other, then 2 ends times 50 genomes=100 in coverage. The simple fact that adaptor-dimers do not amplify with the universal PCR primer contemplated herein but fragments adapted on both ends do means that library quantitation will simply be a matter of measuring library complexity with quantitative PCR (qPCR) using universal primer and calibrating the results against standards with known coverage depth. Here the phrase "genome copies" and "coverage depth" mean the same thing and may be used interchangeably. The present methods will carry forward anywhere from 4-1000, preferably 20-100 fold coverage depth into the next phase of sample processing according to the present invention.

Section 4: Library Amplification

In particular embodiments, a portion of the adaptor ligated genomic fragment library equivalent to 20-100 fold coverage depth will be amplified using standard PCR techniques with a single, universal primer sequence driving amplification. At this stage it is advantageous, in particular embodiments, to convert the picograms of material in the initial library into micrograms of amplified material, implying a 10,000-fold amplification.

Section 5: Hybridization of Target Library Fragments to Capture Probes

Figures 2A, 2B:
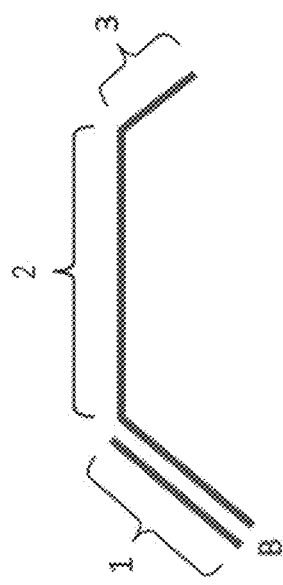
FIG. 2A-FIG. 2B: Genomic capture probe design.
Figure 4A:
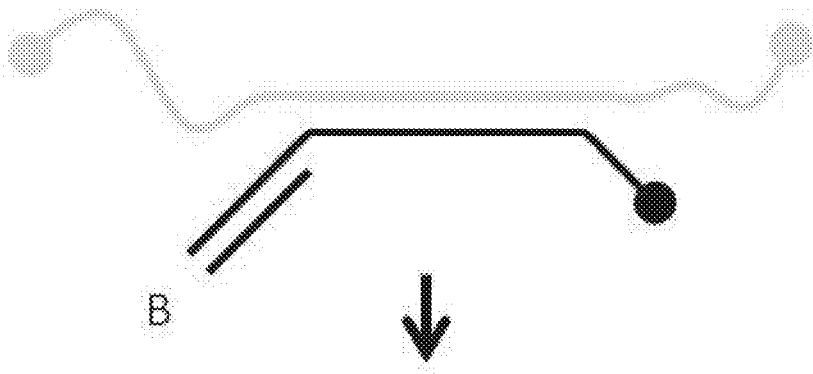
FIG. 4A-FIG. 4D: Enzymatic processing of fragment: probe hybridized complexes.
Figure 4B:
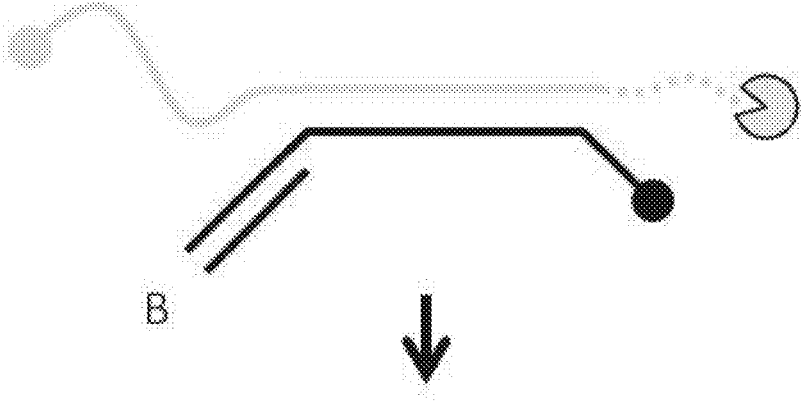
Figure 4C:
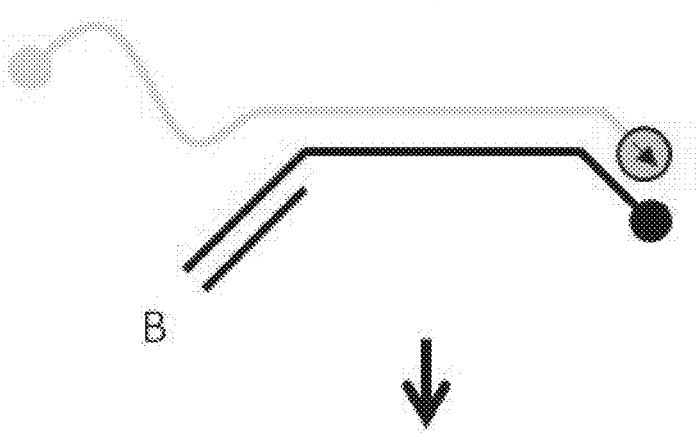
Figure 4D:
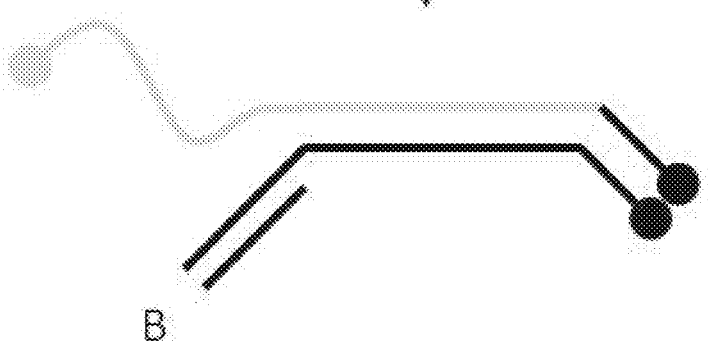

Advances in oligonucleotide synthesis chemistries have created new opportunities for sophisticated genome capture strategies. In particular, the availability of long oligonucleotides (100-200 nt in length) that have reasonable per base synthesis costs, relatively high yields, and exquisite base accuracy are now commercially available from a variety of vendors. This capability has the present inventor to create multifunctional capture probes (FIG. 2). The elements of an illustrative example of a multifunctional capture probe comprises:

Region 1 comprises a 34 nt region common to all probes that hybridizes to a modified complementary oligonucleotide (also referred to as a partner oligonucleotide). This modified oligonucleotide further comprises on the 5' end a biotin—TEG modification that is a biotin capable of binding tightly to streptavidin protein, a long hydrophilic spacer arm that alleviates steric hindrance of biotin binding. On the 3' end, the oligonucleotide terminates with a dideoxy-cytosine residue that renders this partner oligonucleotide inert to primer extension. This element of probe design allows for adapting an unlimited number of probes with biotin capture functionality without having to directly modify said probes.

Region 2 comprises custom 60 nt regions that are target-specific and that interact with gDNA fragment molecules. This region is designed by computational methods that account for uniqueness of sequence within the genome, the presence of common SNPs that may compromise binding efficiency, and secondary structure considerations.

Region 3 comprises a 20 nt segment that will serve as a PCR primer binding site in subsequent fragment amplification. This feature is described in further detail in the next paragraph.

A multiplicity of probes can be used to capture genomic regions of interest (multiplexing of probes). At least two probes may be employed to thoroughly query a typical coding exon of 100-150 bp in length. By way of example, this indicates that 20 probes will be used to capture a typical 10 exon gene and a total of 2000 probes will be used to interrogate a 100 gene panel. The hybridization of genomic library fragments to probes can be performed by thermal denaturation followed by reannealing. In one embodiment, the steps comprise:

1. Combining genomic library fragments with pooled probe sequences (in this case "probe sequences" refers to the combination of individual probes together with an equal molar quantity of the highly modified partner oligonucleotide) at a specific target to probe ratio ranging anywhere from 1 part target to 1 part probe to 1 part target to 1,000,000 parts probe. In one embodiment, the optimal ratio is about 1 part fragment to 10,000 parts probe.
2. Heating the combined fragment+probe in a solution containing 1M NaCl, 10 mM Tris pH 8.0, 1 mM EDTA and 0.1% Tween 20 (non-ionic detergent) to 95° C. for >30 sec to denature all double-strand DNA structure.
3. Cooling the combined probe and fragment in controlled steps, for example 1° C. decrease in temperature every 2 minutes, down to <60° C. This slow cooling will result in duplexes between target genomic fragments and probe sequences.
4. Binding of the probe: fragment complexes to carboxyl coated, streptavidin modified paramagnetic beads and "pull out" of these beads using a strong magnet.
5. Washing of the bound complexes with a solution containing 25% (v/v) formamide, 10 mM Tris pH 8.0, 0.1 mM EDTA and 0.05% Tween 20. In particular embodiments, the wash step is performed at least twice.
6. Resuspension of the washed beads in a solution that is amenable to the subsequent enzyme processing step(s).

Capture Reactions: Embodiments of the capture reaction are demonstrated in Example 3 (Construction of single-adaptor genomic library) and employ qPCR assays developed and further described in Example 5 (Validation of PLP1 qPCR assays).

Section 6: Enzymatic Processing of Hybridized Probe: Target Complexes

As currently practiced in the art, hybridization-based sequence capture methods generally result in a suboptimal enrichment of target sequences. From literature and commercial publications it can be estimated that, at best, about 5%-10% of reads map to their intended target sequences. The remaining reads often map near the intended target and commercial vendors have resorted to redefining "on-target" as reads that land anywhere within ~1000 bases of the intended locus. The reasons for this "spreading" effect are incompletely understood, but they are likely a result of legitimate sequence hybridization events (see, e.g., FIG. 3).

Figures 6A, 6B:
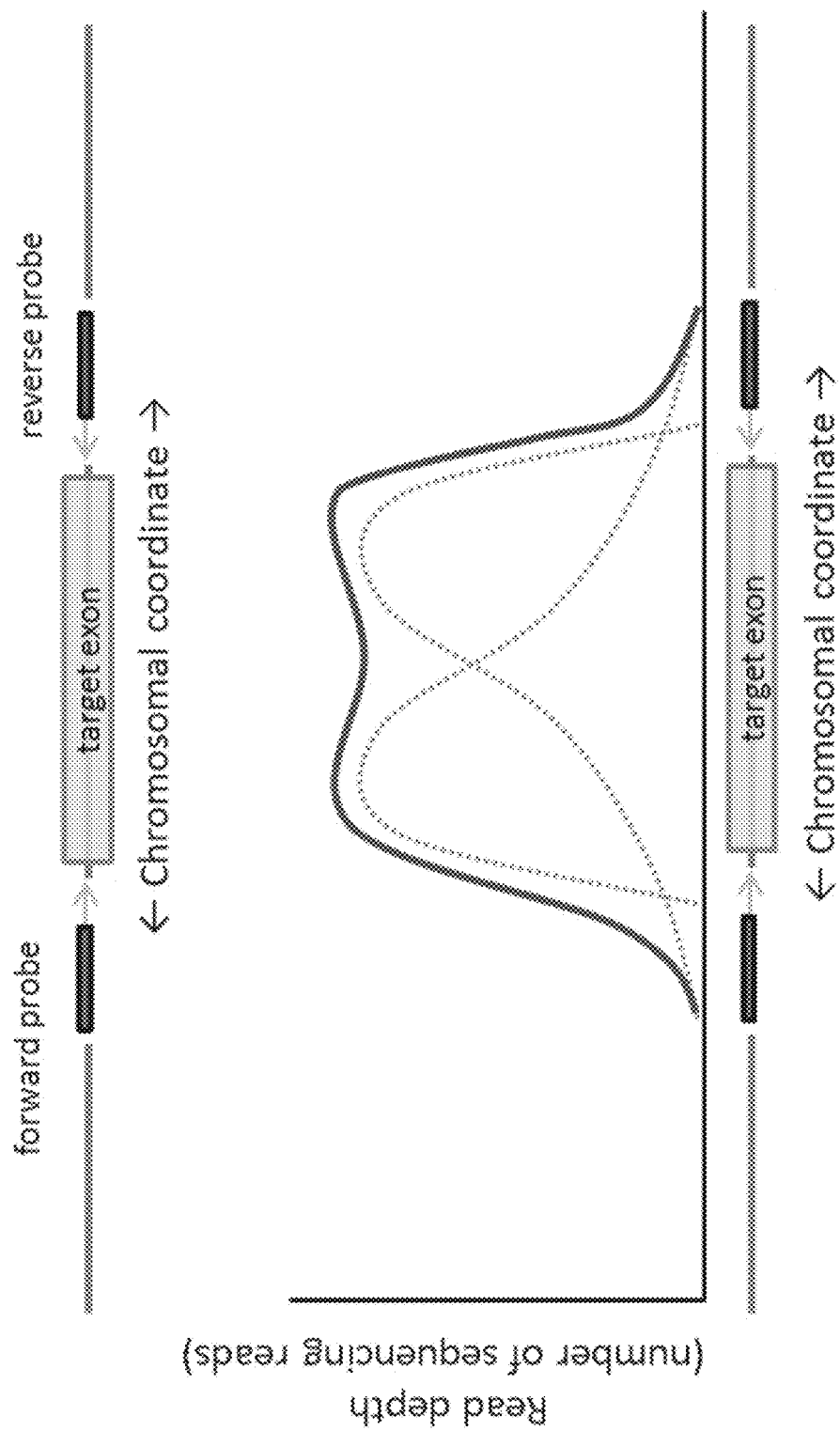
FIG. 6A-FIG. 6B: The "focusing effect" of directional probes.

The enzymatic processing of complexes as contemplated herein more sharply focuses the captured sequences on the exact regions of interest. In this step, a DNA polymerase that also possesses a 3' to 5' exonuclease activity is employed. An illustrative example of such an enzyme is T4 DNA polymerase. This enzyme will "chew off" dangling tail sequences down to the duplex region formed between the probe and target sequence. It will then copy the tail segment on the probe. See, e.g., FIG. 4. Benefits provided by this step include, but are not limited to:

1. By employing this type of enzymatic processing, only those fragments that were in direct, duplexed hybridization with probe will be carried forward. The final sequencing library is a chimeric (hybrid) set of molecules derived from both the fragment and the probe.
2. The probe is strand-specific and therefore the captured target has an inherent directionality to it (illustrated in FIG. 5). This means that only one of two strands generated from a single fragment will interact with probe, and processing will "focus" reads to a region 5' of the probe sequence. At this point, the complementary strand of the fragment becomes a completely independent species. By placing directional probes on either side of a target region (e.g. an exon), the technology enables highly specific focusing of sequencing reads on target regions (FIG. 6).
3. Target molecules that are legitimately cross-hybridized with target fragments (but not with probe; FIG. 3) do not acquire essential probe sequence and are therefore lost in the subsequent amplification step.
4. The actual "tail" sequence of the probe becomes copied into target fragments as part of the amplification sequence. All commercially practicable sequencing platforms (e.g. Illumina's reversible terminator chemistry sequencing platforms) require sequencing libraries in which the target fragments have asymmetric ends; this is often referred to as a "forward" and a "reverse" adaptor sequence, or in the shorthand of sequencing labs, "P1" and "P2". In particular embodiments, up to this point, fragment libraries contemplated herein have a single species on the end; called "P1". The enzymatic processing step achieves two things. First, it "erases" (by 3' to 5' exonuclease activity) one of these P1 ends. Second, it "adds" (by DNA polymerase copying of the probe tail sequence) the basis of a P2 end that is dissimilar from P1.
5. Enzymatically-modified target molecules with legitimate P1-P2 ends can be selectively enriched in the PCR amplification step that follows processing. This is achieved by the use of long PCR primers. In particular long primers are necessary to add the full functionality required for next-generation sequencing, and they also confer selectivity to amplification. Residual P1-P1 library fragments that are "contaminants" from the first round of amplification fail to amplify with longer P1 primers. This is a significant advantage of the present method. The initial P1-P1 library amplifies effectively with a single, 25 nt PCR primer. When this primer length is extended to 57 nt—to add sequencing functionality—these same P1-P1 molecules are not amplified to any appreciable extent. Therefore amplification of the initial library can be "turned on" with a 25 nt primer and "turned off" with a 57 nt primer.

Overall

The inability of P1-insert-P1 libraries to amplify is demonstrated Example 3 (Construction of single-adaptor genomic library). The preferential amplification of P1-insert-P2 processed DNA fragments is shown in Example 3 (Construction of single-adaptor genomic library). Example 3 further demonstrates the substantial improvement in target specificity that accompanies processing. Finally, the "sensitivity" of processing, meaning the percent of initial complexes that are processed, is demonstrated to be on the order of 10% of all captured complexes in Example 9 (Direct measurement of post-capture processing).

Section 7: Amplification and Sequencing

The core adaptor and primer sequences applied to initial proof-of-concept experiments are shown in Table 2. Enzymatically processed complex from step 6 is added directly to a PCR amplification reaction that contains full-length forward and reverse PCR primers. Following amplification, the library can be purified, quantified, loaded on a high-throughput, next-generation sequencer (in this embodiment, the libraries are configured for the Illumina reversible terminator-based platforms), and the sequence of ~millions of fragments is determined. At this stage, single reads of >36 nt, preferably 72 or 100+ nt in length can be observed.

TABLE 2

Genesis of primer sequences

| Description | Sequence (5' to 3') | SEQ ID NO: |
|---|---|---|
| Forward amplification primer for full-length library. | AATGATACGGCGACCACCGA | 65 |
| Forward primer sequence present on Illumina's paired-end (PE) flow cell. | AATGATACGGCGACCACCGAGATCTACAC | 66 |
| Non-palindromic 4mer of all four bases. This was added to make the read 1 sequencing primer the same length and position as the Illumina standard. | GTCA | |
| ACA2. PCR primers ACA2 and CAC3 predate NuGEN | TGCAGGACCAGAGAATTCGAATACA | 67 |
| ACA2 forward sequencing primer (FSP)- read 1 | ACACGTCATGCAGGACCAGAGAATTCGAATACA | 68 |
| ACA2 full length forward amplification primer (FLFP). Final length = 58 nt. | AATGATACGGCGACCACCGAGATCTACACGTCATGCAGGACCAGAGAATTCGAATACA | 69 |
| Reverse amplification primer for full-length library. | CAAGCAGAAGACGGCATACG | 70 |
| PE flow cell reverse primer | CAAGCAGAAGACGGCATACGAGAT | 71 |
| These are the nine 5' bases from the TruSeq Reverse adaptor that were inserted to create a read 2 primer site | GTGACTGG | |

TABLE 2-continued

Genesis of primer sequences

| Description | Sequence (5' to 3') | SEQ ID NO: |
|---|---|---|
| CAC3 reverse primer | CACGGGAGTTGATCCTGGTTTTCAC | 72 |
| CAC3 reverse sequencing primer (RSP)-read 2 | GTGACTGGCACGGGAGTTGATCCTGGTTTTCAC | 73 |
| CAC3 full length reverse primer (FLRP). Final length = 57 nt. | CAAGCAGAAGACGGCATACGAGATGTGACTGGCACGGGAGTTGATCCTGGTTTTCAC | 74 |

Section 8: Data Analysis.

There are at least two major aspects to post-sequencing data analysis. The first is the identification of sequence variants—single nucleotide variants, micro-insertions and/or micro-deletions relative to an established set of reference sequences. While complex, these methods are well documented in the field and one of skill in the art would understand such methods. The second is the determination of copy number variation from the targeted sequencing data.

Example 2: Copy Number Determinations

Copy number determination finds a variety of uses in the field of DNA sequencing. By way of non-limiting example, massive parallel DNA sequencing technologies provide at least two opportunities to interrogate and analyze biological samples. One well-established aspect is determination of DNA sequences, meaning the de novo sequences present in the sample (e.g., the sequencing of a newly isolated microbe) or the resequencing of known regions for variants (e.g., the search for variants within known genes). A second aspect of massive parallel sequencing is quantitative biology and the ability to count the number of times a particular sequence is encountered. This is a fundamental aspect of technologies like "RNA-seq" and "CHIP-seq", where counting is used to infer gene expression or the association of a particular protein with genomic DNA, respectively. This example relates to the quantitative, counting-based aspects of DNA sequencing.

DNA fragments are most often counted as constellations of sequences that share high degrees of similarity (i.e., they align to specific regions of a known genomic sequence). Often the sequences within these clusters are identical. Note that DNA sequences with either a) different starting and ending DNA sequence reads or b) with high quality sequence differences from other reads within the set are most often considered "unique reads". Thus, different starting sequence location and sequence variation are one form of "tagging" that is used to differentiate unique events from clones. In the present example, random nucleotide tags (e.g., random six nucleotide sequences) are also introduced onto genomic fragments during the course of library construction. The combination of 1) the random nucleotide tag sequence with 2) the start point of the DNA sequencing read and 3) the actual sequence of the read collectively make up a tag. This tag enables one to differentiate between convergent events where the same fragment was cloned twice (such fragments will have different random nucleotide tag sequences that were introduced during library construction) and fragments of the same origin that were replicated during library amplification (these "clones" will have the same random nucleotide segment and the same clone start points). This type of tagging further enables quantitative analysis of genomic DNA specifically, and populations of DNA molecules (e.g., RNA-seq libraries) more generally.

The introduction of random nucleotide tags (random Nmer combined with DNA clone ends) into DNA sequencing libraries allows, in theory, each unique clone within the library to be identified by its unique tag sequence. The specification of "in theory" acknowledges confounding features of ordinary experimental data sets that may occur such as errors in sequencing, errors introduced during library amplification, introduction of contaminating clones from other libraries, etc. All of these sources can and will confound the theoretical consideration posed here. In the context of sequence capture and targeted resequencing, the tagging of libraries can enable quantitative analysis of locus copy number within a captured library.

Consider, by way of non-limiting example, a library constructed from the equivalent of 100 diploid genomes of input that was created from a male subject. The prediction is that approximately 200 library clones will be present at each autosomal locus, and 100 clones will be present at each X-chromosome locus. If an autosomal region is captured and sequenced 2000 times, then all 200 tags will be encountered with a confidence interval exceeding 99% certainty. For the X-chromosomal region, 2000 reads would, in theory, reveal a total of 100 tags. By way of illustration, this example supports the general concept that the creation of DNA tags within a DNA sequencing library can preserve copy number differences. This general framework can be applied to the methods described herein. Empirical evidence suggest that adjustments may need to be made for differences in cloning efficiencies on a locus-by-locus basis, for sporadic introduction of artifactual tags from experimental error, etc. The implementation of this concept into practice may differ in different contexts and may involve case-by-case sequence analysis methods, but the general principle outlined here will underlie all such applications.

To this point, the creation of tagged DNA libraries has been considered in the context of genomic DNA analysis, yet it must be emphasized that this concept applies to all counting-based DNA sequencing applications. In particular embodiments, tagging may be applied to RNA-seq, where cDNA molecules produced from mRNA of a sample are cloned by methods that create tags. Such approaches may substantially increase the fidelity of sequence-based gene expression analysis. In certain embodiments, it is contemplated that tagging can increase the resolution of chromatin immunoprecipitation (CHIP-seq) experiments. In various embodiments, tagging will enhance the quantitative aspects of sequence counting used to determine the presence and abundance of microbes in microbiome compartments and environmental samples.

Example 3: Construction of Single Adaptor Genomic Library

Purpose: The goal of this example was to create a genomic DNA library from acoustically fragmented Pro-Mega female hgDNA (~200 bp).

Summary: The results clearly demonstrated the significant features of the present methods for adaptor design. In particular, the adaptor-alone ligation reaction had no detectable adaptor dimer species present. This was very significant in the context of extremely low input sequencing library preparation technology, as with current methods, the limits of input are invariably determined by the background levels of adaptor dimer. Highly specialized technologies have been applied in attempts to keep adaptor dimer contamination in check. These include size exclusion methods such as columns or gel purification, expensive custom oligonucleotide modifications designed to minimize adaptor self-ligation events, and adaptor sequence modifications that allow for restriction digestion destruction of adaptor dimers following library construction.

The simple, single adaptor, single primer concept contemplated herein addresses the adaptor dimer issue with a simple solution that evokes the basic principles of DNA structural principles. This extremely low input technology will be useful for the construction of genomic libraries for genomic analysis, for transcriptome analysis of cloned double-stranded cDNA as, for example, in RNA-seq applications of one or a few specific cells, and in rescuing the few intact fragments that may be present in a highly modified, poorly preserved formalin-fixed, paraffin-embedded (FFPE) nucleic acid sample.

Another essential feature of the adaptor design of the present invention is the ability to "turn on" and "turn off" PCR amplification of the target amplicon library by using different PCR primer lengths. As has been clearly demonstrated, the optimal primer length for library amplification was 25 nt primer species with a projected Tm (under standard ionic strength conditions)≥55° C. A shorter, lower Tm primer displayed less efficient amplification of and appeared to favor amplicons with smaller average insert sizes. There is ample precedent that primers in this size class work well when paired with opposite primers of dissimilar sequence.

Taken together, these data demonstrated that the adaptor and PCR amplification methods of the present invention produce adaptor-dimer-free fragment libraries with "tunable, on/off" amplification properties.

Methods

Hydrated primers that were received from IDT to 100 μM in TEzero (10 mM Tris pH 8.0, 0.1 mM EDTA).

Fragment repair: Thawed gDNA and 500 ng gDNA was end repaired by combining:

14 μL water
5 μL hgDNA
2.5 μL 10× end repair buffer
2.5 μL 1 mM dNTPs
Mix and add 1 μL end repair enzyme and 0.5 μL PreCR enzyme repair mix.

The mixture was incubated at 20° C. for 30 min and 70° C. for 10 min; and held at 10° C.

Adaptor annealing: Combined 68 μL of TEzero, 2 μL of 5M NaCl, 20 μL of oligo 11 and 10 μL of oligo 12. Heated to 95° C. for 10 sec, 65° C. for 5 min and cooled to RT.

TABLE 3

Adapter sequences Adap_P23 and Adapt_L23

| SEQ ID NO: | Oligo ID | Name | Sequence | Description |
|---|---|---|---|---|
| 75 | 11 | Adap_P23 | TCCGTGTATTCGAAT | Number 23 of the initial 64 adapter set, partner strand |
| 23 | 12 | Adap_L23 | GACCAGAGAATTCGAATACACGGA | Number 23 of the initial 64 adapter set, ligation strand |

Ligations: Combined in a total volume of 20 μL; 1=no insert, 2=100 ng end-repaired hgDNA.

13 μL or 8 μL water
0 or 5 μL end-repaired fragment=100 ng.
2 μL 10× T4 ligase buffer
3 μL 50% PEG8000
1 μL 10 μM ACA2 adaptor #23 duplex
Mix and add 1 μL of T4 DNA ligase Incubated at 23° C. for 30 min and 65° C. for 10 min. Added 80 μL/rxn of TEz and 120 μL of beads. Mixed and incubated at RT for 10 min. Washed twice with 200 aliquots of 70% EtOH:water v/v and resuspended in 50 μL of TEz.

PCR amplification: Each 10 μL aliquot of ligation mix=20 ng of library. Planned to amplify for 18 cycles.

TABLE 4

Reaction mixtures

| | 100 μL | 600 μL |
|---|---|---|
| Water | 50 | 300 |
| 10X STD Taq buffer | 10 | 60 |
| 25 mM MgCl$_2$ | 10 | 60 |
| 10 μM PCR primer | 10 | 60 |
| Template | 10 | 60 |
| DMSO | 5 | 30 |
| 10 mM dNTPs | 5 | 30 |
| Taq polymerase | 1 | 6 |

Made 600 μL mix containing all components except primer and template. Made 6 of 80 μL aliquots. Added 10 μL no insert ligation to set 1 and 10 μL of hgDNA insert to set 2. Added 10 μM primer of the primers shown below in pairs to the no insert and hgDNA insert ligation mixes. Mixed. Thermal cycled for 18 cycles of 94° C.-30 sec, 60° C.-30 sec and 72° C.-60 sec; finish for 2 min at 72° C. and held at 10° C.

TABLE 5

Primer sequences

| SEQ ID NO: | Oligo ID | Name | Sequence |
|---|---|---|---|
| 76 | 3 | ACA2_20 | GACCAGAGAATTCGAATACA |
| 77 | 5 | ACA2 | TGCAGGACCAGAGAATTCGAATACA |
| 78 | 8 | ACA2_FLFP | AATGATACGGCGACCACCGAGATCACACGTCATGCAGGACCAGAGAATTCGAATACA |

Purified PCR product with 120 µL of beads. Washed twice with 200 µL of 70% EtOH. Dry beads and elute DNA with 50 µL of TEz. Analyzed 5 µL of each sample on a 2% agarose gel.

Results

Figure 7:
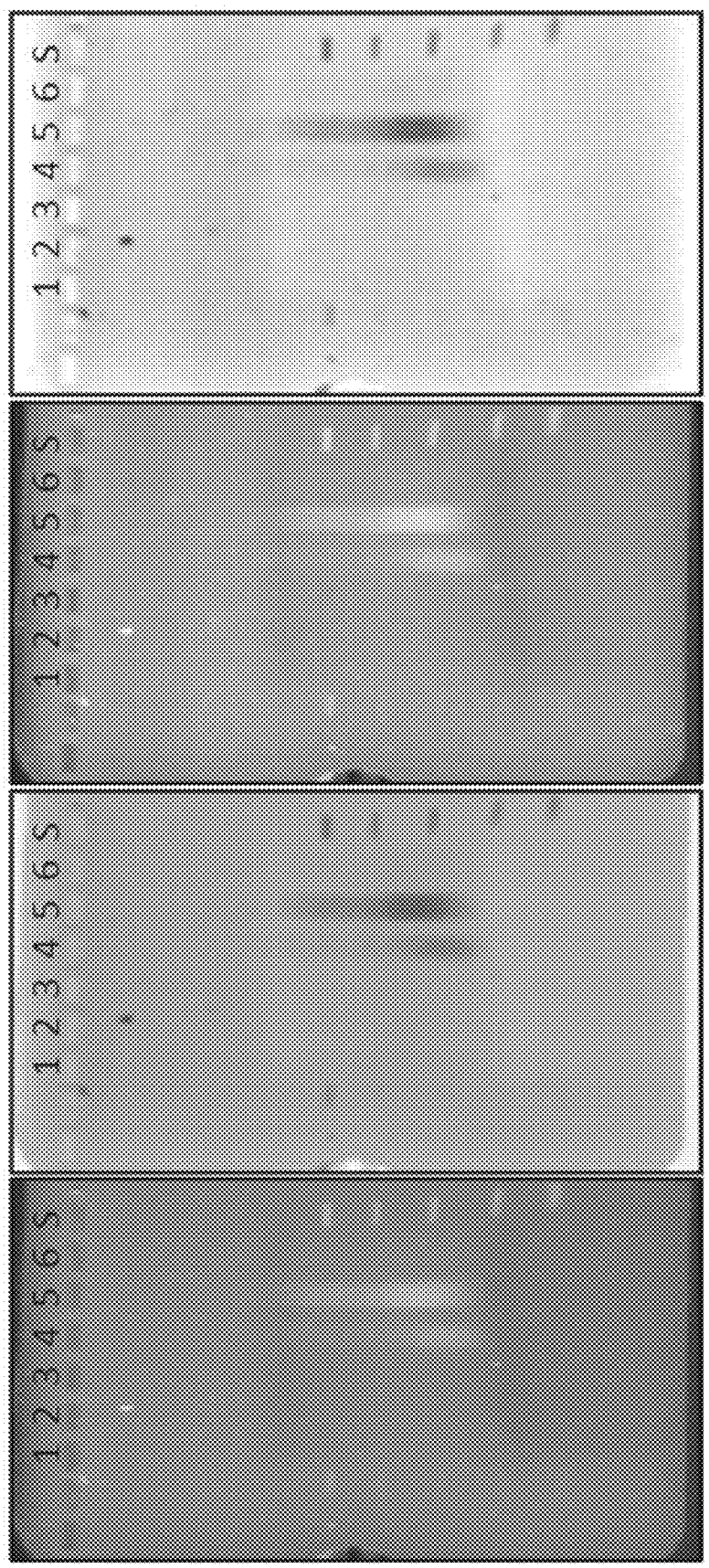
FIG. 7: Demonstration of adaptor-dimer-free fragment libraries with "tunable, on/off" amplification properties. The exact same gel image is shown in four different color and contrast schemes. The samples were: (1) no insert, adaptor-only ligation amplified with ACA2 20; (2) no insert, adaptor-only ligation amplified with ACA2 (normal 25 nt PCR primer); (3) no insert, adaptor-only ligation amplified with ACA2 FLFP (full length forward primer); (4) 20 ng of ~200 bp hgDNA insert+adaptor ligation amplified with ACA2 20; (5) 20 ng of ~200 bp hgDNA insert+adaptor ligation amplified with ACA2 (normal 25 nt PCR primer); and (6) 20 ng of ~200 bp hgDNA insert+adaptor ligation amplified with ACA2 FLFP (full length forward primer). No amplified material was visible in the adaptor alone ligation→PCR products (lanes 1-3). The shorter, 20 nt ACA2 primer showed inefficient amplification (lane 4) relative to the "normal", 25 nt ACA2 primer (lane 5). Only the faintest trace of material was visible with the 58 nt ACA2 FLFP primer (lane 6).

The exact same gel image is shown in four different color and contrast schemes in FIG. 7. The samples loaded on the gel were:
1. No insert, adaptor-only ligation amplified with ACA2 20
2. No insert, adaptor-only ligation amplified with ACA2 (normal 25 nt PCR primer)
3. No insert, adaptor-only ligation amplified with ACA2 FLFP (full length forward primer)
4. 20 ng of ~200 bp hgDNA insert+adaptor ligation amplified with ACA2 20
5. 20 ng of ~200 bp hgDNA insert+adaptor ligation amplified with ACA2 (normal 25 nt PCR primer)
6. 20 ng of ~200 bp hgDNA insert+adaptor ligation amplified with ACA2 FLFP (full length forward primer)

It was clear that there was no amplified material in the adaptor alone ligation→PCR products (lanes 1-3). The shorter, 20 nt ACA2 primer showed inefficient amplification (lane 4) relative to the "normal", 25 nt ACA2 primer (lane 5). Only the faintest trace of material was visible with the 58 nt ACA2 FLFP primer (lane 6).

In further embodiments, it may be useful to titrate in the amount of the ACA2 primer and monitor yield. Normal high-yield PCR primers possess 1 µM of both the forward and reverse primers for a total of 2 µM in primer (per 100 µL PCR reaction). Therefore, addition of ACA2 to 2 µM (since it is both the forward and reverse primer) may increase yield. Similarly, in particular embodiments, it may be useful to monitor amplification characteristics of libraries at primer annealing temperatures lower than 60° C.

Example 4: Fragmentation of gDNA

Purpose: For initial proof-of principle experiments sheared human gDNA from male and female was needed. The present example employs human female and male gDNA from Promega. Based on quantities shown on the tubes, these were diluted to 1000 µL of 100 ng/DNA and subjected them to Covaris conditions that were intended to generate fragments in the range of 200 bp.

Summary: There are at least two components to the laboratory research infrastructure. One is the ability to quantify DNA, and the other is the ability to visualize the size distribution of DNA on gels. In the present example, the Qubit 2.0 instrument from Life Technologies was employed to measure DNA concentration. It was found that the readings recorded were generally lower than our previous experience with Nanodrop. The Qubit reading was based on dsDNA-specific dye binding and fluorescence. One major advantage of the Qubit is that it can be used to quantify DNA amplification reactions (e.g. PCR) without prior clean-up. In these experiments it was found that the Promega gDNA thought to be 100 ng/µL was measured at ~60 ng/µL by Qubit. With respect to gels and qualitative assessment of size distribution, there was electrophoresis and documentation that the system that worked effectively. In the present example, fragmented gDNA was found to have a mean size distribution centered on the desired ~200 bp.

Figure 8:
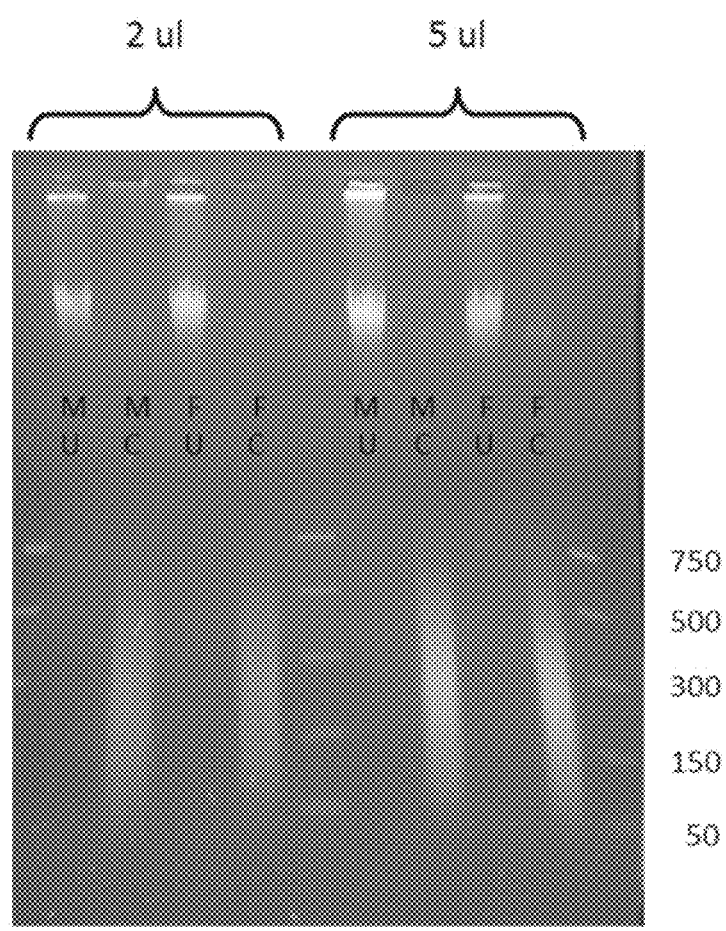
FIG. 8: Even distribution of average fragment size following Covaris fragmentation of gDNA. Male (M) and female (F) human gDNA (received from Promega Corporation, Madison, Wis., USA) was sheared via Covaris conditions, and 24, (~120 ng) or 54, (~300 ng) of the pre-fragmented (U) or the post-fragmented (C) samples were loaded on a 2% agarose gel. The average fragment size was an even distribution centered around 200 bp.

Methods and Results: After Covaris treatment, DNA concentrations were measured using the Qubit instrument. The gDNA was diluted 10-fold, and 2 µL were added to 200 µL final volume of assay solution. The reading for both female and male samples registered at ~60 ng/mL, meaning the starting solutions are 60 ng/µL. While this was below what was initially anticipated, it was well within the appropriate range for particular embodiments. We then loaded 2 (120 ng) and 5 (300 ng) of both pre-fragmented and post-fragmented material on a 2% agarose gel (FIG. 8). In the top row, the labels stand for M—male gDNA and F—female gDNA. In the bottom row, the labels are U—unfragmented and C— Covaris fragmented. One important observation was that the average fragment size was an even distribution centered around 200 bp.

Example 5: Validation of PLP1 qPCR Assays

Purpose: The proteolipid protein 1 (PLP1) gene on chromosome X was examined for initial proof-of-concept capture studies. This gene was chosen because it is relevant to cancer and resides on the X chromosome, meaning it has a natural copy variation between males and females. The 187 nt exon 2 region of Ref-Seq transcript NM000533.3 of PLP1 was used as the target region. For proof of principle studies, the ability to monitor regions in and around PLP1 exon2 by qPCR was needed. This example provides description of the design and validation of eight such assays.

Summary: Eight qPCR assays were designed (in this case, meaning simple primer pairs) to monitor PLP1 exon 2 capture. Five were on-target, meaning they are within a region targeted by capture probes. Two are "near-target," meaning one assay is positioned at a genomic coordinate 200 bp of the target region and one assay is positioned 1000 bp from the target region on the opposite strand. These two assays were designed to quantify "spreading", the phenomenon where region near-by the target locus are pulled along as "hitch-hikers" in capture experiments. Finally, one assay was designed against a region of chromosome 9, and it is designed to monitor an arbitrary and unrelated segment of human gDNA. Here, the example shows that all eight assays produce a PCR fragment that is consistent with the predicted sizes of the amplicons. The example showed that the PLP1 assays, which were situated on chromosome X, appropriately had higher specific activities per ng of input gDNA in females than in males. These data validated the use of these assays in further experiments to monitor gDNA capture.

Method, Results, and Discussion: A 400 bp region centered around the PLP1 exon 2 was submitted to PRIMER3 for generation of amplicons that were 80-100 bp in length, for primers that were 24 nt in length, on average, and that had Tms of 60°-65° C. The search region was manipulated to obtain primer pairs (qPCR amplicons) that "walk" from the 5' intron-exon boundary of exon 2 through the CDS and into the 3' exon-intron boundary. Nearby, proximity capture assays were also designed that were distal to exon 2, toward exon 3, and positioned ~200 nt and ~1000 nt away from exon 2. These would be used to monitor "hitchhiker" genomic fragments that are captured in secondary hybridization events. Finally, one assay was created on chr9 to monitor bulk genomic DNA levels during experiments. The primer sequences of these assays are shown below and the details are appended to the end of this example.

template. These were then amplified by real-time PCR on the Illumina Eco instrument or by conventional PCR. The reasoning was that by qPCR, female should have slightly more PLP1 (chrX) signal than male. By conventional PCR, we were able to check amplicon size and uniqueness. Both tests yielded data consistent with the interpretation that all eight assays performed well.

PCR reaction set up: For each female or male PCR reaction, a 250 μL master mix was made on ice containing:
100 μL of water
25 μL of 10×STD Taq buffer
25 μL of 25 mM MgCl2
25 μL of 60 ng/μL sheared gDNA (female and male were the same concentration by Qubit)
12.5 μL DMSO
12.5 μL 10 mM dNTPs
6.25 μL EvaGreen dye (Biotum)

TABLE 6 qPCR primer sequences "walking" the 5' introns-exon boundary of PLP1 exon 2 through the CDS

| Assay | SEQ ID NO: | Name | Sequence | Description |
|---|---|---|---|---|
| Assay 1 | 79 | F1 | TTAGAGTGCTGTGCAAGATGTCTG | Forward qPCR primer that sits within PLP1 exon2 |
|  | 80 | R1 | ACCCCAAAGAAACACAATCCAGT | Reverse qPCR primer that sits within PLP1 exon2 |
| Assay 2 | 81 | F2 | GCCACTGGATTGTGTTTCTTTG | Forward qPCR primer that sits within PLP 1 exon2 |
|  | 82 | R2 | TCAATTAGCTTTTCTGTGCCAGTG | Reverse qPCR primer that sits within PLP1 exon2 |
| Assay 3 | 83 | F3 | ACTGTTCTGTGGCTGTGGACAT | Forward qPCR primer that sits within PLP1 exon2 |
|  | 84 | R3 | TCTTGGTAGTTTTTGGAGAAATAGGTC | Reverse qPCR primer that sits within PLP1 exon2 |
| Assay 4 | 85 | F4 | ttcttcttccccagGCTTGTTAGA | Forward qPCR primer that sits within and flanks upstream region of PLP1 exon2 (lower case). |
|  | 86 | R4 | CACCCCAAAGAAACACAATCCAGT | Reverse qPCR primer that sits within and flanks upstream region of PLP1 exon2 (lower case). |
| Assay 5 | 87 | F5 | CCCTCACTGGCACAGAAAAGCTAA | Forward qPCR primer that sits within and flanks downstream region of PLP1 exon2 (lower case). |
|  | 88 | R5 | tgggagggcaggtacttacACATT | Reverse qPCR primer that sits within and flanks downstream region of PLP1 exon2 (lower case). |
| Assay 6 | 89 | F6 | CCCCTTGTTTTCTTACACGTGTTCT | Forward qPCR primer that is 200 bp downstream of PLP1 exon2 |
|  | 90 | R6 | CCTCCCTTGGCTTCTCCATACCTA | Reverse qPCR primer that is 200 bp downstream of PLP1 exon2 |
| Assay 7 | 91 | F7 | GTGTGTCATTGTTTGGGAAAATGG | Forward qPCR primer that is 1000 bp downstream of PLP1 exon2 (actually in exon3) |
|  | 92 | R7 | CACCCCTTGTTATTGCCACAAAAT | Reverse qPCR primer that is 1000 bp downstream of PLP1 exon2 (actually in exon3) |
| Assay 8 | 93 | F8 | TACCAGCCAAGCCCATACTAGAGG | Forward qPCR primer unlinked to chrX PLP1 locus that sits in chr9 |
|  | 94 | R8 | GGGATCAACAGTGGCATAATTGAA | Reverse qPCR primer unlinked to chrX PLP1 locus that sits in chr9 |

To validate primer pair performance, PCR reactions were set-up that contained either male or female genomic DNA as 5 μL ROX dye (InVitrogen)
Mix well and add 2.5 μL Taq DNA polymerase.

TABLE 7

Cq values from PLP1 qPCR assay validation

| | Assay 1 chrX | Assay 2 chrX | Assay 3 chrX | Assay 4 chrX | Assay 5 chrX | Assay 6 chrX | Assay 7 chrX | Assay 8 chr9 |
|---|---|---|---|---|---|---|---|---|
| F | 23.27371 | 24.01229 | | 24.19554 | 22.3413 | 22.10594 | 22.65759 | 22.31407 |
| | 23.33794 | 22.49233 | 23.87286 | 22.53665 | 22.49127 | 22.19686 | 22.73586 | 22.0446 |
| | 22.33889 | 22.40355 | 23.68538 | 22.50178 | 22.23099 | 22.23099 | 22.83415 | 22.32891 |
| M | 24.00953 | 23.56869 | | 23.2648 | 23.51487 | 23.11367 | 23.65077 | 22.15477 |
| | 23.63462 | 23.48547 | 23.95081 | 23.18794 | 23.25046 | 22.93675 | 23.66965 | 21.23208 |
| | 23.77216 | 23.16852 | 24.16562 | 23.21774 | 22.93373 | 22.95635 | 23.61168 | 22.16391 |
| F | 22.98351 | 22.96939 | 23.77912 | 22.51921 | 22.42073 | 22.17793 | 22.74253 | 22.2292 |
| M | 23.80544 | 23.40756 | 24.05821 | 23.22349 | 23.23302 | 23.00226 | 23.64403 | 21.85026 |
| M − F | 0.8 | 0.4 | 0.3 | 0.7 | 0.8 | 0.8 | 0.9 | −0.4 |

Figure 9:
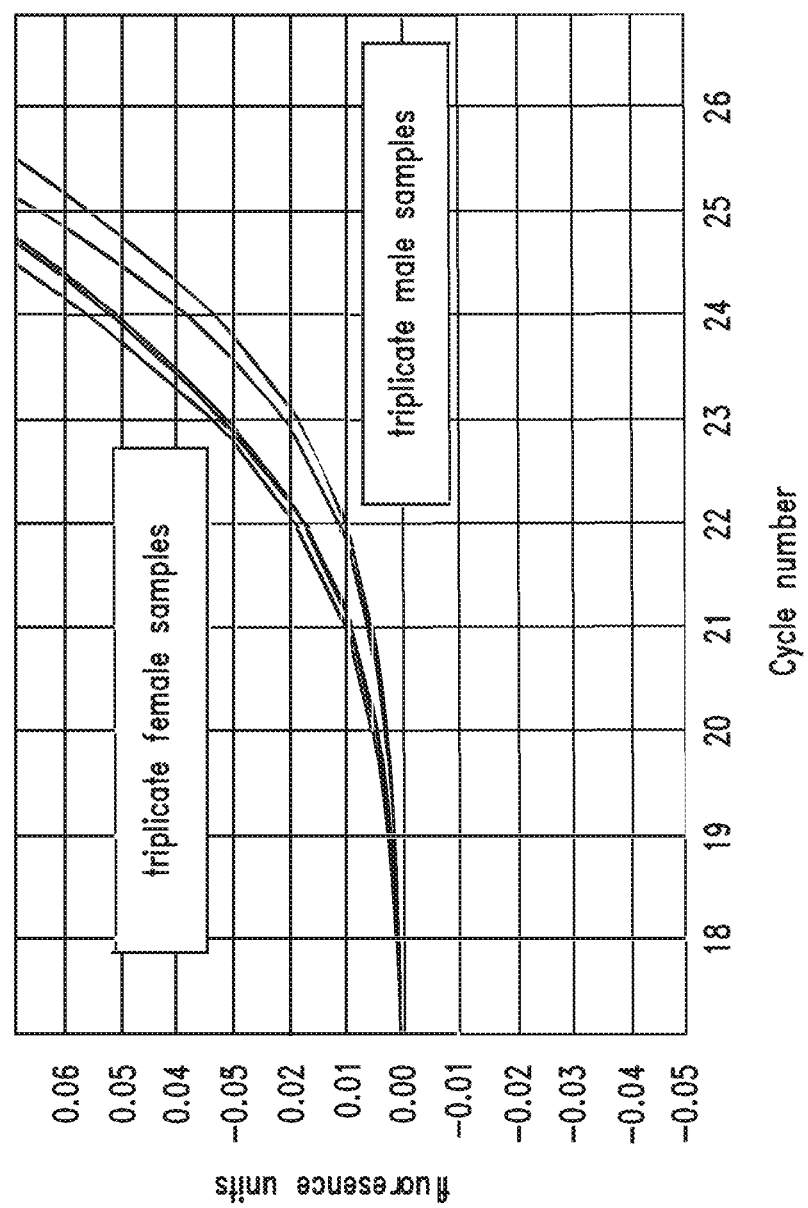
FIG. 9: Amplification traces for proteolipid protein 1 (PLP1) qPCR assay 6 demonstrating expected copy number differences between male and female samples. Triplicate male or female genomic DNA templates were amplified by real-time PCR on the Illumina Eco instrument using PLP1 qPCR assay 6. Amplification traces clearly demonstrated copy number differences between the female and male samples.

For the experiment, 24 µL of mix was aliquoted into two sets of 8 strip tubes (female or male) and added 6 µL of primer mix that contained 10 µM of the forward and reverse primers from each assay. After mixing, three identical 5 µL amounts were aliquoted into columns of a 48-well Eco PCR plate (triplicate female on top in columns, triplicate male samples in columns on the bottom). The instrument was set to monitor SYBR and ROX and to cycle to 95° C. for 30 sec, 60° C. for 30 sec and 72° C. for 30 sec for 40 cycles. A JPG image of the amplification traces for assay 6 is shown in FIG. 9. The copy difference between the female and male samples was clear. All of the "Cq" values were gathered (value where the fluorescence curve passes some auto-defined baseline) for the female and male samples, then differences between averages of triplicate measurements were calculated. This is shown in Table 7 above (bottom line=M-F), where all values are positive except for the chr9 assay. The overall data indicated that all eight assays perform similarly (Cq values from 22-24) and that the chrX assays generally had a higher signal in females.

Figure 10:
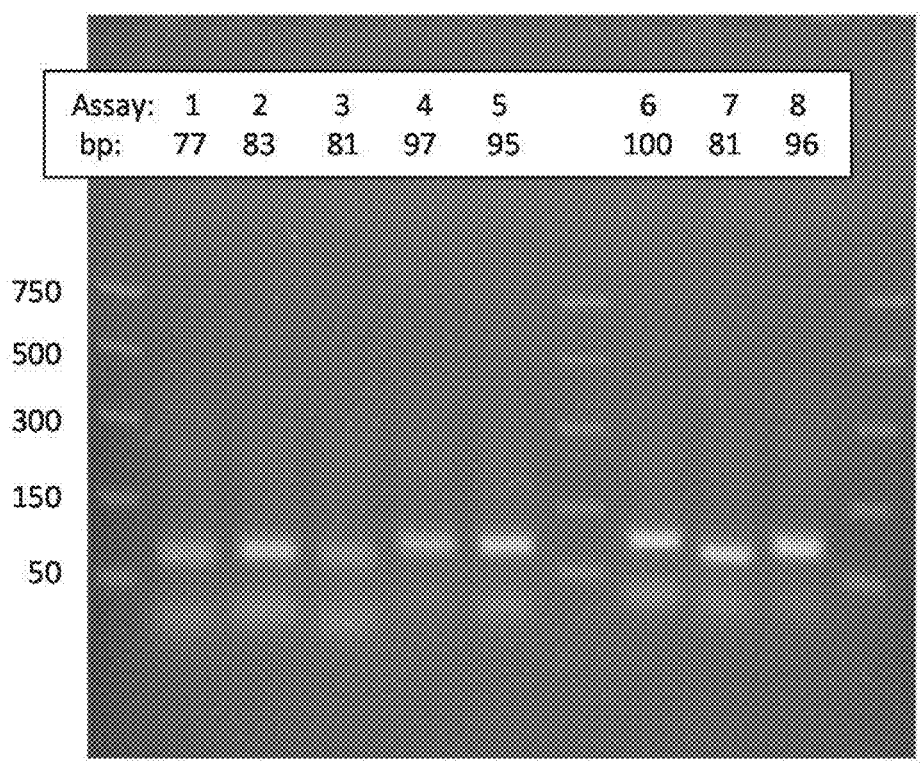
FIG. 10: Demonstration of expected amplicon size and uniqueness following conventional PCR with PLP1 qPCR assay primers. Male or female genomic DNA templates were amplified by conventional PCR using qPCR assay primer sets 1-8 (Example 3) and the unpurified PCR reactions were loaded directly on 2% agarose gels. The upper bands of each doublet were consistent with the projected mobility of the assay PCR products. The lower "fuzzy" material was most likely unused PCR primers.

The conventional PCR reaction was cycled for 30 cycles of 94° C.-30 sec, 60° C.-30 sec and 72° C.-30 sec; 72° C. rest for 2 min, 10° C. hold. A total of 5 µL of product was loaded directly on a 2% agarose gel without purification and is shown in FIG. 10. The upper bands of each doublet were consistent with the projected mobility of the assay PCR products. The lower "fuzzy" material was most likely unused PCR primers.

From the results of real-time PCR and of conventional PCR followed by gel analysis it can be concluded that these eight assays amplify their intended regions exclusively and that they are suitable for monitoring fragment enrichment.

Example 5 Appendix: Details on Assay Design: PLP1 gene: Transcript ID NM_000533.3; Exon 2—187 nt; CDS2 From UCSC browser. CDS in BOLD UPPERCASE UNDERLINED; primer sequences are in italics.
Flanking sequence in lowercase

| SEQ ID NO: NAME | SEQUENCE |
|---|---|
| 95 Forward strand | agtgcccactatctccgagcctgtgagcacagggcctggcag aggggtttgagtggcatgagctacctactggatgtgcctgac tgtttcccttcttcttccccagGCTTGTTAGAGTGCTGTGC AAGATGTCTGGTAGGGGCCCCCTTTGCTTCCCTGGTGGCCAC TGGATTGTGTTTCTTTGGGGTGGCACTGTTCTGTGGCTGTGG ACATGAAGCCCTCACTGGCACAGAAAAGCTAATTGAGACCTA TTTCTCCAAAAACTACCAAGACTATGAGTATCTCATCAATGT gtaagtacctgccctcccacacagacccatctttttttccc tctctccatcctggagatagagaactcttcagtaccttagta actagcaggggactggggtgga |
| 96 Reverse complement | tccacccagtcccctgctagttactaaggtactgaagagtt ctctatctccaggatggagagagggaaaaaaaagatgggtct gtgtgggagggcaggtacttacACATTGATGAGATACTCATA GTCTTGGTAGTTTTTGGAGAAATAGGTCTCAATTAGCTTTTC TGTGCCAGTGAGGGCTTCATGTCCACAGCCACAGAACAGTGC CACCCCAAAGAAACACAATCCAGTGGCCACCAGGGAAGCAAA GGGGGCCCCTACCAGACATCTTGCACAGCACTCTAACAAGCc tggggaagaagaaggggaaacagtcaggcacatccagtaggt agctcatgccactcaaacccctctgccaggccctgtgctcac aggctcggagatagtgggcac |
| 97 qPCR assay 1, 77nt: | agtgcccactatctccgagcctgtgagcacagggcctggcag aggggtttgagtggcatgagctacctactggatgtgcctgac tgtttcccttcttcttccccagGCTTGTTAGAGTGCTGTGC AAGATGTCTGGTAGGGGCCCCCTTTGCTTCCCTGGTGGCCAC TGGATTGTGTTTCTTTGGGGTGGCACTGTTCTGTGGCTGTGG ACATGAAGCCCTCACTGGCACAGAAAAGCTAATTGAGACCTA TTTCTCCAAAAACTACCAAGACTATGAGTATCTCATCAATGT gtaagtacctgccctcccacacagacccatctttttttccc tctctccatcctggagatagagaactcttcagtaccttagta actagcaggggactggggtgga |

| SEQ ID NO: NAME | SEQUENCE |
|---|---|
| 98 qPCR assay 2, 83 nt: | agtgcccactatctccgagcctgtgagcacagggcctggcag<br>aggggtttgagtggcatgagctacctactggatgtgcctgac<br>tgtttccccttcttcttccccagGCTTGTTAGAGTGCTGTGC<br>AAGATGTCTGGTAGGGGCCCCCTTTGCTTCCCTGGTGGCCAC<br>TGGATTGTGTTTCTTTGGGGTGGCACTGTTCTGTGGCTGTGG<br>ACATGAAGCCCTCACTGGCACAGAAAAGCTAATTGAGACCTA<br>TTTCTCCAAAAACTACCAAGACTATGAGTATCTCATCAATGT<br>gtaagtacctgccctcccacacagacccatcttttttttccc<br>tctctccatcctggagatagagaactcttcagtaccttagta<br>actagcaggggactggggtgga |
| 99 qPCR assay 3, 81 nt: | agtgcccactatctccgagcctgtgagcacagggcctggcag<br>aggggtttgagtggcatgagctacctactggatgtgcctgac<br>tgtttccccttcttcttccccagGCTTGTTAGAGTGCTGTGC<br>AAGATGTCTGGTAGGGGCCCCCTTTGCTTCCCTGGTGGCCAC<br>TGGATTGTGTTTCTTTGGGGTGGCACTGTTCTGTGGCTGTGG<br>ACATGAAGCCCTCACTGGCACAGAAAAGCTAATTGAGACCTA<br>TTTCTCCAAAAACTACCAAGACTATGAGTATCTCATCAATGT<br>gtaagtacctgccctcccacacagacccatcttttttttccc<br>tctctccatcctggagatagagaactcttcagtaccttagta<br>actagcaggggactggggtgga |
| 100 qPCR assay 4, 97 nt: | agtgcccactatctccgagcctgtgagcacagggcctggcag<br>aggggtttgagtggcatgagctacctactggatgtgcctgac<br>tgtttccccttcttcttccccagGCTTGTTAGAGTGCTGTGC<br>AAGATGTCTGGTAGGGGCCCCCTTTGCTTCCCTGGTGGCCAC<br>TGGATTGTGTTTCTTTGGGGTGGCACTGTTCTGTGGCTGTGG<br>ACATGAAGCCCTCACTGGCACAGAAAAGCTAATTGAGACCTA<br>TTTCTCCAAAAACTACCAAGACTATGAGTATCTCATCAATGT<br>gtaagtacctgccctcccacacagacccatcttttttttccc<br>tctctccatcctggagatagagaactcttcagtaccttagta<br>actagcaggggactggggtgga |
| 101 qPCR assay 5, 95 nt: | agtgcccactatctccgagcctgtgagcacagggcctggcag<br>aggggtttgagtggcatgagctacctactggatgtgcctgac<br>tgtttccccttcttcttccccagGCTTGTTAGAGTGCTGTGC<br>AAGATGTCTGGTAGGGGCCCCCTTTGCTTCCCTGGTGGCCAC<br>TGGATTGTGTTTCTTTGGGGTGGCACTGTTCTGTGGCTGTGG<br>ACATGAAGCCCTCACTGGCACAGAAAAGCTAATTGAGACCTA<br>TTTCTCCAAAAACTACCAAGACTATGAGTATCTCATCAATGT<br>gtaagtacctgccctcccacacagacccatcttttttttccc<br>tctctccatcctggagatagagaactcttcagtaccttagta<br>actagcaggggactggggtgga |
| 102 qPCR assay 6, 200 bp distal to exon 2, 100bp product<br>>chrX: 103040918 + 103041017<br>100bp | CCCCTTGTTTTCTTACACGTGTTCTgacttctgctaggtgtg<br>gttcatattgcccaagttggagcctccagcgtagTAGGTATG<br>GAGAAGCCAAGGGAGG |
| 103 qPCR assay 7, 1000 bp distal to exon 2 (in exon 3), 81 bp product<br>>chrX: 103041614 + 103041694<br>81bp | GTGTGTCATTGTTTGGGAAAATGGctaggacatcccgacaag<br>gtgatcatcctcaggATTTTGTGGCAATAACAAGGGGTG |
| 104 qPCR assay 8, unlinked assay on chr 9, 96 bp product<br>>chr9: 103041653 + 103041748<br>96bp | TACCAGCCAAGCCCATACTAGAGGctgtccccagatgctagc<br>aaccatctgattgaataaccatctgtatcaTTCAATTATGCC<br>ACTGTTGATCCC |

Example 6: Capture of PLP1 Exon 2

Purpose: In one embodiment, the Clearfork Bioscience v1.0 DNA capture strategy entails the use of multifunctional probes targeted at specific genomic target regions. The goal was to validate the approach using Ultramers™ (Integrated DNA Technologies (IDT), Coralville, Iowa; ultramers is the trade name given to specialty synthesis synthetic oligonucleotides ranging in length from 45-200 nt) targeted to PLP1 exon 2.

Summary: In this example, the capture reaction was demonstrated. Ultramers from IDT-DNA worked well for capture; the basic protocol through the capture step in terms of reagent stochiometries was sound; and PEG molecular crowding agent interfered with effective capture. Post capture enzymatic processing was subsequently addressed.

Brief Description: The multifunctional probes are diagrammed in FIG. 2. The goal of this experimental data set was to test all three features of these probes. Region 1 was the binding site for a 34 nt universal, 5' biotin-TEG and 3' dideoxycytosine-modified universal "pull-down" oligo. Two of these universal regions were designed to validate/verify equivalent (hopefully) performance.

The sequences of these two universal oligos are shown below in Table 8.

TABLE 8

Pull-down oligo sequences targeting PLP exon 2:

| SEQ ID NO: | Name | Sequence | Description |
|---|---|---|---|
| 105 | Univ_seq_1 | /5BioTEG/CACTGGACTATGTAGT ACCTCACTCAGCAATAC/3ddC/ | One of two 5' biotin-TEG and 3' dideoxycytosine modified universal capture oligos |
| 106 | Univ_seq_10 | /5BioTEG/GGCAACGAACGGACTG GAATCTACGGTCACCAA/3ddC/ | One of two 5' biotin-TEG and 3' dideoxycytosine modified universal capture oligos |

Below is a brief description of how these sequences were selected. The functional role of these oligos was to hybridize to capture probes and to thereby provide a stably bound biotin extension that could be used for capture on streptavidin modified magnetic beads.

10 random sequences were generated by a random DNA sequence generator set to have a rough base composition of 50% GC. The University of California, Riverside Computing and Communications web site was used. The ten sequences were then screened by BLAT to the hg19 build of the human genome. Only sequence 3 showed a significant alignment. The two sequences ending in "C" were chosen since these could be blocked with ddC. Both sequences were analyzed by the IDT OligoAnalyzer. Sequence 1 is 47% GC and has a 76° C. melting temp in 1M NaCl. Sequence 2 has a 57% GC content and an 86° C. melting temp in high salt.

The sequences selected, 1 and 10, are the actual "universal" 5' Biotin TEG—ddC complementary probe sequences. The reverse complements of these were used as the tails on capture probes. These sequences were subsequently altered by adding four bases, A, G, C and T, to increase the length to 34 bases. This length worked well with SBC and there was no compelling reason to change. Second, some of the CGCG type motifs were disrupted to lower self-dimer formation.

Region 2 encompassed the portion of the probe that was designed to contact genomic sequences in sample genomic libraries. In this experiment, the target region was exon 2 of PLP1. The DNA sequence of PLP1 exon 2 is shown below. The CDS exon 2 is highlighted in BOLD UPPERCASE UNDERLINED type. The evenly spaced-capture probe sequences are shaded.

| SEQ ID NO: | NAME | SEQUENCE |
|---|---|---|
| 107 | Forward strand | agtgcccactatctccgagcctgtgagcacagggcctggcagaggggtttgagtggcatgagctacctactggatgtgcctgactgtttcccttcttcttccccagGCTTGTTAGAGTGCTGTGCAAGATGTCTGGTAGGGGCCCCCTTTGCTTCCCTGGTGGCCACTGGATTGTGTTTCTTTGGGGTGGCACTGTTCTGTGGCTGTGGACATGAAGCCCTCACTGGCACAGAAAAGCTAATTGAGACCTATTTCTCCAAAAACTACCAAGACTATGAGTATCTCATCAATGTGtaagtacctgccctcccacacagacccatcttttttttccctctctccatcctggagatagagaactcttcagtacttagtaactagcaggggactggggtgga |

Region 3 was complementary to a validated PCR primer called CAC3. The sequence of the CAC3 PCR primer is: CACGGGAGTTGATCCTGGTTTTCAC (SEQ ID NO: 72).

The sequences of the ultramers that include these probe regions are shown in Table 9.

TABLE 9

Sequences of ultramers used in the PLP1 exon 2 capture

| SEQ ID NO: | Name | Sequence | Description |
|---|---|---|---|
| 108 | B1_PLP1ex2_p1 | GAGTTGATCCTGGTTTTCACTTTGAGTGGCAT GAGCTACCTACTGGATGTGCCTGACTGTTTCC CCTTCTTCTTCCCCAGGGTATTGCTGAGTGAG GTACTACATAGTCCAGTG | Ultramer targeted to PLP1 exon 2 and compatible with Universal seq 1 |
| 109 | B1_PLP1ex2_p2 | GAGTTGATCCTGGTTTTCACATGTCTGGTAGG GGCCCCCTTTGCTTCCCTGGTGGCCACTGGAT TGTGTTTCTTTGGGGTGGTATTGCTGAGTGAG GTACTACATAGTCCAGTG | Ultramer targeted to PLP1 exon 2 and compatible with Universal seq 1 |

TABLE 9-continued

Sequences of ultramers used in the PLP1 exon 2 capture

| SEQ ID NO: | Name | Sequence | Description |
|---|---|---|---|
| 110 | B1_PLP1ex2_p3 | GAGTTGATCCTGGTTTTCACCTTGGTAGTTTT TGGAGAAATAGGTCTCAATTAGCTTTTCTGTG CCAGTGAGGGCTTCATGGTATTGCTGAGTGAG GTACTACATAGTCCAGTG | Ultramer targeted to PLP1 exon 2 and compatible with Universal seq 1 |
| 111 | B1_PLP1ex2_p4 | GAGTTGATCCTGGTTTTCACATCTCCAGGATG GAGAGAGGGAAAAAAAAGATGGGTCTGTGTGG GAGGGCAGGTACTTACGGTATTGCTGAGTGAG GTACTACATAGTCCAGTG | Ultramer targeted to PLP1 exon 2 and compatible with Universal seq 1 |
| 112 | B10_PLP1ex2_p1 | GAGTTGATCCTGGTTTTCACTTTGAGTGGCAT GAGCTACCTACTGGATGTGCCTGACTGTTTCC CCTTCTTCTTCCCCAGGTTGGTGACCGTAGAT TCCAGTCCGTTCGTTGCC | Ultramer targeted to PLP1 exon 2 and compatible with Universal seq 10 |
| 113 | B10_PLP1ex2_p2 | GAGTTGATCCTGGTTTTCACATGTCTGGTAGG GGCCCCCTTTGCTTCCCTGGTGGCCACTGGAT TGTGTTTCTTTGGGGTGTTGGTGACCGTAGAT TCCAGTCCGTTCGTTGCC | Ultramer targeted to PLP1 exon 2 and compatible with Universal seq 10 |
| 114 | B10_PLP1ex2_p3 | GAGTTGATCCTGGTTTTCACCTTGGTAGTTTT TGGAGAAATAGGTCTCAATTAGCTTTTCTGTG CCAGTGAGGGCTTCATGTTGGTGACCGTAGAT TCCAGTCCGTTCGTTGCC | Ultramer targeted to PLP1 exon 2 and compatible with Universal seq 10 |
| 115 | B10_PLP1ex2_p4 | GAGTTGATCCTGGTTTTCACATCTCCAGGATG GAGAGAGGGAAAAAAAAGATGGGTCTGTGTGG GAGGGCAGGTACTTACGTTGGTGACCGTAGAT TCCAGTCCGTTCGTTGCC | Ultramer targeted to PLP1 exon 2 and compatible with Universal seq 10 |

Considerations about moles, micrograms and molecules: The genomic library constructed in Example 3 (hgDNA library from Promega female) was used. A large scale (800 µL) amplification of this library was performed starting with 20 µL of ligation mix as input. The purified library (400 µL) had a final concentration of 22 ng/µL. One microgram per experiment described here was used. Furthermore, based on the total adaptor being 50 bp and the inserts being 150-200 bp, there was an assumption that 75% of the library mass is genomic DNA. Based on this assumption, and that one human genome has a mass 3 pg, then there were roughly $(750\times10^{-9}/3\times10^{-12}=250,000)$ 250,000 copies of any given genomic region present. Previous experience and literature suggested that a 10,000-fold molar excess of probes is a reasonable place to start. This implies 2,500,000,000 molecules of probe. $2.5\times10^9$ molecules/$6.02\times10^{23}$ molecules/mole=$4.15\times10^{-15}$ moles=4 amol probe. Translating this to volume of a stock solution, 1 µL of 4 nM (in each probe)=4 amol of probe. Finally, Invitrogen's MyOne strep-coated C1 beads bind about 1 pmol of biotinylated 500 bb dsDNA/1 µL of beads. In this experiment, a total of 4 amol×4 probes=16 amol in probe were added. 1 µL of beads binds 1000 amol, 1 µL is a practical amount of beads to work with, and 1 µL of beads is a 60-fold excess of binding capacity over added probe. Therefore, in this example the following parameters were calculated:
- the number of target molecules in a unit mass of library (250,000 copies of a unique diploid locus/1 µg of library);
- the molarity of probe necessary to address the target loci with a 10,000-fold molar excess of probe (4 amol of each probe, 16 amol total probe (4 probes), 1 µL of a 4 nM solution of probes; and
- the amount of beads necessary to quantitatively capture all of the added probe (1 binds 1000 amol of dsDNA and/or unbound probe).

Buffers and Working Solutions

Solution 1—binding probes: hydrated universal binding partners and PLP1 probes to 100 µM. In two separate tubes, combined 92 µL TEz+0.05% Tween-20 buffer, 4 µL universal oligo and 1 µL each of the four cognate (with the universal oligo) probes. This generated two of 1 µM stock probe solution. Diluted each of these 4 µL into 1000 µL of TEz+Tween to provide a 4 nM working solution of probes.

4× Binding buffer=4M NaCl, 40 mM Tris pH 8.0, 0.4 mM EDTA, and 0.4% Tween 20. Made 50 mls by combining 40 mls of 5M NaCl, 2 mls of 1M Tris pH 8.0, 2 mls of 10% Tween20, 40 µL of 0.5 M EDTA and 6 mls of water.

Wash buffer=25% formamide, 10 mM Tris pH 8.0, 0.1 mM EDTA and 0.05% Tween 20. Made 50 mls by combining 37 mls of water, 12.5 mls of formamide, 500 µL of 1M Tris pH8.0, 10 µL of 0.5M EDTA, and 250 µL of 10% Tween 20.

Beads. Combined 250 µL of 4× bind and 750 µL of water to make 1X binding buffer. Added 10 µL of beads to 90 µL of 1× bind, pulled aside with magnet, washed the beads 2× with 100 µL of 1× bind, and resuspended washed beads in 100 µL 1× bind. Ten microliters of washed beads is equivalent to 1 µL of beads as they come out of the manufacturer's tube.

Methods

The following three parameters were tested:
1. Universal biotin oligo 1 versus oligo 10;
2. Binding in 1× bind versus 1× bind plus 7.5% PEG8000 (a molecular crowding agent that may enhance the rate of annealing); and
3. Fold-enrichment of PLP1 region after straight binding and after binding plus enzymatic processing To test these parameters eight samples (2×2×2) were generated. These samples contained 50 µL of 20 ng/µL genomic DNA, 25 µL of 4× binding buffer, 1 µL of binding probes and either 24 µL of water or 20 µL of 50% PEG8000+4 µL of water (four sample with and 4 samples without PEG). From the IDT DNA website OligoAnalyzer, it was described that the Tm of oligos shifts to dramatically higher temperatures in high salt (e.g., 1M NaCl). Thus, the sample was melted at 95° C. and then dropped the temperature in 1° C. and 2 min increments to 60° C. (35 cycles of AutoX on our ABI2720 thermal cycler where each cycle drops by one degree and each cycle lasts 2 min). After the samples cooled to room temperature (RT), 10 µL of washed beads were added per sample and incubated for 20 min. The beads were pulled out with a strong magnet and the solution aspirated and discarded. The beads were washed four times with 200 µL washes of wash buffer; each time the beads were resuspended, they were incubated a RT for 5 min. After the final wash, the majority of remaining wash was carefully aspirated from the tubes.

A set of four tubes was treated with T4 DNA polymerase. A cocktail was made by combining 10 µL of New England Biolab 10× Quick blunting buffer, 10 µL of 1 mM dNTPs from the same kit, 10 µL of water and 1 µL of T4 DNA polymerase. 20 µL was added to a set of four tubes and the reaction was incubated at 20° C. for 15 min.

For PCR amplification following capture, the non-T4 treated samples (captured only) were amplified with ACA2-25 (TGCAGGACCAGAGAATTCGAATACA; SEQ ID NO: 67) in single primer reactions. The T4-treated samples were amplified with ACA2FL and CAC3FL primers (AATGATACGGCGACCACCGAGATCTACACGT-CATGCAGGACCAGAGAATTCGAATACA (SEQ ID NO: 69) and CAAGCAGAAGACGGCAT-ACGAGATGTGACTGGCACGGGAGTT-GATCCTGGTTTTCA C (SEQ ID NO: 74), respectively). The core reaction mixes contained, per 400 µL reaction, 120 of water, 40 µL of 10×STD Taq buffer (NEB), 40 µL of 25 mM MgCl2, 80 µL of 10 µM single primer or 40 µL+40 µL of F and R primer, 20 µL of DMSO, 20 µL of 10 mM dNTPs and 4 µL of Taq polymerase. 80 µL aliquots were added to beads that had been resuspended in 20 µL of TEz (binding only) or 20 µL of T4 mix. The final volumes were 100 µL. These samples were amplified by PCR for 30 cycles of 94° C.-30 sec, 60° C.-30 sec and 72° C.-60 sec. The gel analysis—5 µL of post-PCR material was loaded per lane—is shown in the results section. Qubit readings indicated that each PCR reaction had a concentration of ~20-25 ng/µL.

For post-amplification analysis, a 500 µL (final volume) master mix of conventional PCR mix was made by combining 200 µL water, 50 µL 10× Taq buffer, 50 µL 25 mM MgCl2, 25 µL of DMSO, 25 µL of 10 mM dNTPs, 12.5 µL EvaGreen (Biotum) and 5 Taq polymerase (NEB). 42 µL aliquots were distributed into 8 tubes and 12 µL of F+R 10 µM PLP1 primer mixes (the assays are described in Example 5: Validation of PLP1 qPCR assays) were added. 9 µL of mix was distributed, each assay in 8 columns. A total of 6 samples, 1 µL of sample per well, was assayed. These samples were:

(a) Row 1: gDNA library starting material
(b) Row 2: Biotin oligo 1 capture material
(c) Row 3: Biotin oligo 1+PEG capture
(d) Row 4: Biotin oligo 10 capture material
(e) Row 5: Biotin oligo 10+PEG capture material
(f) Row 6: TEz NTC control The T4 treated samples were not assayed because gel analysis showed that only aberrant material was treated by PCR amplification.

Results

The capture only libraries produced a smear that looked like the input genomic library, as expected. The samples left to right were (1) oligo 1, (2) oligo 1+PEG, (3) oligo 10, and (4) oligo 10+PEG. The T4-treated samples were contaminated with residual T4 polymerase (5-8). In particular embodiments, T4 polymerase is heat inactivated.

The Qubit measured yields of the four capture only libraries is shown below in Table 10.

TABLE 10

| Qubit measured yields of the four capture only libraries | | |
|---|---|---|
| C1 universal oligo | 23.2 | ng/µL |
| C1 + PEG | 27.2 | ng/µL |
| C10 universal oligo | 24.8 | ng/µL |
| C10 + PEG | 25.6 | ng/µL |

For qPCR, all eight validated PLP1 assays (Example 5) were used in columns and samples in rows. The array of the samples was:

(a) Row 1: 1 µL of 25 gDNA library
(b) Row 2: 1 µL of ~25 ng/µL C1 capture sample
(c) Row 3: 1 µL of ~25 ng/µL C1+P capture sample
(d) Row 4: 1 µL of ~25 ng/µL C10 capture sample
(e) Row 5: 1 µL of ~25 ng/µL C10+P capture sample
(f) Row 6: 1 µL TEz (NTC)

In this configuration, 1 sample per well, the data were meant to be more of a qualitative overview than a rigorous quantitative measurement. The data are shown in the tables below. The top table is raw Cq values. The next table is Cq values converted to absolute values based on the assumption that all samples and assays conform to the same two-fold standard curve. The bottom table shows the quotient of captured sample divided by gDNA library. This provides a sense of fold-enrichment following capture.

TABLE 11

Results of the eight PLP1 qPCR assays demonstrating successful capture-induced enrichment of target sequences

| | Cq Values | | | | | | | |
|---|---|---|---|---|---|---|---|---|
| | Assay 1 | Assay 2 | Assay 3 | Assay 4 | Assay 5 | Assay 6 | Assay 7 | Assay 8 |
| gDNA lib | 22 | 25 | 29 | 25 | 25 | 26 | 25 | 25 |
| C1 | 14 | 11 | 11 | 11 | 9 | 15 | 23 | 22 |
| C1 + P | 18 | 15 | 18 | 14 | 13 | 18 | 29 | 26 |
| C10 | 12 | 12 | 13 | 12 | 10 | 15 | 22 | 25 |
| C10 + P | 16 | 13 | 15 | 13 | 12 | 18 | 27 | 25 |
| NTC | 29 | 25 | 34 | 28 | 30 | 28 | 30 | 31 |

TABLE 11-continued

Results of the eight PLP1 qPCR assays demonstrating successful capture-induced enrichment of target sequences

| | Cq Values | | | | | | | |
|---|---|---|---|---|---|---|---|---|
| | Assay 1 | Assay 2 | Assay 3 | Assay 4 | Assay 5 | Assay 6 | Assay 7 | Assay 8 |
| gDNA lib | 33 | 3 | 0 | 4 | 3 | 2 | 3 | 2 |
| C1 | 4782 | 56660 | 50773 | 43156 | 138885 | 2950 | 10 | 28 |
| C1 + P | 293 | 3196 | 407 | 6187 | 16082 | 450 | 0 | 1 |
| C10 | 29864 | 34343 | 11961 | 28507 | 123383 | 2894 | 31 | 3 |
| C10 + P | 1234 | 11632 | 3976 | 10060 | 25772 | 413 | 1 | 2 |
| NTC | 0 | 3 | 0 | 0 | 0 | 1 | 0 | 0 |

| | cap/gDNA | | | | | | | |
|---|---|---|---|---|---|---|---|---|
| | Assay 1 | Assay 2 | Assay 3 | Assay 4 | Assay 5 | Assay 6 | Assay 7 | Assay 8 |
| C1 | 147 | 19303 | 330609 | 11735 | 48601 | 1720 | 3 | 11 |
| C1 + P | 9 | 1089 | 2649 | 1682 | 5628 | 262 | 0 | 1 |
| C10 | 917 | 1170 | 77886 | 7752 | 43176 | 1688 | 10 | 1 |
| C10 + P | 38 | 3963 | 25890 | 2736 | 9019 | 241 | 0 | 1 |

Several conclusions were drawn from the data: (1) The capture worked. The average capture enrichment across on-target assays 1-5 for C1 was 82,000×. The average for C10 was 28,000×. Anywhere from hundreds to tens of thousands fold enrichment at assay sites was observed. This implies that ultramers work and that the basic probe design is effective. This meant that the basic stoichiometry of gDNA to probe to beads was correct; (2) The two biotin designs worked approximately the same; (3) PEG inhibits rather than enhanced capture efficiency; and (4) Significant "by-catch" at assay 6, which was 200 bp from target was observed. Less stray activity was seen for a region 1000 bp away.

In particular embodiments, it may be important to determine if enzymatic processing of the captured complex contributes to sensitivity (fold-enrichment) and specificity (degree of "by-catch") in this scheme.

Example 7: PLP1 qPCR Assays in SYBR Space

Purpose: In some cases it is useful for real-time conditions to exactly mimic non-real-time amplification conditions. In this example this meant to set up on ice and three stage, relatively slow PCR reactions. Alternatively, some assays do not require replication of a set amplification conditions; rather they are intended strictly to make quantitative measurements. For example, the PLP1 qPCR assays are preferably not used to produce fragments, but only to measure locus enrichment. In this type of situation, qPCR reaction set up at room temperature and fast cycling are advantages. In this experiment, the eight PLP1 assays in ABI 2×SYBR mix were tested. These are the same primer assays as described in the Example 5 (Validation of PLP1 qPCR assays).

Summary: These data suggested that at least six of eight PLP1 qPCR assays could be used with SYBR green qPCR mix and conditions.

Methods: PLP1 assay performance was measured against the female gDNA library (Example 3: hgDNA library from Promega female). Per 10 μL well combined 5 ABI 2×SYBR master mix, 0.2 μL of 10 μM stock F+R primer, 1 μL of gDNA library (20 ng/μL) and 3.8 μL water (larger volume master mixes were made and aliquoted). Made triplicate no-template-control and triplicate gDNA library measurements across each assay. Cycled for 40 cycles on the Illumina Eco real-time PCR using standard 2 step PCR (15 sec at 95° C., 45 sec at 60° C.) with ROX passive reference dye normalization.

Figure 11A:
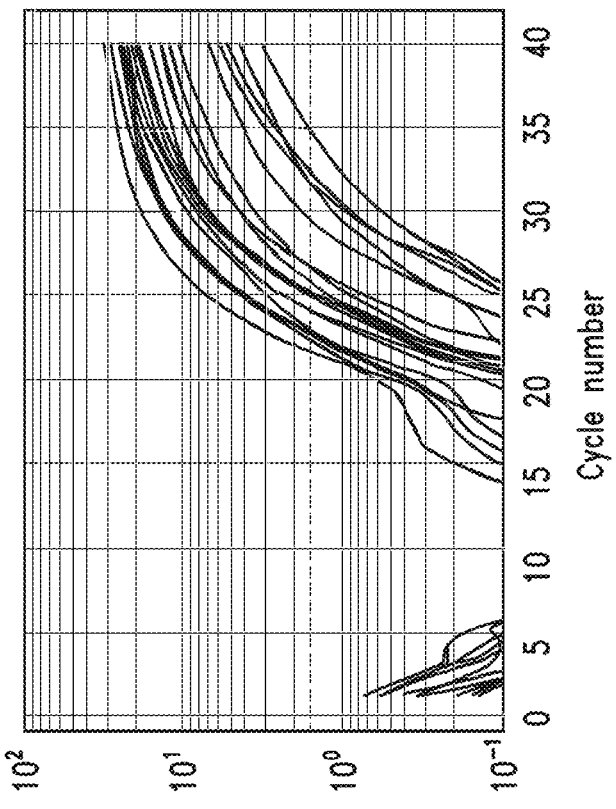
FIG. 11A-FIG. 11B: Analysis of PLP1 qPCR assay performance using ABI 2×SYBR mix and conditions. DNA fragments from genomic library I (constructed in Example 4) were used as template to measure the performance of the PLP1 qPCR assays when set up at room temperature using ABI 2×SYBR master mix in a 2 step PCR reaction. No template control traces (FIG. 11A) and +gDNA traces (FIG. 11B) are shown to provide a qualitative picture of assay performance.
Figure 11B:

Results: The called Cq values for each well are shown in Table 12 below. The NTC is very clean; the gDNA Cq's are variable, likely due to pipetting. The general theme is that Assay 1 and 7 were poor performers while the remaining assays worked reasonably well in SYBR space. In FIG. 11, the NTC traces (A) and +gDNA traces (B) were copied to provide a qualitative picture of assay performance.

TABLE 12

Called Cq values from rapid SYBR-green-based PLP1 assays

| | Assay | | | | | | | |
|---|---|---|---|---|---|---|---|---|
| | 1 | 2 | 3 | 4 | 5 | 6 | 7 | 8 |
| NTC | 38 | 40 | 40 | 40 | 40 | 40 | 40 | 40 |
| | 40 | 40 | 40 | 40 | 40 | 40 | 40 | 40 |
| | 35 | 40 | 40 | 40 | 40 | 40 | 40 | 40 |
| gDNA | 35 | 25 | 25 | 24 | 27 | 22 | 32 | 26 |
| | 35 | 25 | 25 | 24 | 26 | 23 | 32 | 27 |
| | 32 | 24 | 22 | 22 | 23 | 21 | 29 | 24 |

Example 8: Measurement of PLP1 Exon2 Enrichment Before and after Enzymatic Processing of Complexes Purpose: In this example the enzymatic processing of the complex was tested directly for yield by measuring the "specific activity" of PLP1 exon2 DNA in pre- and post-processed capture complex. ultramers support excellent capture efficiency and the core capture protocol performed well.

Summary: This experiment demonstrated that post-capture processing with T4-DNA polymerase dramatically improved the specificity of the capture reaction.

Background: In Example 6 (Capture of PLP1 exon 2) the successful capture was described, however the post-capture processing step where T4 polymerase was not removed prior to PCR yielded an artifactual library. Here, the same basic experiment is repeated except that T4 was heat inactivated at 95° C. for 1 min prior to PCR.

Methods, Results, and Discussion: In this experiment, four samples were generated which included two universal biotin capture probes in order to assess capture efficiency of complexes before and after enzyme processing. Each sample contained 50 µL of 20 genomic DNA, 20 µL of 4× binding buffer, 1 µL of binding probes and either 9 µL of water for a final volume of 80 µL. Samples were melted at 95° C. for one minute and annealed by cooling the temperature in 1° C., 2 min increments to 60° C. (35 cycles of AutoX on our AB12720 thermal cycler) followed by cooling to RT. A total of 10 µL of washed beads (equivalent to 1 µL of MyOne bead solution—streptavidin-coated C1—Invitrogen) were then added per sample and incubated for 20 min. The beads were pulled out with a magnet and the solution aspirated and discarded. The beads were washed four times with 200 µL washes of wash buffer; each time the beads were resuspended, they were incubated at RT for 5 min. After the final wash, the majority of remaining wash was carefully aspirated from the tubes, leaving beads coated with capture complex.

For T4 processing of two of the samples, we prepared 50 µL of enzymatic processing mix that contained 40 µL of water, 5 µL of 10× quick blunt buffer (New England Biolabs), 5 µL of 1 mM dNTPs and 0.5 µL of T4 DNA polymerase. Two aliquots of complex were suspended in 20 µL (each) of T4 mix and incubated at 20° C. for 15 min, 95° C. for 1 min, and cooled to RT. The "untreated" controls were suspended in 20 µL of the same buffer (40 µL of water, 5 µL of 10× quick blunt buffer (New England Biolabs), 5 µL of 1 mM dNTPs) that lacked T4 polymerase.

To measure specific activity, both the capture alone and capture+processing samples were amplified by 30 cycles of PCR. The DNA was then quantified and PLP1 assay signals measured in a specific and known amount of amplified DNA. In this example two amplification reactions were set-up. For capture alone, amplification was performed with

ACA2-25 (TGCAGGACCAGAGAATTCGAATACA; SEQ ID NO: 67)

since these libraries are only amplifiable with this single primer. For enzyme-processed complexes, amplification was performed with ACA2FL and CAC3FL primers (AATGATACGGCGACCACCGAGATCTACACGTCATGCAGGACCAGAGAATTCGAATACA (SEQ ID NO: 69)

CAAGCAGAAGACGGCATACGAGATGTGACTGGCACGGGAGTTGATCCTGGTTTTCAC (SEQ ID NO: 74), respectively). 100 µL of PCR mix contained 10 µL of 10×STD Taq buffer (all reagents NEB unless otherwise specified), 10 µL of 25 mM MgCl2, 20 µL of 10 µM single primer or 10 µL+10 µL of 10 µM dual primers, 20 µL of template (untreated control or T4 processed, beads and all), 5 µL of DMSO, 5 µL of 10 mM dNTPs and 1 µL of Taq DNA polymerase (all set up one ice prior to amplification). Samples were amplified for 30 cycles of PCR in a three step, 95° C.-30 sec, 60° C.-30 sec, 72° C.-60 sec, protocol followed by 72° C. for 2 min and rested at 10° C.

Following amplification, DNA yield was measured and the PCR amplified material examined by DNA gel electrophoresis. Qubit (InVitrogen) measured (DNA HS kit) yields are shown in Table 13 below. These data highlight a basic feature that dual primer amplification supports overall yields than single primer amplification.

TABLE 13

| Qubit quantification of amplified DNA | |
|---|---|
| Sample | Yield (ng/µL) |
| C1 biotin, unprocessed complex | 23 |
| C10 biotin, unprocessed complex | 24 |
| C1 biotin, T4-processed complex | 38 |
| C10 biotin, T4-processed complex | 34 |

Figure 12:
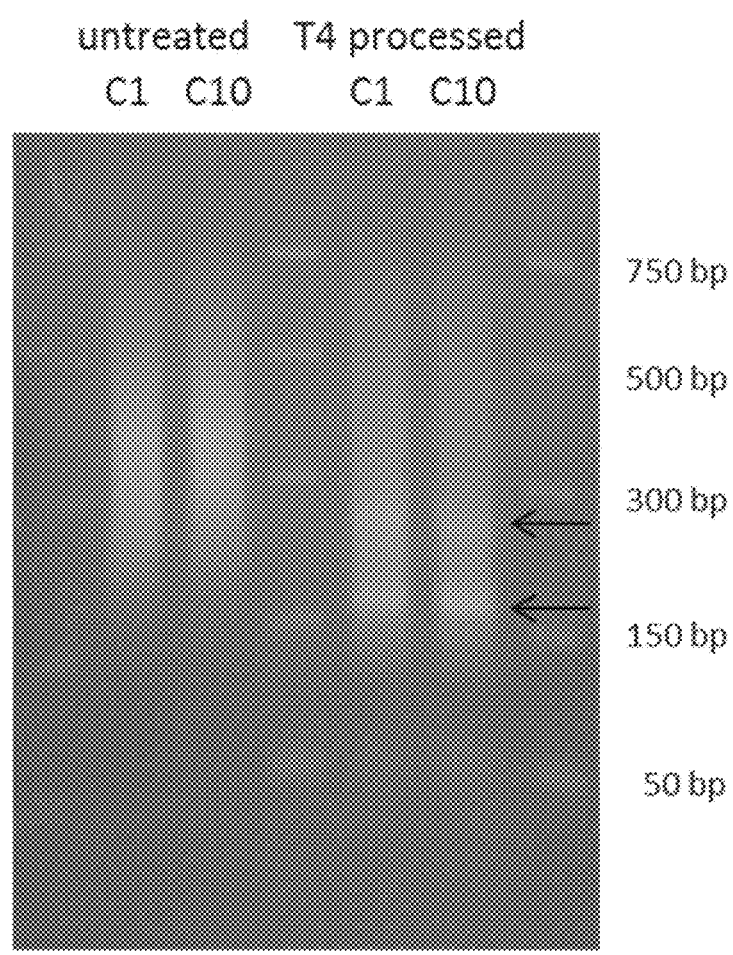
FIG. 12: Reduced insert size following post-capture processing with T4-DNA polymerase. Four samples of adapter ligated gDNA fragments from genomic library I (constructed in Example 4) were captured as described (Example 6—PLP1 EXON 2). Two of these samples utilized universal binding oligo C1, while the other two samples were bound with oligo C10. Samples were then either treated with T4-DNA polymerase (T4 processed) or processed similarly in a reaction solution lacking the T4 polymerase (untreated). Post-capture processing with T4-polymerase induced an overall reduction in the size distribution of the sample, suggesting a reduction in the average size of insert. Additionally, T4 processing resulted in the appearance of two faint bands (~250 bp and ~175 bp).

The gel image (2% agarose, 100 ng of material loaded) is shown in FIG. 12. Processing had two noticeable effects. First, it produced two faint bands of ~250 bp (upper arrow) and ~175 bp (lower arrow) in addition to an expected smear. The lower band was consistent with inadvertent cloning of probe (115 bp of adaptor+60 bp probe=175 bp). Second, processing reduced the overall size distribution of the sample. This was noteworthy since the 50 bp single adaptors were replaced by 115 bp full-length adaptors, which was expected to create an overall upward shift of 65 bp in processed material. The interpretation was that processing reduced the average insert size of the library significantly.

Two efforts were made to measure enrichment efficiency by qPCR. In the first, more qualitative effort, all eight PLP1 assays (described in detail in Example 5: Validation of PLP1 qPCR assays) were used to measure six samples:
1. 25 ng/assay of starting gDNA library
2. 0.25 ng/assay of untreated C1
3. 0.25 ng/assay of untreated C10
4. 0.25 ng/assay of T4 treated C1
5. 0.25 ng/assay of T4 treated C10
6. No template control The Cq values from these single measurements are shown in Table 14 below. The gDNA and NTC controls did perform well (top and bottom, lightest shades) and were not evaluated further.

TABLE 14

| | Cq values of qualitative PLP1 assay analysis of enrichment efficiencies | | | | | | | |
|---|---|---|---|---|---|---|---|---|
| | Assay 1 | Assay 2 | Assay 3 | Assay 4 | Assay 5 | Assay 6 | Assay 7 | Assay 8 |
| gDNA | N/A | 27 | 29 | 40 | 27 | 30 | 23 | 32 |
| un-C1 | 12 | 8 | 8 | 9 | 5 | 11 | 24 | 29 |
| un-C10 | 16 | 14 | 14 | 15 | 9 | 10 | 30 | 31 |
| T4-C1 | 7 | 6 | 3 | 3 | 4 | 19 | 25 | N/A |
| T4-C10 | 4 | 3 | 4 | 6 | 3 | 17 | 26 | 28 |
| NTC | 32 | 32 | 31 | 23 | 24 | 28 | 24 | 30 |

The T4-treated samples (darkest shading) had so much signal (Cq's less than 10) that quantitative analysis was not very informative. But at a qualitative level, two trends were clear in comparison to untreated capture complexes (middle shading). One was that on-target signal from assays 1-5 increases (lower Cq's) dramatically. The other was that off-target signal from Assay 6, which is 200 bp away from the target region, decreased significantly upon processing. While the data have some bumps and warts the central message was that processing greatly enhanced specificity of PLP1 exon2 signal.

To capture more quantitative aspects of this experiment, the untreated C10 capture amplicons were diluted 1000-fold and the processed C10 amplicons 15,000 fold prior to qPCR; this was done to bring Cq values into a measurable range. The starting gDNA library was then examined and these diluted samples in quadruplicate wells of the qPCR plate across two on-target assays (Assays 2 and 5) and two off-target assays (Assays 6 and 7). The Cq values of the quadruplicate wells were averaged and these values are shown in Table 15 below. Once again the gDNA signal was poor; the impact of poor signal on data interpretation was not terribly significant because the goal of these experiments was to compare PLP1 exon2 signal in unprocessed versus T4 polymerase treated capture complexes. The Cq values were converted to absolute values using a "universal" standard curve that assumes 2-fold amplification with every PCR cycle. The third segment of the table shows the adjustment for dilutions. The fourth segment, ratios of unprocessed and T4-treated to gDNA is not as useful; however, at the bottom of the table is the quantitative ratios of unprocessed versus T4-treated complex. In Example 6, it was observed that untreated capture enrichment of 82,000× for C1 and 28,000× for C10 (as in all these experiments, the gDNA denominator was derived from very low signal, so the fold range had a qualitative aspect to it), so a reasonable estimate was that capture alone produced a 50,000× enrichment of the 300 bp PLP1 exon2 region. Processing increased this enrichment another 50-fold (average of 83× and 24× from the Table 15), pushing enrichment to 2.5 million-fold and 10 million fold (3 billion bases per genome over 300 bp target). At the level of qPCR measurements, capture+processing therefore appeared to approach best-case scenarios in terms of enrichment. It was noteworthy that the off-target signal that was 200 bp removed from the target monitored by Assay 6, while greatly enriched by capture alone (the hitch-hiker, cross-hyb effect), dropped significantly with processing.

TABLE 15

Cq values of quantitative PLP1 assay analysis of enrichment efficiencies

| | Assay 2 | Assay 5 | Assay 6 | Assay 7 |
|---|---|---|---|---|
| Raw Cq values | | | | |
| Cq | | | | |
| gDNA | 27 | 33 | 35 | 27 |
| capture | 15 | 12 | 17 | 32 |
| cap + enz | 13 | 11 | 24 | 31 |
| Cq converted to absolute values | | | | |
| abs val | | | | |
| gDNA | 81 | 1 | 0 | 95 |
| capture | 253464 | 2538822 | 89450 | 3 |
| cap + enz | 1408479 | 4050620 | 506 | 4 |
| Absolute value adjusted for dilutions of samples | | | | |
| abs val | | | | |
| gDNA | 81 | 1 | 0 | 95 |
| capture | 253465648 | 2538821701 | 89449912 | 2573 |
| cap + enz | 21127189405 | 60759299218 | 7584546 | 66931 |
| Ratios of captured samples to gDNA | | | | |
| /gDNA | | | | |
| capture | 3126652 | 2394181716 | 239697693 | |
| cap + enz | 260618748 | 57297762664 | 20324204 | |
| Ratios of unprocessed to processed sample | | | | |
| enz/cap | | | | |
| cap + enz | 83 | 24 | 0.08 | |

This experiment addressed the specificity of capture+processing—the non-target qPCR signal. The specific activity per ng of amplified DNA—from PLP1 exon 2 was greatly enhanced by post-capture processing. This experiment did not address sensitivity, that is, the percent of capture complexes that are converted by enzyme. A quantitative understanding of both specificity and sensitivity of the present method may also be important in particular embodiments.

Example 9: Direct Measurement of Post-Capture Processing

Purpose: In the Example 8, it was determined that post-capture processing achieved the desired aim of substantially increasing target capture specificity. The other critical parameter to be examined is sensitivity, i.e. the percentage of the initially captured complexes that are recovered in the final sequencing library. In this example, we demonstrated by direct measurement of sensitivity that enzymatic processing is effective for >10% of the initially captured sequences.

Summary: The data from this experiment indicated that 10% of the on-target capture complexes were processed by T4 polymerase into post-capture sequencing library fragments.

Figure 13A:
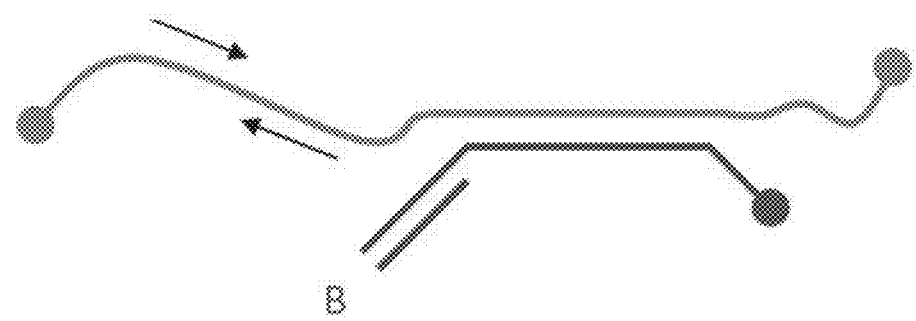
FIG. 13A-FIG. 13C: Direct measurement of post-capture processing sensitivity. First, PLP1 exon 2 specific genomic DNA fragments were isolated by pull down/pull out from the female gDNA library (Example 1) using single PLP1 capture probes in independent reactions. Captured material was quantified using an adjacent PLP1 qPCR assay primer pair, as illustrated in (FIG. 13A). Following enzymatic processing the amount of processed complex was measured again by qPCR using one PLP1 specific primer and one probe-specific primer, as show in (FIG. 13B). The ratio of the measurements in [B/A×100%] will yield an estimate of processing efficiency. The PCR products from real-time reactions were extracted and subjected to gel analysis to verify that amplicons of the expected length were produced (FIG. 13C). This was possible since both PCR reactions had discrete start and stop points. Processing efficiency was inferred from pull-outs that yielded interpretable data from A+B+C.
Figure 13B:
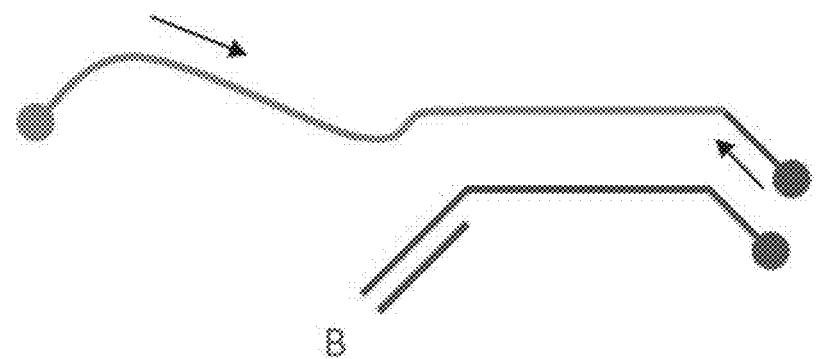
Figure 13C:
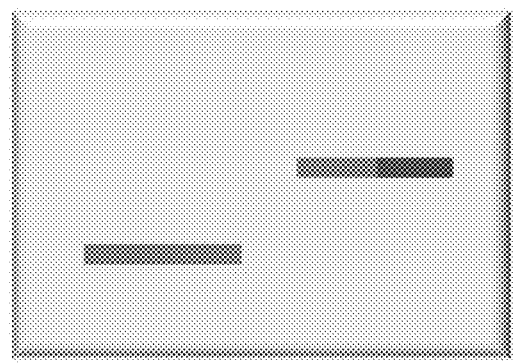

Considerations: By way of reference, a schematic illustration of post-capture processing is shown in FIG. 4. Here, the sensitivity of processing was measured in a three-step procedure, which is illustrated on the lower right of FIG. 13. First, single PLP1 capture probes were used in independent reactions to pull down/pull out PLP1 exon 2 specific genomic DNA fragments from the female gDNA library (Example 3: hgDNA library from Promega female). As there were four probes, four pull-downs were performed. The amount of captured material was measured using an adjacent PLP1 qPCR assay primer pair, as illustrated in FIG. 13(A). Following enzymatic processing of the complex, again by qPCR, the amount of processed complex was measured by using one PLP1 specific primer and one probe-specific primer, as show in FIG. 13(B). The ratio of the measurements in [B/A×100%] yielded an estimate of processing efficiency. Critical to the correct interpretation of the experimental results, the PCR products were extracted from real-time reactions and verified that amplicons of the expected length were produced by gel analysis FIG. 13(C). This was possible because both PCR reactions had discrete start and stop points. Pull-outs that yield interpretable data from A+B+C were used to determine processing efficiency.

Assays: Individual probes needed to be matched to qPCR assays. Six combinations of probes matched to pre- and post-process qPCR assays were elected. These are shown below with probe sequences in italics, PLP1 exon2 specific primers shaded. The darker shaded primers are those that are paired with the CAC3 primer after processing. The expected product sizes of the PCR amplicons are also shown for each assay set:

| SEQ ID NO: | NAME | SEQUENCE |
|---|---|---|
| 116 | Probe 1 and assay 1; qPCR assay 1 = 77 bp; CAC3⇆R1 = 167 bp | agtgcccactatctccgagcctgtgagcacagggcctggcag agggg*tttgagtggcatgagctacctactggatgtgcctgac tgtttcccttcttcttccccag*GCTTGTTAGAGTGCTGTGC AAGATGTCTGGTAGGGGCCCCCTTTGCTTCCCTGGTGGCCAC TGGATTGTGTTTCTTTGGGGTGGCACTGTTCTGTGGCTGTGG ACATGAAGCCCTCACTGGCACAGAAAAGCTAATTGAGACCTA TTTCTCCAAAAACTACCAAGACTATGAGTATCTCATCAATGT gtaagtacctgccctcccacacagacccatctttttttttccc tctctccatcctggagatagagaactcttcagtaccttagta actagcaggggactggggtgga |
| 117 | Probe 1 and assay 2; qPCR assay 2 = 83 bp; CAC3⇆R2 = 224 bp: | agtgcccactatctccgagcctgtgagcacagggcctggcag agggg*tttgagtggcatgagctacctactggatgtgcctgac tgtttcccttcttcttccccag*GCTTGTTAGAGTGCTGTGC AAGATGTCTGGTAGGGGCCCCCTTTGCTTCCCTGGTGGCCAC TGGATTGTGTTTCTTTGGGGTGGCACTGTTCTGTGGCTGTGG ACATGAAGCCCTCACTGGCACAGAAAAGCTAATTGAGACCTA TTTCTCCAAAAACTACCAAGACTATGAGTATCTCATCAATGT gtaagtacctgccctcccacacagacccatctttttttttccc tctctccatcctggagatagagaactcttcagtaccttagta actagcaggggactggggtgga |
| 118 | Assay 3 and probe 4; qPCR assay 3 = 81 bp; F3⇆CAC3 = 187 bp: | agtgcccactatctccgagcctgtgagcacagggcctggcag agggg*tttgagtggcatgagctacctactggatgtgcctgac tgtttcccttcttcttccccag*GCTTGTTAGAGTGCTGTGC AAGATGTCTGGTAGGGGCCCCCTTTGCTTCCCTGGTGGCCAC TGGATTGTGTTTCTTTGGGGTGGCACTGTTCTGTGGCTGTGG ACATGAAGCCCTCACTGGCACAGAAAAGCTAATTGAGACCTA TTTCTCCAAAAACTACCAAGACTATGAGTATCTCATCAATGT *gtaagtacctgccctcccacacagacccatctttttttttccc tctctccatcctggagat*agagaactcttcagtaccttagta actagcaggggactggggtgga |
| 119 | Assay 2 and probe 4; qPCR assay 2 = 83 bp; F2⇆CAC3 = 216 bp: | agtgcccactatctccgagcctgtgagcacagggcctggcag agggg*tttgagtggcatgagctacctactggatgtgcctgac tgtttcccttcttcttccccag*GCTTGTTAGAGTGCTGTGC AAGATGTCTGGTAGGGGCCCCCTTTGCTTCCCTGGTGGCCAC TGGATTGTGTTTCTTTGGGGTGGCACTGTTCTGTGGCTGTGG ACATGAAGCCCTCACTGGCACAGAAAAGCTAATTGAGACCTA TTTCTCCAAAAACTACCAAGACTATGAGTATCTCATCAATGT *gtaagtacctgccctcccacacagacccatctttttttttccc tctctccatcctggagat*agagaactcttcagtaccttagta actagcaggggactggggtgga |
| 120 | Probe 2 and assay 5; qPCR assay 5 = 95 bp; CAC3⇆R5 = 209 bp: | agtgcccactatctccgagcctgtgagcacagggcctggcag agggg*tttgagtggcatgagctacctactggatgtgcctgac tgtttcccttcttcttccccag*GCTTGTTAGAGTGCTGTGC AAG*ATGTCTGGTAGGGGCCCCCTTTGCTTCCCTGGTGGCCAC TGGATTGTGTTTCTTTGGGGT*GGCACTGTTCTGTGGCTGTGG ACATGAAGCCCTCACTGGCACAGAAAAGCTAATTGAGACCTA TTTCTCCAAAAACTACCAAGACTATGAGTATCTCATCAATGT gtaagtacctgccctcccacacagacccatctttttttttccc tctctccatcctggagatagagaactcttcagtaccttagta actagcaggggactggggtgga |
| 121 | Assay 4 and probe 3; qPCR assay 4 = 97 bp; F4⇆CAC3 = 204 bp: | agtgcccactatctccgagcctgtgagcacagggcctggcag agggg*tttgagtggcatgagctacctactggatgtgcctgac tgtttcccttcttcttccccag*GCTTGTTAGAGTGCTGTGC AAGATGTCTGGTAGGGGCCCCCTTTGCTTCCCTGGTGGCCAC TGGATTGTGTTTCTTTGGGGTGGCACTGTTCTGTGGCTGTGG AC*ATGAAGCCCTCACTGGCACAGAAAAGCTAATTGAGACCTA TTTCTCCAAAAACTACCAAG*ACTATGAGTATCTCATCAATGT gtaagtacctgccctcccacacagacccatctttttttttccc tctctccatcctggagatagagaactcttcagtaccttagta actagcaggggactggggtgga |

Methods

Probes. In these assays the B10 universal oligo set of probes (24 Aug. 2012 Experiment 4—Capture of PLP1 exon 2) was chosen. To make individual capture probes, 1 of universal oligo 10 (100 μM) was combined with 1 μL of 100 μM probe ultramer and 98 of TEz+0.05% Tween20. This was further diluted 4 μL into 996 μL TEz+Tween to provide a 4 nM working solution.

Capture. For capture 50 μL of 22 ng/μL gDNA library, 20 μL of 4× binding buffer, 1 μL of probe and 9 μL of water were combined. There were six independent capture reactions (two with probe #1, two with probe #4, one with probe #2 and one with probe #3). These were heated to 95° C. for 1 min then cooled in 35 "cycles" of −1° C. and 2 min to 60° C. as described earlier. Following annealing, 10 μL of washed beads (=1 μL of stock beads) was added and binding was incubated for 20 min at RT. Beads were then pulled aside and washed 4 times, 5 min each, with 200 µL aliquots of wash buffer. After the last wash, all remaining accessible fluid was aspirated from the beads.

Processing. Beads were resuspended in 10 µL of quick blunt solution (200 µL=20 µL of 10× quick blunting buffer, 20 µL of 1 mM dNTP and 160 µL water). Each of the six aliquots of beads was split into two 5 µL aliquot. 5 µL of QB buffer without enzyme was added to one set of tubes (these are the capture-only aliquot). To the other 5 µL aliquots, 5 of QB buffer containing 0.025 µL of T4 polymerase (this was made by combining 100 QB buffer with 0.5 µL of T4 polymerase and distributing 5 µL aliquots) was added. Both the capture only and the capture+processing tubes were incubated at 20° C. for 15 min, 98° C. for 1 min, cooled to RT and placed immediately on magnets. ~10 µL of supernatant was pulled from the six pairs of capture-only and T4-processed complexes (now 12 tubes total). These supernatants were used directly in qPCR as described below.

qPCR For these assays, standard Taq reaction mix and 3 step thermal cycling were chosen. Twelve of 40 µL qPCR mix were constructed, each containing:

14 µL of water

4 µL of 10×STD Taq buffer

4 µL of 25 mM MgCl2

4 µL of a blend of F and R primer at 10 µM each

8 µL of template (supernatant from above)

2 µL of DMSO

2 µL of 10 mM dNTPs

1 µL of EvaGreen 0.8 µL of ROX 0.4 µL of Taq polymerase

Reactions were distributed in quads and cycled for 40 cycles of 94° C.-30 sec, 55° C.-30 sec, 72° C.-60 sec. Following PCR, reaction mix was pooled from each of the four wells of the quad and 5 µL was analyzed on 2% agarose gels.

Results

Figure 14:
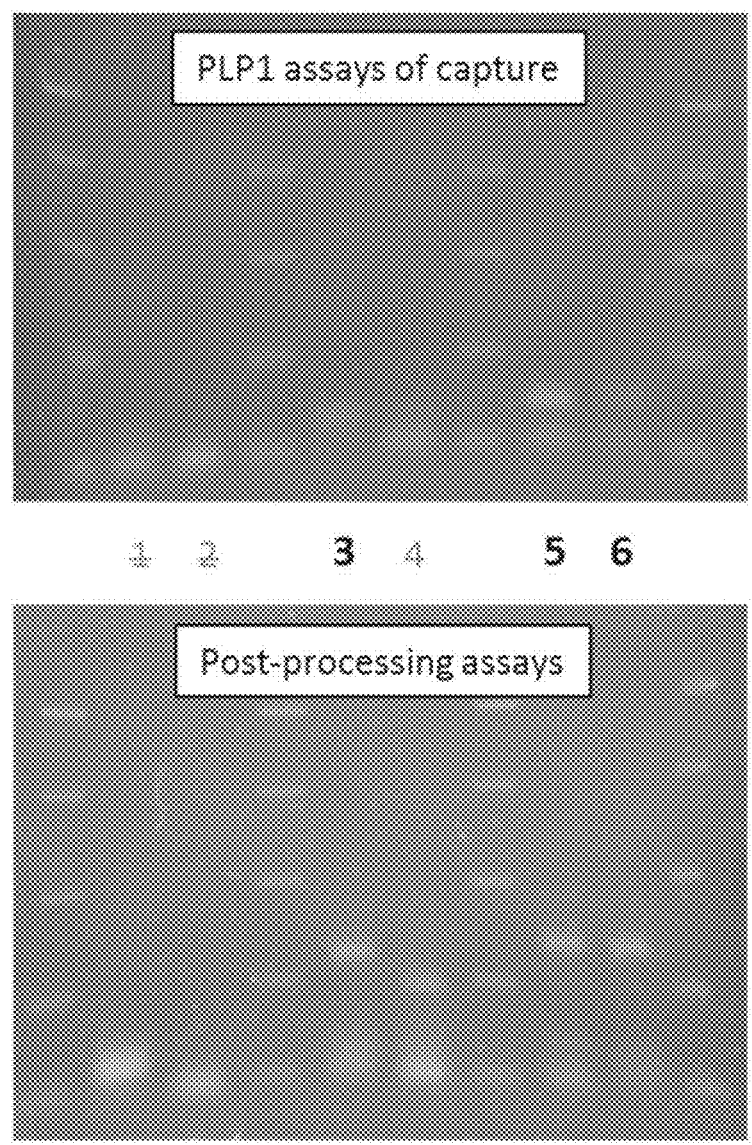
FIG. 14: Gel analysis of qPCR products from real-time quantification of pre- and post-processed PLP1 exon 2 captured DNA fragments. Six independent capture reactions (two with probe #1, two with probe #4, one with probe #2, and one with probe #3) were processed as described in FIG. 16. The probes were from the B10 universal oligo set (Example 4) and comprised universal oligo and probe ultramer. Under these conditions, assay sets 3 (probe 4), 5 (probe 2) and 6 (probe 3) yielded PCR products consistent with the assay amplicon (top gel) or the post-processed PLP1 to adaptor amplicons (bottom gel), while no detectable products were observed in the other assay sets.

To interpret the experimental data, the agarose gels that are shown in FIG. 14 were examined. Under the cycling conditions used with the primers used (etc.) it was observed that assay sets 3, 5 and 6 yielded PCR products consistent with the assay amplicon (top gel) or the post-processed PLP1 to adaptor amplicons (bottom gel). The more successful assay sets corresponded to:

Probe 4 with assay 3

Probe 2 with assay 5

Probe 3 with assay 4

The qPCR Cq values are shown in Table 16 below. Assays 1 and 2 failed gel analysis. Successful assays are shown in assays 3, 5 and 4. To derive % processing values, Cq's were converted to absolute values (In "Excel speak", Abs value=power(10,log 10(½)*Cq+10). The quotient of post-processed over capture only was then expressed as a percentage. This measurement assumed that the amplification efficiency of the all amplicons was the same and conforms to an idealized standard curve (probably reasonably accurate). Assuming this was correct, then approximately 10% of captured material appears to be processed.

TABLE 16 qPCR analysis of post-capture processing sensitivity

| | probe 1 assay 1 | probe 1 assay 2 | probe 4 assay 3 | probe 4 assay 2 | probe 2 assay 5 | probe 3 assay 4 |
|---|---|---|---|---|---|---|
| capture | 23 | 21 | 25 | 21 | 25 | 26 |
| post-process | 16 | 23 | 29 | 22 | 28 | 29 |
| % processed | | | 7% | | 17% | 10% |

Example 10: Construction of Expanded Code Male and Female gDNA Libraries

Purpose: Build set of 16 coded male and female gDNA libraries that will be used to test multiple capture parameters in a single MiSeq sequencing run.

Methods

Step 1: gDNA. Repaired gDNA was prepared.

Step 2: All 16 possible adaptor codes were generated. These codes are four base structures in which the base positions at −4 and −3 (relative to the insert) are random bases and the base positions at −2 and +1 are sample codes. There are four "clusters" of sample codes. These are:

Cluster 1: AC, GA, CT, TG

Cluster 2: AA, GC, CG, TT

Cluster 3: AG, GT, CA, TC

Cluster 4: AT, GG, CC, TA

Clusters 2-4 were ordered as 100 µM oligos in plates. One set of plates had ligation strand and one set of plates had partner strands. The plate array was A1-H1, A2-H2, etc. To anneal adaptors in two sets of 96 well PCR plates, 70 µL/well of "annealing solution" containing 68 µL of TEz and 2 µL of 5M NaCl was added to 20 µL partner strand oligo and 10 ligation strand oligo, covered with tape, and annealed 10 sec at 95° C., 5 min 65° C., and cooled to RT. Pooled sets of 16—random codes that have the same sample code—into sets of four. Red=set AA, GC, CG and TT. Purple=set AG, GT, CA and TC. Blue=set AT, GG, CC and TA (laid out in this order).

Step 3: It is easiest to create 16 ligation for female DNA and 16 ligations for male DNA in which both types received the same set of 16 unique adaptor types. This will allow us to decide later which combinations of samples we want to create with maximum flexibility. To do this, End-repaired gDNA from the experiment was used. I will perform the requisite 32 ligation in 20 µL/rxn as follows:

Two gDNA cocktails were made, one female and one male, that contain:

144 µL water

32 µL 10× lig buffer

48 µL 50% PEG8000

64 µL gDNA

The cocktails were mixed and aliquoted into 16 tubes with 18 µL each. 2 of adaptors and 0.5 µL HC T4 ligase were added and the resulting reactions were incubated at 22° C. for 60 min, 65° C. for 10 min, and cooled to RT. 80 µL TEz, then 120 µL Ampure beads were also added to the reactions, mixed and incubated 10 min at RT. The reactions were wash twice with 200 µL of 70% EtOH/water (v/v), air dried, and resuspended in 100 µL TEz.

Step 4: qPCR. Make qPCR master mix containing:

175 µL of water

50 µL of 10×STD Taq buffer

50 µL of 25 mM MgCl2

100 µL of ACA2 primer (10 µM)

(50 µL of template—added later)

25 µL of DMSO

25 µL of 10 mM dNTPs
12.5 µL of Eva green
10 µL of ROX
5 µL of Taq DNA polymerase
9 µL was distributed into the 48 wells of an Illumina Eco qPCR plate. Two serial dilutions of library calibration standard were made that are 10 pg/µL and 1 pg/µL. The remainder of the plate was loaded with libraries as shown in the tables below.

TABLE 17

Sample key for 48 well assay plate 1

|   | 1 | 2 | 3 | 4 | 5 | 6 | 7 | 8 |
|---|---|---|---|---|---|---|---|---|
| A | 10 pg/µL STD | 1 pg/µL STD | F1 | F2 | F3 | F4 | F5 | F6 |
| B | 10 pg/µL STD | 1 pg/µL STD | F1 | F2 | F3 | F4 | F5 | F6 |
| C | F7 | F8 | F9 | F10 | F11 | F12 | F13 | F14 |
| D | F7 | F8 | F9 | F10 | F11 | F12 | F13 | F14 |
| E | F15 | F16 | M1 | M2 | M3 | M4 | M5 | M6 |
| F | F15 | F16 | M1 | M2 | M3 | M4 | M5 | M6 |

The second plate had the layout shown in Table 18 below.

TABLE 18

Sample key for 48 well assay plate 2

|   | 1 | 2 | 3 | 4 | 5 | 6 | 7 | 8 |
|---|---|---|---|---|---|---|---|---|
| A | 100 pg/µL STD | 10 pg/µL STD | 1 pg/µL STD | NTC | F15 | M1 | M2 | M3 |
| B | 100 pg/µL STD | 10 pg/µL STD | 1 pg/µL STD | NTC | F15 | M1 | M2 | M3 |
| C | M1 | M2 | M3 | M4 | M5 | M6 | M7 | M8 |
| D | M1 | M2 | M3 | M4 | M5 | M6 | M7 | M8 |
| E | M9 | M10 | M11 | M12 | M13 | M14 | M15 | M16 |
| F | M9 | M10 | M11 | M12 | M13 | M14 | M15 | M16 |

Ligation efficiency was measured by the following cycling program:
72° C.-2 min
94° C.-30 sec, 60° C.-30 sec, and 72° C.-60 sec; 40 cycles
Results: FIG. 49 shows the Cq values of STDs and samples (the average of duplicate measurements except (i) the experiment repeated on plate 2 and (ii) M1, M2 and M3 were measured in three sets of duplicates—average of the three measurements taken).

These were converted to arbitrary absolute values by the equation quantity=power (10,log 10(½)*Cq+8) in Excel.

Values were then normalized to the known standards by multiplying abs values by 10/1583 (plate 1) or 10/1469 (plate 2). Genomes per µL was calculated by multiplying by ⅞ (to account for adaptor mass) and then dividing by 3 pg/genome. The ligation efficiency was calculated (20 ng/ligation & ¹/₁₀₀th measured=200 pg into ligation), and the calculated efficiency indicated that ~5% conversion to library is about average. This was the same for libraries made without fill-in, which suggested that the fill-in reaction has rapid kinetics and can occur as the sample heats to 94° C. in the first cycle.

The goal of this experiment was to create ligation mixes containing gDNA library and to quantify genome equivalents per µL of ligation mix so that measured numbers of genomes can be amplified into microgram quantities of library material. FIG. 50 shows the genomes per µL for each library that was made. The goal of FIG. 51 was to convert designated samples (picked by random drawing) into 10 copy, 20 copy, 40 copy, 80 copy, etc. libraries for downstream capture tests. The table transposes the genomes per µL into µL per PCR reaction to achieve the indicated depth of coverage. The table assumes a 200 µL PCR per sample and 40 of template input. These experiments may be used as guides where actual libraries are generated and purified.

Example 11: Validation of 8 New Capture qPCR Assays

Purpose: Validate the performance of eight new qPCR primer sets designed to follow capture efficiency of the expanded probe collection.

Summary: All eight assays produced amplicons of the expected size when used to amplify human gDNA. Quantitative analysis of the chrX:154376051 region (4× in females, 2× in males) showed a surprisingly tight correlation between observed and expected copies.

Methods: Eight segments for assay design that represent a sampling of the 49 probe target regions were chosen. To design assays, the DNA segment that is within 200 bp of the 5' end of the probe was identified. The eight regions, as shown in Table 19 below, were chosen to be a more-or-less random selection of target regions. The 200 bp segments were submitted to PRIMER3 PCR primer picking in which we specified amplicons of 50-100 bp, primer Tm's of 65° C. (optimal) and primer lengths of 24 nt (optimal). Table 19 below shows the region and unique genomic attributes, the forward (F) and reverse (R) primer sequences, the expected amplicon length, and the actual amplicon within the context of the genomic sequence.

TABLE 19

Genomic capture targets, and primers for their interrogation

| SEQ ID NO: | Assay | Region | Feature | Name | Sequence | Product |
|---|---|---|---|---|---|---|
| 122 | 9 | CYP2D6 | 4X in males and females | CYP2D6_F | GGCTTCGACTGAACGTCTCCA | 53 bp |
| 123 |   |   |   | CYP2D6_R | AGTGCTCCATGGCTGCTCAGTT |   |
| 124 | 10 | chrX-154376051 | 4X in females, 2X in males | chrX-15_1_F | GAACCAGAGGAACGCTGTGGTAACT | 52 bp |

TABLE 19-continued

Genomic capture targets, and primers for their interrogation

| SEQ ID NO: | Assay | Region | Feature | Name | Sequence | Product |
|---|---|---|---|---|---|---|
| 125 | | | | chrX-15_1_R | GACGTGTGCCTAGATGCGTTTTC | |
| 126 | 11 | chrX-154376051 | 4X in females, 2X in males | chrX-15_2_F | TGGCTGAAAAGTCTCCTTGAAACTG | 53 bp |
| 127 | | | | chrX-15_2_R | CTCAGTGGGTCTCCTTGAGAGAGGT | |
| 128 | 12 | chrX-6929264 | 6X in females, 5X in males (2 on chr19, one on chrX) | chrX-69_F | CTTTCCTCCAGTCACAAGCCATCTA | 78 bp |
| 129 | | | | chrX-69_R | CATGCTGATAGAAAGTCCCCTGGTA | |
| 130 | 13 | KRAS region 1 | 2X in females and males | KRAS_r1_F | TTTTCACACAGCCAGGAGTCTTTTC | 66 bp |
| 131 | | | | KRAS_r1_R | GGGAGATCCGACAATACAGATTGAA | |
| 132 | 14 | KRAS region 2 | 2X in females and males | KRAS_r2_F | CCTGTCTTGTCTTTGCTGATGTTTC | 73 bp |
| 133 | | | | KRAS_r2_R | ACAAAACAGGCTCAGGACTTAGCAA | |
| 134 | 15 | MYC region 2 | 2X in females and males | MYC_r2_1_F | CAACGTTAGCTTCACCAACAGGAAC | 92 bp |
| 135 | | | | MYC_r2_1_R | GCTGGTAGAAGTTCTCCTCCTCGTC | |
| 136 | 16 | MYC region 2 | 2X in females and males | MYC_r2_2_F | GTCTGCTCCACCTCCAGCTTGTA | 93 bp |
| 137 | | | | MYC_r2_2_R | GTTGAGAGGGTAGGGGAAGACCAC | |

The performance of each primer pair was investigated by performing 100 PCR reactions that contained 200 ng (2 ng/µL) of female genomic DNA. The reaction mixes contained, per 100 µL, 50 µL water, 10 µL 10×STD Taq buffer, 10 µL 25 mM MgCl2, 10 of an F+R primer blend in which each primer was present at 10 µM, 10 µL of 20 ng/µL gDNA, 5 of DMSO, 5 µL of 10 mM dNTPs, and 1 µL of Taq polymerase. Reactions were set up on ice. Amplifications were performed for 30 cycles of 94° C.-30 sec, 60° C.-30 sec, and 72° C.-30 sec, followed by a 2 min incubation at 72° C. and hold at 10° C. Five µL of PCR product was examined on a 2% agarose gel.

PCR products were purified on Qiagen PCR purification columns by combining the remaining 95 µL of PCR product with 500 µL PB. The material was spun through the column at 6 KRPM for 30 sec and washed with 750 µL PE, spun at 13.2 KRPM. The products were eluted from the columns with 50 µL of EB and quantified by Qubit.

For qPCR analysis, the chrX-154376051 region (assays 10 & 11) was examined in more detail. The purified PCR products were diluted to 100 fg/µL, 10 fg/µL and 1 fg/µL. Genomic DNA was diluted to 10 ng/µL. Two microliters of either standards or gDNA was combined with 8 µL of PCR master mix per well of the 48-well Eco qPCR plate. Master mix contained, per 500 µL of final reaction volume (that accounts for the addition of template) 175 of water, 50 µL of 10×STD Taq buffer, 50 µL of 25 mM MgCl2, 50 µL of F+R 10 µM primer blend, 25 µL of DMSO, 25 µL of 10 mM dNTPs, 12.5 µL EvaGreen, 10 µL of ROX and 5 µL of Taq polymerase. Thirty two µL of mix was distributed to 16 wells and 8 µL of templates were added. These were then distributed in quads to the qPCR plate. The plate layout is shown in Table 20 below. Conditions for Assay 10 are indicated in bold. Conditions for Assay 11 are indicated in underlined italics.

TABLE 20

Plate layout for qPCR interrogation of chrX-154376051 region

|   | 1 | 2 | 3 | 4 | 5 | 6 | 7 | 8 |
|---|---|---|---|---|---|---|---|---|
| A | 100 fg PCR prod | | 10 fg PCR prod | | 1 fg PCR prod | | NTC | |
| B | | | | | | | | |
| C | *100 fg PCR prod* | | *10 fg PCR prod* | | *1 fg PCR prod* | | *NTC* | |
| D | | | | | | | | |
| E | F-gDNA | | M-gDNA | | *F-gDNA* | | *M-gDNA* | |
| F | | | | | | | | |

Results and Discussion: Gel analysis of the PCR products amplified from genomic DNA showed that all eight PCR reactions produced unique products of the expected size (data not shown). The amplicons were sufficiently clean (no extra bands, no left-over primer) and were useful for generating standard curves for quantitative analysis. The amplicons were purified using Qiagen PCR spin columns and eluted products in 50 µL. The product yields were: Assay 9—18.4 ng/µL; Assay 10—26.1 ng/µL; Assay 11—13.9 ng/µL; Assay 12—26.6 ng/µL; Assay 13—7.9 ng/µL; Assay 14—19.2 ng/µL; Assay 15—23.1 ng/µL; and Assay 16—20.4 ng/µL.

Quantitative analysis was performed with assays 10 & 11 that correspond to a cryptic segmental duplication on chromosome X such that females have four copies and males have two copies.

The average Cq values are shown in Table 21 below. These were used to generate the standard curves shown. The two reactions were basically superimposable. Using these curves we calculated the absolute quantities in units of femtograms of both the STD curve wells and the genomic input wells. The data are shown in Table 21 below the standard curve data.

TABLE 21

Cq values of standard samples analyzed with assays 10 and 11

| STD Curve 10 | 13 | 17 | 20 | 31 |
|---|---|---|---|---|
| STD Curve 11 | 13 | 16 | 20 | 33 |
| F then M Samples | 21 | 22 | 21 | 22 |

One point of this example was to emphasize the strength of quantitative molecular biology. In this experiment, 2 µL of STDs were added and sampled, meaning that the 1 fg/µL STD really had 2 fg in the qPCR reaction. This corresponds to 17,500 molecules of the 53 bp fragment of Assay 10. 20 ng of genomic DNA were put into the reaction. This corresponds to 6667 genomes worth of DNA. The genomic DNA was fragmented to an average size of 200 bp, meaning that only 75% of the target regions will remain intact. Hence, the gDNA had about 5000 "qPCR actionable" genome copies. Finally, in males the expected average of one copy of the duplicated X region per genome, and in females the expected average was two. The expected versus observed values, broken out by numbers of molecules observed, turned out to be as follows: Expected males=5000 copies; Observed males=3500 copies; Expected females=10000 copies; and Observed females=7000 copies.

TABLE 22

Expected vs. Observed Values

| STD curve 10 | 102.8004 | 9.421966 | 1.02996 |
|---|---|---|---|
| F then M samples | 0.447179 | 0.204926 | |
| STD curve 11 | 98.27451 | 10.35326 | 0.983644 |
| F then M samples | 0.388559 | 0.174757 | |

Example 12: Further Post-Capture Processing Strategy

Figure 15:
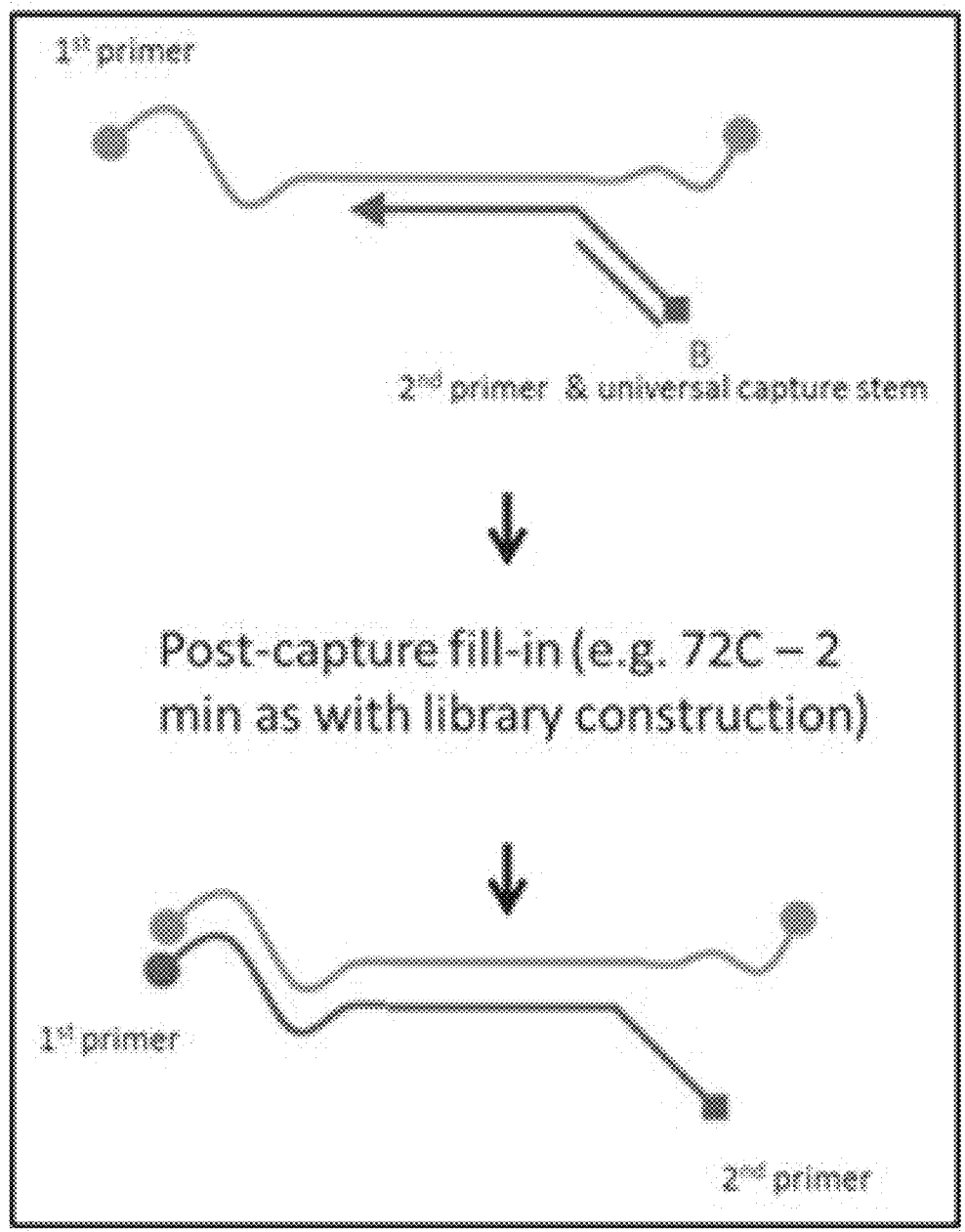
FIG. 15: Alternative enzymatic processing of fragment: probe hybridized complexes. In contrast to the method outlined in FIG. 4, this alternative approach shifted from having the clone copy the probe to having the probe copy the clone. This reversal in polarity means that the 5' end of the probe was used as both the pull-down sequence and the reverse PCR sequence. The 3' end of the probe was left unmodified thus it was able to copy the clone using DNA polymerase; 5'-3' DNA polymerase extended the multifunctional capture probe utilizing the isolated tagged DNA library fragments as template.

Purpose: An alternative method to achieve post-capture processing (see FIG. 15) was developed.

Summary: Post-capture processing steps performed with redesigned probes appeared to enhance the already robust capture by an additional 5-9-fold. Overall the test was very successful.

Background: In other embodiments of the assay design, it was contemplated to use an exonuclease step at the 3' end of clones prior to copying of the probe tail sequence that added a PCR priming site. The particular embodiments, it was further contemplated to shift from having the clone copy the probe to having the probe copy the clone. The reversal in polarity means that we use the 5' end of the probe as both the pull-down sequence and the reverse PCR primer sequence. The 3' end of the probe is left unmodified and can then copy the clone using DNA polymerase. Conceptually, there are some advantages to this approach. First, because there was a shift from a step that required both exonuclease activity and polymerization to a simple polymerization step, this step can be done in concert with PCR. Moreover, this step can be done at 72° C. with a thermostable polymerase enzyme, meaning potential secondary structures of single strand clones are less of an issue. Finally, the implication was that probes were shortened from 114 nt to 95 nt; and this provided a cost saving advantage.

Figure 16:
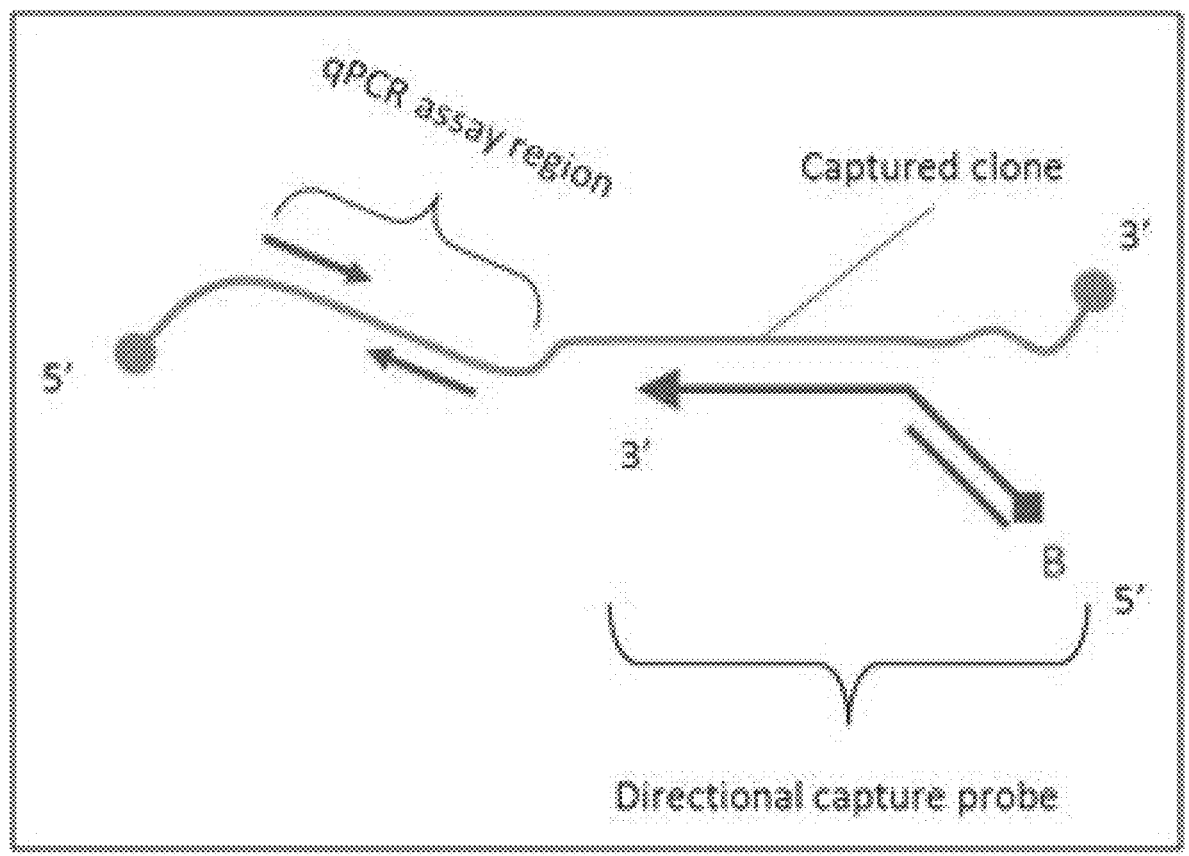
FIG. 16: Experimental design employed to test the alternative enzymatic processing concept. Four well behaved qPCR assays, (10, 14, 15 and 16) were matched with probes that "pointed" at those assays. Importantly, although the target sequences of the probe and qPCR assays were directed to regions within proximity to one another, they did not overlap. Thus the effect of the processing could be directly tested using these well-established assay sets.

Four well behaved qPCR assays (Example 11: Validation of eight new capture qPCR assays), assays 10, 14, 15 and 16 with probes that "point" at those assays were matched. While the probe and qPCR assays were within proximity to one another, their DNA sequences did not overlap with one another (See FIG. 16). The sequences of the probes and corresponding assays are shown in Tables 23 and 24 below.

TABLE 23

Genomic capture targets and primers for their interrogation

| SEQ ID NO: | Assay | Region | Feature | Name | Sequence | Product |
|---|---|---|---|---|---|---|
| 138 | 10 | chrX-154376051 | 4X in females, 2X in males | chrX-15_1_F | GAACCAGAGGAACGCT GTGGTAACT | 52 bp |
| 139 | | | | chrX-15_1_R | GACGTGTGCCTAGATG CGTTTTC | |
| 140 | 14 | KRAS region 2 | 2X in females and males | KRAS_r2_F | CCTGTCTTGTCTTTGC TGATGTTTC | 73 bp |
| 141 | | | | KRAS_r2_R | ACAAAACAGGCTCAGGACTTAGCAA | |
| 142 | 15 | MYC region 2 | 2X in females and males | MYC_r2_1_F | CAACGTTAGCTTCACC AACAGGAAC | 92 bp |
| 143 | | | | MYC_r2_1_R | GCTGGTAGAAGTTCTCCTCCTCGTC | |
| 144 | 16 | MYC region 2 | 2X in females and males | MYC_r2_2_F | GTCTGCTCCACCTCCA GCTTGTA | 93 bp |
| 145 | | | | MYC_r2_2_R | GTTGAGAGGGTAGGGGAAGACCAC | |

TABLE 24

Capture probe sequences and genomic targets

| SEQ ID NO: | Assay | Region | 60 mer probe sequence |
|---|---|---|---|
| 146 | 10 | chrX-154376051_2x_chrX: 154376979: region_1: 1011 nt: 929: 988: - | AGAATTCATTGCCAGCTATAAATC TGTGGAAACGCTGCCACACAATCT TAGCACACAAGA |
| 147 | 14 | KRAS_NM_033360_chr12: 25378485: region_2: 161 nt: -62: -3: + | TAAATGACATAACAGTTATGATTT TGCAGAAAACAGATCTGTATTTAT TTCAGTGTTACT |
| 148 | 15 | MYC_NM_002467_chr8: 128750431: region_2: 773 nt: -62: -3: + | AGGTTTCCGCACCAAGACCCCTTT AACTCAAGACTGCCTCCCGCTTTG TGTGCCCCGCTC |
| 149 | 16 | MYC_NM_002467_chr8: 128751122: region_2: 773 nt: 630: 689: - | AGAGCAGAGAATCCGAGGACGGAG AGAAGGCGCTGGAGTCTTGCGAGG CGCAGGACTTGG |

Methods: A gDNA library was remade from samples F13-F16 (Example 10) by combining 20 µL of each ligation mix into 80 µL total and amplifying in 800 µL total. Beads were cleaned to 400 µL and pool concentration at 32 ng/µL was measured by Qubit.

Oligos from IDT, listed below, were resuspended to 100 µM. ultramers come as 4 nmol, so these were suspended in 40 µL TEzero. Four 2 µL aliquots of the four test probes were combined with 8 µL of 100 µM universal tail sequence (derived from the first 35 bases of the full length reverse primer #9) to give a 50 µM tube of duplex. This duplex was diluted 10 µL into 990 µL of TEzero+Tween to give 500 nM, and 10 into 990 again to get 5 nM.

Combined 40 µL of gDNA was combined with 15 µL of 4× bind and 5 of capture duplex. The reaction mix was annealed and captured on 2 µLs of washed MyOne strep coated beads. The reaction was washed four times with wash buffer and aspirated wash buffer from bead pellet. To measure capture alone, one bead pellet was resuspended in 100 PCR mix that contained single PCR primer ACA2. To measure capture+processing, another bead pellet was resuspended in 100 µL of PCR mix that contained the full-length ACA2 forward primer (oligo #8) and full-length CAC3 reverse primer (oligo #9). The latter sample was incubated for 72° C. for 2 min. Both samples were amplified for 25 cycles of 94° C.-30 sec, 60° C.-30 sec, and 72° C.-60 sec. After a hold at 72° C. for 2 min and cooling to RT, the PCR amplicons were purified on bead and resuspended in 50 µL of TEzero.

For qPCR, samples were assayed with assays 9-16 (assays 10, 14, 15, and 16 are targets), using EvaGreen as the reporter dye, ROX as the STD dye, and 3 step PCR of 94° C.-30 sec, 60° C.-30 sec and 72° C.-60 sec for 40 cycles. The original gDNA library was present at 2 ng/µL final concentration. The captured sample and capture+processed samples were present at 2 pg/µL final concentration (diluted in TEzero+0.05% Tween20).

Figure 17:
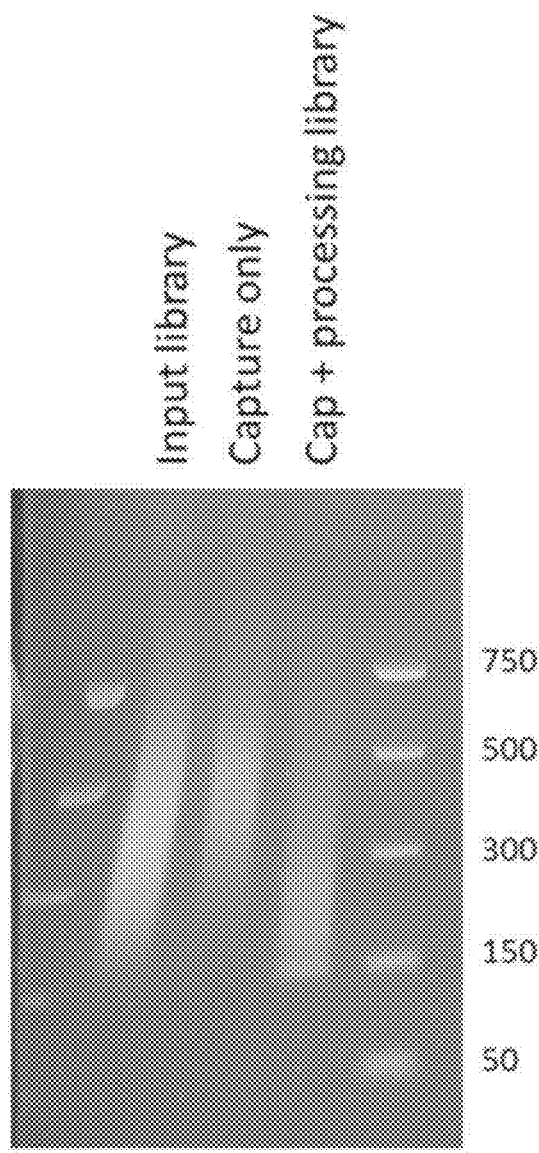
FIG. 17: Decrease in the average insert size of the library induced by the alternative processing method. DNA fragments were hybridized to capture probes/ultramers, and captured on streptavidin beads as previously described (FIG. 12). Post-capture processing was performed using the alternative method described in FIG. 17, and input samples as well as pre- and post-processed samples were analyzed by 2% agarose gel electrophoresis. As was expected, the average insert size of the library was decreased in the processed samples, thus supporting the conclusion that the processing worked. Collapsing of the library into an apparent band at the bottom of the processed sample was also observed, indicating some priming off of probe may have occurred.

Results and Discussion: PCR yields of the capture only was 27.8 ng/µL and of the capture+processing was 40.4 ng/µL. These robust yields indicated that amplification went to completion. The 2% agarose gel image shows the starting input library, the captured library and the capture+processing library (FIG. 17). If processing worked, the average insert size of the library should decrease, which it did. The fact that the bottom end of the library is more or less "a band" indicates that there may be some priming off of probe. Because the 3' end of our probes are exposed in this format, it may be possible to eliminate residual, unbound probe with Exonuclease I, a ssDNA specific, 3'→5' exonuclease.

An important metric in this experiment was qPCR measurement of capture sensitivity and specificity. qPCR data is shown in FIG. 52.

With respect to specificity, only those regions targeted (light gray highlight) exhibited significant enrichment. Moreover, the processed library had a significant increase in specific activity for all target regions relative to capture alone. These data indicated that this additional probe design embodiment could be used for efficient post-capture processing.

Example 13: Sequence Analysis of Post-Capture Processing Strategy

Purpose: The purpose of this experiment was to assess the enrichment and coverage of target regions in sequencing libraries.

Summary: The level of enrichment and focusing of target sequences was dramatically improved by coupling hybridization-based capture with enzymatic processing, compared to capture alone.

Background: Prior experiments disclosed herein have demonstrated that post-capture processing increases the target content and specific activity of enrichment libraries as measured by qPCR. In this experiment, next generation DNA sequencing was used to compare the representation and distribution of target sequences in libraries generated by capture alone or by the alternative processing method.

Methods: Two enrichment library pools were constructed from an equal mix of male and female human genomic DNA using a set of 49 capture probes that target sites within specific genes (KRAS, MYC, PLP1, CYP2D6 and AMY1) and duplicated regions on the X chromosome. Probe sequences are shown in Table 25 below

TABLE 25 qPCR analysis of capture sensitivity and specificity

| SEQ ID NO: | Probe No. | Probe Name | Probe Sequence |
|---|---|---|---|
| 150 | 1 | CYP2D6_F | ATGTGACTGGCACGGGAGTTGATCCTGGTTTTCACAAGCACCTAGCCC CATTCCTGCTGAGCAGGAGGTGGCAGGTACCCCAGACTGGGAGGTAA |
| 151 | 2 | CYP2D6_R | ATGTGACTGGCACGGGAGTTGATCCTGGTTTTCACAGTCGGTGGGGCC AGGATGAGGCCCAGTCTGTTCACACATGGCTGCTGCCTCTCAGCTCT |
| 152 | 3 | AMY1_F | ATGTGACTGGCACGGGAGTTGATCCTGGTTTTCACACCTGAGTAGCAT CATTGTAGTTCTCGATATCTCCACTTCCAGTTTTACATTTACCATCA |
| 153 | 4 | chrX_15_F | ATGTGACTGGCACGGGAGTTGATCCTGGTTTTCACCCTGGCCCTCAGC CAGTACAGAAAGTCATTTGTCAAGGCCTTCAGTTGGCAGACGTGCTC |
| 154 | 5 | chrX_15_R | ATGTGACTGGCACGGGAGTTGATCCTGGTTTTCACAGAATTCATTGCC AGCTATAAATCTGTGGAAACGCTGCCACACAATCTTAGCACACAAGA |
| 155 | 6 | chrX_477_F | ATGTGACTGGCACGGGAGTTGATCCTGGTTTTCACGACTTCAAAGAAA TTACAAGTTGACATCTTGGACTCTACCCCTCGTACTTTATCTCCTAT |
| 156 | 7 | chrX_477_R | ATGTGACTGGCACGGGAGTTGATCCTGGTTTTCACTCTCTTTGGGGTC AAGAAAGAATCCCTAGTGGATTTGGGATTCTAGAGGAGGTGTTATAA |
| 157 | 8 | chrX_478_F | ATGTGACTGGCACGGGAGTTGATCCTGGTTTTCACTGCGATACCATGC TGAAGATGAGCTAACCCAACCAGCCAAGCAGGCAGGGCTGCGAAGGA |
| 158 | 9 | chrX_478_R | ATGTGACTGGCACGGGAGTTGATCCTGGTTTTCACGGGGTAGGTGGAA AACCCAAGTAATGTGATTTTGTAACATCCACTGCTGCATTTGTTTGC |
| 159 | 10 | chrX_69_F | ATGTGACTGGCACGGGAGTTGATCCTGGTTTTCACTTACTTCCCTCCA GTTTTGTTGCTTGCAAAACAACAGAATCTTCTCTCCATGAAATCATG |
| 160 | 11 | chrX_69_R | ATGTGACTGGCACGGGAGTTGATCCTGGTTTTCACCAGGGGTATCTAT TATCCCCATTTTCTCACAAAGGAAACCAAGATAAAAGGTTTAAATGG |
| 161 | 12 | PLP1_ex1_F | ATGTGACTGGCACGGGAGTTGATCCTGGTTTTCACGAAATTCTCTTGT GAATTCCTGTGTCCTCTTGAATCTTCAATGCTAAAGTTTTTGAAACT |
| 162 | 13 | PLP1_ex2_F | ATGTGACTGGCACGGGAGTTGATCCTGGTTTTCACGGGTTTGAGTGGC ATGAGCTACCTACTGGATGTGCCTGACTGTTTCCCCTTCTTCTTCCC |
| 163 | 14 | PLP1_ex2_R | ATGTGACTGGCACGGGAGTTGATCCTGGTTTTCACCTATCTCCAGGAT GGAGAGAGGGAAAAAAAAGATGGGTCTGTGTGGGAGGGCAGGTACTT |
| 164 | 15 | PLP1_ex3_F | ATGTGACTGGCACGGGAGTTGATCCTGGTTTTCACGAAAGAAGCCAGG TCTTCAATTAATAAGATTCCCTGGTCTCGTTTGTCTACCTGTTAATG |
| 165 | 16 | PLP1_ex3_M | ATGTGACTGGCACGGGAGTTGATCCTGGTTTTCACCAGACTCGCGCCC AATTTTCCCCCACCCCTTGTTATTGCCACAAAATCCTGAGGATGATC |

TABLE 25-continued qPCR analysis of capture sensitivity and specificity

| SEQ ID NO: | Probe No. | Probe Name | Probe Sequence |
|---|---|---|---|
| 166 | 17 | PLP1_ex3_R | ATGTGACTGGCACGGGAGTTGATCCTGGTTTTCACTCTTTCTTCTTCC TTTATGGGGCCCTCCTGCTGGCTGAGGGCTTCTACACCACCGGCGCA |
| 167 | 18 | PLP1_ex4_F | ATGTGACTGGCACGGGAGTTGATCCTGGTTTTCACGTTTGTGTTTCTA CATCTGCAGGCTGATGCTGATTTCTAACCACCCCATGTCAATCATTT |
| 168 | 19 | PLP1_ex4_R | ATGTGACTGGCACGGGAGTTGATCCTGGTTTTCACAACCAAATATATA GTGCTTCCATAGTGGGTAGGAGAGCCAAAGCACCCGTACCCTAACTC |
| 169 | 20 | PLP1_ex5_F | ATGTGACTGGCACGGGAGTTGATCCTGGTTTTCACAGTCTCCATGTGG CCCCGTAACTCCATAAAGCTTACCCTGCTTGCTTTTTGTGTCTTACT |
| 170 | 21 | PLP4_ex5_R | ATGTGACTGGCACGGGAGTTGATCCTGGTTTTCACCCATGGGTGTAAT TTGTATGGTATTAGCTACTCCCTTGTAAAATAACCCAAATAACCCAC |
| 171 | 22 | PLP1_ex6_F | ATGTGACTGGCACGGGAGTTGATCCTGGTTTTCACTTTACAGTGGAGC ATATTACTGCTGTTGCAAGAAACAGTTCTTCCTCTTTCATTTTCCTG |
| 172 | 23 | PLP1_ex6_R | ATGTGACTGGCACGGGAGTTGATCCTGGTTTTCACATAGCTGTACCCA CACTATCTCAGGCCTATTTACTTGCCAAGATCATTCAAAGTCAACTC |
| 173 | 24 | PLP1_ex7_F | ATGTGACTGGCACGGGAGTTGATCCTGGTTTTCACGATTTGAGGAGGG AGTGCTTTCTTTTCTACTCTCATTCACATTCTCTCTTCTGTTCCCTA |
| 174 | 25 | PLP1_ex7_R | ATGTGACTGGCACGGGAGTTGATCCTGGTTTTCACCAGCATTGTAGGC TGTGTGGTTAGAGCCTCGCTATTAGAGAAAGGGGGATTTCTACGGGG |
| 175 | 26 | KRAS_ex1_F | ATGTGACTGGCACGGGAGTTGATCCTGGTTTTCACTGTTACCTTTAAA AGACATCTGCTTTCTGCCAAAATTAATGTGCTGAACTTAAACTTACC |
| 176 | 27 | KRAS_ex1_R | ATGTGACTGGCACGGGAGTTGATCCTGGTTTTCACTTCCCAGTAAATT ACTCTTACCAATGCAACAGACTTTAAAGAAGTTGTGTTTTACAATGC |
| 177 | 28 | KRAS_ex2_F | ATGTGACTGGCACGGGAGTTGATCCTGGTTTTCACTAAATGACATAAC AGTTATGATTTTGCAGAAAACAGATCTGTATTTATTTCAGTGTTACT |
| 178 | 29 | KRAS_ex2_R | ATGTGACTGGCACGGGAGTTGATCCTGGTTTTCACGACAGGTTTTGAA AGATATTTGTGTTACTAATGACTGTGCTATAACTTTTTTTTCTTTCC |
| 179 | 30 | KRA S_ex3_F | ATGTGACTGGCACGGGAGTTGATCCTGGTTTTCACACTCAAAAAATAA AAACTATAATTACTCCTTAATGTCAGCTTATTATATTCAATTTAAAC |
| 180 | 31 | KRAS_ex3_R | ATGTGACTGGCACGGGAGTTGATCCTGGTTTTCACAACACCTTTTTTG AAGTAAAAGGTGCACTGTAATAATCCAGACTGTGTTTCTCCCTTCTC |
| 181 | 32 | KRAS_ex4_F | ATGTGACTGGCACGGGAGTTGATCCTGGTTTTCACGAAACCTTTATCT GTATCAAAGAATGGTCCTGCACCAGTAATATGCATATTAAAACAAGA |
| 182 | 33 | KRAS_ex4_R | ATGTGACTGGCACGGGAGTTGATCCTGGTTTTCACGTGTATTAACCTT ATGTGTGACATGTTCTAATATAGTCACATTTTCATTATTTTTATTAT |
| 183 | 34 | MYC_r1_F1 | ATGTGACTGGCACGGGAGTTGATCCTGGTTTTCACCCCCAGCCAGCGG TCCGCAACCCTTGCCGCATCCACGAAACTTTGCCCATAGCAGCGGGC |
| 184 | 35 | MYC_r1_R1 | ATGTGACTGGCACGGGAGTTGATCCTGGTTTTCACCGACTCATCTCAG CATTAAAGTGATAAAAAAATAAATTAAAAGGCAAGTGGACTTCGGTG |
| 185 | 36 | MYC_r2_F1 | ATGTGACTGGCACGGGAGTTGATCCTGGTTTTCACCTGTGGCGCGCAC TGCGCGCTGCGCCAGGTTTCCGCACCAAGACCCCTTTAACTCAAGAC |
| 186 | 37 | MYC_r2_F2 | ATGTGACTGGCACGGGAGTTGATCCTGGTTTTCACTTCTACTGCGACG AGGAGGAGAACTTCTACCAGCAGCAGCAGCAGAGCGAGCTGCAGCCC |
| 187 | 38 | MYC_r2_F3 | ATGTGACTGGCACGGGAGTTGATCCTGGTTTTCACACCGAGCTGCTGG GAGGAGACATGGTGAACCAGAGTTTCATCTGCGACCCGGACGACGAG |
| 188 | 39 | MYC_r2_F4 | ATGTGACTGGCACGGGAGTTGATCCTGGTTTTCACGCCGCCGCCTCAG AGTGCATCGACCCCTCGGTGGTCTTCCCCTACCCTCTCAACGACAGC |
| 189 | 40 | MYC_r2_R1 | ATGTGACTGGCACGGGAGTTGATCCTGGTTTTCACGGCGGCTAGGGGA CAGGGGCGGGGTGGGCAGCAGCTCGAATTTCTTCCAGATATCCTCGC |

TABLE 25-continued qPCR analysis of capture sensitivity and specificity

| SEQ ID NO: | Probe No. | Probe Name | Probe Sequence |
|---|---|---|---|
| 190 | 41 | MYC_r2_R2 | ATGTGACTGGCACGGGAGTTGATCCTGGTTTTCACAGACGAGCTTGGC GGCGGCCGAGAAGCCGCTCCACATACAGTCCTGGATGATGATGTTTT |
| 191 | 42 | MYC_r2_R3 | ATGTGACTGGCACGGGAGTTGATCCTGGTTTTCACAGGAGAGCAGAGA ATCCGAGGACGGAGAGAAGGCGCTGGAGTCTTGCGAGGCGCAGGACT |
| 192 | 43 | MYC_r2_R4 | ATGTGACTGGCACGGGAGTTGATCCTGGTTTTCACTAAGAGTGGCCCG TTAAATAAGCTGCCAATGAAAATGGGAAAGGTATCCAGCCGCCCACT |
| 193 | 44 | MYC_r3_F1 | ATGTGACTGGCACGGGAGTTGATCCTGGTTTTCACTTGTATTTGTACA GCATTAATCTGGTAATTGATTATTTTAATGTAACCTTGCTAAAGGAG |
| 194 | 45 | MYC_r3_F2 | ATGTGACTGGCACGGGAGTTGATCCTGGTTTTCACGAGGCCACAGCAA ACCTCCTCACAGCCCACTGGTCCTCAAGAGGTGCCACGTCTCCACAC |
| 195 | 46 | MYC_r3_F3 | ATGTGACTGGCACGGGAGTTGATCCTGGTTTTCACAGAGGAGGAACGA GCTAAAACGGAGCTTTTTTGCCCTGCGTGACCAGATCCCGGAGTTGG |
| 196 | 47 | MYC_r3_R1 | ATGTGACTGGCACGGGAGTTGATCCTGGTTTTCACTCCAACTTGACCC TCTTGGCAGCAGGATAGTCCTTCCGAGTGGAGGGAGGCGCTGCGTAG |
| 197 | 48 | MYC_r3_R2 | ATGTGACTGGCACGGGAGTTGATCCTGGTTTTCACGCTTGGACGGACA GGATGTATGCTGTGGCTTTTTTAAGGATAACTACCTTGGGGGCCTTT |
| 198 | 49 | MYC_r3_R3 | ATGTGACTGGCACGGGAGTTGATCCTGGTTTTCACGCATTTGATCATG CATTTGAAACAAGTTCATAGGTGATTGCTCAGGACATTTCTGTTAGA |

The first library pool was generated as described for the 'capture plus processing' library in Example 12. The second pool was generated as described for the 'capture only' library in Example 12 except for the following modification. After capture, a second round of PCR was performed to convert single primer, ACA2-amplified libraries into dual primer, heterologous end libraries suitable for Illumina sequencing. To do this, libraries were diluted and re-amplified with the following primers: primer #55

(SEQ ID NO: 199)
AATGATACGGCGACCACCGAGATCTACACGTCATGCAGGACCAGAG and primer #56

(SEQ ID NO: 200)
CAAGCAGAAGACGGCATACGAGATGTGACTGGCACGGGAGTTGAGAATT CGAATACA.

The 100 μL reaction mix contained 40 ng of library, 10 μL of 10×STD Taq buffer, 10 μL of 25 mM MgCl2, 10 μL of 55 and 10 μL of 56 primer that were both at 10 uM, 5 μL of DMSO, 5 μL of dNTP and 1 μL of Taq DNA polymerase. The samples were amplified for 2 cycles of 94° C.-30 sec, 50° C.-30 sec, 52.5° C.-30 sec, 55° C.-30 sec, 57.5° C.-30 sec, 60° C.-30 sec, 72° C.-1 min. They were then amplified for 8 cycles of 94 C-30 sec, 60 C-30 sec and 72 C-60 sec followed by 72° C. for 2 min. PCR mixes were purified with beads and resuspended in 50 μL each.

Results and Discussion: Both pools were analyzed using an Illumina MiSeq Personal Sequencer. The 50 nucleotide sequence reads from each library pool were trimmed to remove 4 base barcode sequences and mapped to the human genome reference sequence (version hg19) using the Bowtie sequence alignment program. Approximately 80% of reads in both libraries aligned unambiguously to the reference sequence. Further characterization of aligned reads revealed that coupling hybridization-based capture with enzymatic processing resulted in a 979,592-fold enrichment of the 4.9 kilobase target region relative to the input genomic DNA. This represented a 3-fold improvement in library content when compared to the unprocessed, 'capture only' approach. Overall, nearly 4 out of 5 sequences obtained by this alternative processing method mapped to genomic sites that were specifically targeted by capture probes.

A summary of alignment statistics for each library pool are shown in FIG. 53.

Reads from each library pool were also displayed in the UCSC Genome Browser to assess local sequence coverage and distribution around target sites. A close-up view of two segments of the X chromosome shows that processed libraries produced sequence coverage that was more highly concentrated within targeted sites than 'capture only' libraries did (FIG. 18). Moreover, the sequences mapping to target regions were more uniformly distributed in the processed libraries than the unprocessed controls. Taken together, these data indicated that the alternative processing method dramatically improved the quantity and quality of target sequences present in enriched libraries.

Example 14: Bioinformatics

Overview: Traditional Next Generation Sequencing (NGS) analysis is "vertical." The unique design of the inventive molecules contemplated herein enables a "horizontal" approach that will revolutionize the approach to clinical resequencing.

"Vertical" as used herein, with regard to sequence alignments, refers to approaches exemplified by FIG. 19. Previous approaches to informatics analysis involve a first step in which short reads are aligned to a reference genome. Following alignment, overlapping reads are analyzed for base changes that may be indicative of a SNV (single nucleotide variant). The approach was nick-named here as "vertical" because it relies on alignments that are often depicted as vertical stacks of reads. Various programs make allowances for SNVs and Indels (insertions/deletions), but the core approach is alignment-recognition-based.

In contrast, the paired-end read data obtained by the methods contemplated herein will have DNA tagged sequence information in read 1 and probe ID information in read 2. The first step in data analysis is to match reads to probes. Step two is analyzing the sequence information connected "horizontally" to each probe. See, e.g., FIG. 20.

At sufficient read depth, horizontal, probe-based sequence association does not rely on alignment. Rather, reads can be assembled into contigs de novo. The advantage of the method is that it is extremely robust to insertions/deletions and multiple sequence changes in a short stretch of sequence, both situations where conventional, alignment-based methods struggle and have the most difficulty detecting. Moreover, the combination of horizontal association with probes and tagging facilitates more accurate hypothesis generation (i.e., determination if an observed sequence variant is likely to be true or false).

CNV and Structural Variation I: In large scale copy number variation (CNV) analyses, the method comprises determination of unique read numbers associated with captured sequence regions. The vast majority of observed CNV is "micro-CNV" that involves base insertions and deletions that are on the order of 2-100 bp in length. Vertical alignment methods struggle with micro insertions/deletions (indel) because they require relaxation of alignment stringency that promotes large numbers of false-positive hypotheses. Horizontal methods and de novo contig assembly require no such relaxation of alignment parameters and they demand that structural variation is accounted for.

Figure 21:
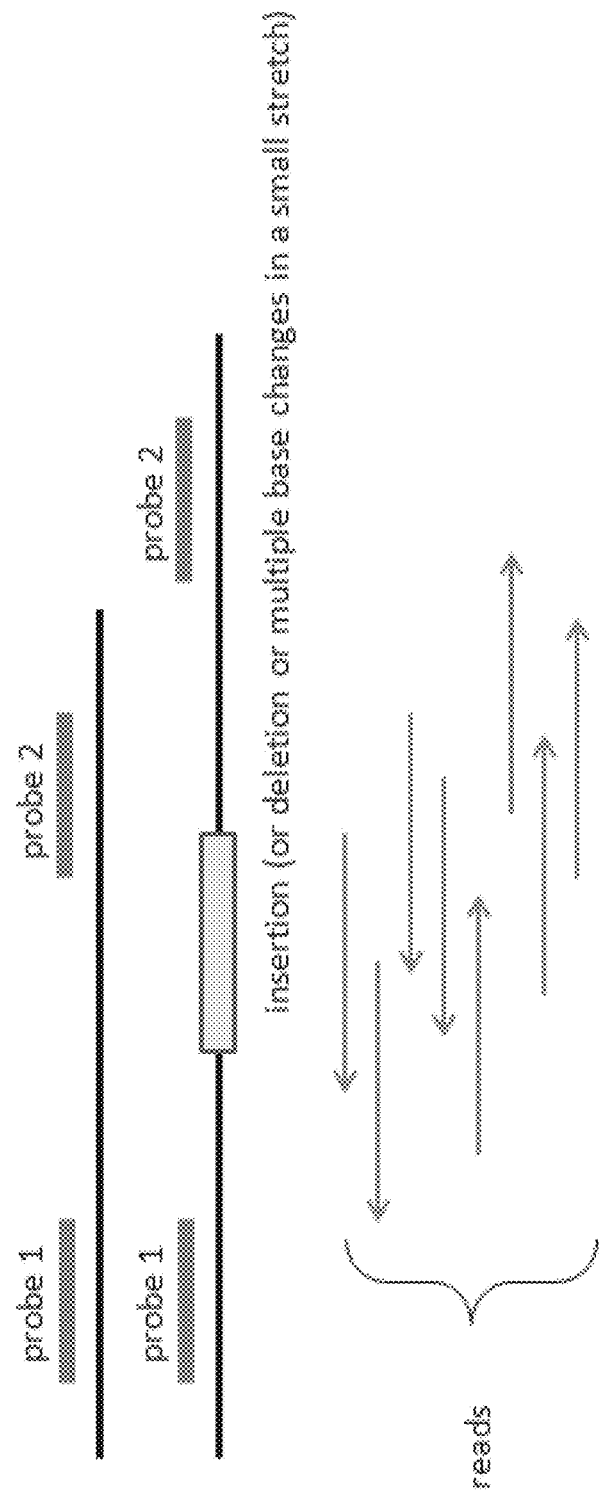
FIG. 21: Diagram of horizontal alignment "forces" reads associated with probe 1 and probe 2. Assembly will generate two contigs, one with a wild-type exon structure and one with an insertion structure. Two important principles emerge: 1) Overlapping reads from adjacent probes will support or refute the hypothesis of an indel-containing allele of the captured exon and 2) micro-CNV alleles outside of capture probes are readily detectable by horizontal methodologies.

Consider the simple case of a small insertion within one allele of an exon, as exemplified in FIG. 21. In this example, horizontal alignment "forces" reads to be associated with probe 1 and probe 2. Assembly will generate two contigs, one with a wild-type exon structure and one with an insertion structure. Two principles emerge from this analysis: 1) Overlapping reads from adjacent probes will support or refute the hypothesis of an indel-containing allele of the captured exon; and 2) micro-CNV alleles outside of capture probes are readily detectable by horizontal methodologies.

CNV and Structural Variation II: Validation of CNV often involves vertical alignment methods. In these studies, typically perfect alignments to a reference sequence are demanded. Such methods are vulnerable to SNVs (such as common SNPs) where reads crossing SNVs that differ from the reference will be discarded. The net result will be chronic underestimation of copy number. The horizontal methods possible with the present invention methods should be used going forward.

Horizontal hypothesis testing of SNVs I: Vertical, alignment-based methods for SNV detection are difficult to analyze. Homozygous variant alleles involving a single base are fairly straightforward to identify, but these changes are rare. More commonly, SNVs are heterozygous, and variants may occur at several contiguous or closely spaced positions (error prone repair tends to lay down tracks where several bases are non-consensus). The heterozygous SNV hypotheses run the spectrum from true, high coverage detection where (strictly as an hypothetical example) 49 reads possess a SNV and 47 reads possess the wild-type, reference base. Calls become much more speculative when read depth thins and the numbers of SNV versus WT reads deviate significantly from 50/50 (e.g., 10 total reads where 8 are WT and 2 are variant). Hypotheses nominated for orthogonal validation are invariably subject to an arbitrary cut-off.

Figure 22:
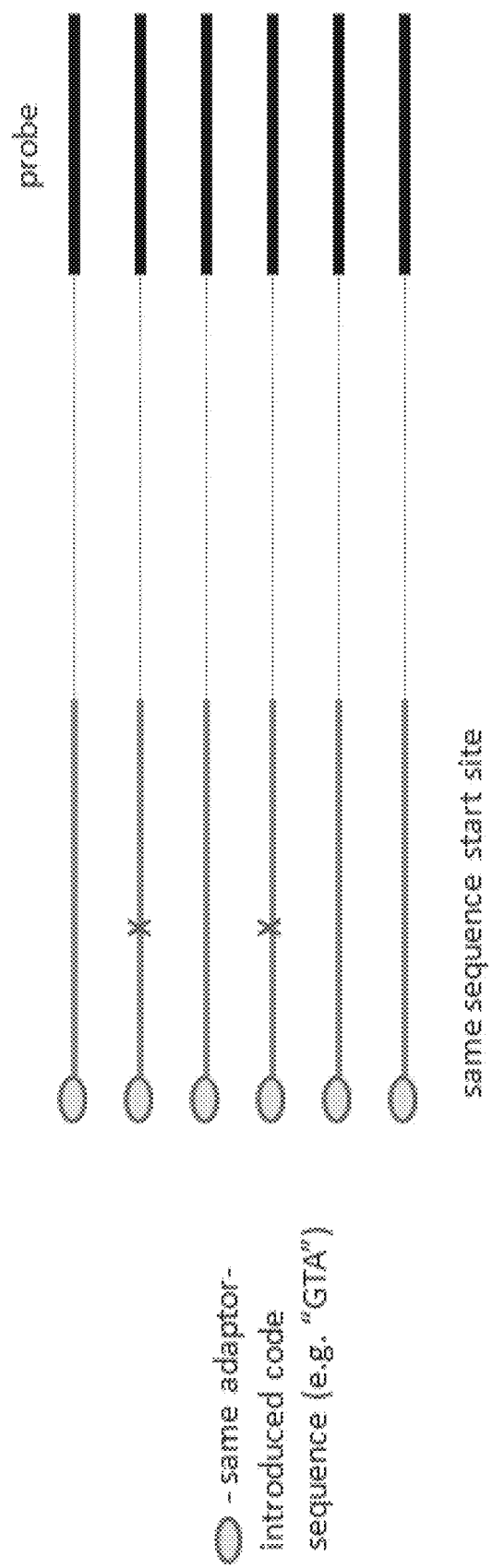
FIG. 22: Diagram of "low confidence" SNV calls. Candidate nucleotide variants can be actual events harbored in the individual from whom the sample was collected and processed, but they can also be artifacts introduced during processing and sequencing of samples. The methods described here were designed to differentiate between actual, "high confidence" variant calls and artifactual "low confidence" variant calls. Sequencing reads covering a target region are collected from multiple different clones in both possible sequencing orientations, and each read is annotated with tag information. The tags allow reads derived from the same cloning event to be identified and grouped. SNVs and indels that arise within only one set of clones that are all derived from the same cloning event are low confidence calls that are discarded from further analysis.

In particular embodiments, where horizontal probe-based association is combined with tags, far greater granularity in SNV hypotheses is achieved. SNVs that reside on a single tag (tag=code+end-point), especially in cases where reads within the same tag are WT, are disregarded. See, e.g., FIG. 22.

Horizontal hypothesis testing of SNVs II. SNV hypotheses that arise on two different tags, even if the read start sites are identical (A), or that arise on different reads that horizontally associate with the same probe (B), or that arise from different probe associations at the same exon (C) are necessarily hypotheses that must be seriously considered. See, e.g., FIG. 23.

Example 15: Molecular Annotation

Overview: This example describes the interplay between "molecular annotation" of sequencing libraries (FIG. 24) and the informatics used in subsequent steps to evaluate the resulting sequencing information. The reverse read from a probe has utility. Reverse read 2, which determines the DNA sequence of the probe region, has significant utility in all downstream analysis considerations. For example, utility can be found in variant calling and the output from this in copy number determination. These two aspects of data analysis are described below.

Read 2 probe sequence: A probe set is a unique and known collection of sequences, which can include one or two probes or even tens of thousands of probes. This means that read_2 can be used to identify any and all of the probes within an experiment. This of course assumes that read 2 is of sufficient length and that probes are designed such that the region interrogated by read_2 constitutes a unique identifier. Table 26 describes a collection of 192 probes and the 10 nt read_2 sequence that serves as a unique identifier for each probe. Note that two probes (CYP2C19_r5_F and CYP2C9_r5_F) naturally share identical 10 nt 5' DNA sequences, and a 2 nt code of "AG" or "CT" was added to distinguish between them.

TABLE 26

Collection of 192 probes

| Name | Sequence | SEQ ID NO: | 10 nt read_2 | SEQ ID NO: |
|---|---|---|---|---|
| CYP2D6_F | AAGCACCTAGCCCCATTCCTGCT GAGCAGGAGGTGGCAGGTACCCC AGACTGGGAGGTAA | 201 | AAGCACCTAG | 393 |

TABLE 26-continued

Collection of 192 probes

| Name | Sequence | SEQ ID NO: | 10 nt read_2 | SEQ ID NO: |
|---|---|---|---|---|
| CYP2D6_R | AGTCGGTGGGGCCAGGATGAGGC CCAGTCTGTTCACACATGGCTGC TGCCTCTCAGCTCT | 202 | AGTCGGTGGG | 394 |
| AMY1_F | ACCTGAGTAGCATCATTGTAGTT CTCGATATCTCCACTTCCAGTTT TACATTTACCATCA | 203 | ACCTGAGTAG | 395 |
| chrX_15_F | CCTGGCCCTCAGCCAGTACAGAA AGTCATTTGTCAAGGCCTTCAGT TGGCAGACGTGCTC | 204 | CCTGGCCCTC | 396 |
| chrX_15_R | AGAATTCATTGCCAGCTATAAAT CTGTGGAAACGCTGCCACACAAT CTTAGCACACAAGA | 205 | AGAATTCATT | 397 |
| chrX_477_F | GACTTCAAAGAAATTACAAGTTG ACATCTTGGACTCTACCCCTCGT ACTTTATCTCCTAT | 206 | GACTTCAAAG | 398 |
| chrX_477_R | TCTCTTTGGGGTCAAGAAAGAAT CCCTAGTGGATTTGGGATTCTAG AGGAGGTGTTATAA | 207 | TCTCTTTGGG | 399 |
| chrX_478_F | TGCGATACCATGCTGAAGATGAG CTAACCCAACCAGCCAAGCAGGC AGGGCTGCGAAGGA | 208 | TGCGATACCA | 400 |
| chrX_478_R | GGGGTAGGTGGAAAACCCAAGTA ATGTGATTTTGTAACATCCACTG CTGCATTTGTTTGC | 209 | GGGGTAGGTG | 401 |
| chrX_69_F | TTACTTCCCTCCAGTTTTGTTGC TTGCAAAACAACAGAATCTTCTC TCCATGAAATCATG | 210 | TTACTTCCCT | 402 |
| chrX_69_R | CAGGGGTATCTATTATCCCCATT TTCTCACAAAGGAAACCAAGATA AAAGGTTTAAATGG | 211 | CAGGGGTATC | 403 |
| PLP1_ex1_F | GAAATTCTCTTGTGAATTCCTGT GTCCTCTTGAATCTTCAATGCTA AAGTTTTTGAAACT | 212 | GAAATTCTCT | 404 |
| PLP1_ex2_F | GGGTTTGAGTGGCATGAGCTACC TACTGGATGTGCCTGACTGTTTC CCCTTCTTCTTCCC | 213 | GGGTTTGAGT | 405 |
| PLP1_ex2_R | CTATCTCCAGGATGGAGAGAGGG AAAAAAAAGATGGGTCTGTGTGG GAGGGCAGGTACTT | 214 | CTATCTCCAG | 406 |
| PLP1_ex3_F | GAAAGAAGCCAGGTCTTCAATTA ATAAGATTCCCTGGTCTCGTTTG TCTACCTGTTAATG | 215 | GAAAGAAGCC | 407 |
| PLP1_ex3_M | CAGACTCGCGCCCAATTTTCCCC CACCCCTTGTTATTGCCACAAAA TCCTGAGGATGATC | 216 | CAGACTCGCG | 408 |
| PLP1_ex3_R | TCTTTCTTCTTCCTTTATGGGGC CTCCTGCTGGCTGAGGGCTTCT ACACCACCGGCGCA | 217 | TCTTTCTTCT | 409 |
| PLP1_ex4_F | GTTTGTGTTTCTACATCTGCAGG CTGATGCTGATTTCTAACCACCC CATGTCAATCATTT | 218 | GTTTGTGTTT | 410 |
| PLP1_ex4_R | AACCAAATATATAGTGCTTCCAT AGTGGGTAGGAGAGCCAAAGCAC CCGTACCCTAACTC | 219 | AACCAAATAT | 411 |

TABLE 26-continued

Collection of 192 probes

| Name | Sequence | SEQ ID NO: | 10 nt read_2 | SEQ ID NO: |
|---|---|---|---|---|
| PLP1_ex5_F | AGTCTCCATGTGGCCCCGTAACTCCATAAAGCTTACCCTGCTTGCTTTTTGTGTCTTACT | 220 | AGTCTCCATG | 412 |
| PLP1_ex5_R | CCATGGGTGTAATTTGTATGGTATTAGCTACTCCCTTGTAAAATAACCCAAATAACCCAC | 221 | CCATGGGTGT | 413 |
| PLP1_ex6_F | TTTACAGTGGAGCATATTACTGCTGTTGCAAGAAACAGTTCTTCCTCTTTCATTTTCCTG | 222 | TTTACAGTGG | 414 |
| PLP1_ex6_R | ATAGCTGTACCCACACTATCTCAGGCCTATTTACTTGCCAAGATCATTCAAAGTCAACTC | 223 | ATAGCTGTAC | 415 |
| PLP1_ex7_F | GATTTGAGGAGGGAGTGCTTTCTTTTCTACTCTCATTCACATTCTCTCTTCTGTTCCCTA | 224 | GATTTGAGGA | 416 |
| PLP1_ex7_R | CAGCATTGTAGGCTGTGTGGTTAGAGCCTCGCTATTAGAGAAAGGGGGATTTCTACGGGG | 225 | CAGCATTGTA | 417 |
| KRAS_ex1_F | TGTTACCTTTAAAAGACATCTGCTTTCTGCCAAAATTAATGTGCTGAACTTAAACTTACC | 226 | TGTTACCTTT | 418 |
| KRAS_ex1_R | TTCCCAGTAAATTACTCTTACCAATGCAACAGACTTTAAAGAAGTTGTGTTTTACAATGC | 227 | TTCCCAGTAA | 419 |
| KRAS_ex2_F | TAAATGACATAACAGTTATGATTTTGCAGAAAACAGATCTGTATTTATTTCAGTGTTACT | 228 | TAAATGACAT | 420 |
| KRAS_ex2_R | GACAGGTTTTGAAAGATATTTGTGTTACTAATGACTGTGCTATAACTTTTTTTTCTTTCC | 229 | GACAGGTTTT | 421 |
| KRAS_ex3_F | ACTCAAAAATAAAAACTATAATTACTCCTTAATGTCAGCTTATTATATTCAATTTAAAC | 230 | ACTCAAAAAA | 422 |
| KRAS_ex3_R | AACACCTTTTTTGAAGTAAAAGGTGCACTGTAATAATCCAGACTGTGTTTCTCCCTTCTC | 231 | AACACCTTTT | 423 |
| KRAS_ex4_F | GAAACCTTTATCTGTATCAAAGAATGGTCCTGCACCAGTAATATGCATATTAAAACAAGA | 232 | GAAACCTTTA | 424 |
| KRAS_ex4_R | GTGTATTAACCTTATGTGTGACATGTTCTAATATAGTCACATTTTCATTATTTTTATTAT | 233 | GTGTATTAAC | 425 |
| MYC_r1_F1 | CCCCAGCCAGCGGTCCGCAACCCTTGCCGCATCCACGAAACTTTGCCCATAGCAGCGGGC | 234 | CCCCAGCCAG | 426 |
| MYC_r1_R1 | CGACTCATCTCAGCATTAAAGTGATAAAAAAATAAATTAAAAGGCAAGTGGACTTCGGTG | 235 | CGACTCATCT | 427 |
| MYC_r2_F1 | CTGTGGCGCGCACTGCGCGCTGCGCCAGGTTTCCGCACCAAGACCCCTTTAACTCAAGAC | 236 | CTGTGGCGCG | 428 |
| MYC_r2_F2 | TTCTACTGCGACGAGGAGGAGAACTTCTACCAGCAGCAGCAGAGCGAGCTGCAGCCC | 237 | TTCTACTGCG | 429 |

TABLE 26-continued

Collection of 192 probes

| Name | Sequence | SEQ ID NO: | 10 nt read_2 | SEQ ID NO: |
|---|---|---|---|---|
| MYC_r2_F3 | ACCGAGCTGCTGGGAGGAGACATGGTGAACCAGAGTTTCATCTGCGACCCGGACGACGAG | 238 | ACCGAGCTGC | 430 |
| MYC_r2_F4 | GCCGCCGCCTCAGAGTGCATCGACCCCTCGGTGGTCTTCCCCTACCCTCTCAACGACAGC | 239 | GCCGCCGCCT | 431 |
| MYC_r2_R1 | GGCGGCTAGGGGACAGGGGCGGGGTGGGCAGCAGCTCGAATTTCTTCCAGATATCCTCGC | 240 | GGCGGCTAGG | 432 |
| MYC_r2_R2 | AGACGAGCTTGGCGGCGGCCGAGAAGCCGCTCCACATACAGTCCTGGATGATGATGTTTT | 241 | AGACGAGCTT | 433 |
| MYC_r2_R3 | AGGAGAGCAGAGAATCCGAGGACGGAGAGAAGGCGCTGGAGTCTTGCGAGGCGCAGGACT | 242 | AGGAGAGCAG | 434 |
| MYC_r2_R4 | TAAGAGTGGCCCGTTAAATAAGCTGCCAATGAAAATGGGAAAGGTATCCAGCCGCCCACT | 243 | TAAGAGTGGC | 435 |
| MYC_r3_F1 | TTGTATTTGTACAGCATTAATCTGGTAATTGATTATTTTAATGTAACCTTGCTAAAGGAG | 244 | TTGTATTTGT | 436 |
| MYC_r3_F2 | GAGGCCACAGCAAACCTCCTCACAGCCCACTGGTCCTCAAGAGGTGCCACGTCTCCACAC | 245 | GAGGCCACAG | 437 |
| MYC_r3_F3 | AGAGGAGGAACGAGCTAAAACGGAGCTTTTTTGCCCTGCGTGACCAGATCCCGGAGTTGG | 246 | AGAGGAGGAA | 438 |
| MYC_r3_R1 | TCCAACTTGACCCTCTTGGCAGCAGGATAGTCCTTCCGAGTGGAGGGAGGCGCTGCGTAG | 247 | TCCAACTTGA | 439 |
| MYC_r3_R2 | GCTTGGACGGACAGGATGTATGCTGTGGCTTTTTAAGGATAACTACCTTGGGGGCCTTT | 248 | GCTTGGACGG | 440 |
| MYC_r3_R3 | GCATTTGATCATGCATTTGAAACAAGTTCATAGGTGATTGCTCAGGACATTTCTGTTAGA | 249 | GCATTTGATC | 441 |
| AMY1A_r_9 | CATCATTGTTGAAAACAATGAATCCTCTGTTTCCTCTCCCAAAAGCCACTTGGTTGCTCC | 250 | CATCATTGTT | 442 |
| AMY1A_r-10 | TTTATCTCCAGAAATGACATCACAGTATGTGCCAGCAGGAAGACCAGTTTGCAAAGTTAA | 251 | TTTATCTCCA | 443 |
| AMY1A_r_8 | CTATTAGAGGACATGTCTAAATACATATTCTCACCTTATTTGGCGCATCGATGTTCACA | 252 | CTATTAGAGG | 444 |
| AR_r1_F | TCTGAGCAAGAGAAGGGGAGGCGGGGTAAGGGAAGTAGGTGGAAGATTCAGCCAAGCTCA | 253 | TCTGAGCAAG | 445 |
| AR_r1_R | CCAGAACACAGAGTGACTCTGCCCTGGGCCGAAAGGCGACATTTCTGGAAGGAAAAACTT | 254 | CCAGAACACA | 446 |
| AR_r2_F | CTTCACTTGCCTATTTCTGCCATTCAGTGACATGTGTTGCATTGGTTTTTTGTGTCTTTC | 255 | CTTCACTTGC | 447 |

TABLE 26-continued

Collection of 192 probes

| Name | Sequence | SEQ ID NO: | 10 nt read_2 | SEQ ID NO: |
|---|---|---|---|---|
| AR_r2_R | GTGTCTCTCTCTGGAAGGTAAAGGAGAAAGGGAAAGAGAAGTGCATGTGCAAGACCCTTT | 256 | GTGTCTCTCT | 448 |
| AR_r3_F | CCGAAGAAAGAGACTCTGGAAACTCATTATCAGGTCTATCAACTCTTGTATTTGTTCTCC | 257 | CCGAAGAAAG | 449 |
| AR_r3_R | ACTAGAAAATGAGGGAGAAGGGGGAGAGAGGAAGGAGGAGGAAGAGAAAGAAAAGTATCT | 258 | ACTAGAAAAT | 450 |
| AR_r4_F | GTAGTTGCATTGTGTGTTTTGACCACTGATGATAAATTCAAGTCTCTCTTCCTTCCCAA | 259 | GTAGTTGCAT | 451 |
| AR_r4_R | CATAGGAGCGTTCACTAAATATGATCCCCCTTATCTCATGCTCCCACTTCCCTTTTCCTT | 260 | CATAGGAGCG | 452 |
| AR_r5_F | CTCAGACTTAGCTCAACCCGTCAGTACCCAGACTGACCACTGCCTCTGCCTCTTCTTCTC | 261 | CTCAGACTTA | 453 |
| AR_r5_R | CACCAACCAGGTCTGGCCAAGCTGCTGTATTTTAGTGAGGTCTGGGCCCCAGGAGCACTT | 262 | CACCAACCAG | 454 |
| ATR_r44_F | GGAAGATACAGTTGTTGAGAAAAGGAAATTGAGAGAAAACACAATTAGTAAGAGTAACTC | 263 | GGAAGATACA | 455 |
| ATR_r44_R | TTTTAGATTTATATTGGCCTCATATGTATATGGATATTTCATAGGCATTGTGTTTCTTTT | 264 | TTTTAGATTT | 456 |
| ATR_r45_F | TGTAGGGGCCAATAATTATATTCGAGGTTACTGTTAAATTATTTACAAAGTATAGGTGAT | 265 | TGTAGGGGCC | 457 |
| ATR_r45_R | TTTGAGTAAAGATTTTTAAATTCTAACATTGTTAGTTTGTAATAAAATGTATTGTTTCTA | 266 | TTTGAGTAAA | 458 |
| ATR_r46_F | CATATCAAGTTCATTTGTAGAGATGAGGACTACAGCCCATATCAAGCTATACCTTCTACT | 267 | CATATCAAGT | 459 |
| ATR_r46_R | ATGTCAGCAAGATTTCTTCTTGCAAAGATAACATCATACCATAATATTTGTTTCAATTTT | 268 | ATGTCAGCAA | 460 |
| ATR_r47_F | CAACCACAGATTCATACCAAATGCATTACTTTTAGATTATTAACATATTCTTTTACATAA | 269 | CAACCACAGA | 461 |
| ATR_r47_R | AAGAAAGGTAGTAATTCCAAATTATTAACATCTGTTTTTGGTTTTATGTTTCTTCTTTTT | 270 | AAGAAAGGTA | 462 |
| C4A_r20_F | GGCCTATGTGTGGCCACCCCAGTCCAGCTCCGGGTGTTCCGCGAGTTCCACCTGCACCTC | 271 | GGCCTATGTG | 463 |
| C4A_r24_R | AGGCGTGGCCTCCCTCTTGAGGCTTCCTCGAGGCTGTGGGGAGCAAACCATGATCTACTT | 272 | AGGCGTGGCC | 464 |
| C4A_r1_F | CCTAGCTTGGCCAGAAGGTAGCAGACAGACAGACGGATCTAACCTCTCTTGGATCCTCCA | 273 | CCTAGCTTGG | 465 |

TABLE 26-continued

Collection of 192 probes

| Name | Sequence | SEQ ID NO: | 10 nt read_2 | SEQ ID NO: |
|---|---|---|---|---|
| C4A_r1_R | TGAATCGGGTCCCGATGCCAGCCCTGCCCCAATCCAAGCACCCAGCATCCCGCCTCCAGG | 274 | TGAATCGGGT | 466 |
| C4A_r2_F | AGGGAGAGCAGGGGTGGAGGTGTCAGAGCGAAGTCTGACTGCTGATCCTGTCTGTTCTCC | 275 | AGGGAGAGCA | 467 |
| C4A_r2_R | TGACACTTACAAGACAGATGGGAACAGGGCAGGAGGCCCCCACAAGCAGCAGGAGGGCAT | 276 | TGACACTTAC | 468 |
| C4A_r3_F | CCTTTTTGGTCAGCTGTCTCTTGCTCTGTGACCCGCTCCCTCTCCCTCTCCCTCTCCTGA | 277 | CCTTTTTGGT | 469 |
| C4A_r3_R | CAAACTCATCCTGAGAGGGCTCGGAGGGGGTTAAAGGTTGAGGCCCTGGGGCTGAGACTC | 278 | CAAACTCATC | 470 |
| C4A_r4_F | AGTTTGACCCACCCTCCCCTTGCACATGGACCCCTGCTCACCTCTCTCCTCCTCCACTCC | 279 | AGTTTGACCC | 471 |
| C4A_r4_R | AAGGGGAGAAGTGCTCACAGGCAGGAGGTCACATCAGTGGCCAGGATCAGGAAGGCCAGA | 280 | AAGGGGAGAA | 472 |
| CCL4_r1_F | GTTCTGAAGCTTCTGAGTTCTGCAGCCTCACCTCTGAGAAAACCTCTTTGCCACCAATAC | 281 | GTTCTGAAGC | 473 |
| CCL4_r2_F | GGCAGTGTTGATCTCACCCTGGCCTTTCCTTTCAGTGGGCTCAGACCCTCCCACCGCCTG | 282 | GGCAGTGTTG | 474 |
| CCL4_r2_R | ACCACAGCTGGCTGGGAGCAGAGGCTGCTGGTCTCATAGTAATCTACCACAAAGTTGCGA | 283 | ACCACAGCTG | 475 |
| CCL4_r3_F | TCAGGTGACCTTCCCTGAAGACTTCCTGTCTCTGAGCAGCTCAGTTCAGTTCCAGGTCAT | 284 | TCAGGTGACC | 476 |
| CYP2C19_r1_F | GGAGCATATAGTGGGCCTAGGTGATTGGCCACTTTATCCATCAAAGAGGCACACACACTT | 285 | GGAGCATATA | 477 |
| CYP2C19_r1_R | CCTTTCAAAGTATTTTACTTTACAATGATCTCTTGTAACATTGTACCTCTAGGGATATAC | 286 | CCTTTCAAAG | 478 |
| CYP2C19_r3_F | ATGGGAGGATGGAAAACAGACTAGCAGAGCTTCTCGGGCAGAGCTTGGCCCATCCACAT | 287 | ATGGGAGGA | 479 |
| CYP2C19_r3_R | GATCTGGCCACCCCTGAAATGTTTCCAAGAATGTCAGTAGAGAGGAGAGCAGTCCAGAAA | 288 | GATCTGGCCA | 480 |
| CYP2C19_r5_F | AGCAACCAGAGCTTGGCATATTGTATCTATACCTTTATTAAATGCTTTTAATTTAATAAATT | 289 | AGCAACCAGA | 481 |
| CYP2C19_r5_R | CAAAACTAGTCAATGAATCACAAATACGCAAGCAGTCACATAACTAAGCTTTTGTTAACA | 290 | CAAAACTAGT | 482 |
| CYP2C9_r1_F | AAGGAGCATATAGTGGACCTAGGTGATTGGTCAATTATCCATCAAAGAGGCACACACCG | 291 | AAGGAGCATA | 483 |

TABLE 26-continued

Collection of 192 probes

| Name | Sequence | SEQ ID NO: | 10 nt read_2 | SEQ ID NO: |
|---|---|---|---|---|
| CYP2C9_r1_F | AGCCTTTCAAAGTATTTTACTTTACCATTACCTCTTGTAACATGTACCTCTAGGGATACA | 292 | AGCCTTTCAA | 484 |
| CYP2C9_r3_F | GGGGAGGATGGAAAACAGAGACTTACAGAGCTCCTCGGGCAGAGCTTGGCCCATCCACAT | 293 | GGGGAGGATG | 485 |
| CYP2C9_r3_R | GATATGGCCACCCCTGAAATGTTTCCAAGAATGTCAGTAGAGAAGATAGTAGTCCAGTAA | 294 | GATATGGCCA | 486 |
| CYP2C9_r5_F | CTCAACCAGAGCTTGGTATATGGTATGTATGCTTTTATTAAAATCTTTTAATTTAATAAATT | 295 | CTCAACCAGA | 487 |
| CYP2C9_r5_R | CAGAACTAGTCAACAAATCACAAATTCACAAGCAGTCACATAACTAAGCTTTTGTTTACA | 296 | CAGAACTAGT | 488 |
| CYP2D6_r1_F | GGAAGTCCCCCAAACCTGCTTCCCCTTCTCAGCCTGGCTTCTGGTCCAGCCTGTGGTTTC | 297 | GGAAGTCCCC | 489 |
| CYP2D6_r1_R | GCCTGGTGGGTGGGGTGCCAGGTGTGTCCAGAGGAGCCCATTTGGTAGTGAGGCAGGT | 298 | GCCTGGTGGG | 490 |
| CYP2D6_r2_F | GCCCAGCTCGGACTACGGTCATCACCCACCCGGGTCCCACGGAAATCTGTCTCTGTCCCC | 299 | GCCCAGCTCG | 491 |
| CYP2D6_r2_R | AATAGGACTAGGACCTGTAGTCTGGGGGGATCCTGGCTTGACAAGAGGCCCTGACCCTCC | 300 | AATAGGACTA | 492 |
| CYP2D6_r5_F | AAGTTCATGGGCCCCCGCCTGTACCCTTCCTCCCTCGGCCCCTGCACTGTTTCCCAGATG | 301 | AAGTTCATGG | 493 |
| CYP2D6_r5_R | GGGCTGACAGGTGCAGAATTGGAGGTCATTTGGGGGCTACCCCGTTCTGTCCCGAGTATG | 302 | GGGCTGACAG | 494 |
| CYP2D6_r8_F | CATTGCTTTATTGTACATTAGAGCCTCTGGCTAGGGAGCAGGCTGGGGACTAGGTACCCC | 303 | CATTGCTTTA | 495 |
| CYP2D6_r8_R | TGGAGTCTTGCAGGGGTATCACCCAGGAGCCAGGCTCACTGACGCCCCTCCCCTCCCCAC | 304 | TGGAGTCTTG | 496 |
| DCC_r1_F | AGTGCATGTGTGTGAGTGCTGCCGCTGCCCGCGACCCCTGGCCCCGAAGGTGTTGGCTGA | 305 | AGTGCATGTG | 497 |
| DCC_r1_R | AATGAGAAGGGAAGTGGGGTACGGAAGGGGGTGCGACGAGAAGAAAGGAAAGAGCCACTT | 306 | AATGAGAAGG | 498 |
| DCC_r2_F | GGAATCTAAGCCTGAGATTTATTTGAATACATGAACATATTTCCCTGTGCTCTCTTGTTC | 307 | GGAATCTAAG | 499 |
| DCC_r2_R | AAGATGGCATTCATCTGGCCTTGGGAATGGATGAAAGGAAGCAGCAACTTTCAAATGGGT | 308 | AAGATGGCAT | 500 |
| DCC_r2 | GGTAAAGTCCCTCATCTGGCTTGTGGTGTCTGGAATGAAGTATGTTTTGTATCAGCAGAG | 309 | GGTAAAGTCC | 501 |

TABLE 26-continued

Collection of 192 probes

| Name | Sequence | SEQ ID NO: | 10 nt read_2 | SEQ ID NO: |
|---|---|---|---|---|
| DCC_r3_F | TTTATTGGCGATTATTGTGCTTT ATTTGGAAGACTTATTCTTCCTT CTTTGTTTTTCTCC | 310 | TTTATTGGCG | 502 |
| DCC_r3_R | GAAAAAAATTGTTTTTCAACTTA TTCCAGAGAATATCATTCTGAAG GCAACAAAGAGCAT | 311 | GAAAAAAATT | 503 |
| DCC_r4_F | ATATATCATTTATCTTTGCAATG TTTTTCATATATCATATGATACT GTGTTTTCCCCTCA | 312 | ATATATCATT | 504 |
| DCC_r4_R | ATTAGAGAAATATAAATAGCAGC ATATACCATACAAAAGTACACTT TACAAAAAGTCTT | 313 | ATTAGAGAAA | 505 |
| EP300_r18_F | ATACTCCATCTCCCGTAAAAATA GTGAGACTTGAGTAATGTTTGAT GTCACTTGTCTTTC | 314 | ATACTCCATC | 506 |
| EP300_r18_R | CAGTCACCACTATATTATTCTAG GTATCCCAGAAAAGTTAAAGTCA AATCTGAAACACAT | 315 | CAGTCACCAC | 507 |
| EP300_r19_F | TTCTTACTGTTCTAGCTTGTCCT TAAGGCCTCTGTGCTTTTTAACA AATGGTTTCTTTTG | 316 | TTCTTACTGT | 508 |
| EP300_r19_R | TCCGCATGCACTCCCTGGACATG TGGACACATGGACCATGGTCCAC ACCTGGCCAAGCTT | 317 | TCCGCATGCA | 509 |
| EP300_r20_F | CTTGGCTTGGGCTGTGTTGTGTG AACGGAACAGTTCACCCCAGTAT GGCCTTCTTGCCGA | 318 | CTTGGCTTGG | 510 |
| EP300_r20_R | GCTGTGCATAATCACTGGACAAC AAACTAATTAGCACTTTTCAAAA TAATGCAGTTACTT | 319 | GCTGTGCATA | 511 |
| EP300_r21_F | GAACAGCAGTCAGATTGCTCATC TCTATCACTTTTTCTCATTGTGT CCCTTTTCTCTCCT | 320 | GAACAGCAGT | 512 |
| EP300_r21_R | AGAGAATGAAAGGGAAAAAGAAA AGCCAAAGCGTACTGACTATTCA AGGGGATCGTACTT | 321 | AGAGAATGAA | 513 |
| EP300_r22_F | TATTGCAAGTTTTCATTTGGTTA AGGTTTGGGGTTAATTTTGGAAT TGGCTCTGCTCTTC | 322 | TATTGCAAGT | 514 |
| EP300_r22_R | AAAACTTGTTAATATTCACGATA AGAAAAATTCCAGAGAAAGTAA CAACGTTAAGACTT | 323 | AAAACTTGTT | 515 |
| PTEN_r1_F | GCAGAAGAAGCCCCGCCACCAGC AGCTTCTGCCATCTCTCTCCTCC TTTTTCTTCAGCCA | 324 | GCAGAAGAAG | 516 |
| PTEN_r1_R | CTACTCCCACGTTCTAAGAGAGT GACAGAAAGGTAAAGAGGAGCAG CCGCAGAAATGGAT | 325 | CTACTCCCAC | 517 |
| PTEN_r2_F | AGTATTCTTTTAGTTTGATTGCT GCATATTTCAGATATTTCTTTCC TTAACTAAAGTACT | 326 | AGTATTCTTT | 518 |

TABLE 26-continued

Collection of 192 probes

| Name | Sequence | SEQ ID NO: | 10 nt read_2 | SEQ ID NO: |
|---|---|---|---|---|
| PTEN_r2_R | AATGAAAACACAACATGAATATAAACATCAATATTTGAAATAGAAAATCAAAGCATTCTT | 327 | AATGAAAACA | 519 |
| PTEN_r3_F | GTAATTTCAAATGTTAGCTCATTTTTGTTAATGGTGGCTTTTTGTTTGTTTGTTTTGTTT | 328 | GTAATTTCAA | 520 |
| PTEN_r3_R | CTTTCACTTAATAGTTGTTTTAGAAGATATTTGCAAGCATACAAATAAGAAAACATACTT | 329 | CTTTCACTTA | 521 |
| PTEN_r4_F | GTACTTTTTTTCTTCCTAAGTGCAAAAGATAACTTTATATCACTTTTAAACTTTTCTTT | 330 | GTACTTTTTT | 522 |
| PTEN_r4_R | ACAGTAAGATACAGTCTATCGGGTTTAAGTTATACAACATAGTACAGTACATTCATACCT | 331 | ACAGTAAGAT | 523 |
| PTEN_r5_F | TACTTGTTAATTAAAAATTCAAGAGTTTTTTTTTCTTATTCTGAGGTTATCTTTTTACCA | 332 | TACTTGTTAA | 524 |
| PTEN_r5_R | CCAAAATCTGTTTTCCAATAAATTCTCAGATCCAGGAAGAGGAAAGGAAAAACATCAAAA | 333 | CCAAAATCTG | 525 |
| RHD_r1_F | TCAAGTAGGTGTTGGAGAGAGGGGTGATGCCTGGTGCTGGTGGAACCCCTGCACAGAGAC | 334 | TCAAGTAGGT | 526 |
| RHD_r2_F | CCTGTCCTTTCGGGGTCCATTCCCTCTATGACCCAGAAGTGATCCAGCCACCATCCCAAT | 335 | CCTGTCCTTT | 527 |
| RHD_r5_F | AACCCCTCGAGGCTCAGACCTTTGGAGCAGGAGTGTGATTCTGGCCAACCACCCTCTCTG | 336 | AACCCCTCGA | 528 |
| RHD_r5_R | CATAAATATGTGTGCTAGTCCTGTTAGACCCAAGTGCTGCCCAAGGGCAGCGCCCTGCTC | 337 | CATAAATATG | 529 |
| RHD_r6_F | TTGCAGCAAGATGGTGTTCTCTCTCTACCTTGCTTCCTTTACCCACACGCTATTCTTTG | 338 | TTGCAGCAAG | 530 |
| RHD_r7_F | GAGATCAAGCCAAAATCAGTATGTGGGTTCATCTGCAATAAAAATGTTTGTTTTGCTTTT | 339 | GAGATCAAGC | 531 |
| RHD_r7_R | GCAACAGTGAGAGGAAGTTGTCTTGTTTTTGAACAGGCCTTGTTTTTCTTGGATGCTTTT | 340 | GCAACAGTGA | 532 |
| RUNX1_r1_F | CTGCCATTTCATTACAGGCAAAGCTGAGCAAAAGTAGATATTACAAGACCAGCATGTACT | 341 | CTGCCATTTC | 533 |
| RUNX1_r1_R | AAGGTAAAAGAAATCATTGAGTCCCCCGCCTTCAGAAGAGGGTGCATTTTCAGGAGGAAG | 342 | AAGGTAAAAG | 534 |
| RUNX1_r3_F | GCGGATCTCCCCCGGCCTCGCCGGCCTCCGCCTGTCCTCCCACCACCCTCTCCGGGCCAG | 343 | GCGGATCTCC | 535 |
| RUNX1_r3_R | CTGGTAGGAGCTGTTTGCAGGGTCCTAACTCAATCGGCTTGTTGTGATGCGTATCCCCGT | 344 | CTGGTAGGAG | 536 |

TABLE 26-continued

Collection of 192 probes

| Name | Sequence | SEQ ID NO: | 10 nt read_2 | SEQ ID NO: |
|---|---|---|---|---|
| RUNX1_r4_F | TTTTGAAATGTGGGTTTGTTGCCATGAAACGTGTTTCAAGCATAGTTTTGACAGATAACG | 345 | TTTTGAAATG | 537 |
| RUNX1_r4_R | TGCCCTAAAAGTGTATGTATAACATCCCTGATGTCTGCATTTGTCCTTTGACTGGTGTTT | 346 | TGCCCTAAAA | 538 |
| RUNX1_r5_F | GTATACCAGCCTGGAGGGTGTACCAGCCTGGAGGGTGTACCAGCCCCAAGTGGATGCACT | 347 | GTATACCAGC | 539 |
| RUNX1_r5_R | TTCAACAGATATGTTCAGGCCACCAACCTCATTCTGTTTTGTTCTCTATCGTGTCCCCAC | 348 | TTCAACAGAT | 540 |
| SKI_r4_F | AGGATGTGTCTGGGTGGTGCTTGGGGACAGAGGCACCTTCCCGACACCCGCCTGCCCCTC | 349 | AGGATGTGTC | 541 |
| SKI_r4_R | CCTCAGCCAGTGCCACCCCACAGCCCACAGGGAGGAGGCACAGAAAGCGACTCACACGT | 350 | CCTCAGCCAG | 542 |
| SKI_r5_F | CTGGTGTGGAGCTGCCGGGCACTTCCATGACTTTGTTTCTGTCTCTGCTTCCTCCTCAGT | 351 | CTGGTGTGGA | 543 |
| SKI_r5_R | CTGGTGCAGGCTGTGCTCACTGCCCGTGCCCTGGACCTCCCAGCACCACTCGCCCCGCTC | 352 | CTGGTGCAGG | 544 |
| SKI_r6_F | GTCATGGTGAGGGGTGTGCTGGGACCGGCTGGGCAGTGACCCCGAGCCGCCTCCGGCCCC | 353 | GTCATGGTGA | 545 |
| SKI_r6_R | CCGGGGCCCACGGCGGCTCCACGCCCACCGTGCTGCGTGCCTCAGTCTCCCCACCCGCAT | 354 | CCGGGGCCCA | 546 |
| SRY_r1_F | CTGTAAGTTATCGTAAAAGGAGCATCTAGGTAGGTCTTTGTAGCCAATGTTACCCGATT | 355 | CTGTAAGTTA | 547 |
| SRY_r1_M1 | AGTAAAATAAGTTTCGAACTCTGGCACCTTTCAATTTTGTCGCACTCTCCTTGTTTTTGA | 356 | AGTAAAATAA | 548 |
| SRY_r1_M2 | GAAGCAAACTGCAATTCTTCGGCAGCATCTTCGCCTTCCGACGAGGTCGATACTTATAAT | 357 | GAAGCAAACT | 549 |
| SRY_r1_M3 | AATGGCCATTCTTCCAGGAGGCACAGAAATTACAGGCCATGCACAGAGAGAAATACCCGA | 358 | AATGGCCATT | 550 |
| SRY_r1_M4 | CTTGCGCCTCTGATCGCGAGACCACACGATGAATGCGTTCATGGGTCGCTTCACTCTATC | 359 | CTTGCGCCTC | 551 |
| SRY_r1_R | GAAAGCTGTAACTCTAAGTATCAGTGTGAAACGGGAGAAAACAGTAAAGGCAACGTCCAG | 360 | GAAAGCTGTA | 552 |
| TNFRSF14_r1_F | AGTTCCTCTGCTGGAGTTCATCCTGCTAGCTGGGTTCCCGAGCTGCCGGTCTGAGCCTGA | 361 | AGTTCCTCTG | 553 |
| TNFRSF14_r1_R | TCTGTGGGAGGCCCTGGGGTCAGAACTGGGATCTGCGAGCAGACGGAGAGGAGGCTCGGG | 362 | TCTGTGGGAG | 554 |

TABLE 26-continued

Collection of 192 probes

| Name | Sequence | SEQ ID NO: | 10 nt read_2 | SEQ ID NO: |
|---|---|---|---|---|
| TNFRSF14_r2_F | CAAGCCTGGCAGAGCCCACAGGG CAGCCAGGGCATCTCCCAATGCC TGTCCTGACCCCCT | 363 | CAAGCCTGGC | 555 |
| TNFRSF14_r2_R | TGTCTGGGGCAGAAGGGGGCAAG AGTGTCTGCCCTCGGCCCACAGA GCTGGCCCGCCAAA | 364 | TGTCTGGGGC | 556 |
| TNFRSF14_r3_F | TGATGGGTGGGCTCCCGAAGGGG CCTCCCGCAGACTTGCGAAGTTC CCACTCTCTGGGCG | 365 | TGATGGGTGG | 557 |
| TNFRSF14_r3_R | CAGGGTGCGGGGGCATCCAGGCT GCCCAAGCGGAGGCTGGGCCGGC TGTGCTGGCCTCTT | 366 | CAGGGTGCGG | 558 |
| UGT1A1_rP_P | CTCCACCTTCTTTATCTCTGAAA GTGAACTCCCTGCTACCTTTGTG GACTGACAGCTTTT | 367 | CTCCACCTTC | 559 |
| UGT1A1_r1_F | TCGATCCAAAGTAATACATCTGA AAGAATATACGCATGTAAAAGTC CCACTCCAATACAC | 368 | TCGATCCAAA | 560 |
| UGT1A1_r1_M1 | CTGCAGCAGAGGGGACATGAAAT AGTTGTCCTAGCACCTGACGCCT CGTTGTACATCAGA | 369 | CTGCAGCAGA | 561 |
| UGT1A1_r1_M2 | ACTCTTTCACATCCTCCCTTTGG AATGGCACAGGGTACGTCTTCAA GGTGTAAAATGCTC | 370 | ACTCTTTCAC | 562 |
| UGT1A1_r1_M3 | GCGTGTGATCAAAACATACAAGA AAATAAAAAAGGACTCTGCTATG CTTTTGTCTGGCTG | 371 | GCGTGTGATC | 563 |
| UGT1A1_r1_M4 | ACATCAAAGCTGCTTTCTGCCAG GGAGGCCATGAGCTCCTTGTTGT GCAGTAAGTGGGAA | 372 | ACATCAAAGC | 564 |
| UGT1A1_r1_M5 | CTCTGCCCACTGTATTCTTCTTG CATGCACTGCCATGCAGCCTGGA ATTTGAGGCTACCC | 373 | CTCTGCCCAC | 565 |
| UGT1A1_r1_M6 | TCATGTGATCTGAATGAGAGGAG AGAGGCCTGGGCACGTAGGAGAA TGGGTTGGGGCACT | 374 | TCATGTGATC | 566 |
| UGT1A1_r1_M7 | TGCGACGTGGTTTATTCCCCGTA TGCAACCCTTGCCTCAGAATTCC TTCAGAGAGAGGTG | 375 | TGCGACGTGG | 567 |
| UGT1A1_r1_R | CTTCACAAAGTCACTTCTAAACA GCCAGACAGATGCAGAGCTCAAT AGGTCCTGGACAGT | 376 | CTTCACAAAG | 568 |
| UGT1A1_r2_F | ACTGTATGTAGTCATCAAAGAAT ATGAGAAAAATTAACTGAAAAT TTTTCTTCTGGCTC | 377 | ACTGTATGTA | 569 |
| UGT1A1_r2_R | ATTAATCTGGAAGCTGGAAGTCT GGGATTAGCGCTCCTGTGAAAAT AGATATGAGGCCAT | 378 | ATTAATCTGG | 570 |
| UGT1A1_r3_F | CAGATTTGTTTTCTAATCATATT ATGTTCTTTCTTTACGTTCTGCT CTTTTTGCCCCTCC | 379 | CAGATTTGTT | 571 |
| UGT1A1_r3_R | GCTTAAGCCATTTTCTTAATTTG ACCCTGGTTTGACCTATACATCC AATCCGCCCAACAT | 380 | GCTTAAGCCA | 572 |

TABLE 26-continued

Collection of 192 probes

| Name | Sequence | SEQ ID NO: | 10 nt read_2 | SEQ ID NO: |
|---|---|---|---|---|
| UGT1A1_r4_F | TGTGTCCAGCTGTGAAACTCAGAGATGTAACTGCTGACATCCTCCCTATTTTGCATCTCA | 381 | TGTGTCCAGC | 573 |
| UGT1A1_r4_R | ATTTGAAACAATTTTATCATGAATGCCATGACCAAAGTATTCTTCTGTATCTTCTTTCTT | 382 | ATTTGAAACA | 574 |
| UGT1A1_r5_F | ATAAAGAGAGGATTGTTCATACCACAGGTGTTCCAGGCATAACGAAACTGTCTTTGTGTT | 383 | ATAAAGAGAG | 575 |
| UGT1A1_r5_R | TTTTCAAGTTTGGAAATGACTAGGGAATGGTTCAAAATTTTACCTTATTTCCCACCCACT | 384 | TTTTCAAGTT | 576 |
| VHL_r1_F | CGCCCCGCGTCCGACCCGCGGATCCCGCGGCGTCCGGCCCGGGTGGTCTGGATCGCGGAG | 385 | CGCCCCGCGT | 577 |
| VHL_r1_M1 | TAGAGGGGCTTCAGACCGTGCTATCGTCCCTGCTGGGTCGGGCCTAAGCGCCGGGCCCGT | 386 | TAGAGGGGCT | 578 |
| VHL_r1_M2 | GGCGCCGAGGAGGAGATGGAGGCCGGGCGGCCGCGGCCCGTGCTGCGCTCGGTGAACTCG | 387 | GGCGCCGAGG | 579 |
| VHL_r1_R | CCATACGGGCAGCACGACGCGCGGACTGCGATTGCAGAAGATGACCTGGGAGGGCTCGCG | 388 | CCATACGGGC | 580 |
| VHL_r2_F | GGTGTGGGCCACCGTGCCCAGCCACCGGTGTGGCTCTTTAACAACCTTTGCTTGTCCCGA | 389 | GGTGTGGGCC | 581 |
| VHL_r2_R | AAGTGGTCTATCCTGTACTTACCACAACAACCTTATCTTTTAAAAAGTAAAACGTCAGT | 390 | AAGTGGTCTA | 582 |
| VHL_r3_F | CTTGTTCGTTCCTTGTACTGAGACCCTAGTCTGCCACTGAGGATTTGGTTTTTGCCCTTC | 391 | CTTGTTCGTT | 583 |
| VHL_r3_R | ATCAAGACTCATCAGTACCATCAAAAGCTGAGATGAAACAGTGTAAGTTTCAACAGAAAT | 392 | ATCAAGACTC | 584 |

In paired-end sequencing experiments, read_1 and read_2 are derived from the same DNA clone. This implies that the read_1 genomic sequence (parts (3) and (4) in FIG. 24) is present because it was associated with a particular probe (part (5) in FIG. 24). Taken in total, this data indicates that each DNA sequence present in a collection of next-generation sequences can be associated with the probe sequence that targeted it. All DNA sequences associated with a particular probe can be retrieved.

Figure 25:
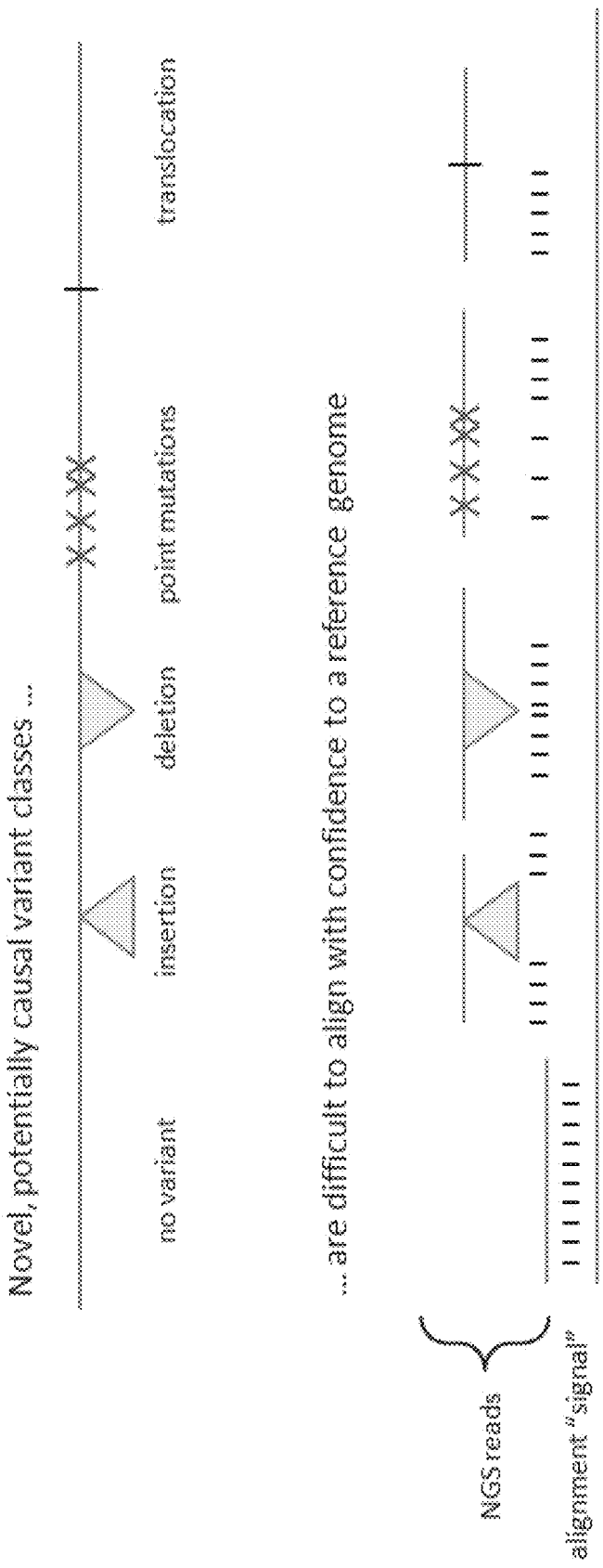
FIG. 25: The most significant classes of DNA sequence variants (insertions, deletions, runs of point mutations and/or translocations) are also the most difficult to detect by alignment based methods.

The present paradigm for next-generation resequencing analysis (targeted or otherwise) is to align reads back to a reference genome. Knowledge of the targeting probe association affords a novel workflow in which reads are first sorted by probe and then analyzed by either alignment-based methods, de novo assembly methods, or both. As described in Example 14, probe-associated-read-scaffold-assembly (PARSAR) solves one of the more complex and difficult issues in variant discovery, which is that the most interesting variants are those that deviate most significantly from the reference sequence, yet these are the very sequences that will be most refractile to conventional sequence based alignment (FIG. 25). Using probe-association followed by de novo local assembly, such variants are easily identified.

Probe-based read grouping is used in conjunction with other aspects of molecular design to identify variants with a high-degree of first-pass confidence. As shown in FIG. 26, probes are generally designed to bracket target regions. The overlapping aspect of reads allows potential variant sites to be queried by independent reads in both orientations. In addition, this dual-probe design ensures that adjacent probe binding sites themselves are sequenced. This is an important feature where probe capture performance may be in question. As an example, variant alleles where single nucleotide variants underlie one of the capture probe sequences are identified by this molecular design and can be accounted for in downstream informatics analysis.

Figure 24:
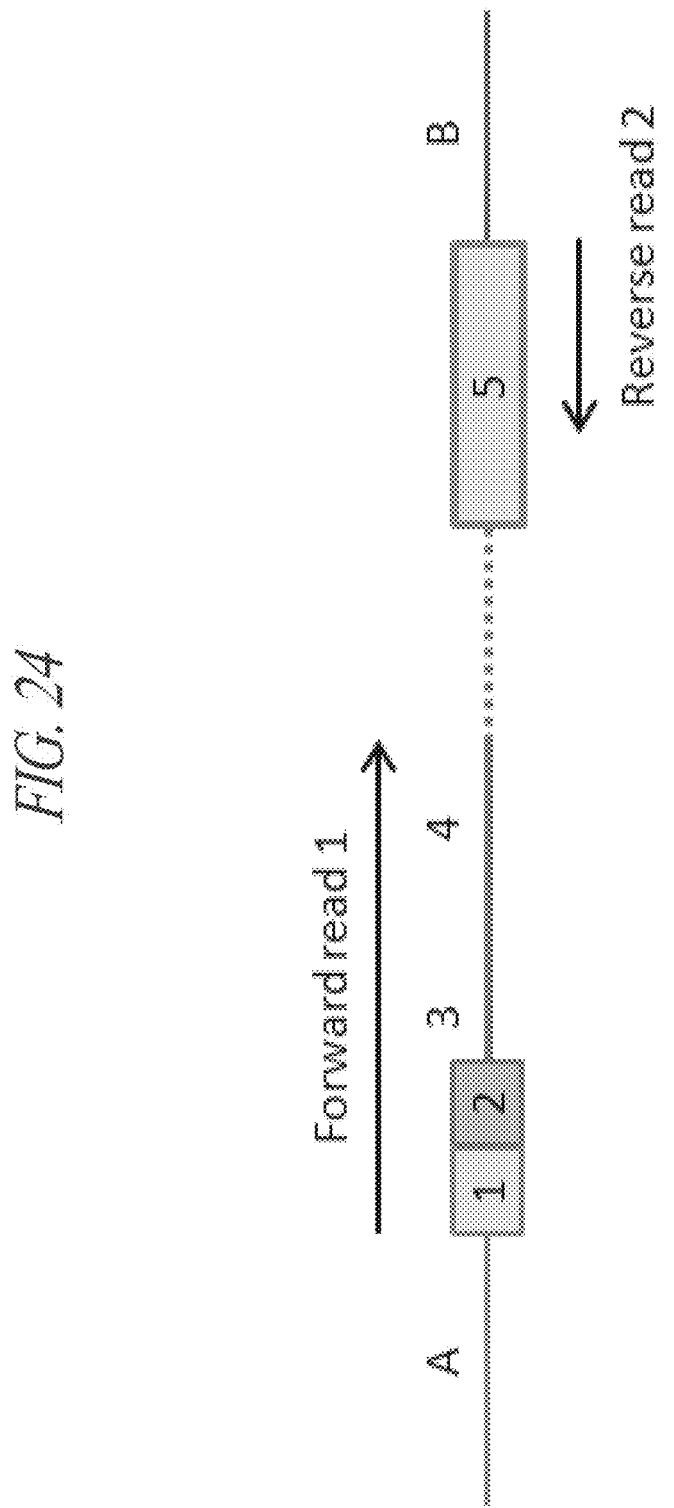
FIG. 24: Molecularly annotated sequencing read. (A) Forward flow cell (Illumina chemistry) graft sequences and sequencing primer binding site. (B) Reverse flow cell graft sequence and reverse sequencing primer annealing site. (1) Sequence label. (2) Sample label. (3) Forward read start site. (4) Sequence of genomic fragment. (5) Genomic index (probe sequence). The combination of (1)+(3) constitutes the unique read tag that is critical for both variant calling and copy number determination.
Figure 27A:
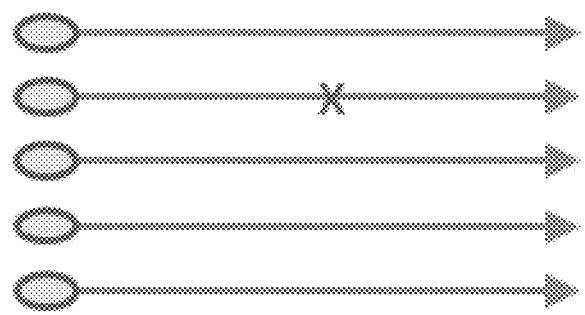
FIG. 27A-FIG. 27B: The role of sequence tags in variant calling. Sequence "tags" are comprised of a nucleotide code (ovals; in the case of Clearfork a collection of 16 possible three nucleotide sequences) and a ragged, arbitrary clone fragment end sequence.
Figure 27B:
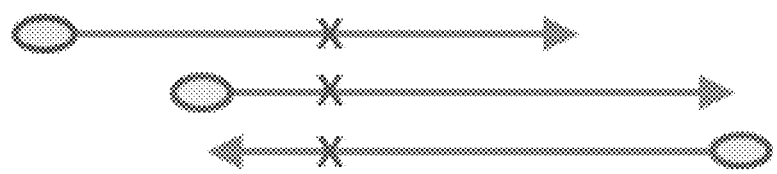

An additional aspect of flow of information from molecular annotation to downstream variant analysis involves sequence "tags", defined as the combination of a three base sequence label and ragged sequence start sites ((1)+(3) in FIG. 24). Sequence tags define the uniqueness of each sequencing clone. As illustrated in FIG. 27, variants that occur within a collection of sibling clones that share identical sequence tags are likely to be false positives. In contrast, variants are shared among sequences with different tags—even if they occur at low frequency—have a higher probability of being true positive variants. This system of tagging sequences and using tags to assign confidence predictions to variant calling has the prospect of substantially decreasing the burden of downstream variant validation (which can be costly and time consuming). Molecular annotation is described in more detail in the document Example 16, which describes the molecular technology sequencing platform.

Figure 28:
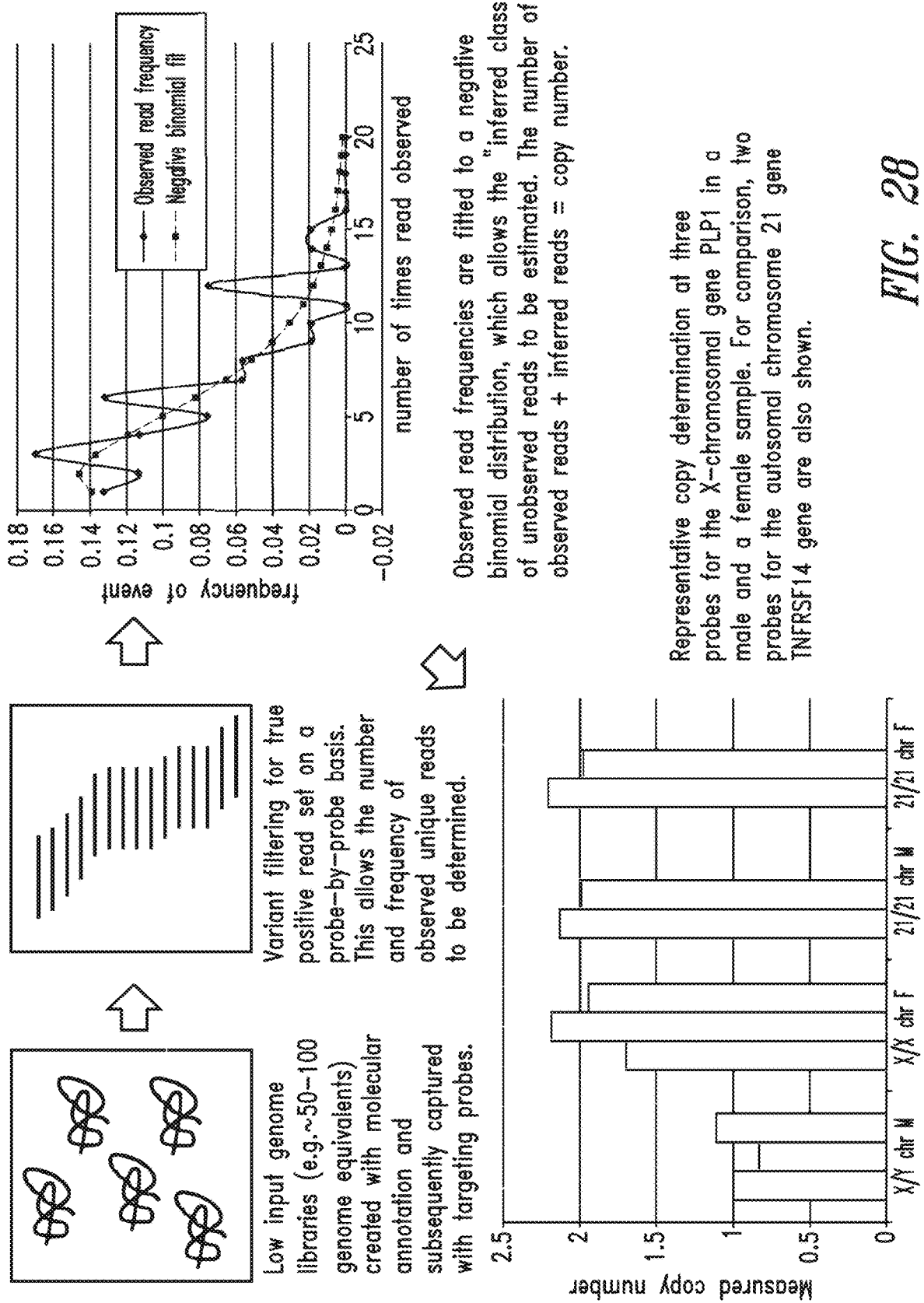
FIG. 28: Copy determination using read observation statistics.

In summary, one of the distinguishing features of the technology platforms contemplated herein is the fact that all "annealing probe" events are copied into DNA clones that also possess additional molecular annotation. Sequences are segregated by probe and by sample labels into a collection belonging to a specific target region of a specific input sample. Combinations of alignment and de novo assembly can then be used for variant detection. Finally, redundancy in the appearance of candidate variants can be used to assign confidence in variant calling. In addition to variant analysis, methods for copy number determination were also provided. These two elements are tightly coupled, specifically because copy number determination is dependent on high confidence sequencing reads. The overall schema for determining copy number from sequence information is shown in FIG. 28.

Example 16: Molecular Technology Sequencing Platform

Overview: The genomic sequencing platforms contemplated herein provide methods to: (1) Address genomic samples from multiple individuals in a single sequencing run; (2) Detect single (and/or multiple) nucleotide variants (SNVs) and single (and/or multiple) nucleotide insertions and deletions (SNIDs) with high confidence; (3) Detect large and small scale copy number variations (CNVs) in all queried gene environments; (4) Detect micro-scale translocations, inversions and insertion/deletion events in queried gene environments; (5) Develop a technological system that is scalable from ≥exome-scale investigation (≥1-2% of the overall human genome sequence) to ≤single gene-scale validation; (6) Achieve high specificity (low false-negative rate) and high sensitivity (low false-positive rate) in genomic variation tests; (7) Create a molecular and bioinformatics technology that is simple, portable and scalable in its execution; and (8) Provide molecular methods that are readily amenable to quality control measurements.

Figure 29:
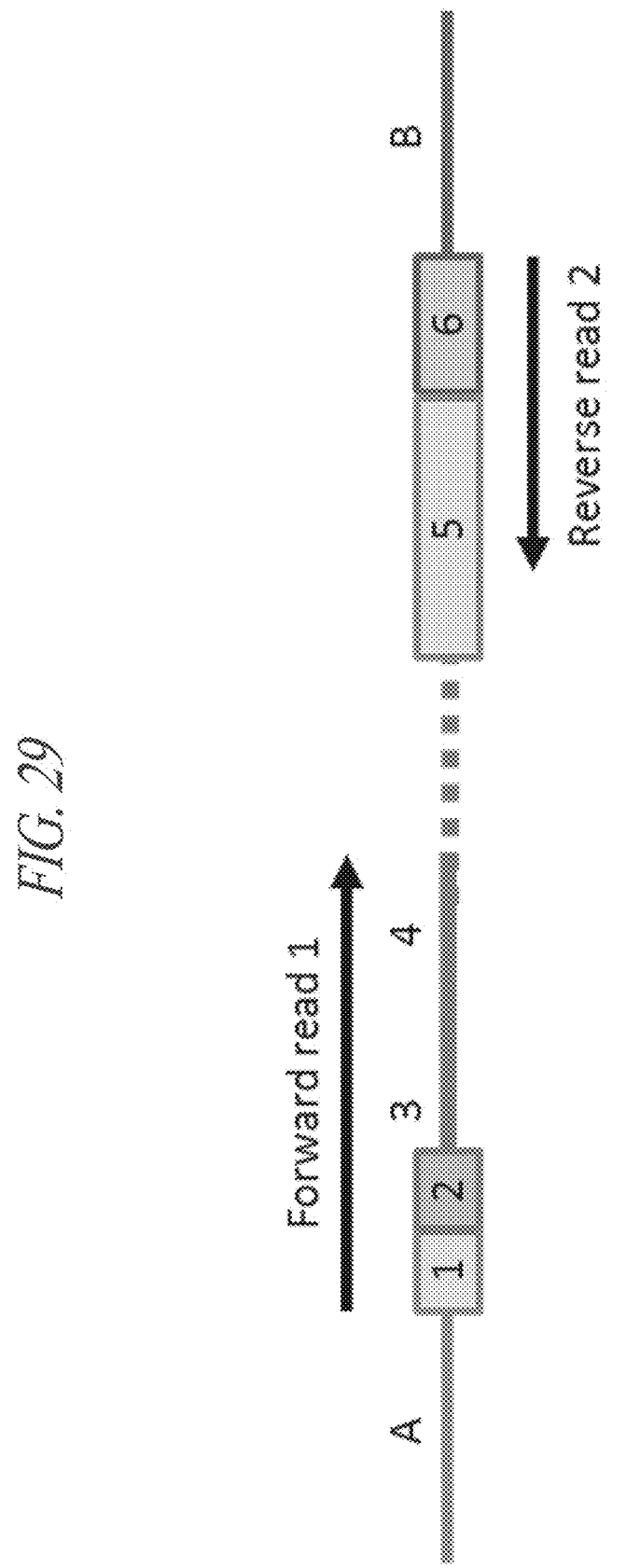
FIG. 29: Molecularly annotated sequencing read. (A) Forward flow cell (Illumina SBS chemistry) graft sequences and sequencing primer binding site. (B) Reverse flow cell graft sequence and reverse sequencing primer annealing site. (1) Sequence label. (2) Sample label. (3) Forward read start site. (4) Sequence of genomic fragment. (5) Genomic index (probe sequence). (6) Capture label. The combination of (1)+(3) constitutes the unique read tag that is critical for copy number determination. The combination of (5)+(6) constitutes a genomic index tag that can be used to monitor and quantify capture events. The forward sequencing read 1 that determines the sequences of annotation elements 1, 2, 3, and 4, and paired-end reverse read 2 that determines the sequences of annotation elements 5 and 6 are indicated.

The overall schematic of genomic sequencing read is shown in FIG. 29. A description of each element is as follows:

(1) The "sequence label" is a set of (contiguous*) nucleotides (i.e. a unique set of 3 mers) that is used in conjunction with the read start position (3) to establish the uniqueness of each sequencing read. In founding documents, the combination of this label and the read start point were referred to as the "unique sequence tag." Because the sequence label is the first set of bases encountered in sequencing-by-synthesis (SBS) chemistry all four DNA bases must be equally represented at each read position, the constraints on the sequencing label are not only uniqueness, but also that the collection of bases used in the collective set of sequence labels must have all four bases present at all positions sequenced. The use of unique sequence tags to determine local CNVs is described in the bioinformatics section of this document.

(2) The "sample label" is a set of (contiguous*) nucleotide codes that uniquely identify a particular sample within a set of multiplexed samples. As with the sequencing label, the collection of sample labels must also contain all four bases to satisfy the requirements of SBS sequence base calling. The sample codes are intentionally positioned next to genomic DNA fragments. The driver for this design is ligation bias, meaning that there are base preferences for DNA ligation efficiency in the ~2 bases upstream and the 1-2 bases downstream of the ligation junction. By placing the sample code at the ligation junction, all fragments within a specific sample experience the ligation influences/biases.

Without wishing to be bound to any particular theory, it is contemplated that the sequence labels and sample labels could be created as inter-digitated nucleotide sequences.

(3) The "read start point" within genomic fragments is one of two key elements that define a "unique sequence read." As discussed in section (1) above, the unique identifying "tag" for each read is comprised of the sequencing label AND the read start point. As considered in more detail below, the collection of unique [(1)+(3)] sequence tags is essential for determination of large scale CNV. Here "large scale CNV" is defined as any CNV that involves the entirety of at least one probe binding region plus some adjacent sequence. Large scale CNV can be as large as gain or loss of entire chromosomes.

[(1)+(2)] The sequence label and sample label are embedded in adaptor sequences that are ligated to end-repaired genomic fragments in the initial stage of library construction process where a whole genome library is created.

(4) The sequencing read. The sequence information from genomic fragments is, of course, a central focus of the genomic assays. Each read is considered in the context of multiple, overlapping reads produced within the same assay.

(5) The probe level—"genomic indexing." The overall genomics assay strategy is to combine multiple sequence labels into a composite "molecular annotation" that places each sequencing read into a larger framework of genomic analysis. Within this operational paradigm, Read 1 reveals elements (1-4) of each annotated clone. Read 2 reveals the probe sequence that retrieved each clone by hybridization based capture and subsequent enzymatic processing. The probe sequence information is central to the genomics strategy because all reads are initially clustered according to the probe that captured them. This clustering of information on a probe-by-probe basis is termed "genomic indexing" because each read is indexed to a genomic probe prior to analysis.

One of the interesting features of the probe label is that the constellation of all probe sequences within a capture reaction is well-defined (we know which probes went into the capture reaction). This implies that Read 2 does not necessarily need to cover the entire 60 nt probe sequence. Rather, Read 2 only needs to be of sufficient length to enable unambiguous identification of all probes within a specific reaction. As one non-limiting example, the probe set discussed in Example 15 consists of 192 probes that can be differentiated based on only 7 nt of 5' probe sequence (two of the probes with identical 7 nt 5' termini were tagged with dinucleotide codes so they could be informatically differentiated).

(6) The capture label. The composition of the libraries is determined by the intimate molecular interaction between probes and target sequences. The performance of each unique probe sequence can be monitored using the capture label, which can be as simple as a string of several (4-6) random bases. The diversity and statistical distribution of capture labels detected in sequencing is a direct measure of probe performance. By way of example, imagine a case where very few sequences are associated with a particular probe sequence. It may be tempting to attribute this deficit of sequences to poor probe performance, and therefore to initiate iterative cycles of probe redesigns. However, sequence under-representation may also be a consequence of sequences that do not ligate well to adaptors and or sequences that do not amplify well with the particular PCR regimen that is used. The use of capture labels allows differentiation of these failure modes. With poor probe performance, the very few capture events that do occur will manifest as very few capture labels that show up multiple times. In contrast, poor representation for reasons upstream of the actual capture reaction (ligation, PCR, end-repair, etc.) will result in a large constellation of capture labels that will be, by and large, uniquely represented. In particular embodiments, as one transitions into automated designs of thousands of probes, the ability to informatically QC probe performance will become increasingly important.

Example 17: Probe Selection and Implementation

Summary: Probe sequence selection and the methods to use them have, necessarily, been developed in concert. This example describes probe selection criterion in Section I and the laboratory methods that make them most effective in Section II. See, e.g., FIG. 30.

Section I. Selection of Targeting Probes.

Figure 30:
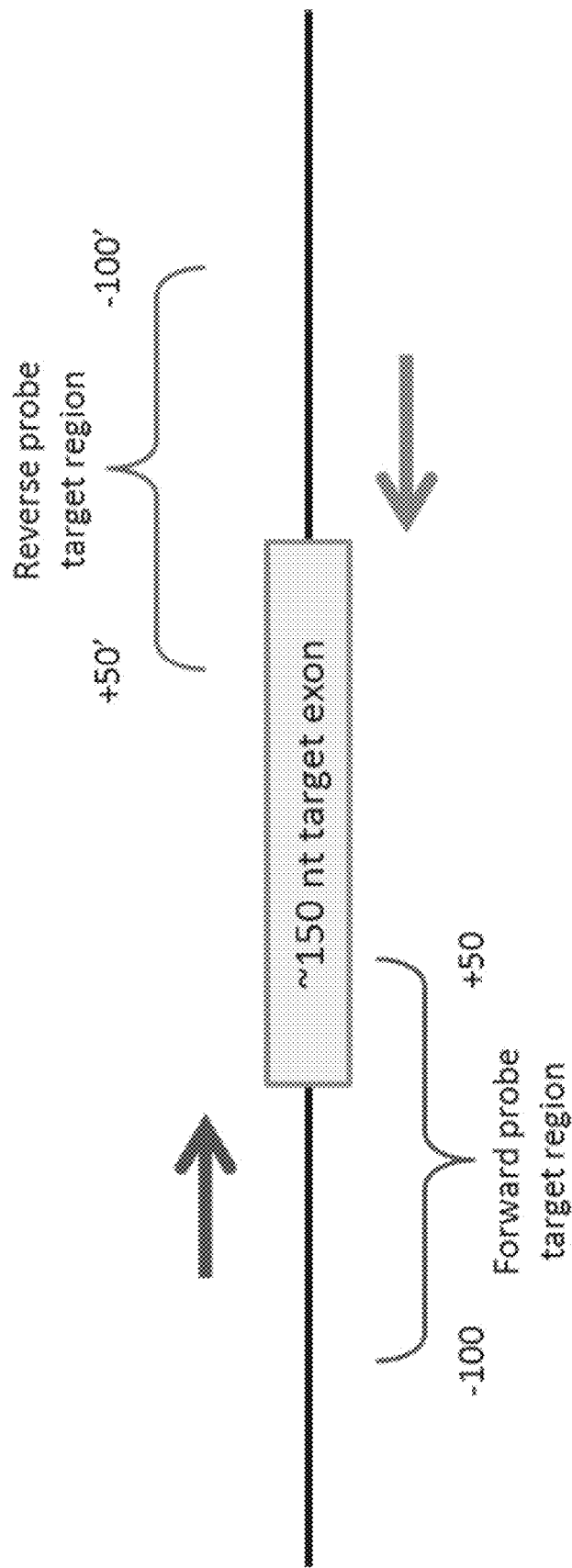
FIG. 30: Probes (e.g., multifunctional capture probes) are generally directional, meaning they capture sequences on one side (generally the 3'3' side) of their position. Tail sequences that add additional functionality (e.g., PCR primer binding site, binding site for partner oligo that enables biotin pull-out, etc.) are added in addition to the core targeting 60-mer. Sixty nucleotide targeting sequences are chosen with the following constraints and criterion: (1) The probe is positioned from −100 to +50 nt relative to the start of the target sequence. In the illustration at right, the "start" of the target sequence is the intron:exon junction; (2) Probes are designed with redundancy, as illustrated, such that the resulting sequences from a pair of probes are overlapping in opposite orientations; (3) Probes are selected (where possible) to possess GC content not less than 33% (>20 G's or C's per 60 mer) and not more than 67% (<40 G's or C's per 60 mer); (4) Probes are selected to avoid repeats wherever possible. This is done with the help of REPEATMASKER and/or unique alignability criterion, both of which can be viewed on the UCSC genome browser; (5) In cases the position requirement, GC requirement, and the uniqueness requirement cannot be met, selection rules are relaxed in the following order (GC>position>uniqueness). In other words, GC and positioning are flexible; the uniqueness criterion is not.

In the most general terms, target enrichment probes are 60 nt in length. Probes are generally directional, meaning they capture sequences on one side (generally the 3' side) of their position. Tail sequences that add additional functionality (e.g., PCR primer binding site, binding site for complementary oligo that enables biotin pull-out, etc) are added in addition to the core targeting 60-mer. Sixty nucleotide targeting sequences are chosen with the following constraints and criterion: (1) The probe is positioned from −100 to +50 nt relative to the start of the target sequence. In FIG. 30, the "start" of the target sequence is the intron:exon junction; (2) Probes are designed with redundancy, as illustrated, such that the resulting sequences from a pair of probes are overlapping in opposite orientations; (3) Probes are selected (where possible) to possess GC content not less than 33% (>20 G's or C's per 60 mer) and not more than 67% (<40 G's or C's per 60 mer); (4) Probes are selected to avoid repeats wherever possible. This is done with the help of REPEATMASKER and/or unique alignability criterion, both of which can be viewed on the UCSC genome browser; and (5) In case the position requirement, GC requirement, and the uniqueness requirement cannot be met, selection rules are relaxed in the following order (GC>position>uniqueness). In other words, GC and positioning are flexible; the uniqueness criterion is not.

Section II. Laboratory Methods.

The input to target enrichment is probes, a gDNA library, and buffers, which have been described elsewhere herein. The first step in targeted enrichment is melting of the gDNA library, which begins in a form as double-stranded PCR fragments. This is achieved by denaturation of the gDNA, preferably at a concentration of 100 ng/μL in a total volume of 10 at 98° C. for 2 min followed by immediate transfer to ice. The gDNA library is suspended in a low salt buffer that contains 10 mM Tris pH 8.0 and 0.1 mM EDTA. The second step is to add 5 of concentrated binding buffer (4M NaCl, 40 mM Tris pH 8.0, 0.4 mM EDTA and 0.4% Tween20). While these conditions are specific, the overarching concept is that the concentration of salt must be increased to 2N osmolarity to achieve rapid kinetic association of complementary DNA strands. Five microliters of probe is also added such that the final concentration of probe is 250 pM in each probe. The mixture of gDNA library, buffer and probe is heated to 98° C. for 2 min and cooled in 1° C. increments for four min each down to 68° C. In the third step, probe:gDNA complexes (the probe has a biotin associated with it) are bound to magnetic beads that are coated with streptavidin. In the fourth step, stringent washing is used to remove unwanted associations between probe and non-target sequences that may occur because of, for example, short matches of nucleotide sequence between probe and gDNA. Stringency is achieved by using low-salt, high-formamide wash buffer as, for example, a buffer containing 30%-35% formamide (v/v), 10 mM Tris pH 8.0, 0.1 mM EDTA and 0.5% Tween 20). Several washes of the beads are used to achieve the desired purity of target sequence (e.g., four). The washed beads possess target sequences bound to probe that are processed, amplified, and sequenced. In summary, low salt melting of the gDNA library, high salt probe annealing, and high formamide washes are used in concert with probe designs to achieve high levels of target sequence enrichment.

Example 18: Exemplary Sequences

Overview: Exemplary genome tags, sample codes and library information are shown in Tables 27-29 below.

TABLE 27

Exemplary Genome tags
Genome tags

| AAC | CAA | GAT | TAG |
| ACA | CCC | GCG | TCT |
| AGT | CGG | GGC | TGA |
| ATG | CTT | GTA | TTC |

TABLE 28

Exemplary Sample Codes
Sample codes

| GAA | TCA | CGA | ATA |
| TAC | GCC | AGC | CTC |
| AAG | CCG | TGG | GTG |
| CAT | ACT | GGT | TTT |

TABLE 29

Exemplary Library

| Genome tags | Sample codes | Sample ID | Input |
|---|---|---|---|
| AAC | ATA | NA18917 | 50 genomes |
| ACA | CCG | NA18917 | 100 genomes |
| AGT | GGT | NA18917 | 200 genomes |
| ATG | TAC | NA18917 | 400 genomes |
| CAA | AGC | NA12878 | 50 genomes |
| CCC | CAT | NA12878 | 100 genomes |
| CGG | GTG | NA12878 | 200 genomes |
| CTT | TCA | NA12878 | 400 genomes |
| GAT | | | |
| GCG | | | |
| GGC | | | |
| GTA | | | |
| TAG | | | |
| TCT | | | |
| TGA | | | |
| TTC | | | |

Example 19: Construction of Tagged, Targeted, Genomic Library

Summary: Several ways to construct tagged, targeted genomic sequencing libraries are contemplated herein. In this embodiment, DNA repair is used to attach probe-associated sequences to captured genomic fragments. This approach worked well for creating sequence-ready targeted genomic libraries.

Concept: An important principle of the library construction is that the sequence ready clones are comprised of DNA sequences derived from both genomic fragments and capture probes. This "recombination" of parts greatly enriches for those genomic fragments that are in direct contact with probe, and it enables focused sequencing reads on one side of a probe sequence. In this design, the tripartite complex formed between the target genomic library fragment, the capture probe and the common partner oligo possesses a structure reminiscent of a DNA replication fork. Such forks occur during normal DNA replication, but they also occur during DNA repair processes. In the latter case, it is often necessary to trim 5' displaced strands to enable joining of the newly polymerized strand to the adjacent 3' sequence. This repair process requires two enzymes and three enzymatic activities. DNA polymerase holoenzymes like E. coli DNA polymerase or Bst DNA polymerase possess two of these activities, a 5' to 3' endonuclease activity that removes these 5' displaced flaps and, of course, DNA polymerase activity.

Figure 31A:
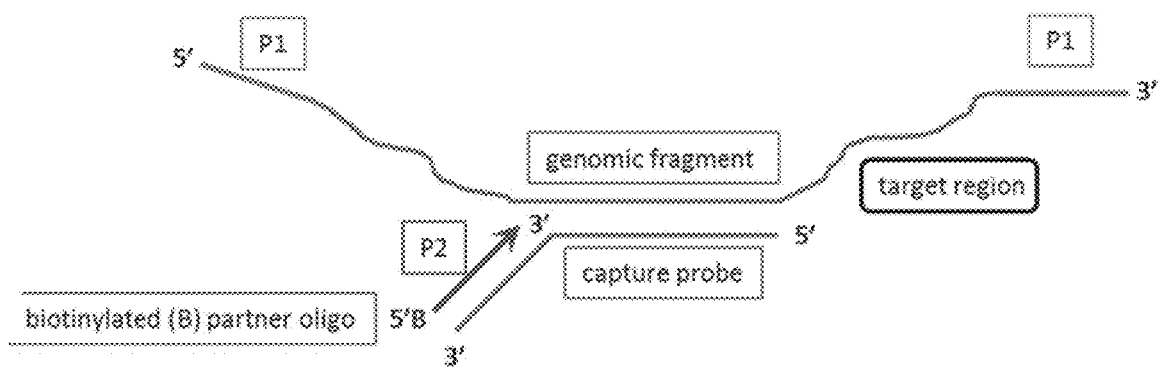
FIG. 31A-FIG. 31B: Processing to create targeted genomic sequencing libraries.
Figure 31B:
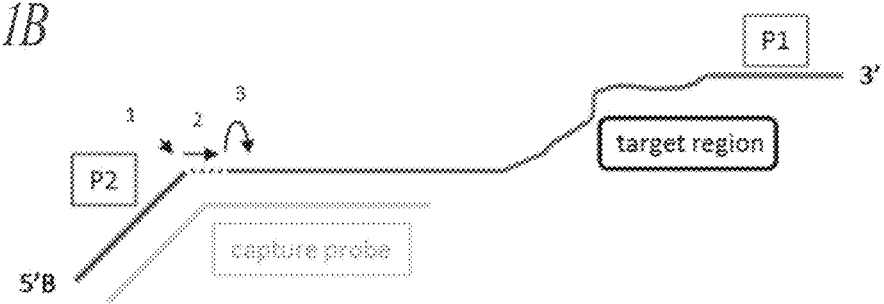
Figure 32:
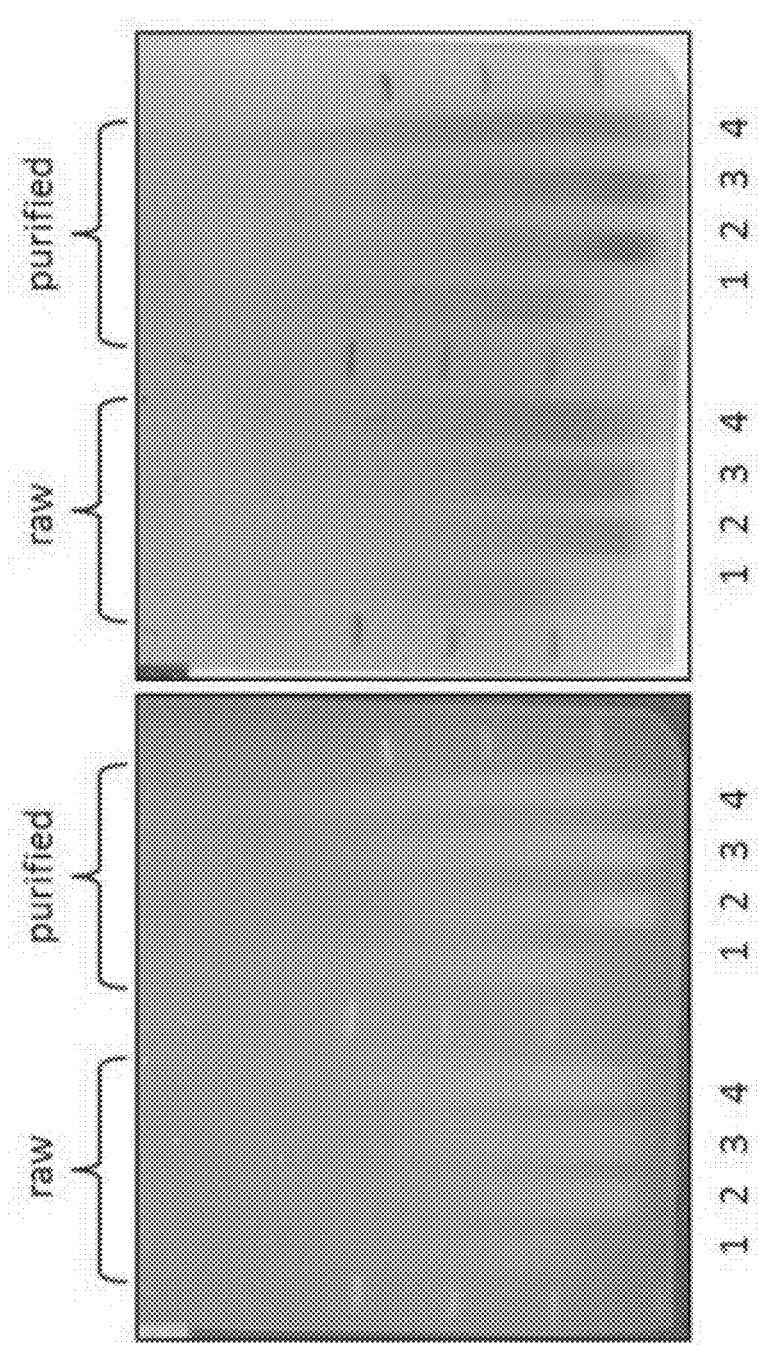
FIG. 32 shows post-capture/processing of PCR products. Lane 1 is ACA2 single primer amplified, unprocessed capture complex. Lanes 2-4 were amplified with AF+CR dual PCR primers.

In particular embodiments, Bst polymerase is preferred because it also lacks 3' to 5' nuclease activity that is often associated with DNA polymerase holoenzymes. See, e.g., FIG. 31. This feature is useful because it suggests that the single-stranded 3' DNA protrusions of the target genomic clones do not require protection. The other enzyme and activity required is a nick-closing DNA ligase such as the $NAD^+$-requiring Taq DNA ligase. Following processing, processed fragments are amplified by PCR to allow for size selection and quantification prior to sequencing.

Proof of principle oligonucleotides: For this experiment, eight target regions were chosen that correspond to eight genomic regions for which we have qPCR assays. The forward and reverse primers for these eight regions are shown in Table 30. The capture probes are the exact reverse complement of capture probes that were used and validated elsewhere herein. These probes span a % GC range from 22% to 73% as noted in Table 32.

TABLE 30

Proof of principle oligonucleotides

| SEQ ID NO: | qPCR Assay | Name | Sequence |
|---|---|---|---|
| 585 | 17 | SRY_F | CTGGTGCTCCATTCTTGAGTGTGT |
| 586 | | SRY_R | GGACAACAGGTTGTACAGGGATGA |
| 587 | 18 | VHL_F | TACAGGAGACTGGACATCGTCAGG |
| 588 | | VHL_R | CTTTCTGCACATTTGGGTGGTCTT |
| 589 | 19 | UGT_F | GGTGATCAGATGGACAATGCAAAG |
| 590 | | UGT_R | TCATTTCCAGAACATTCAGGGTCA |
| 591 | 20 | TNF_F | ACCTCAATGGCCTAAGCAAGTGTC |
| 592 | | TNF_R | GCCTCTTACCTGGGTCACACATTT |
| 593 | 21 | RUNX_F | ATCTTGCAACCTGGTTCTTCATGG |
| 594 | | RUNX_R | GCTGGCAATGATGAAAACTACTCG |
| 595 | 22 | RHD_F | CCAAGTTTCAACTCTGCTCTGCTG |
| 596 | | RHD_R | GTTGAACACGGCATTCTTCCTTTC |
| 597 | 23 | PTEN_F | GGAAAGGGACGAACTGGTGTAATG |
| 598 | | PTEN_R | AAATCTAGGGCCTCTTGTGCCTTT |
| 599 | 24 | EP300_F | AGCCCCATGGATCTTTCTACCATT |
| 600 | | EP300_R | ATACTGCCAGGGCTCCTGATACTG |

TABLE 30-continued

Proof of principle oligonucleotides

| | Capture probe | Name | Sequence |
|---|---|---|---|
| 601 | 17 | SRY_rlf_V3 | AATCGGGTAACATTGGCTACAAAGACCTACCTAGATGC TCCTTTTTACGATAACTTACAGGTGAAAACCAGGATCA ACTCCCGTGCCAGTCACATCTCGT |
| 602 | | SRY_rlr_V3 | ATTATAAGTATCGACCTCGTCGGAAGGCGAAGATGCTG CCGAAGAATTGCAGTTTGCTTCGTGAAAACCAGGATCA ACTCCCGTGCCAGTCACATCTCGT |

Probes were synthesized as ultramers by IDT, rehydrated to 100 uM, and pooled; each probe in the pool is present at 6.25 uM. To create a 100× stock solution in which each probe was present at 100 nM, 10 uM of pool and 10 µL of 100 uM common, biotinylated partner oligo were combined in 605 µL of TEzero+0.05% Tween 20 (TT). The 100× stock was further diluted 100-fold (10 µL into 990 µL TT) to give a working solution in which each probe is present at a concentration of 1 nM.

Capture/Processing Protocols: One objective of the proof of principle study was to validate probe performance and test the efficiency of processing on sequence-ready library yield. The genomic library pool was derived from a 16 sample set library. For probe annealing, four of 10 µL library aliquots in separate PCR strip tubes were heated to 98° C. for 2 min and cooled on ice. Five µL of 4× bind buffer and five µL of probe were added to each tube, and the solution was annealed using a 1° C. step for four min thermal cycler program from 98° C. to 69° C. Annealed complexes were bound to streptavidin-coated magnetic beads, washed four times with 25% formamide-containing wash buffer and one time with TEzero. The final complexes were suspended in 2 µL of TEzero.

Four treatments of the four complexes were investigated: (1) No processing, amplification with ACA2 primer alone to determine raw capture efficiency; (2) No processing, amplification with AF and CR to determine unprocessed amplification and capture efficiency; (3) PreCR processing in 10 µL prior to AF and CR amplification to explore low volume processing; and (4) PreCR processing in 50 µL prior to AF and CR amplification to establish high volume processing effects.

PreCR processing was accomplished by adding the manufacturer's recommended solution that contained per 100

82 µL of water
10 µL of Thermopol buffer
1 µL of 100×NAD$^+$
1 µL of 10 mM dNTPs
2 µL of PreCR enzyme mix Ten µL of PreCR cocktail was added to tube 3 and 50 µL was added to tube 4. These were incubated at 37 C for 20 min.

Following PreCR treatment, all four samples were resuspended to 50 µL by the addition of TEzero, and Q5 PCR cocktail with the appropriate PCR primers was added to a final volume of 250 µL. Each aliquot of PCR cocktail contained:

125 µL water
50 µL 5× Q5 reaction buffer
25 µL of 10 uM primer (either ACA2 or a 1:1 blend of AF and CR)
5 µL of 10 mM dNTPs
2.5 µL of Q5 hot start enzyme 50 µL of each PCR reaction mix was aliquoted to a tube containing 1.25 EvaGreen and 1 µL ROX dyes, mixed, and quadruplicate 10 µL aliquots were added to a qPCR optical PCR plate. The remaining 200 µL was split into to 100 µL aliquots. Both the qPCR and conventional PCR reaction were cycled as:

98° C.-30 sec
98° C.-10 sec, 69° C.-10 sec, 72° C.-10 sec for 40 cycles (qPCR) and plateau cycle (conventional).

The real-time PCR reaction was monitored to determine the optimal stopping point for the conventional PCR reactions. For the ACA2 reaction, the stopping point was at 21 cycles. For the remaining reactions, the stopping point was at 28 cycles. These qPCR reactions are further described in the Results section, infra.

Ten µL of raw PCR was collected for gel analysis and a remaining aliquot of 100 µL was purified 1:1 with beads. The purified PCR product was eluted with 50 µL TEzero and quantified by Qubit. The DNA yields were: (1) 7.44 ng/µL; (2) 10.6 ng/µL; (3) 12.1 ng/µL; and (4) 15.7 ng/µL.

qPCR analysis of capture/processing: A single Eco qPCR plate containing an array of eight assays—Assays 17-24 (Table 32) by six samples was used to assess capture efficiency. The six samples were:

1. 10 ng/µL of original gDNA library
2. NTC
3. 0.01 ng/µL of sample 1
4. 0.01 ng/µL of sample 2
5. 0.01 ng/µL of sample 3
6. 0.01 ng/µL of sample 4

The Q5 hot start assay mixture contained:
237.5 µL H$_2$O
100 µL 5× Q5 reaction buffer
10 µL dNTPs
12.5 µL EvaGreen
10 µL ROX
5 µL Q5 hot start enzyme This cocktail was distributed in 48 µL aliquots and 3 µL of Assay primer (10 uM in both F and R primer) was added. This was distributed in columns. Two µL of sample was added in rows and the plate was cycled as described above.

Results: Amplification of complexes: While the fluorescence profile of amplifying complexes is used primarily to identify the amplification plateau (which occurs much sooner for single primer than dual primer amplicons), the Cq value can be used to look at the content of amplicon between samples. In this experiment, the observed Cq values were:

| Sample | Conditions | Cq |
|---|---|---|
| 1 | no PreCR, ACA2 single primer | 15 |
| 2 | no PreCR, AF + CR | 21 |

-continued

| Sample | Conditions | Cq |
|---|---|---|
| 3 | 10 µL PreCR, AF + CR | 20 |
| 4 | 50 µL PreCR, AF + CR | 19 |

These data demonstrated that PreCR treatment increased the abundance of P1+P2 (AF+CR) amplicons.

Figure 33:
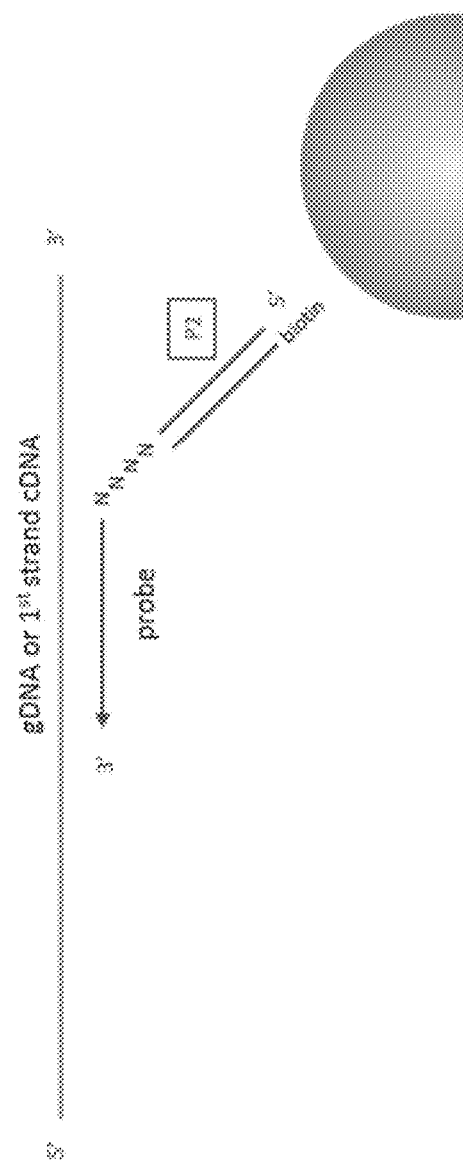
FIG. 33 shows Steps 1 and 2 of a library free method for generating tagged genomic DNAs and related capture, processing, and analysis methods.

Gel images of the post-processing PCR products shown in FIG. 33 show that PreCR treatment supported the amplification of a larger size distribution of clones. The untreated, sample 2 amplicon is primarily a cluster of small size fragments. Sample 3 and to a greater extent sample 4 are more broadly distributed smears.

The qPCR results showing target enrichment are shown in Table 31 below. The raw sequence capture in sample 1 was surprisingly high. At least two factors may have contributed to such an unexpected improvement over historical data sets: (1) The core annealing process (pre-melt, higher temps, low salt binding to strep beads) has been optimized; and (2) A longer partner oligo (40 nt vs 35 nt) was used.

Even with no PreCR treatment, P1+P2 (AF+CR) amplifiable material was made (sample 2) and substantial enrichment of target signal over gDNA (and/or NTC) was observed.

PreCR treated complex also yielded enrichment levels comparable to unprocessed (sample 1) control. This is a fantastic demonstration of the fact that PreCR processing can stimulate the recombination of the probe-based partner oligo with the genomic library-based target clones. While the levels of enrichment are not remarkable, the majority of clone material is small and falls outside the range of the qPCR assay. As noted elsewhere herein, judicious bead enrichment can dramatically increase the proportion of the library that covers the qPCR site.

In addition, the results indicated that more PreCR is not necessarily better. Sample 3 (10 µL PreCR treatment) outperformed Sample 4 (50 µL PreCR treatment) with respect to enrichment specific activity in 6 of 8 assays.

TABLE 31 qPCR enrichment data for V3 experimental samples

| | Cqs | | | | | | | |
|---|---|---|---|---|---|---|---|---|
| | Assay 17 | Assay 18 | Assay 19 | Assay 20 | Assay 21 | Assay 22 | Assay 23 | Assay 24 |
| gDNA lib | 24 | 21 | 21 | 22 | 22 | 22 | 22 | 22 |
| NTC | 35 | 31 | 34 | 26 | 33 | N/A | 30 | 29 |
| sample 1 | 16 | 13 | 13 | 12 | 14 | 13 | 15 | 14 |
| sample 2 | 21 | 18 | 19 | 16 | 18 | 18 | 22 | 20 |
| sample 3 | 16 | 14 | 15 | 13 | 14 | 15 | 17 | 15 |
| sample 4 | 16 | 14 | 15 | 13 | 15 | 15 | 17 | 15 |

| | Abs value | | | | | | | |
|---|---|---|---|---|---|---|---|---|
| | Assay 17 | Assay 18 | Assay 19 | Assay 20 | Assay 21 | Assay 22 | Assay 23 | Assay 24 |
| gDNA lib | 5 | 40 | 36 | 32 | 20 | 22 | 34 | 29 |
| NTC | 0 | 0 | 0 | 1 | 0 | | 0 | 0 |
| sample 1 | 1918 | 14374 | 9372 | 20243 | 8444 | 10189 | 2820 | 8133 |
| sample 2 | 59 | 382 | 172 | 1526 | 295 | 403 | 34 | 87 |
| sample 3 | 1085 | 5090 | 3051 | 10275 | 5213 | 4144 | 1068 | 2822 |
| sample 4 | 1492 | 5381 | 2751 | 8770 | 3866 | 2777 | 777 | 2233 |

| | Adj value | | | | | | | |
|---|---|---|---|---|---|---|---|---|
| | Assay 17 | Assay 18 | Assay 19 | Assay 20 | Assay 21 | Assay 22 | Assay 23 | Assay 24 |
| gDNA lib | 5 | 40 | 36 | 32 | 20 | 22 | 34 | 29 |
| NTC | 0 | 0 | 0 | 1 | 0 | 0 | 0 | 0 |
| sample 1 | 1918016 | 14374082 | 9372333 | 20243011 | 8443797 | 10188837 | 2820166 | 8132920 |
| sample 2 | 59292 | 381694 | 171590 | 1526000 | 295038 | 403467 | 33575 | 87344 |
| sample 3 | 1085442 | 5089739 | 3050781 | 10275412 | 5212989 | 4143563 | 1068184 | 2821950 |
| sample 4 | 1491501 | 5380882 | 2751029 | 8770152 | 3865764 | 2777330 | 777035 | 2232604 |

| | Fold enrich | | | | | | | |
|---|---|---|---|---|---|---|---|---|
| | Assay 17 | Assay 18 | Assay 19 | Assay 20 | Assay 21 | Assay 22 | Assay 23 | Assay 24 |
| sample 1 | 378673 | 356798 | 262412 | 641805 | 415341 | 453405 | 84090 | 281573 |
| sample 2 | 11706 | 9475 | 4804 | 48382 | 14513 | 17954 | 1001 | 3024 |
| sample 3 | 214298 | 126339 | 85418 | 325782 | 256421 | 184389 | 31850 | 97700 |
| sample 4 | 294466 | 133566 | 77025 | 278058 | 190152 | 123592 | 23169 | 77296 |

Discussion: The capture and processing methods disclosed in this example performed well using untreated complexes. Without wishing to be bound to any particular theory, it is contemplated that one reason that the untreated complexes performed so well was because both the capture probe and genomic fragments possess primer binding sites.

Appendix to Example 19: The primer and amplicon designs for this example are shown below in Table 32.

TABLE 32

Sequences used to perform Example 19

| SEQ ID NO: | Target | Name | Sequence | % GC |
|---|---|---|---|---|
| 603 | SRY_r1, Assay 17 | F qPCR primer | CTGGTGCTCCATTCTTGAGTGTGT | |
| 604 | | R qPCR primer | GGACAACAGGTTGTACAGGGATGA | |
| 605 | | qPCR Amplicon | CTGGTGCTCCATTCTTGAGTGTGTGGCTTTCGTACAGTCATCCCTGTACAACCTGTTGTCC | |
| 606 | | F-probe | CTGTAAGTTATCGTAAAAAGGAGCATCTAGGTAGGTCTTTGTAGCCAATGTTACCCGATT | 40% |
| 607 | | R-probe | GAAGCAAACTGCAATTCTTCGGCAGCATCTTCGCCTTCCGACGAGGTCGATACTTATAAT | 47% |
| 608 | | F-probe reverse complement | AATCGGGTAACATTGGCTACAAAGACCTACCTAGATGCTCCTTTTTACGATAACTTACAG | |
| 609 | | R-probe reverse complement | ATTATAAGTATCGACCTCGTCGGAAGGCGAAGATGCTGCCGAAGAATTGCAGTTTGCTTC | |
| 610 | VHL_r3 Assay 18 | F qPCR primer | TACAGGAGACTGGACATCGTCAGG | |
| 611 | | R qPCR primer | CTTTCTGCACATTTGGGTGGTCTT | |
| 612 | | qPCR Amplicon | TACAGGAGACTGGACATCGTCAGGTCGCTCTACGAAGATCTGGAAGACCACCCAAATGTGCAGAAAG | |
| 613 | | F-probe | CTTGTTCGTTCCTTGTACTGAGACCCTAGTCTGCCACTGAGGATTTGGTTTTTGCCCTTC | 48% |
| 614 | | R-probe | ATCAAGACTCATCAGTACCATCAAAAGCTGAGATGAAACAGTGTAAGTTTCAACAGAAAT | 35% |
| 615 | | F-probe reverse complement | GAAGGGCAAAAACCAAATCCTCAGTGGCAGACTAGGGTCTCAGTACAAGGAACGAACAAG | |
| 616 | | R-probe reverse complement | ATTTCTGTTGAAACTTACACTGTTTCATCTCAGCTTTTGATGGTACTGATGAGTCTTGAT | |
| 617 | UGT1A1_r4, Assay 19 | F qPCR primer | GGTGATCAGATGGACAATGCAAAG | |
| 618 | | R qPCR primer | TCATTTCCAGAACATTCAGGGTCA | |
| 619 | | qPCR Amplicon | GGTGATCAGATGGACAATGCAAAGCGCATGGAGACTAAGGGAGCTGGAGTGACCCTGAATGTTCTGGAAATGA | |
| 620 | | F-probe | TGTGTCCAGCTGTGAAACTCAGAGATGTAACTGCTGACATCCTCCCTATTTTGCATCTCA | 45% |
| 621 | | R-probe | ATTTGAAACAATTTTATCATGAATGCCATGACCAAAGTATTCTTCTGTATCTTCTTTCTT | 28% |
| 622 | | F-probe reverse complement | TGAGATGCAAAATAGGGAGGATGTCAGCAGTTACATCTCTGAGTTTCACAGCTGGACACA | |
| 623 | | R-probe reverse complement | AAGAAAGAAGATACAGAAGAATACTTTGGTCATGGCATTCATGATAAAATTGTTTCAAAT | |
| 624 | TNFRSF14_r3, Assay 20 | F qPCR primer | ACCTCAATGGCCTAAGCAAGTGTC | |
| 625 | | R qPCR primer | GCCTCTTACCTGGGTCACACATTT | |
| 626 | | qPCR Amplicon | ACCTCAATGGCCTAAGCAAGTGTCTGCAGTGCCAAATGTGTGACCCAGGTAAGAGGC | |

TABLE 32-continued

Sequences used to perform Example 19

| SEQ ID NO: | Target | Name | Sequence | % GC |
|---|---|---|---|---|
| 627 | | F-probe | TGATGGGTGGGCTCCCGAAGGGGCCTCCCGCAGACTTG CGAAGTTCCCACTCTCTGGGCG | 67% |
| 628 | | R-probe | CAGGGTGCGGGGGCATCCAGGCTGCCCAAGCGGAGGCT GGGCCGGCTGTGCTGGCCTCTT | 73% |
| 629 | | F-probe reverse complement | CGCCCAGAGAGTGGGAACTTCGCAAGTCTGCGGGAGGC CCCTTCGGGAGCCCACCCATCA | |
| 630 | | R-probe reverse complement | AAGAGGCCAGCACAGCCGGCCCAGCCTCCGCTTGGGCA GCCTGGATGCCCCCGCACCCTG | |
| 631 | RUNX_r4, Assay 21 | F qPCR primer | ATCTTGCAACCTGGTTCTTCATGG | |
| 632 | | R qPCR primer | GCTGGCAATGATGAAAACTACTCG | |
| 633 | | qPCR Amplicon | AATCTTGCAACCTGGTTCTTCATGGCTGCGGTAGCATT TCTCAGCTCAGCCGAGTAGTTTTCATCATTGCCAGC | |
| 634 | | F-probe | TTTTGAAATGTGGGTTTGTTGCCATGAAACGTGTTTCA AGCATAGTTTTGACAGATAACG | 37% |
| 635 | | R-probe | TGCCCTAAAAGTGTATGTATAACATCCCTGATGTCTGC ATTTGTCCTTTGACTGGTGTTT | 40% |
| 636 | | F-probe reverse complement | CGTTATCTGTCAAAACTATGCTTGAAACACGTTTCATG GCAACAAACCCACATTTCAAAA | |
| 637 | | R-probe reverse complement | AAACACCAGTCAAAGGACAAATGCAGACATCAGGGATG TTATACATACACTTTTAGGGCA | |
| 638 | RHD_r5 Assay 22 | F qPCR primer | CCAAGTTTCAACTCTGCTCTGCTG | |
| 639 | | R qPCR primer | GTTGAACACGGCATTCTTCCTTTC | |
| 640 | | qPCR Amplicon | CCAAGTTTCAACTCTGCTCTGCTGAGAAGTCCAATCGA AAGGAAGAATGCCGTGTTCAAC | |
| 641 | | F-probe | AACCCCTCGAGGCTCAGACCTTTGGAGCAGGAGTGTGA TTCTGGCCAACCACCCTCTCTG | 58% |
| 642 | | R-probe | CATAAATATGTGTGCTAGTCCTGTTAGACCCAAGTGCT GCCCAAGGGCAGCGCCCTGCTC | 55% |
| 643 | | F-probe reverse complement | CAGAGAGGGTGGTTGGCCAGAATCACACTCCTGCTCCA AAGGTCTGAGCCTCGAGGGGTT | |
| 644 | | R-probe reverse complement | GAGCAGGGCGCTGCCCTTGGGCAGCACTTGGGTCTAAC AGGACTAGCACACATATTTATG | |
| 645 | PTEN_r5, Assay 23 | F qPCR primer | GGAAAGGGACGAACTGGTGTAATG | |
| 646 | | R qPCR primer | AAATCTAGGGCCTCTTGTGCCTTT | |
| 647 | | qPCR Amplicon | GGAAAGGGACGAACTGGTGTAATGATATGTGCATATTT ATTACATCGGGGCAAATTTTTAAAGGCACAAGAGGCCC TAGATTT | |
| 648 | | F-probe | TACTTGTTAATTAAAAATTCAAGAGTTTTTTTTTCTTA TTCTGAGGTTATCTTTTTACCA | 22% |
| 649 | | R-probe | CCAAAATCTGTTTTCCAATAAATTCTCAGATCCAGGAA GAGGAAAGGAAAAACATCAAAA | 33% |
| 650 | | F-probe reverse complement | TGGTAAAAAGATAACCTCAGAATAAGAAAAAAAACTC TTGAATTTTTAATTAACAAGTA | |

TABLE 32-continued

Sequences used to perform Example 19

| SEQ ID NO: | Target | Name | Sequence | % GC |
|---|---|---|---|---|
| 651 | | R-probe reverse complement | TTTTGATGTTTTTCCTTTCCTCTTCCTGGATCTGAGAA TTTATTGGAAAACAGATTTTGG | |
| 652 | EP300_r18, Assay 24 | F qPCR primer | AGCCCCATGGATCTTTCTACCATT | |
| 653 | | R qPCR primer | ATACTGCCAGGGCTCCTGATACTG | |
| 654 | | qPCR Amplicon | AGCCCCATGGATCTTTCTACCATTAAGAGGAAGTTAGA CACTGGACAGTATCAGGAGCCCTGGCAGTAT | |
| 655 | | F-probe | ATACTCCATCTCCCGTAAAAATAGTGAGACTTGAGTAA TGTTTGATGTCACTTGTCTTTC | 37% |
| 656 | | R-probe | CAGTCACCACTATATTATTCTAGGTATCCCAGAAAAGT TAAAGTCAAATCTGAAACACAT | 33% |
| 657 | | F-probe reverse complement | GAAAGACAAGTGACATCAAACATTACTCAAGTCTCACT ATTTTTACGGGAGATGGAGTAT | |
| 658 | | R-probe reverse complement | ATGTGTTTCAGATTTGACTTTAACTTTTCTGGGATACC TAGAATAATATAGTGGTGACTG | |
| 659 | Additional oligos | Tail sequence for capture probes | GTGAAAACCAGGATCAACTCCCGTGCCAGTCACATCTC GT | |
| 660 | | Common partner oligo sequence | /5BioTEG/ACGAGATGTGACTGGCACGGGAGTTGATC CTGGTTTTCAC | |
| 661 | | Forward amplification primer AF | AATGATACGGCGACCACCGAGATCTACACGTCATGCAG GACCAGAGAATTCGAATACA | |
| 662 | | Reverse amplification primer CR | CAAGCAGAAGACGGCATACGAGATGTGACTGGCACGGG AGTTGATCCTGGTTTTCAC | |

Example 20: Library-Free Targeted Genomic Analysis

Summary: This example demonstrates a library-free genomic analysis. The goals were to identify the most useful parameters for implementing such methods in a reliable, reproducible, low-cost, and high-throughput format. In particular, it was discovered that T4 polymerase can copy many and diverse genomic sequences provided it is supplemented with T4 gene 32 protein in the presence of PEG8000—a molecular crowding agent. In addition, it was found that suppression PCR just upstream of sequence library construction is a powerful method to enrich for long insert sequencing clones.

Figure 34:
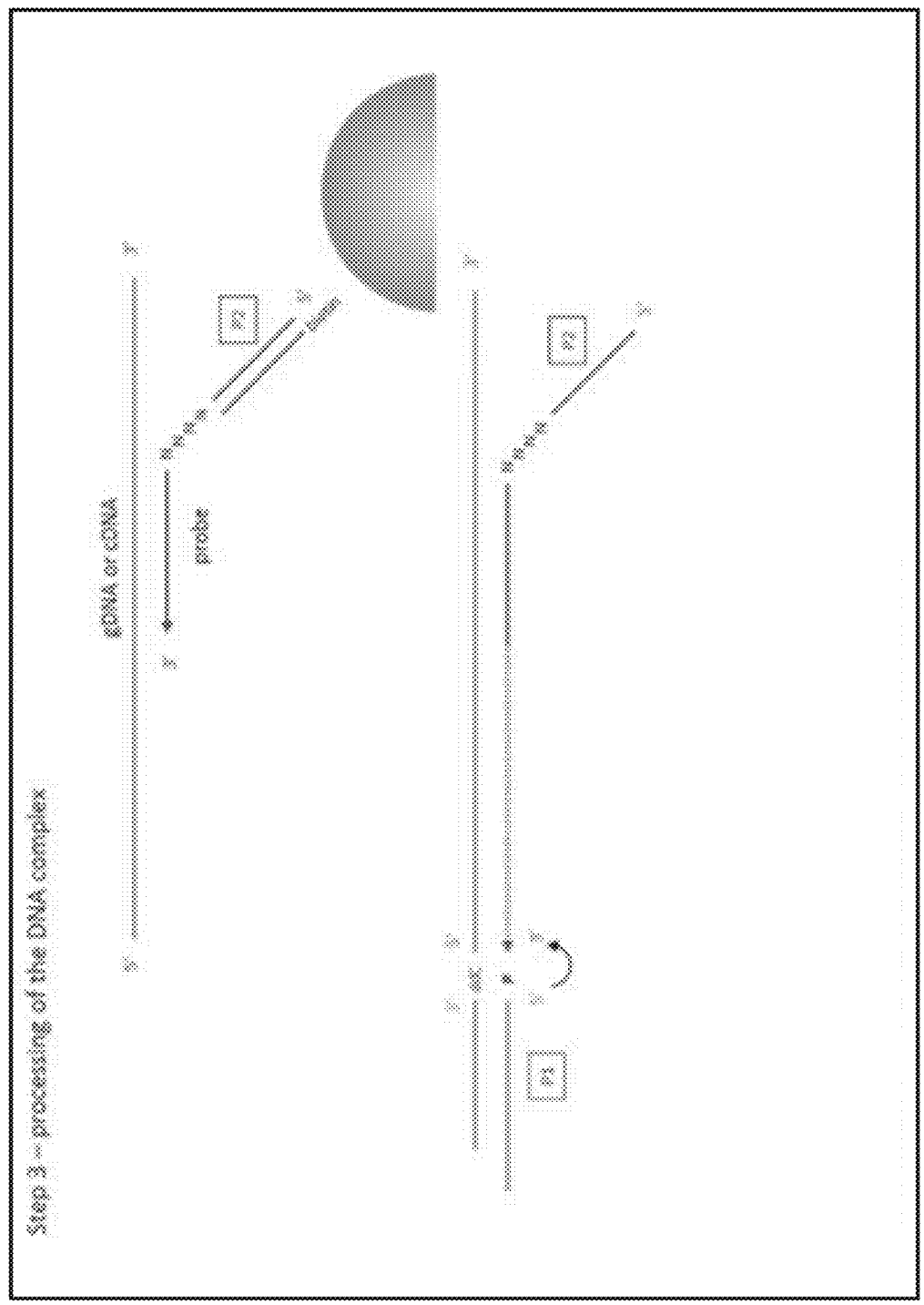
FIG. 34 shows Step 3 of a library free method for generating tagged genomic DNAs and related capture, processing, and analysis methods
Figure 35:
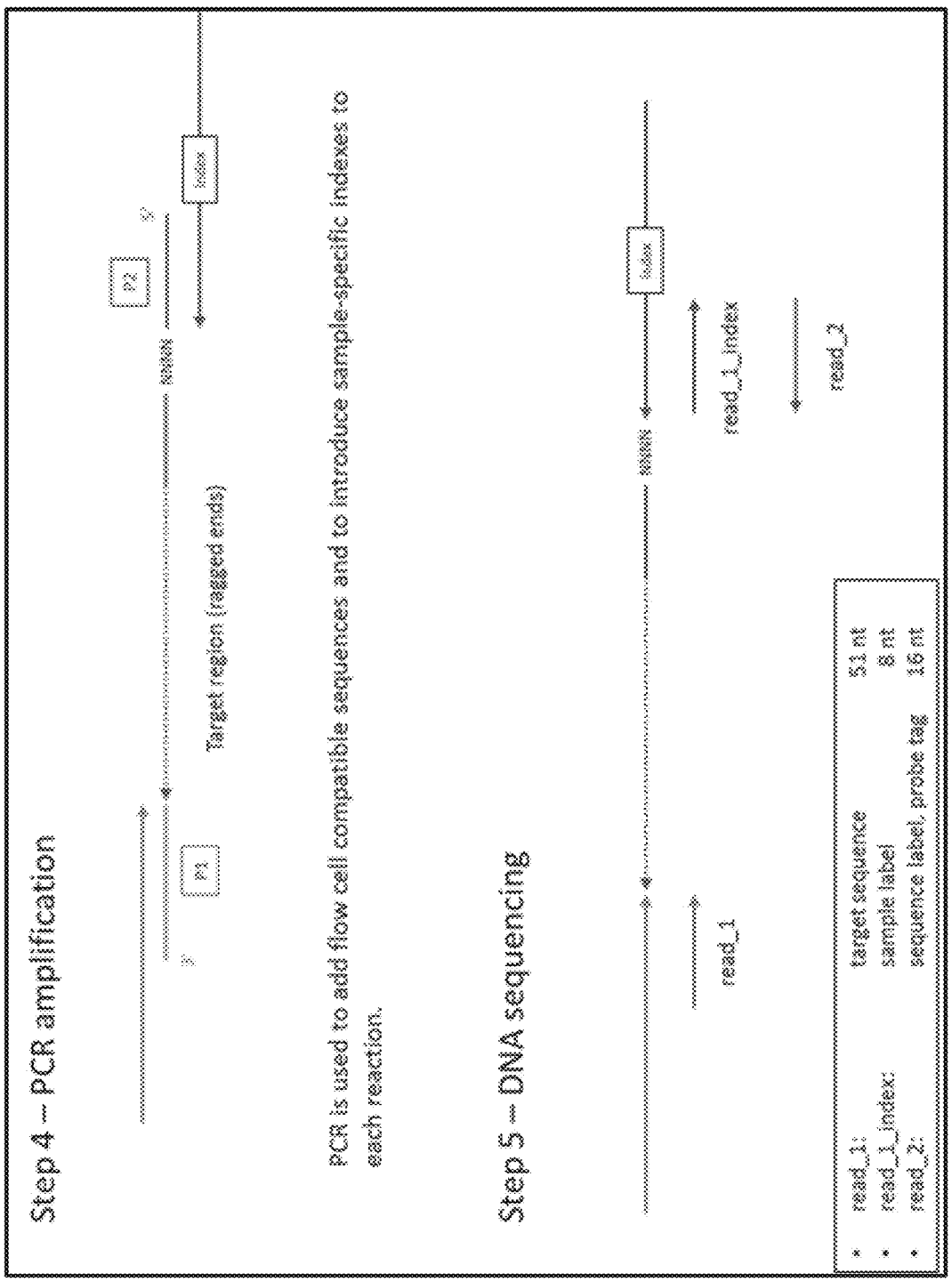
FIG. 35 shows Steps 4 and 5 a library free method for generating tagged genomic DNAs and related capture, processing, and analysis methods.

Background: The molecular concepts behind library-free methods include:
(1) fragmenting gDNA to ~400 bp or performing 1$^{st}$ strand cDNA synthesis with random 15-mers in the presence of ddNTPs (FIG. 33);
(2) melting the gDNA or cDNA with labeled capture probes and purify the end-repaired gDNA/cDNA. For gDNA, the genomic sequence is repaired with a sequence tag that comprises a random hexamer sequence contained within the tail portion (FIG. 33);
(3) processing the DNA complex in a single reaction at 20° C. The Buffer used is NEB CutSmart (NEB #4 and BSA), ATP, dNTPs, and PEG8000. The complex is processed with T4 DNA polymerase, T4 gene 32 protein (SB), and T4 DNA ligase. The adapter ligation strand is 5' phosphorylated and the partner strand comprises a 3' ddC. The opposite end of the adapter is staggered and can be blocked. A blunt configuration makes no self-dimer, is extremely efficiency and attaches the P1 containing ligation strand to the P2 containing target. (FIG. 34);
(4) PCR amplification to add flow cell compatible sequences and to introduce sample-specific index sequence to each reaction (FIG. 35); and
(5) DNA sequencing (FIG. 35).

Figure 36:
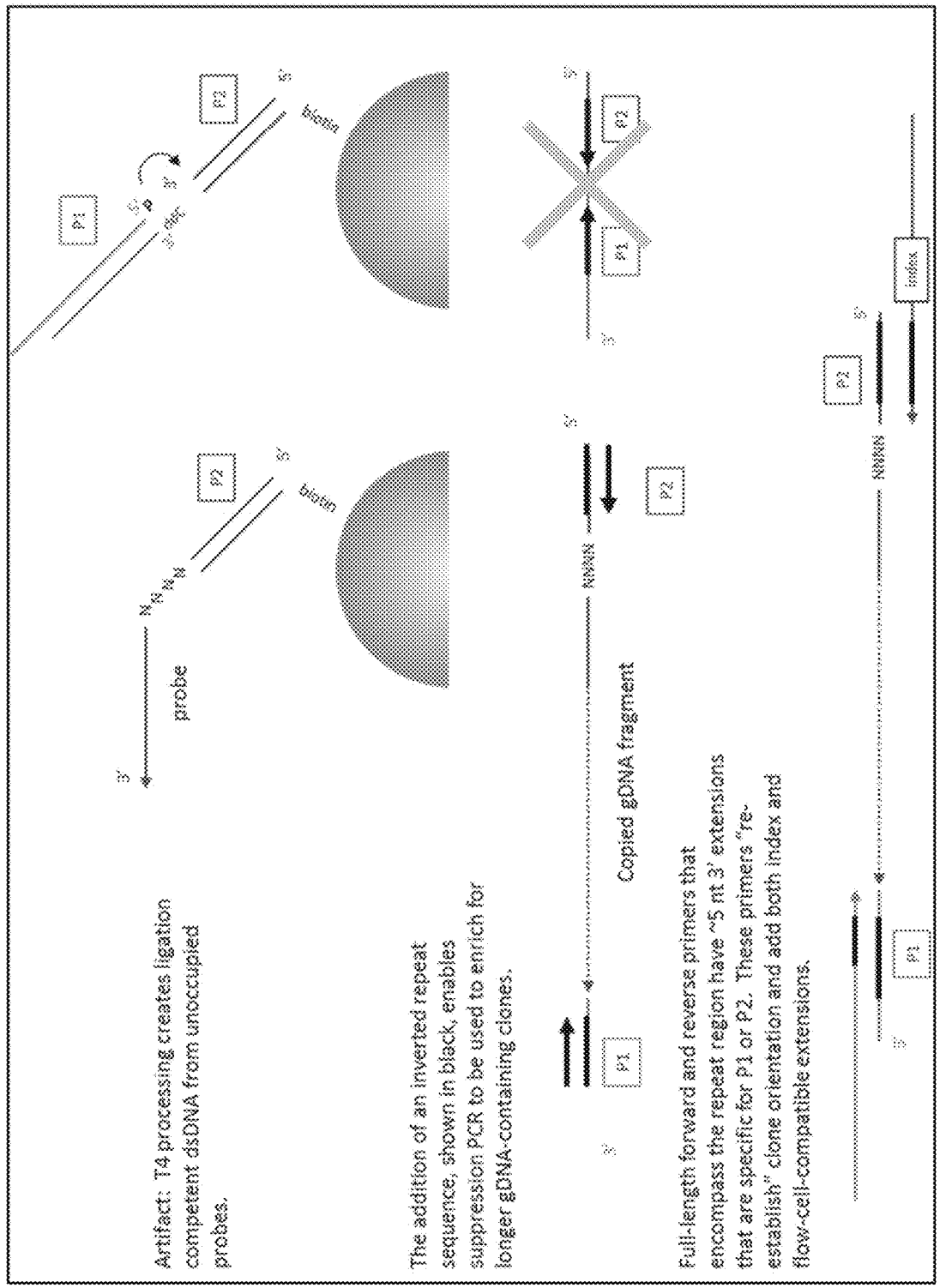
FIG. 36 shows a suppressive PCR strategy for avoiding primer-dimer artifacts in library free methods for generating tagged genomic DNAs.

One potential artifact that may occur in particular embodiments is associated with the abundance of unoccupied probes. The 3' to 5' exonuclease activity of T4 DNA polymerase is capable of generating a blunt end on these molecules, which then becomes a substrate for ligation to the P1 adaptor sequence (FIG. 36). These short "oligo-dimer" products will, without intervention, overwhelm the subsequent PCR reaction. To circumvent the potential artifact, a suppressive PCR design was used, in which a 25 nt segment of P2 was included in the P1 adaptor. Following suppression PCR amplification with this segment, forward and reverse primers with P1 or P2-specific extensions are used to add the index sequence and the flow cell-compatible extensions.

The oligonucleotides that enable post-processing suppressive PCR, full-length amplification and sequencing are shown in the Table 33 below.

TABLE 33

| SEQ ID NO: | Name | Sequence | Description |
|---|---|---|---|
| 663 | LF_part strand | AGTTGATCCTGGTTATACA/3ddC/ | Adaptor partner strand |
| 664 | LF_lig strand | /5Phos/GTGTATAACCAGGATCAACTCC CGTGCCAGT | Adaptor ligation strand |
| 665 | LF_I1P | GTGAAAACCAGGATCAACTCCCGTGCCAG TCAC | Index 1 sequencing primer |
| 666 | LF_FSP | GTCATGCAGGAGTTGATCCTGGTTATACA C | Library-free Forward sequencing primer |
| 667 | LF_Single primer sequence | ACTGGCACGGGAGTTGATCCTGGTT | Post-processing amplification primer |
| 668 | LF_FLFP | AATGATACGGCGACCACCGAGATCTACAC GTCATGCAGGAGTTGATCCTGGTTATACA C | Library-free forward amplification primer |
| 669 | LF_FLRP_N701 | CAAGCAGAAGACGGCATACGAGATTCGCC TTAGTGACTGGCACGGGAGTTGATCCTGG TTTTCAC | Index N701 reverse primer |
| 670 | LF_FLRP_N702 | CAAGCAGAAGACGGCATACGAGATCTAGT ACGGTGACTGGCACGGGAGTTGATCCTGG TTTTCAC | Index N702 reverse primer |
| 671 | LF_FLRP_N703 | CAAGCAGAAGACGGCATACGAGATTTCTG CCTGTGACTGGCACGGGAGTTGATCCTGG TTTTCAC | Index N703 reverse primer |
| 672 | LF_FLRP_N704 | CAAGCAGAAGACGGCATACGAGATGCTCA GGAGTGACTGGCACGGGAGTTGATCCTGG TTTTCAC | Index N704 reverse primer |

Materials: Genomic DNA samples were collected from 4 subjects and purified using the Oragene saliva collection kit. The samples that were sequenced in this study were:

Genomic DNA samples and Illumina Indexes used in this study

| Coriel ID # | Sample description | Illumina Index ID |
|---|---|---|
| NA19240 | Yoruba female | Index N701 reverse primer |
| GM03623 | Aneuploid XXX and chr18 trisomy | Index N702 reverse primer |
| GM11226 | XXXX | Index N703 reverse primer |
| GM18917 | Yoruban/Nigerian-harbors deletion 1, 2, 4, 9 | Index N704 reverse primer |

The probes used in these experiments are provided in Table 34 below. Hexamer tags are required to establish independent capture events with the same sequencing start site from sibling clones that arise during post-capture amplification.

TABLE 34

| SEQ ID NO: | Name | Sequence |
|---|---|---|
| 673 | CYP2D6_F | ATGTGACTGGCACGGGAGTTGATCCTGGTTTTCACNNNNNNAAGC ACCTAGCCCCATTCCTGCTGAGCAGGAGGTGGCAGGTACCCCAGA CTGGGAGGTAA |
| 674 | CYP2D6_R | ATGTGACTGGCACGGGAGTTGATCCTGGTTTTCACNNNNNNAGTC GGTGGGCCAGGATGAGGCCCAGTCTGTTCACACATGGCTGCTGC CTCTCAGCTCT |
| 675 | AMY1_F | ATGTGACTGGCACGGGAGTTGATCCTGGTTTTCACNNNNNNACCT GAGTAGCATCATTGTAGTTCTCGATATCTCCACTTCCAGTTTTAC ATTTACCATCA |
| 676 | chrX_15_F | ATGTGACTGGCACGGGAGTTGATCCTGGTTTTCACNNNNNNCCTG GCCCTCAGCCAGTACAGAAAGTCATTTGTCAAGGCCTTCAGTTGG CAGACGTGCTC |

TABLE 34-continued

| SEQ ID NO: | Name | Sequence |
|---|---|---|
| 677 | chrX_15_R | ATGTGACTGGCACGGGAGTTGATCCTGGTTTTCACNNNNNNAGAA TTCATTGCCAGCTATAAATCTGTGGAAACGCTGCCACACAATCTT AGCACACAAGA |
| 678 | chrX_477_F | ATGTGACTGGCACGGGAGTTGATCCTGGTTTTCACNNNNNNGACT TCAAAGAAATTACAAGTTGACATCTTGGACTCTACCCCTCGTACT TTATCTCCTAT |
| 679 | chrX_477_R | ATGTGACTGGCACGGGAGTTGATCCTGGTTTTCACNNNNNNTCTC TTTGGGGTCAAGAAAGAATCCCTAGTGGATTTGGGATTCTAGAGG AGGTGTTATAA |
| 680 | chrX_478_F | ATGTGACTGGCACGGGAGTTGATCCTGGTTTTCACNNNNNNTGCG ATACCATGCTGAAGATGAGCTAACCCAACCAGCCAAGCAGGCAGG GCTGCGAAGGA |
| 681 | chrX_478_R | ATGTGACTGGCACGGGAGTTGATCCTGGTTTTCACNNNNNNGGGG TAGGTGGAAAACCCAAGTAATGTGATTTTGTAACATCCACTGCTG CATTTGTTTGC |
| 682 | chrX_69_F | ATGTGACTGGCACGGGAGTTGATCCTGGTTTTCACNNNNNNTTAC TTCCCTCCAGTTTTGTTGCTTGCAAAACAACAGAATCTTCTCTCC ATGAAATCATG |
| 683 | chrX_69_R | ATGTGACTGGCACGGGAGTTGATCCTGGTTTTCACNNNNNNCAGG GGTATCTATTATCCCCATTTTCTCACAAAGGAAACCAAGATAAAA GGTTTAAATGG |
| 684 | PLP1_ex1_F | ATGTGACTGGCACGGGAGTTGATCCTGGTTTTCACNNNNNNGAAA TTCTCTTGTGAATTCCTGTGTCCTCTTGAATCTTCAATGCTAAAG TTTTTGAAACT |
| 685 | PLP1_ex2_F | ATGTGACTGGCACGGGAGTTGATCCTGGTTTTCACNNNNNNGGGT TTGAGTGGCATGAGCTACCTACTGGATGTGCCTGACTGTTTCCCC TTCTTCTTCCC |
| 686 | PLP1_ex2_R | ATGTGACTGGCACGGGAGTTGATCCTGGTTTTCACNNNNNNCTAT CTCCAGGATGGAGAGAGGGAAAAAAAAGATGGGTCTGTGTGGGAG GGCAGGTACTT |
| 687 | PLP1_ex3_F | ATGTGACTGGCACGGGAGTTGATCCTGGTTTTCACNNNNNNGAAA GAAGCCAGGTCTTCAATTAATAAGATTCCCTGGTCTCGTTTGTCT ACCTGTTAATG |
| 688 | PLP1_ex3_M | ATGTGACTGGCACGGGAGTTGATCCTGGTTTTCACNNNNNNCAGA CTCGCGCCCAATTTTCCCCCACCCCTTGTTATTGCCACAAAATCC TGAGGATGATC |
| 689 | PLP1_ex3_R | ATGTGACTGGCACGGGAGTTGATCCTGGTTTTCACNNNNNNTCTT TCTTCTTCCTTTATGGGGCCCTCCTGCTGGCTGAGGGCTTCTACA CCACCGGCGCA |
| 690 | PLP1_ex4_F | ATGTGACTGGCACGGGAGTTGATCCTGGTTTTCACNNNNNNGTTT GTGTTTCTACATCTGCAGGCTGATGCTGATTTCTAACCACCCCAT GTCAATCATTT |
| 691 | PLP1_ex4_R | ATGTGACTGGCACGGGAGTTGATCCTGGTTTTCACNNNNNNAACC AAATATATAGTGCTTCCATAGTGGGTAGGAGAGCCAAAGCACCCG TACCCTAACTC |
| 692 | PLP1_ex5_F | ATGTGACTGGCACGGGAGTTGATCCTGGTTTTCACNNNNNNAGTC TCCATGTGGCCCCGTAACTCCATAAAGCTTACCCTGCTTGCTTTT TGTGTCTTACT |
| 693 | PLP1_ex5_R | ATGTGACTGGCACGGGAGTTGATCCTGGTTTTCACNNNNNNCCAT GGGTGTAATTTGTATGGTATTAGCTACTCCCTTGTAAAATAACCC AAATAACCCAC |
| 694 | PLP1_ex6_F | ATGTGACTGGCACGGGAGTTGATCCTGGTTTTCACNNNNNNTTTA CAGTGGAGCATATTACTGCTGTTGCAAGAAACAGTTCTTCCTCTT TCATTTTCCTG |
| 695 | PLP1_ex6_R | ATGTGACTGGCACGGGAGTTGATCCTGGTTTTCACNNNNNNATAG CTGTACCCACACTATCTCAGGCCTATTTACTTGCCAAGATCATTC AAAGTCAACTC |

TABLE 34-continued

| SEQ ID NO: | Name | Sequence |
|---|---|---|
| 696 | PLP1_ex7_F | ATGTGACTGGCACGGGAGTTGATCCTGGTTTTCACNNNNNNNGATT TGAGGAGGGAGTGCTTTCTTTTCTACTCTCATTCACATTCTCTCT TCTGTTCCCTA |
| 697 | PLP1_ex7_R | ATGTGACTGGCACGGGAGTTGATCCTGGTTTTCACNNNNNNNCAGC ATTGTAGGCTGTGTGGTTAGAGCCTCGCTATTAGAGAAAGGGGGA TTTCTACGGGG |
| 698 | KRAS_ex1_F | ATGTGACTGGCACGGGAGTTGATCCTGGTTTTCACNNNNNNNTGTT ACCTTTAAAAGACATCTGCTTTCTGCCAAAATTAATGTGCTGAAC TTAAACTTACC |
| 699 | KRAS_ex1_R | ATGTGACTGGCACGGGAGTTGATCCTGGTTTTCACNNNNNNNTTCC CAGTAAATTACTCTTACCAATGCAACAGACTTTAAAGAAGTTGTG TTTTACAATGC |
| 700 | KRAS_ex2_F | ATGTGACTGGCACGGGAGTTGATCCTGGTTTTCACNNNNNNNTAAA TGACATAACAGTTATGATTTTGCAGAAAACAGATCTGTATTTATT TCAGTGTTACT |
| 701 | KRAS_ex2_R | ATGTGACTGGCACGGGAGTTGATCCTGGTTTTCACNNNNNNNGACA GGTTTTGAAAGATATTTGTGTTACTAATGACTGTGCTATAACTTT TTTTTCTTTCC |
| 702 | KRAS_ex3_F | ATGTGACTGGCACGGGAGTTGATCCTGGTTTTCACNNNNNNNACTC AAAAAATAAAAACTATAATTACTCCTTAATGTCAGCTTATTATAT TCAATTTAAAC |
| 703 | KRAS_ex3_R | ATGTGACTGGCACGGGAGTTGATCCTGGTTTTCACNNNNNNNAACA CCTTTTTTGAAGTAAAAGGTGCACTGTAATAATCCAGACTGTGTT TCTCCCTTCTC |
| 704 | KRAS_ex4_F | ATGTGACTGGCACGGGAGTTGATCCTGGTTTTCACNNNNNNNGAAA CCTTTATCTGTATCAAAGAATGGTCCTGCACCAGTAATATGCATA TTAAAACAAGA |
| 705 | KRAS_ex4_R | ATGTGACTGGCACGGGAGTTGATCCTGGTTTTCACNNNNNNNGTGT ATTAACCTTATGTGTGACATGTTCTAATATAGTCACATTTTCATT ATTTTTATTAT |
| 706 | MYC_r1_F1 | ATGTGACTGGCACGGGAGTTGATCCTGGTTTTCACNNNNNNNCCCC AGCCAGCGGTCCGCAACCCTTGCCGCATCCACGAAACTTTGCCCA TAGCAGCGGGC |
| 707 | MYC_r1_R1 | ATGTGACTGGCACGGGAGTTGATCCTGGTTTTCACNNNNNNNcgac tcatctcagcattaaagtgataaaaaaataaattaaaaggcaagt ggacttcggtg |
| 708 | MYC_r2_F1 | ATGTGACTGGCACGGGAGTTGATCCTGGTTTTCACNNNNNNNctgt ggcgcgcactgcgcgctgcgccaggttttccgcaccaagacccctt taactcaagac |
| 709 | MYC_r2_F2 | ATGTGACTGGCACGGGAGTTGATCCTGGTTTTCACNNNNNNNTTCT ACTGCGACGAGGAGGAGAACTTCTACCAGCAGCAGCAGCAGAGCG AGCTGCAGCCC |
| 710 | MYC_r2_F3 | ATGTGACTGGCACGGGAGTTGATCCTGGTTTTCACNNNNNNNACCG AGCTGCTGGGAGGAGACATGGTGAACCAGAGTTTCATCTGCGACC CGGACGACGAG |
| 711 | MYC_r2_F4 | ATGTGACTGGCACGGGAGTTGATCCTGGTTTTCACNNNNNNNGCCG CCGCCTCAGAGTGCATCGACCCCTCGGTGGTCTTCCCCTACCCTC TCAACGACAGC |
| 712 | MYC_r2_R1 | ATGTGACTGGCACGGGAGTTGATCCTGGTTTTCACNNNNNNNGGCG GCTAGGGGACAGGGGGGGGGTGGGCAGCAGCTCGAATTTCTTCCA GATATCCTCGC |
| 713 | MYC_r2_R2 | ATGTGACTGGCACGGGAGTTGATCCTGGTTTTCACNNNNNNNAGAC GAGCTTGGCGGCGGCCGAGAAGCCGCTCCACATACAGTCCTGGAT GATGATGTTTT |
| 714 | MYC_r2_R3 | ATGTGACTGGCACGGGAGTTGATCCTGGTTTTCACNNNNNNNAGGA GAGCAGAGAATCCGAGGACGGAGAGAAGGCGCTGGAGTCTTGCGA GGCGCAGGACT |

TABLE 34-continued

| SEQ ID NO: | Name | Sequence |
|---|---|---|
| 715 | MYC_r2_R4 | ATGTGACTGGCACGGGAGTTGATCCTGGTTTTCACNNNNNNNtaag agtggcccgttaaataagctgccaatgaaaatgggaaaggtatcc agccgcccact |
| 716 | MYC_r3_F1 | ATGTGACTGGCACGGGAGTTGATCCTGGTTTTCACNNNNNNNttgt atttgtacagcattaatctggtaattgattattttaatgtaacct tgctaaaggag |
| 717 | MYC_r3_F2 | ATGTGACTGGCACGGGAGTTGATCCTGGTTTTCACNNNNNNGAGG CCACAGCAAACCTCCTCACAGCCCACTGGTCCTCAAGAGGTGCCA CGTCTCCACAC |
| 718 | MYC_r3_F3 | ATGTGACTGGCACGGGAGTTGATCCTGGTTTTCACNNNNNNAGAG GAGGAACGAGCTAAAACGGAGCTTTTTTGCCCTGCGTGACCAGAT CCCGGAGTTGG |
| 719 | MYC_r3_R1 | ATGTGACTGGCACGGGAGTTGATCCTGGTTTTCACNNNNNNNTCCA ACTTGACCCTCTTGGCAGCAGGATAGTCCTTCCGAGTGGAGGGAG GCGCTGCGTAG |
| 720 | MYC_r3_R2 | ATGTGACTGGCACGGGAGTTGATCCTGGTTTTCACNNNNNNGCTT GGACGGACAGGATGTATGCTGTGGCTTTTTTAAGGATAACTACCT TGGGGGCCTTT |
| 721 | MYC_r3_R3 | ATGTGACTGGCACGGGAGTTGATCCTGGTTTTCACNNNNNNGCAT TTGATCATGCATTTGAAACAAGTTCATAGGTGATTGCTCAGGACA TTTCTGTTAGA |

Figure 37:
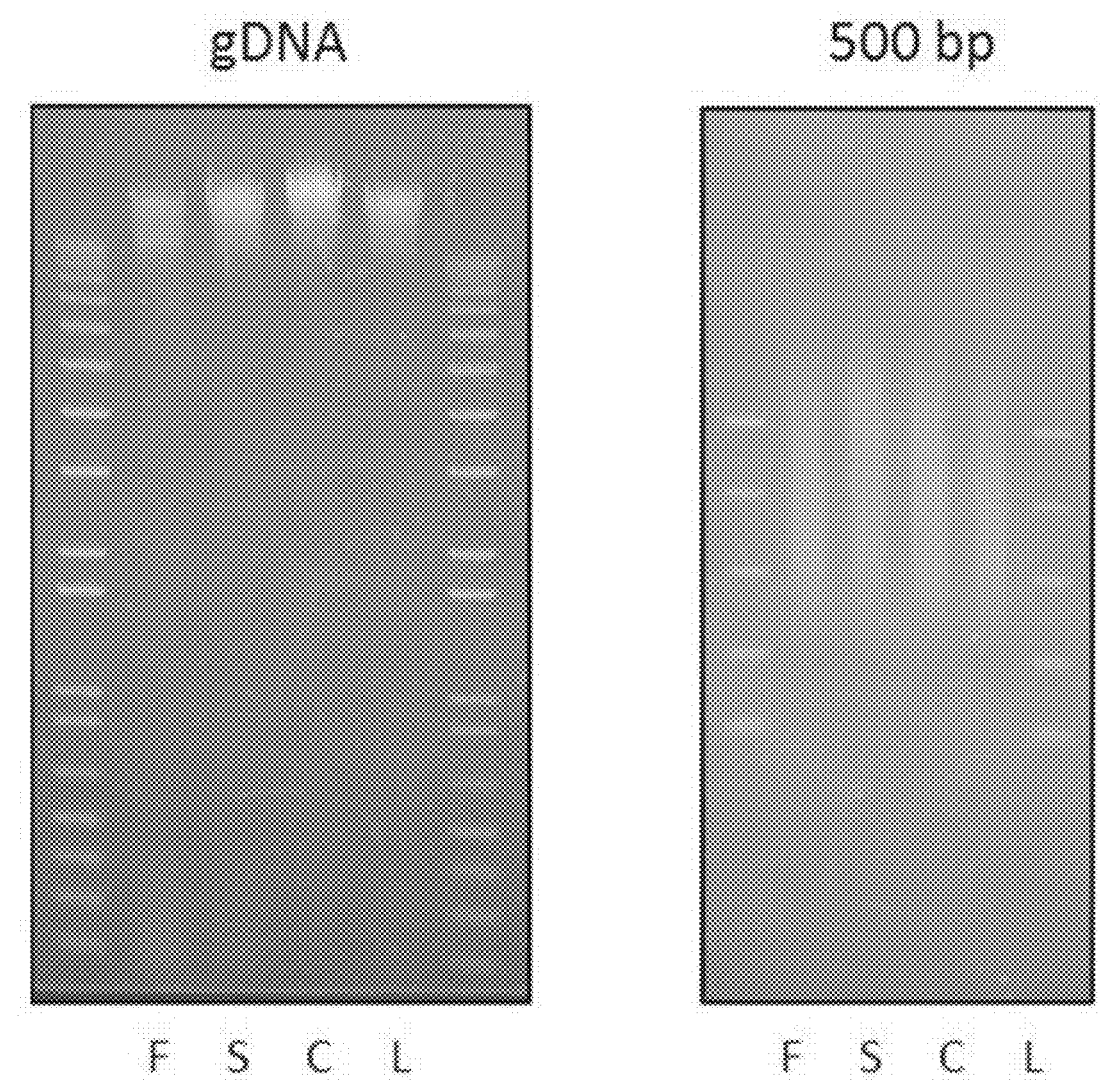
FIG. 37 shows gel electrophoresis results of raw and sonicated gDNAs used in library free methods for generating tagged genomic DNAs.

Methods, Results and Discussion: PART I. Four gDNAs (F, S, C and L) were diluted to 20 ng/μL in 150 μL final volume. The samples were sonicated to 500 bp and 125 μL was purified with 125 μL of beads. The starting material and purified, fragmented gDNA are shown in FIG. 37. The concentrations of gDNA were: (1) F—137 ng/μL; (2) S—129 ng/μL; (3) C—153 ng/μL; and (4) L—124 ng/μL.

For capture, 10 μL of gDNA sample was heated to 98° C. for 2 min (to achieve strand dissociation) and cooled on ice. 5 μL of 4× bind and 5 μL of the 49 probe pool (SEQ ID NOs: 150-198) (1 nM in each probe combined with 50 nM universal oligo 61, were added and the mix was annealed (98° C. 2 min followed by 4 min incubations at successive 1° C. lower temperatures down to 69° C.). The complexes were bound to 2 μL of MyOne strep beads that were suspended in 180 μL TEzero (total volume 200 μL) for 30 min, washed four times, 5 min each with 25% formamide wash, washed once with TEzero, and the supernatants were withdrawn from the bead complexes.

For processing and adaptor ligation, 100 μL of T4 mix was made that contained: 60 μL water; 10 μL NEB "Cut-Smart" buffer; 15 μL 50% PEG8000; 10 μL 10 mM ATP; 1 μL 1 mM dNTP blend; 1 μL T4 gene 32 protein (NEB); and 0.5 μL T4 DNA polymerase (NEB). 25 μL of mix was added to each of the four samples and incubated at 20° C. for 15 min followed by a 70° C. incubation for 10 min to heat inactivate the T4 polymerase. Following the inactivation step, 1.25 μL of adaptor (10 μM) and 1.25 μL of HC T4 DNA ligase were added. This mixture was further incubated at 22° C. for 30 min and 65° C. for 10 min.

One attractive feature of the library free methods is that processed complexes are still attached to beads. Beads were pulled from the ligation buffer and washed once with 200 μL of TEzero. The complexes were then resuspended in 2 μL. For amplification, single primer amplification in a 20 μL volume was used to both amplify target fragments and to enrich for long genomic fragments over probe "stubs".

Following the amplification, a larger volume PCR reaction with full length primers were used to create a "sequence-ready" library.

Figure 38:
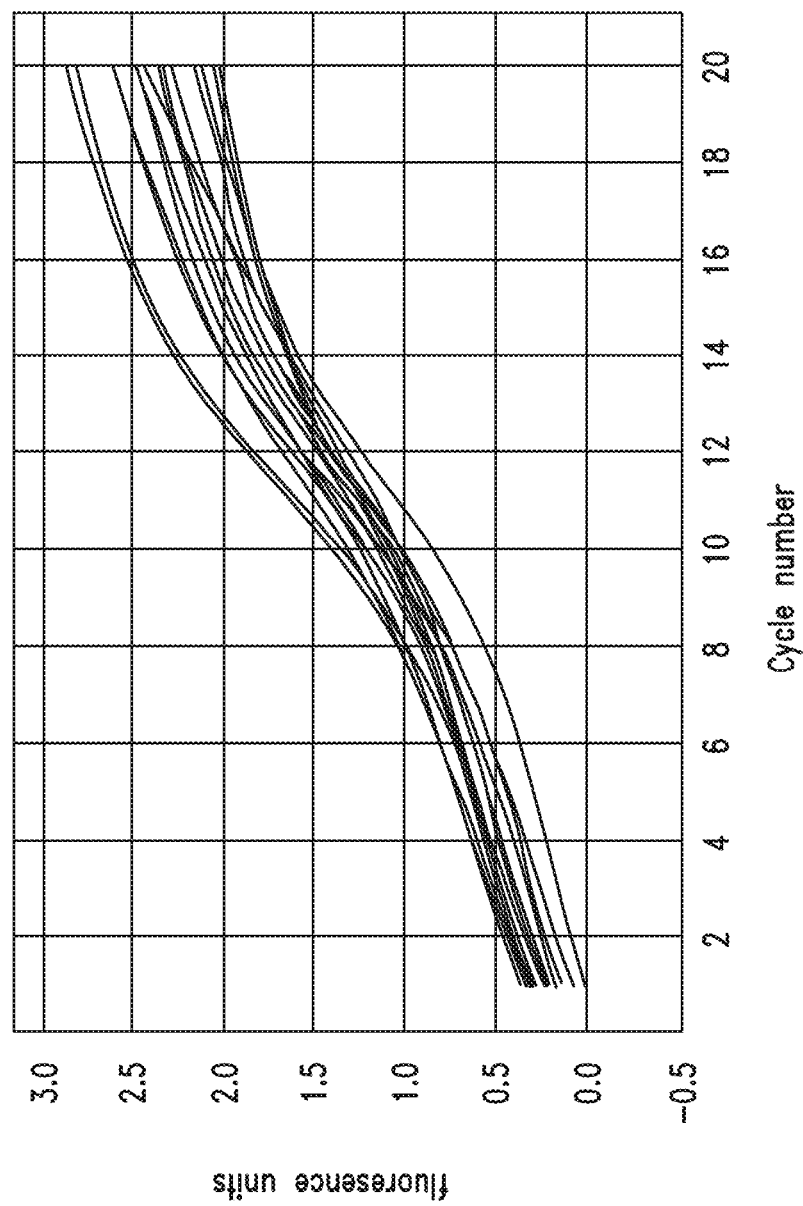
FIG. 38 shows a qPCR amplification plot of four gDNA samples prepared by the library free method.
Figure 39:
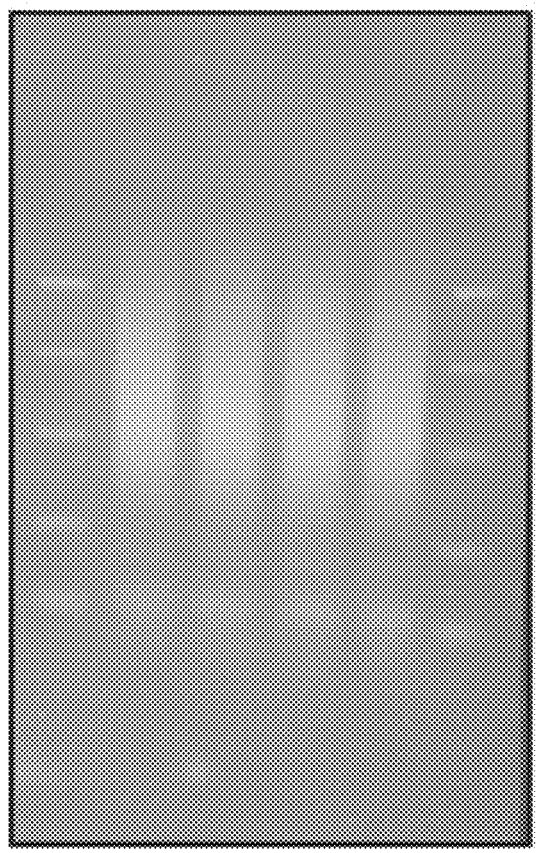
FIG. 39 shows the gel electrophoresis results from raw PCR products amplified from samples prepared by the library free methods.
Figure 40:
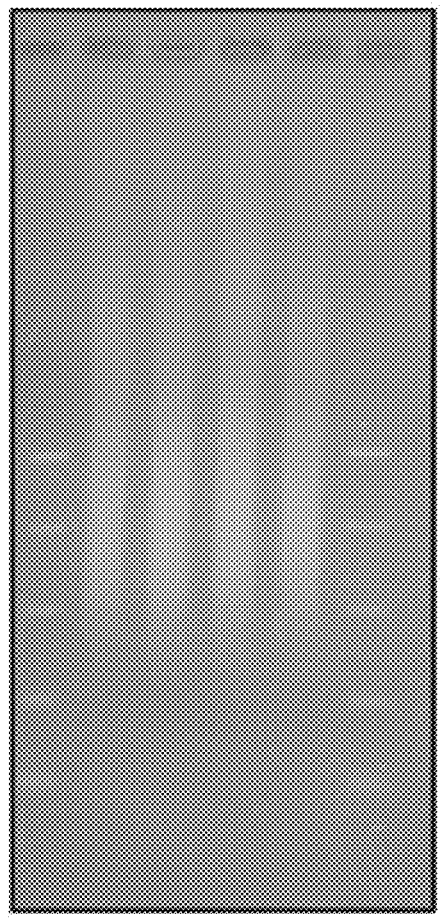
FIG. 40 shows the gel electrophoresis results from bead-cleaned PCR products amplified from samples prepared by the library free methods.

A Q5-based single primer PCR amplification buffer was made by combining 57 μL water, 20 μL 5× Q5 reaction buffer, 10 μL of single primer 117 (see Table 33), 2 μL of 10 mM dNTPs, and 1 μL of Q5 hot start polymerase. Eighteen μL was added to each tube followed by amplification for 20 cycles (98° C.-30 sec; 98° C.-10 sec, 69° C.-10 sec, 72° C.-10 sec for 20 cycles; 10° C. hold). Following the PCR, the beads were pulled out and the 20 μL of pre-amp supernatant was transferred to 280 μL of PCR mix that contained 163.5 water, 60 μL 5× Q5 buffer, 15 μL of forward primer 118 (10 uM), 15 uM of reverse primer 119 (10 uM), 6 μL of 10 mM dNTPs, 13.5 μL of EvaGreen+ROX dye blend (1.25 parts EG to 1 part ROX), and 3 μL of Q5 hot start polymerase (adding the dye to all reactions was unintended). Two 100 μL aliquots were amplified by conventional PCR (98° C.-10 sec, 69° C.-10 sec, 72° C.-10 sec) and quadruplicate ten μL aliquots were amplified under qPCR conditions. FIG. 38 shows the amplification plot that was observed for all four samples. The reaction seems to go through an inflection/plateau reminiscent of PCR and the conventional reactions were stopped at 20 cycles (now 40 total cycles of PCR). FIG. 39 shows a 2% agarose gel containing the products of these amplification reactions. FIG. 40 shows a 2% agarose gel containing the amplification products following bead purification.

The library-free samples were assayed to determine if gene specific targets were captured and selectively amplified using the well-validated qPCR capture assays described elsewhere herein. The target regions for Assays 1-16 are shown in Table 35.

TABLE 35

Target regions for assays 1-16.

| Assay | Sequence |
|---|---|
| Assay 1 | PLP1 exon 2 |
| Assay 2 | PLP1 exon 2 |
| Assay 3 | PLP1 exon 2 |
| Assay 4 | PLP1 upstream of exon 2 |
| Assay 5 | PLP1 downstream of exon 2 |
| Assay 6 | PLP1 200 bp downstream of exon 2 |
| Assay 7 | PLP1 exon 3 |
| Assay 8 | Chr 9, off target |
| Assay 9 | CYP2D6 |
| Assay 10 | Chr X: 154376051 |
| Assay 11 | Chr X: 154376051 |
| Assay 12 | Chr X: 6929264 |
| Assay 13 | KRAS Region 1 |
| Assay 14 | KRAS Region 2 |
| Assay 15 | Myc Region 2 |
| Assay 16 | Myc Region 2 |

For qPCR analysis, genomic DNA from sample F at 10 ng/μL (2 μL is added to 8 μL of PCR mix to give a final volume and concentration of 10 μL and 2 ng/μL, respectively) was used as control. Purified processed material from the F and S samples was diluted to 0.01 ng/μL=10 pg/μL and 2 μL was added to each 8 μL PCR reaction to give a final concentration of 2 pg/μL. The results are shown in Table 36.

TABLE 36 qPCR Results

Cqs

| | Assay 1 | Assay 2 | Assay 3 | Assay 4 | Assay 5 | Assay 6 | Assay 7 | Assay 8 |
|---|---|---|---|---|---|---|---|---|
| gDNA | 23 | 22 | 25 | 22 | 22 | 23 | 23 | 19 |
| F-lib | 13 | 13 | 13 | 13 | 13 | 20 | 12 | 35 |
| S-lib | 14 | 14 | 13 | 13 | 14 | 20 | 13 | N/A |

| | Assay 9 | Assay 10 | Assay 11 | Assay 12 | Assay 13 | Assay 14 | Assay 15 | Assay 16 |
|---|---|---|---|---|---|---|---|---|
| gDNA | 21 | 21 | 22 | 22 | 22 | 21 | 21 | 21 |
| F-lib | 11 | 13 | 13 | 16 | 18 | 17 | 14 | 13 |
| S-lib | 11 | 13 | 14 | 17 | 17 | 16 | 13 | 12 |

Abs

| | Assay 1 | Assay 2 | Assay 3 | Assay 4 | Assay 5 | Assay 6 | Assay 7 | Assay 8 |
|---|---|---|---|---|---|---|---|---|
| gDNA | 16 | 24 | 4 | 17 | 22 | 15 | 8 | 146 |
| F-lib | 12150 | 13296 | 8874 | 16739 | 13738 | 79 | 22495 | 0 |
| S-lib | 6142 | 7704 | 10410 | 10093 | 6425 | 132 | 14648 | |

| | Assay 9 | Assay 10 | Assay 11 | Assay 12 | Assay 13 | Assay 14 | Assay 15 | Assay 16 |
|---|---|---|---|---|---|---|---|---|
| gDNA | 60 | 39 | 18 | 30 | 17 | 43 | 49 | 37 |
| F-lib | 45447 | 11671 | 11034 | 1288 | 440 | 853 | 6373 | 16448 |
| S-lib | 68935 | 12477 | 7634 | 678 | 1077 | 1203 | 10171 | 19305 |

Adj

| | Assay 1 | Assay 2 | Assay 3 | Assay 4 | Assay 5 | Assay 6 | Assay 7 | Assay 8 |
|---|---|---|---|---|---|---|---|---|
| gDNA | 16 | 24 | 4 | 17 | 22 | 15 | 8 | 146 |
| F-lib | 12150333 | 13296288 | 8874203 | 16739230 | 13737864 | 79482 | 22495321 | 2 |
| S-lib | 6141637 | 7703565 | 10410406 | 10093396 | 6424647 | 131876 | 14648060 | 0 |

| | Assay 9 | Assay 10 | Assay 11 | Assay 12 | Assay 13 | Assay 14 | Assay 15 | Assay 16 |
|---|---|---|---|---|---|---|---|---|
| gDNA | 60 | 39 | 18 | 30 | 17 | 43 | 49 | 37 |
| F-lib | 45447322 | 11670722 | 11034289 | 1288163 | 440236 | 852919 | 6373326 | 16447972 |
| S-lib | 68934509 | 12476684 | 7634492 | 677562 | 1077493 | 1203428 | 10170993 | 19304903 |

Adj

| | Assay 1 | Assay 2 | Assay 3 | Assay 4 | Assay 5 | Assay 6 | Assay 7 | Assay 8 |
|---|---|---|---|---|---|---|---|---|
| F-lib | 778820 | 562525 | 2393851 | 987542 | 627702 | 5247 | 2657954 | 0 |
| S-lib | 393671 | 325914 | 2808248 | 595466 | 293551 | 8706 | 1730754 | 0 |

| | Assay 9 | Assay 10 | Assay 11 | Assay 12 | Assay 13 | Assay 14 | Assay 15 | Assay 16 |
|---|---|---|---|---|---|---|---|---|
| F-lib | 757399 | 300823 | 627284 | 42799 | 25665 | 19716 | 130461 | 439562 |
| S-lib | 1148823 | 321597 | 434010 | 22512 | 62817 | 27819 | 208198 | 515912 |

The qPCR data indicated that the library-free technology is very effective at retrieving the targeted genomic regions and at leaving off-target regions behind (e.g., Assays 6, 8). The fold purifications, often >500,000-fold, were directly comparable to data from earlier experiments generated with libraries as disclosed elsewhere herein.

Methods, Results and Discussion: Part II—Leave-one-out analysis: The enzymatic requirements for complex processing were evaluated: the design of experiment is shown in FIG. 54.

Figure 41:
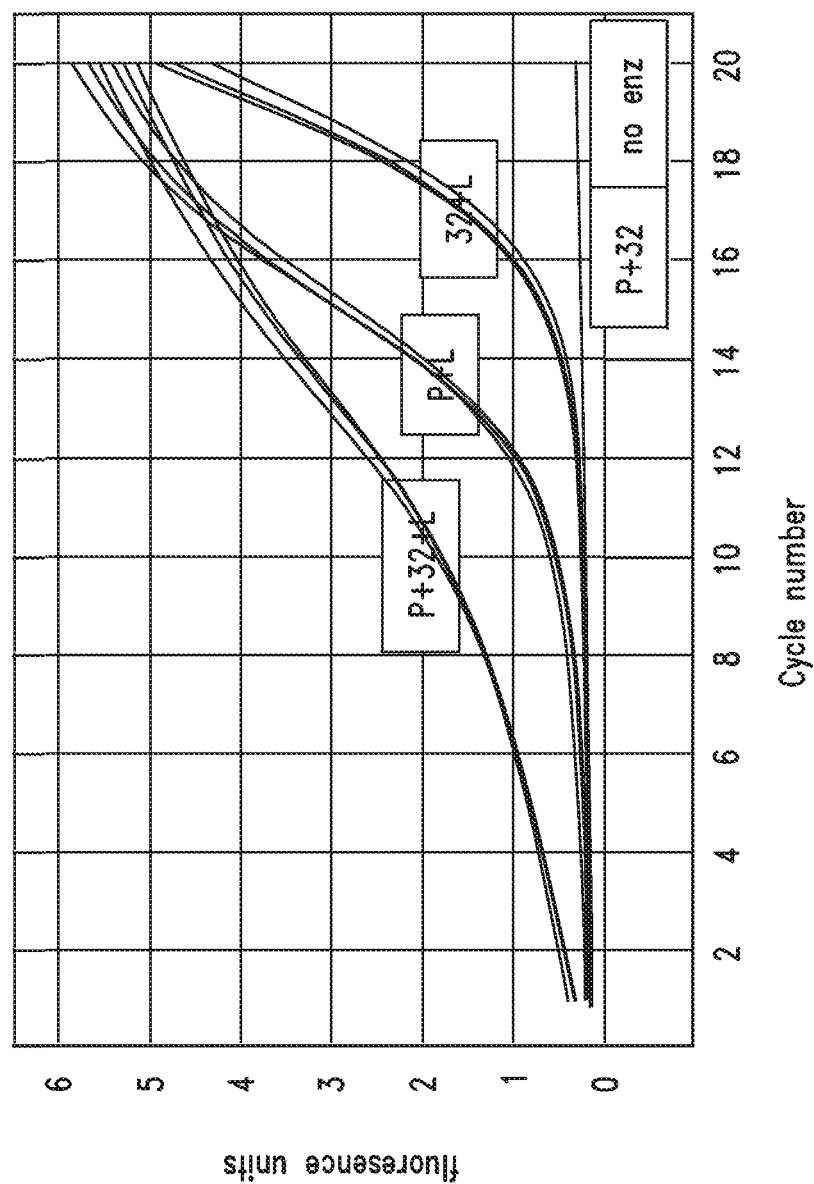
FIG. 41 shows a qPCR amplification plot of samples prepared by the library free methods using different combinations of enzymes: T4 DNA polymerase (P), T4 DNA ligase (L), and T4 gene 32 protein (32), or no enzyme control.

To make capture complexes for analysis, twelve identical reactions were created. Ten μL of 135 ng/μL sonicated gDNA was melted, annealed with a tagged, bound to streptavidin coated beads, washed and resuspended in TEzero as described supra. Five hundred μL of processing master mix was prepared by combining 270 μL water, 50 μL 10× CutSmart buffer, 50 μL of 10 mM ATP, 75 μL of 50% PEG8000, and 5 μL of 10 mM dNTPs. This buffer was divided into 10 90 μL aliquots (duplicate tests were performed) and enzyme was added in the amounts described above (per 90 μL of master mix was added 1 μL of T4 gene 32 protein, 0.5 μL of T4 polymerase, 5 μL of adaptor and/or 5 μL of HC T4 ligase). Following T4 fill-in and ligation as described supra, the complexes were washed free of processing mix in TEzero and resuspended in 2 μL TEzero. Complexes were resuspended in 20 μL final volume each of single primer amplification mix and amplified for 20 cycles as described supra. The beads were then pulled aside using a magnet and the 20 μL clarified amplification was diluted into 180 μL of full-length F+R (118+119) PCR amplification mix. Fifty μL was pulled aside for qPCR analysis and the remaining 150 μL was split in two and amplified by conventional PCR. The 50 μL qPCR samples were mixed with 2.5 μL of dye blend and 10 μL aliquots were monitored by fluorescence change. The traces of this experiment are shown in FIG. 41.

Figure 42:
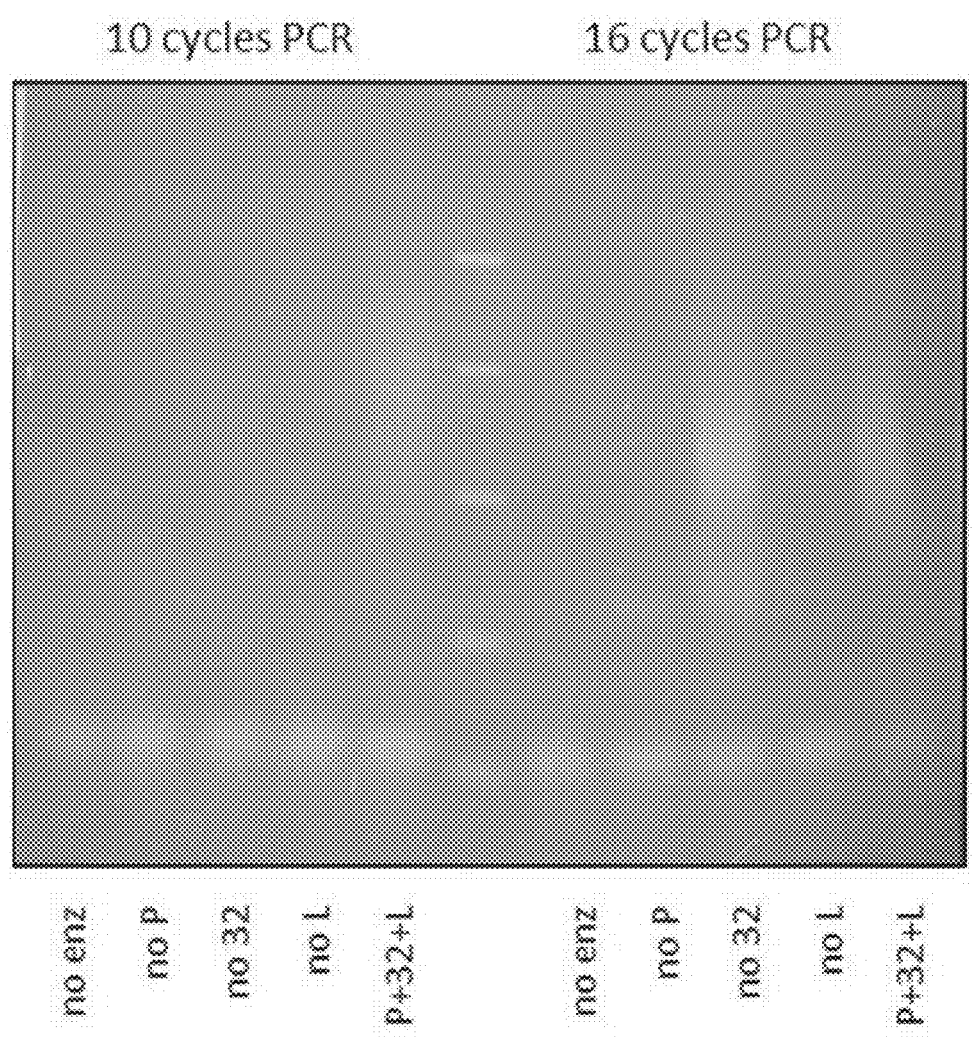
FIG. 42 shows the gel electrophoresis results of PCR amplified (10 cycles or 16 cycles) samples prepared by the library free methods using different combinations of enzymes: T4 DNA polymerase (P), T4 DNA ligase (L), and T4 gene 32 protein (32), or no enzyme control.

One of the two conventional PCR aliquots was pulled at 10 cycles and the other at 16 cycles of PCR. Aliquots of these raw PCR reactions (5 μL of each reaction) were analyzed on 2% agarose gels. The results are shown in FIG. 42. The surprising result is that all three enzymes are required for the efficient production of amplifiable library material. A more subtle observation is that the size distribution of all-three-enzyme-material at 10 cycles is significantly larger than the size distribution of P+L alone that appears at 16 cycles.

These data together with the qPCR from the initial investigation support the interpretation that T4 DNA polymerase in conjunction with T4 gene 32 protein in the presence of the molecular crowding agent PEG8000 (the latter contribution has not been evaluated) is capable of efficiently copying captured genomic material onto capture probes.

Figure 43:
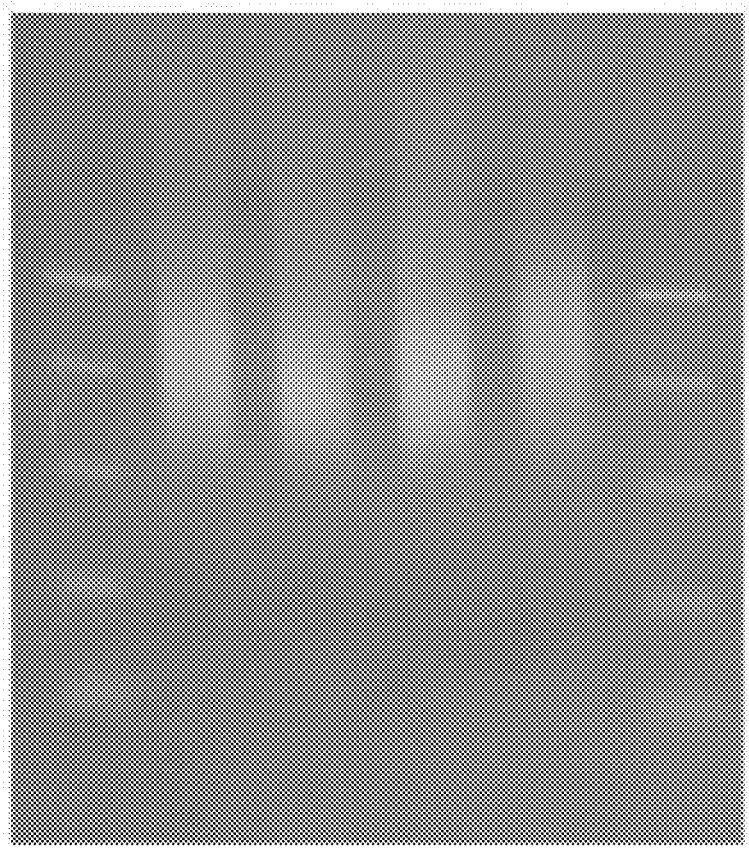
FIG. 43 shows the gel electrophoresis results of individual samples prepared by the library free methods prior to pooling.

Methods, Results and Discussion: Part III—Generation of a library-free sequencing library: The methods described above were used to produce a DNA sequencing library with the four Coriel samples shown in the "Materials" section of this report. Each one of the four samples was coded with an individual index code in the final PCR step. The final library constituents (shown separately prior to pooling) are shown in the gel image in FIG. 43. The "normal" library smear usually stretches from 175 bp upward. Here, the smallest fragments are >300 bp. Similarly, the largest fragments appear to be 750 bp or larger. Larger fragments do not give rise to optimal libraries. These samples were all twice purified on 80% bead:sample ratios. These samples were pooled into a 16.9 ng/μL pool that, with an estimated average insert size of 400 bp, is ~65 nM. The samples were sequenced.

Figure 44:
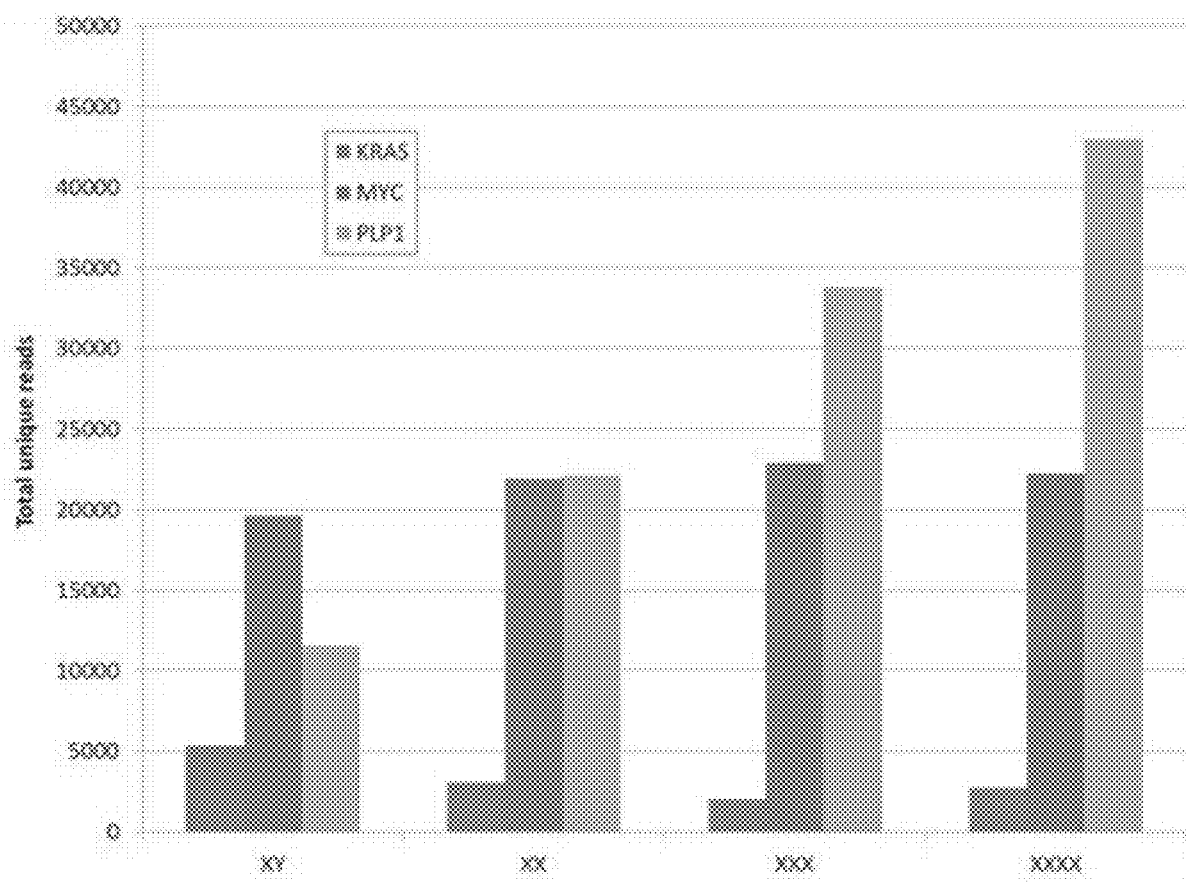
FIG. 44 shows CNV for PLP1 in relation to the normalizing autosomal loci KRAS and MYC across samples with variable dosages of the X chromosome. Samples were prepared using library free methods.
Figure 45:
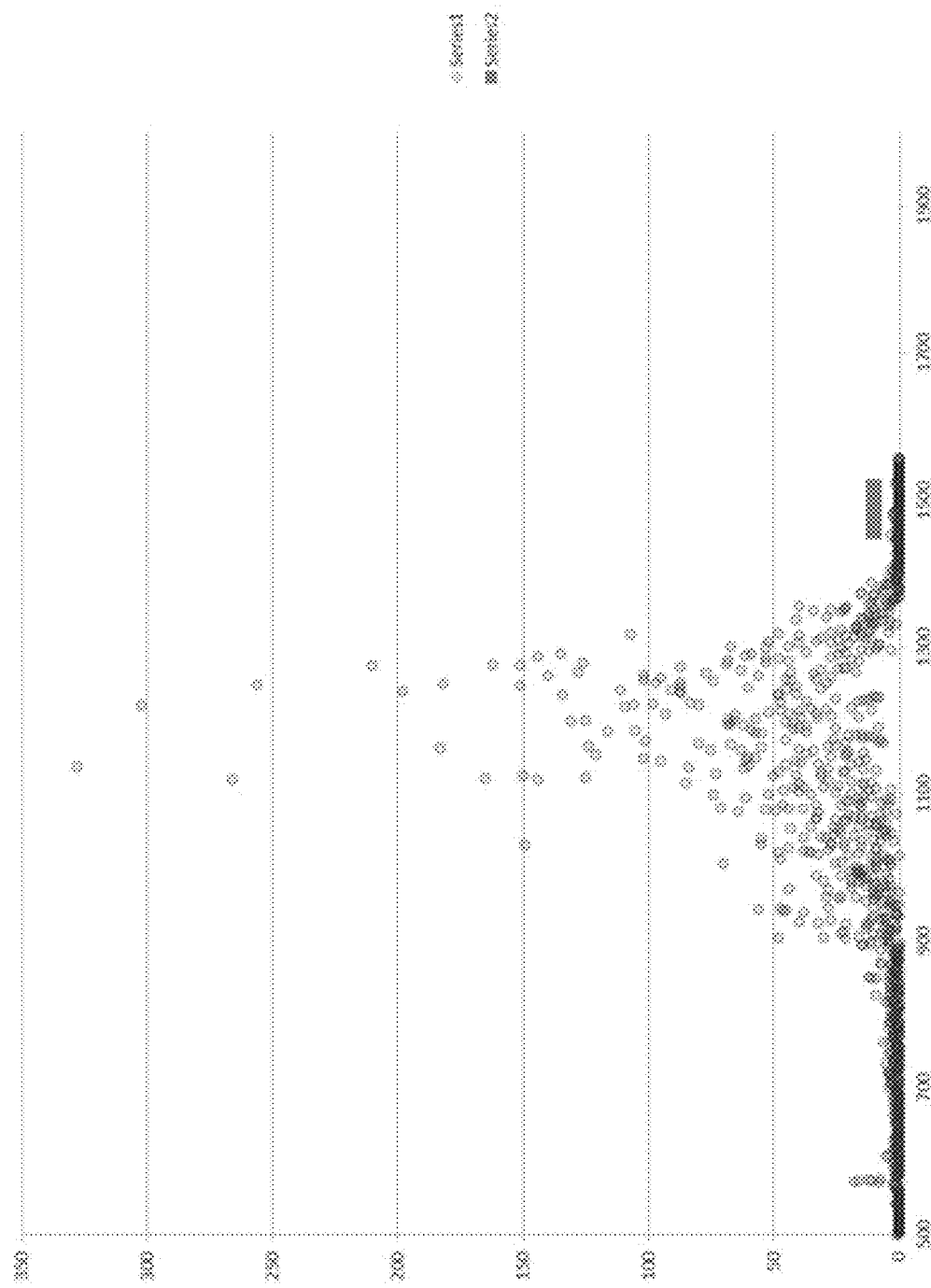
FIG. 45 shows the DNA sequence start points for chrX region 15 in the XXXX (4× dosage) sample relative to the capture probe sequence. Reads go from left to right and samples were prepared using library free methods.

The library-free methods worked well for CNV analyses. Unique read counts for the X-linked genePLP1 were normalized to the autosomal loci KRAS and MYC and the plot of these data is shown in FIG. 44. The data illustrate that absolute copy number is lost with the library-free procedure (the "copies" of KRAS relative to MYC are no longer comparable). However, relative copy number (the change of PLP1 relative to the autosomal normalizers) is robustly detected. The sequencing results also showed striking features related to read start sites relative to probe. FIG. 45 shows that reads are detected as far as 900 bp from the probe; and between coordinates 1100 and 1300 every single start point is used multiple times. These data indicated that reads start at every single possible base position and that there is little ligation/processing bias. In addition, there are very few reads that start within 100 bp of the probe, consistent with the very large size distribution of the library that was observed on gels.

Example 21: Targeted Gene Expression Analysis

Overview: This example demonstrates the development of targeted gene expression libraries. The input is RNA, not DNA, and therefore double-strand cDNA synthesis step is required. A preferred method is $1^{st}$ strand synthesis using an RNAse H$^-$ reverse transcriptase or a kit that exhibits RNAse H$^-$ like activity (e.g., Promega's GoScript) and priming with random hexamers. A preferred method for $2^{nd}$ strand synthesis is to use a kit that includes E. coli DNA polymerase holoenzyme, NAD$^+$-dependent ligase and RNAse H (e.g., New England Biolabs $2^{nd}$ strand cDNA synthesis module).

Because there is a very wide range of transcript copies, there must be a correspondingly wide range of random tags that are introduced on adaptors to sheared and end-repaired cDNA. Accordingly, random 8-mers (65,536 possible sequences) were used. The adaptor was engineered with a random 8-mer sequence followed by 10-12 fixed bases that can both serve as an annealing site for a complementary 10-12 that facilitates ligation and that is used as a sample identifier in the case of multiplexed samples.

The actual number of unique versus duplicated reads—in other words the statistical distribution of reads—is one important factor in determining expression levels. One potential source of error are reads that are duplicated after the capture event. To identify these errors, a random tag was added to the capture probe such that each capture event is labeled.

The treatment and sequencing of targeted RNA-seq libraries follows the same procedure as treatment of genomic libraries.

The informatics analysis starts with the removal of post-capture duplicate reads and alignment to the target transcriptome. The unique read counts among aligning reads are then determined. While the data can then be fit to a statistical distribution, it was found that the raw unique read counts are a very close approximation to actual expression levels.

Purpose: The purpose of these experiments was to make targeted expression sequencing libraries from heart and liver total RNAs and to make both total RNA and targeted RNA libraries from the same starting material a direct comparison could be made.

Summary: The RNA counts from total RNA libraries and from targeted RNA libraries showed good agreement along two parameters. First, the expression ratios between heart vs liver samples were well correlated. Second, the measurement of absolute abundance of different transcripts within a given sample was in good agreement when total RNA counts were compared to targeted RNA counts. These first-pass data indicated that quantitative targeted nucleic acid methods can be extended beyond genomic DNA into the analysis of cDNA libraries.

Strategy: To create a reasonable total RNA library that is depleted of rRNA, dT priming was used. To create targeted RNA libraries, total RNA samples were initially primed with IDT-supplied random hexamers. Random hexamer priming likely provides the most comprehensive coverage of the transcriptome. The total RNA libraries were sequenced after amplification with PCR primers that introduce P1 and P2 flow cell sequences. For targeted analysis, the capture, washing, processing and amplification steps were performed as contemplated elsewhere herein. The targeted clones were then sequenced.

Methods

Oligonucleotides: For total RNA libraries the poly-dT primer:

TTTTTTTTTTTTTTTTTVN (SEQ ID NO: 722)

was used. For targeted RNA-seq, an adaptor design was created in which the first 8 bases were random and the next 12 served as a "code" and an anchor sequence for a 12 mer partner strand oligo that could therefore form a ligatable duplex. The sequences of these adaptors were:

| SEQ ID NO: | Name | Sequence |
|---|---|---|
| 723 | RNA_L_1 | TGCAGGACCAGAGAATTCGAATACANNNNNNNNNGACTCCGATCCC |
| 724 | RNA_P_1 | GGGATCGGAGTC |
| 725 | RNA_L_2 | TGCAGGACCAGAGAATTCGAATACANNNNNNNNNCGGAACTCGGAG |
| 726 | RNA_P_2 | CTCCGAGTTCCG | cDNA library construction: The following methods were used to synthesize the four following cDNA libraries: (1) Heart total RNA (dT primed); (2) Heart targeted RNA (N6 primed); (3) Liver total RNA; and (4) Liver targeted RNA (N6 primed). One μg/μL total RNA was diluted 10-fold to 100 ng/μL in TEz. The following components were combined in a total volume of 10 heated to 65° C. and transferred to ice: 2 μL of diluted total RNA (100 ng); 2 μL of 5 uM poly-dTVN primer or 2 μL of 50 uM N6 (IDT); and 6 μL of water.

The mix was combined with 10 μL of 1$^{st}$ strand cocktail (4 μL 5× GoScript buffer; 1.6 μL 25 mM Mg$^{++}$ (2 mM final concentration); 1.0 μL 10 mM dNTPs (500 uM final concentration); 1.0 μL GoScript enzyme; and 2.4 μL water) and incubated at 42° C. for 30 min, then 70° C. for 10 min. Sixty microliters of 2$^{nd}$ strand synthesis reagents (48 μL water, mix; 8 μL 10× second strand synthesis buffer; 4 μL second strand enzyme mix) were added to each reaction and incubated at 16° C. for 2 hours.

Following the second strand synthesis 55 μL TEz was added to each reaction and reactions were transferred to glass Covaris sonication tubes and sonicated to about 500 bp. 125 μL of the sonicated sample was transferred to a PCR strip tube and 125 μL beads were added. Following purification, the sample was resuspended to a final volume of 20 μL.

End repair was carried out for 19 μL of the reaction using the methods contemplated herein. The end repaired fragments were then ligated to adaptors at 22° C. for 30 min and heat inactivated at 65° C. for 10 min. Ligation was carried out in a 40 μL final volume: 25 μL of repaired fragments; 2 μL of 10 uM adaptor (10 uM in L strand, 20 uM in P strand); 4 μL 10× buffer; 6 μL 50% PEG8000; 1 μL water; and 2 μL HC T4 ligase. 60 μL TEz and 100 beads were added to each reaction and the sample was purified to a final volume of 20 μL.

Library amplification was monitored using qPCR and each library was amplified by PCR by combining 20 μL of purified ligation mix with 130 μL PCR mix (75 μL 2× NEBNext master mix, 15 μL ACA2-20, 40 μL water). 50 μL was aliquoted into a well that contains 2.5 μL EvaGreen+ ROX and further aliquoted to 10 μL in qPCR plate. The remaining 100 μL was kept in PCR strip tube. The PCR amplification was carried out at 72° C.-30 sec, 98° C.-30 sec, and variable cycles of 98° C.-10 sec, 60° C.-10 sec, 72° C.-10 sec.

For dT libraries, 100 μL PCR reactions were purified with 120 μL beads. ACA2-20 (a 20 nt PCR primer) amplified material was diluted 20-fold—5 μL into 95 μL of PCR mix—that contains 50 μL 2×NEBNext master mix, 5 μL of F primer, 5 μL of R-primer and 35 of water. The F primer is oligo #8, ACA2 FLFP

ACA2_FLFP
(SEQ ID NO: 69)
AATGATACGGCGACCACGAGATCTACACGTCATGCAGGACCAGAGAATTC

GAATACA and the reverse primer is oligo

CAC3_FLRP
(SEQ ID NO: 74)
CAAGCAGAAGACGGCATACGAGATGTGACTGGCACGGGACCAGAGAATTC

GAATACA.

Amplification was carried out for 8 cycles. This step was included to grow the shorter, 20 bp ACA2 terminal sequences into longer P1 and P2, flow cell-compatible and sequencable sequences. Constructs that pick up the two different primers will amplify while those that have only one sequence will be suppressed. The resulting DNA was purified by adding 100 μL beads to the 100 μL PCR rxn and resuspended in a final volume of 50 μL.

DNA was quantified by Qubit and examined by gel electrophoresis. The DNA was sequenced using the forward primer oligo #7,

```
ACA2_FSP
                                  (SEQ ID NO: 68)
ACACGTCATGCAGGACCAGAGAATTCGAATACA
``` and the reverse primer oligo #62, exome

```
CAC3_RSP
                                  (SEQ ID NO: 73)
GTGACTGGCACGGGACCAGAGAATTCGAATACA.
``` dT-primed RNA was sequenced in runs_48 & 49.

Figure 46:
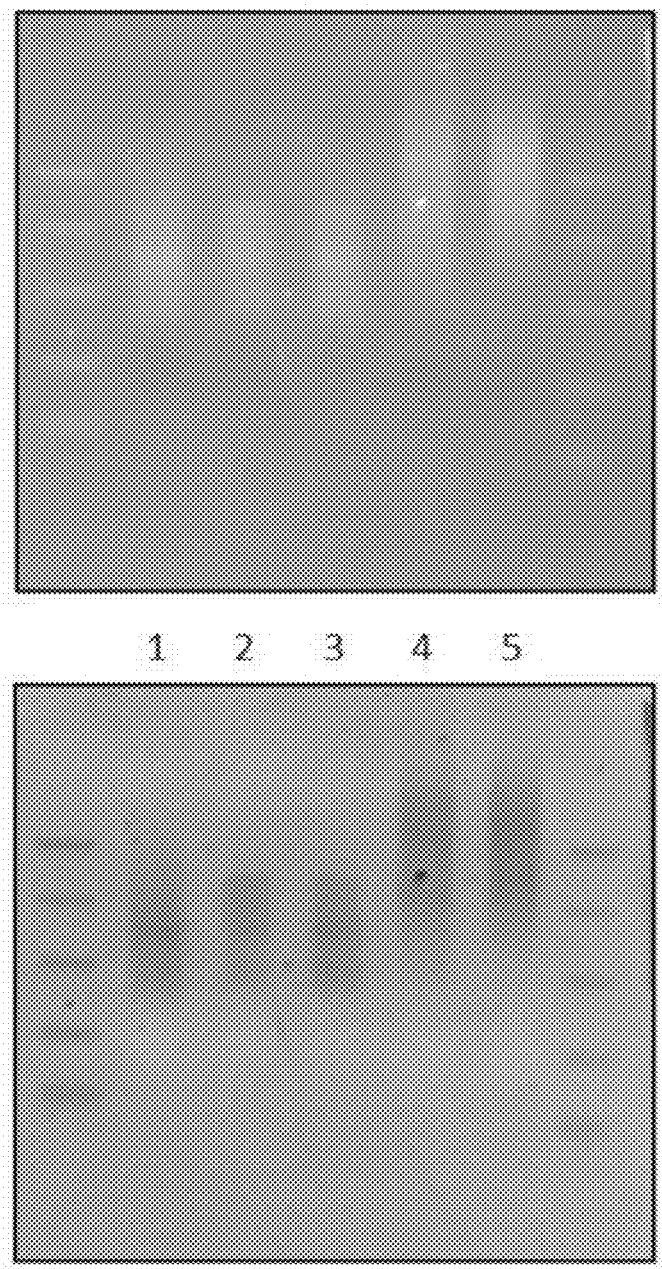
FIG. 46 shows the gel electrophoresis results of cDNA prepared from RNA samples using the RNA-seq methods contemplated herein, captured cDNAs, and cDNA preps sized with the Pippin automated DNA size selector.

The DNA gel of samples is shown in FIG. 46. The large fragment size distribution of dT-primed total RNA libraries was somewhat surprising.

For targeted RNA sequencing, Ns-primed libraries were resuspended in 40 of TEz. Fragment content in heart and liver libraries was quantified: 153 fg/μL of heart sample cDNA and 760 fg/μL of liver sample cDNA. Based on these data, 40 μL of the heart ligation sample and 8 μL of the liver ligation sample were carried into downstream PCR amplification.

Progress of library amplification was monitored using qPCR and the library was amplified by PCR combining 40 μL of purified ligation mix (heart) or 8 μL of ligation mix+32 μL of TEz (liver) with 210 μL PCR mix (125 μL 2×NEB Next master mix, 25 ACA2, 60 μL water). 50 μL was aliquoted into a well that contains 2.5 μL EvaGreen+ROX and further aliquoted into 10 μL aliquots in a qPCR plate. The remaining 100 μL was placed in a PCR strip tube. The PCR amplification was carried out at 72° C.-30 sec, 98° C.-30 sec, and variable cycles of 98° C.-10 sec, 60° C.-10 sec, 72° C.-10 sec. 200 μL of PCR products were purified with 200 μL beads and resuspended in a final volume of 25 μL. The concentration of PCR products was 41 ng/μL for the heart library and 42 ng/μL for the liver library.

For capture, heart and liver samples were combined and two of "2×" capture reactions were performed with tagged RNA-seq-specific probes (see Appendix, infra for sequences), washed, processed C+P (final yield=40 μL of 23 ng/μL), and size selected 240-600 bp fragments on a Pippin automated DNA size selector. 5.4 ng/μL of fragments were recovered from the Pippin=20.8 nM. A flow cell was loaded with the fragments and 51 nt first reads and 24 nt second reads were collected.

Results and Discussion: To determine useful RNA-seq data, a heart versus liver sample was chosen for comparison. 21 transcripts were parsed out of transcripts reported in the RNA-seq Atlas (medicalgenomics.org/rna_seq_atlas) based on their absolute abundance in one or the other tissue (RPKM values of about 100, 10, 1 etc. in heart or liver) and on their ratios between tissues (again about 100, 10, 1, 0.1, 0.01 for heart vs liver ratios). The list of candidate transcripts and their reported RPKM values are shown in FIG. 55.

The targeted RNA-seq library was compared to an untargeted, total RNA library made from the same total RNA sample. Poly dT priming was used to convert total RNA, which is primarily rRNA, into non-rRNA transcript libraries. For targeted RNA-seq, random hexamers were used. For the dT primed total RNA libraries, reads can be derived along the entire length of a transcript, some of which are quite long. As an example, the distribution of reads along MYH7 in heart was examined and reads derived from near the 5' end of this long transcript were found. To compare one (long) transcript to another (short) transcript, counts were normalized by transcript length (often referred to as the reads per million per Kb or RPKM method). Following this 1$^{st}$ degree normalization, counts were also normalize between total and targeted samples. The final read count data set is shown in FIG. 56.

Visual inspection revealed a good correlation between all three types of data (Atlas, Total and Targeted). One important comparison was between that total RNA-seq sample prepared herein and the targeted RNA-seq sample prepared herein, because both data sets were derived from the same total RNA samples. Two important points of comparison include: (1) The correlation of the actual heart versus liver expression ratio; and (2) the correlation of the absolute abundances of transcripts within a specific sample between total and targeted counts.

Figure 47:
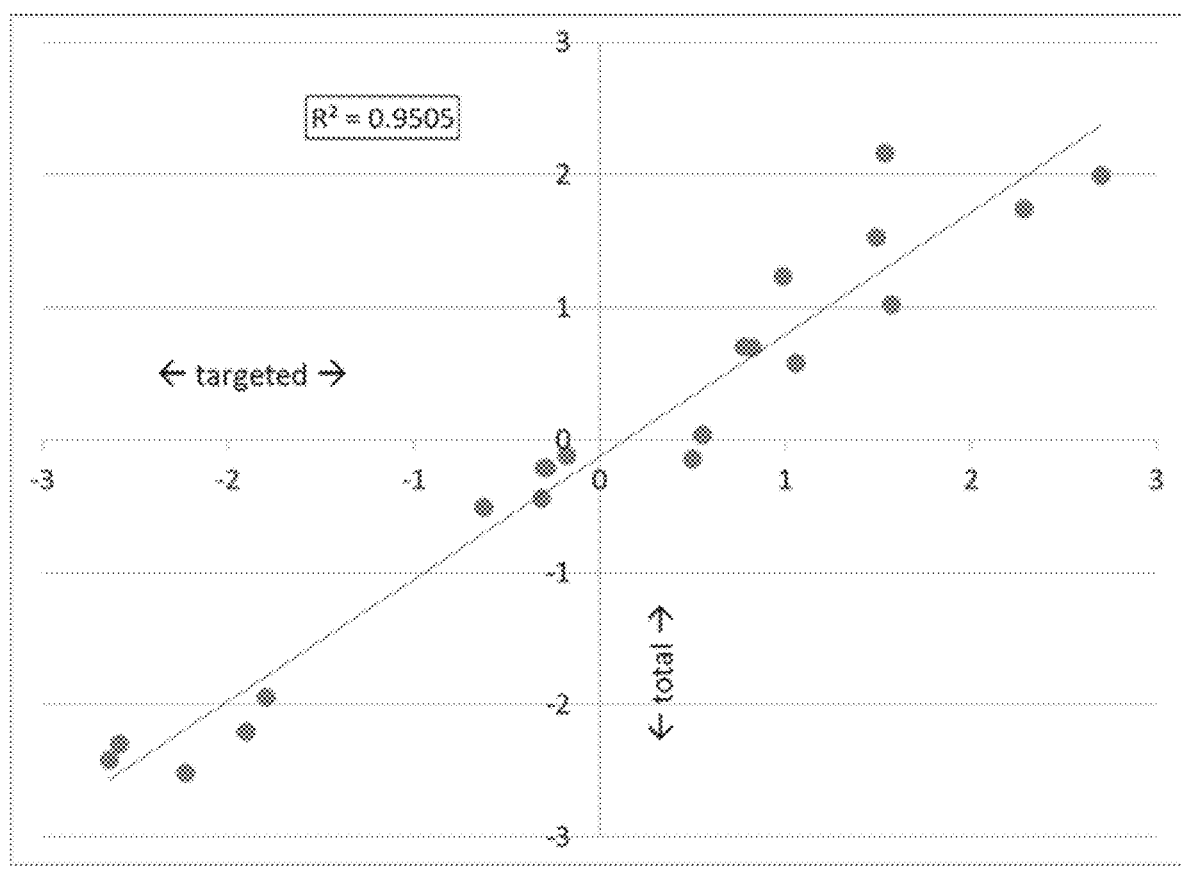
FIG. 47 shows the correlations of the gene expression of various transcripts in heart versus liver in libraries prepared using a total RNA versus targeted expression strategy for the library preparation.

The first point addresses the preservation of expression profiles, but ignores the actual magnitude of counts being compared. An expression ratio heart versus liver comparison plot for total versus targeted expression ratios is shown in FIG. 47. This plot shows an exceptional correlation ($r^2$=0.95) between "expression profiles" generated by the two methods.

Figure 48:
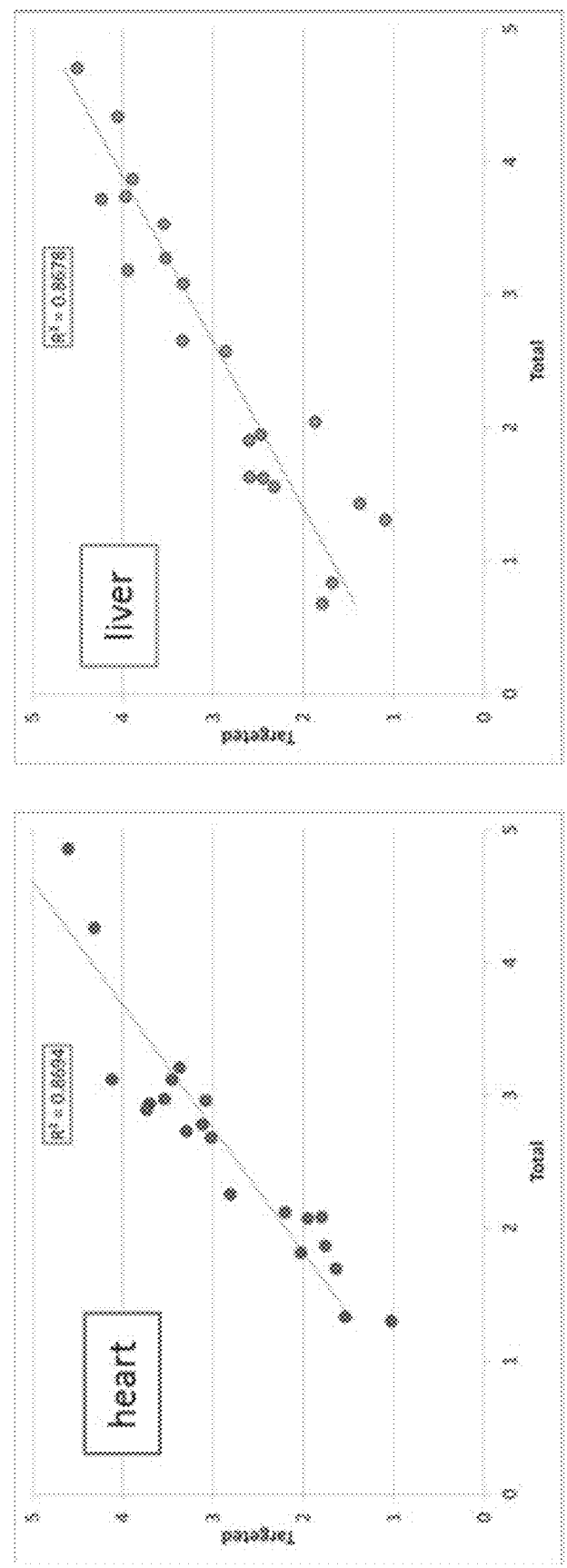
FIG. 48 shows the correlation of absolute expression levels of various transcript measured in total RNA-seq compared to targeted RNA-seq.

The second point can be more rigorous because it asks for an absolute comparison between the two methods. A comparison of absolute expression levels as measured in total RNA-seq or targeted RNA-seq is shown in FIG. 48, where log 10(count) values are plotted against one another. This comparison was sensitive not only to targeting, but also to the fact that the RNA-seq libraries were prepared by fundamentally different methods (dT priming for total, random hexamer priming for targeted). Despite the different methods of preparation there was an excellent correlation between the two methods.

This study demonstrated that the core methods of labeling with random tags combined with sequence-specific capture can produce target-specific RNA transcript data that preserves absolute expression abundance, reveals transcript-specific sequence information, and dramatically reduces the complexity of transcriptome data.

APPENDIX

PROBE SEQUENCES USED FOR RNA-SEQ ANALYSIS.

| SEQ ID NO: | Name | Sequence |
|---|---|---|
| 727 | APOB_1 | ATGTGACTGGCACGGGAGTTGATCCTGGTTTTCACNNNNNNNGCCGAAGAGGAAA TGCTGGAAAATGTCAGCCTGGTCTGTCCAAAAGATGCGACCCGATTC |
| 728 | APOB_2 | ATGTGACTGGCACGGGAGTTGATCCTGGTTTTCACNNNNNNNCAGCTGACCTCAT CGAGATTGGCTTGGAAGGAAAAGGCTTTGAGCCAACATTGGAAGCT |
| 729 | ATP5E_1 | ATGTGACTGGCACGGGAGTTGATCCTGGTTTTCACNNNNNNNTACTGGAGACAGG CTGGACTCAGCTACATCCGATACTCCCAGATCTGTGCAAAAGCAGTG |

APPENDIX-continued

PROBE SEQUENCES USED FOR RNA-SEQ ANALYSIS.

| SEQ ID NO: | Name | Sequence |
|---|---|---|
| 730 | ATP5E_2 | ATGTGACTGGCACGGGAGTTGATCCTGGTTTTCACNNNNNNNCTGAAGACAGAAT TCAAAGCAAATGCTGAGAAGACTTCTGGCAGCAACGTAAAAATTGTG |
| 731 | BVES_1 | ATGTGACTGGCACGGGAGTTGATCCTGGTTTTCACNNNNNNNACAGAGTCCAGCC CATTGAGAGAATCAACTGCCATAGGTTTTACACCTGAGTTAGAAAGT |
| 732 | BVES_2 | ATGTGACTGGCACGGGAGTTGATCCTGGTTTTCACNNNNNNNAGCCAGCTCCAGT GACAGTGACGACGGCTTGCACCAGTTTCTTCGGGGTACCTCCAGCA |
| 733 | DKK3_1 | ATGTGACTGGCACGGGAGTTGATCCTGGTTTTCACNNNNNNNGACACGCAGCACA AATTGCGCAGCGCGGTGGAAGAGATGGAGGCAGAAGAAGCTGCTGC |
| 734 | DKK3_2 | ATGTGACTGGCACGGGAGTTGATCCTGGTTTTCACNNNNNNNTGGTGTATGTGTG CAAGCCGACCTTCGTGGGGAGCCGTGACCAAGATGGGGAGATCCTG |
| 735 | FGA_1 | ATGTGACTGGCACGGGAGTTGATCCTGGTTTTCACNNNNNNNATGAGGATCGTCT GCCTGGTCCTAAGTGTGGTGGGCACAGCATGGACTGCAGATAGTGGT |
| 736 | FGA_2 | ATGTGACTGGCACGGGAGTTGATCCTGGTTTTCACNNNNNNNATTTTTTCTGTTT ATTGCGATCAAGAGACCAGTTTGGGAGGATGGCTTTTGATCCAGCA |
| 737 | FGL1_1 | ATGTGACTGGCACGGGAGTTGATCCTGGTTTTCACNNNNNNNGTGTTCAGTTTCA TCCTTGTTACCACCGCTCTGACAATGGGCAGGGAAATTTCGGCGCTC |
| 738 | FGL1_2 | ATGTGACTGGCACGGGAGTTGATCCTGGTTTTCACNNNNNNNTGCAAACCTGAAT GGTGTATACTACAGCGGCCCCTACACGGCTAAAACAGACAATGGGA |
| 739 | HAND2_1 | ATGTGACTGGCACGGGAGTTGATCCTGGTTTTCACNNNNNNNCATCCCCAACGTA CCCGCCGACACCAAACTCTCCAAAATCAAGACCCTGCGCCTGGCCA |
| 740 | HAND2_2 | ATGTGACTGGCACGGGAGTTGATCCTGGTTTTCACNNNNNNNCGACCAGAATGGC GAGGCGGAGGCCTTCAAGGCAGAGATCAAGAAGACCGACGTGAAAG |
| 741 | MGP_1 | ATGTGACTGGCACGGGAGTTGATCCTGGTTTTCACNNNNNNNCTGATCCTTCTTG CCATCCTGGCCGCCTTAGCGGTAGTAACTTTGTGTTATGAATCACAT |
| 742 | MGP_2 | ATGTGACTGGCACGGGAGTTGATCCTGGTTTTCACNNNNNNNCGAGCTCAATAGG GAAGCCTGTGATGACTACAGACTTTGCGAACGCTACGCCATGGTTT |
| 743 | MGST1_1 | ATGTGACTGGCACGGGAGTTGATCCTGGTTTTCACNNNNNNNAAGAAGTATCTTC GAACAGATGACAGAGTAGAACGTGTACGCAGAGCCCACCTGAATGA |
| 744 | MGST1_2 | ATGTGACTGGCACGGGAGTTGATCCTGGTTTTCACNNNNNNNTATTCCTTGAGTG GTCCCGACCCCTCTACAGCCATCCTGCACTTCAGACTATTTGTCGG |
| 745 | MYH7_1 | ATGTGACTGGCACGGGAGTTGATCCTGGTTTTCACNNNNNNNCAGACCAGGCCTT TTGACCTCAAGAAGGATGTCTTCGTGCCTGATGACAAACAGGAGTTT |
| 746 | MYH7_2 | ATGTGACTGGCACGGGAGTTGATCCTGGTTTTCACNNNNNNNAGAGCTCTTCAAA CTCAAGAACGCCTATGAGGAGTCCCTGGAACATCTGGAGACCTTCA |
| 747 | NEBL_1 | ATGTGACTGGCACGGGAGTTGATCCTGGTTTTCACNNNNNNNCAGGTCTTCTATA AGCCTGTTATTGAAGACTTAAGCATGGAATTGGCCAGAAAATGCACG |
| 748 | NEBL_2 | ATGTGACTGGCACGGGAGTTGATCCTGGTTTTCACNNNNNNNAAAGAGCAAAACT ACAAGGCCACTCCGGTAAGCATGACCCCGGAGATAGAGAGAGTGAG |
| 749 | PDE4DIP_1 | ATGTGACTGGCACGGGAGTTGATCCTGGTTTTCACNNNNNNNGGATATCGCACTC TGTCCCAGCACCTCAATGACCTGAAGAAGGAGAACTTCAGCCTCAAG |
| 750 | PDE4DIP_2 | ATGTGACTGGCACGGGAGTTGATCCTGGTTTTCACNNNNNNNGAAAGCCAAGCTG CTGCAGAGAAGTTGGTGCAAGCCTTAATGGAAAGAAATTCAGAATT |
| 751 | PDIA4_1 | ATGTGACTGGCACGGGAGTTGATCCTGGTTTTCACNNNNNNNCCGGACGAGGATT CTTCTAACAGAGAAAATGCCATTGAGGATGAAGAGGAGGAGGAGGAG |
| 752 | PDIA4_2 | ATGTGACTGGCACGGGAGTTGATCCTGGTTTTCACNNNNNNNCGTCAAGGTCGTG GTGGGAAAGACCTTTGACTCCATTGTGATGGACCCCAAGAAGGACG |
| 753 | RP9P_1 | ATGTGACTGGCACGGGAGTTGATCCTGGTTTTCACNNNNNNNAGATCACGAGTTA TGAAAAACCTCCTCCTGGGCTTATCAAGGTTGGCATTGCAAATGGT |

APPENDIX-continued

PROBE SEQUENCES USED FOR RNA-SEQ ANALYSIS.

| SEQ ID NO: | Name | Sequence |
|---|---|---|
| 754 | RP9P_2 | ATGTGACTGGCACGGGAGTTGATCCTGGTTTTCACNNNNNNAAAGTTTCTTCAT CGTTGTCCTCCCTGCTGGTCACATGAGTTTACGATTCCTTAGAAGTG |
| 755 | SERPINF2_1 | ATGTGACTGGCACGGGAGTTGATCCTGGTTTTCACNNNNNNCCCGGCGCGTTCC GACTGGCTGCCAGGATGTACCTGCAGAAAGGATTTCCCATCAAAGA |
| 756 | SERPINF2_2 | ATGTGACTGGCACGGGAGTTGATCCTGGTTTTCACNNNNNNGCCTGAAAGGCTT CCCCCGCGGAGACAAGCTTTTCGGCCCTGACTTAAAACTTGTGCCC |
| 757 | SOD2_1 | ATGTGACTGGCACGGGAGTTGATCCTGGTTTTCACNNNNNNAACAACCTGAACG TCACCGAGGAGAAGTACCAGGAGGCGTTGGCCAAGGGAGATGTTAC |
| 758 | SOD2_2 | ATGTGACTGGCACGGGAGTTGATCCTGGTTTTCACNNNNNNAGGAGAAGCTGAC GGCTGCATCTGTTGGTGTCCAAGGCTCAGGTTGGGGTTGGCTTGGT |
| 759 | STARD10_1 | ATGTGACTGGCACGGGAGTTGATCCTGGTTTTCACNNNNNNGACCAAGACTTTC GCAGCTTCCGGTCAGAGTGTGAGGCTGAGGTGGGCTGGAACCTGACC |
| 760 | STARD10_2 | ATGTGACTGGCACGGGAGTTGATCCTGGTTTTCACNNNNNNAGATGTACAAGGC GTGCCTCAAGTACCCCGAGTGGAAACAGAAGCACCTGCCTCACTTCA |
| 761 | TAF1A_1 | ATGTGACTGGCACGGGAGTTGATCCTGGTTTTCACNNNNNNTTCAGTGAAGAAT TAAAAGGGCCTGTGACAGATGATGAAGAAGTGGAAACATCTGTGCTC |
| 762 | TAF1A_2 | ATGTGACTGGCACGGGAGTTGATCCTGGTTTTCACNNNNNNGAAACCACCTTGC GTGGGTTCAAGAAGAGTGGAACTCCAGGAAAAACTGGTGGCCAGGC |
| 763 | TFR2_1 | ATGTGACTGGCACGGGAGTTGATCCTGGTTTTCACNNNNNNCTTTGGGGTCTAT TCCAGAGAGCGCAACAACTGTCCCCAAGATCCTCTCAGACCGTCTAC |
| 764 | TFR2_2 | ATGTGACTGGCACGGGAGTTGATCCTGGTTTTCACNNNNNNAGGCCTACCCATT CCTGCACACAAAGGAGGACACTTATGAGAACCTGCATAAGGTGCTG |
| 765 | TMEM14A_1 | ATGTGACTGGCACGGGAGTTGATCCTGGTTTTCACNNNNNNATCGGTTTTGGTT ATGCAGCCCTCGTGACATTTGGAAGCATTTTTGGATATAAGCGGAGA |
| 766 | TMEM14A_2 | ATGTGACTGGCACGGGAGTTGATCCTGGTTTTCACNNNNNNGCTTTCTTCCTGG CTACCATAATGGGTGTGAGATTTAAGAGGTCCAAGAAAATAATGCC |
| 767 | TRAPPC1_1 | ATGTGACTGGCACGGGAGTTGATCCTGGTTTTCACNNNNNNCACAACCTGTACC TGTTTGACCGGAATGGAGTGTGTCTGCACTACAGCGAATGGCACCGC |
| 768 | TRAPPC1_2 | ATGTGACTGGCACGGGAGTTGATCCTGGTTTTCACNNNNNNATCCGAGATGTGC TGCACCACATCTACAGTGCGCTGTATGTGGAGCTGGTGGTGAAGAA |
| 769 | APOB_1 | ATGTGACTGGCACGGGAGTTGATCCTGGTTTTCACNNNNNNGCCGAAGAGGAAA TGCTGGAAAATGTCAGCCTGGTCTGTCCAAAAGATGCGACCCGATTC |
| 770 | APOB_2 | ATGTGACTGGCACGGGAGTTGATCCTGGTTTTCACNNNNNNCAGCTGACCTCAT CGAGATTGGCTTGGAAGGAAAAGGCTTTGAGCCAACATTGGAAGCT |
| 771 | ATP5E_1 | ATGTGACTGGCACGGGAGTTGATCCTGGTTTTCACNNNNNNTACTGGAGACAGG CTGGACTCAGCTACATCCGATACTCCCAGATCTGTGCAAAAGCAGTG |
| 772 | ATP5E_2 | ATGTGACTGGCACGGGAGTTGATCCTGGTTTTCACNNNNNNCTGAAGACAGAAT TCAAAGCAAATGCTGAGAAGACTTCTGGCAGCAACGTAAAAATTGTG |
| 773 | BVES_1 | ATGTGACTGGCACGGGAGTTGATCCTGGTTTTCACNNNNNNACAGAGTCCAGCC CATTGAGAGAATCAACTGCCATAGGTTTTACACCTGAGTTAGAAAGT |
| 774 | BVES_2 | ATGTGACTGGCACGGGAGTTGATCCTGGTTTTCACNNNNNNAGCCAGCTCCAGT GACAGTGACGACGGCTTGCACCAGTTTCTTCGGGGTACCTCCAGCA |
| 775 | DKK3_1 | ATGTGACTGGCACGGGAGTTGATCCTGGTTTTCACNNNNNNGACACGCAGCACA AATTGCGCAGCGCGGTGGAAGAGATGGAGGCAGAAGAAGCTGCTGC |
| 776 | DKK3_2 | ATGTGACTGGCACGGGAGTTGATCCTGGTTTTCACNNNNNNTGGTGTATGTGTG CAAGCCGACCTTCGTGGGAGCCGTGACCAAGATGGGGAGATCCTG |
| 777 | FGA_1 | ATGTGACTGGCACGGGAGTTGATCCTGGTTTTCACNNNNNNATGAGGATCGTCT GCCTGGTCCTAAGTGTGGTGGGCACAGCATGGACTGCAGATAGTGGT |

APPENDIX-continued

PROBE SEQUENCES USED FOR RNA-SEQ ANALYSIS.

| SEQ ID NO: | Name | Sequence |
|---|---|---|
| 778 | FGA_2 | ATGTGACTGGCACGGGAGTTGATCCTGGTTTTCACNNNNNNATTTTTTCTGTTT<br>ATTGCGATCAAGAGACCAGTTTGGGAGGATGGCTTTTGATCCAGCA |
| 779 | FGL1_1 | ATGTGACTGGCACGGGAGTTGATCCTGGTTTTCACNNNNNNGTGTTCAGTTTCA<br>TCCTTGTTACCACCGCTCTGACAATGGGCAGGGAAATTTCGGCGCTC |
| 780 | FGL1_2 | ATGTGACTGGCACGGGAGTTGATCCTGGTTTTCACNNNNNNTGCAAACCTGAAT<br>GGTGTATACTACAGCGGCCCCTACACGGCTAAAACAGACAATGGGA |
| 781 | HAND2_1 | ATGTGACTGGCACGGGAGTTGATCCTGGTTTTCACNNNNNNCATCCCCAACGTA<br>CCCGCCGACACCAAACTCTCCAAAATCAAGACCCTGCGCCTGGCCA |
| 782 | HAND2_2 | ATGTGACTGGCACGGGAGTTGATCCTGGTTTTCACNNNNNNCGACCAGAATGGC<br>GAGGCGGAGGCCTTCAAGGCAGAGATCAAGAAGACCGACGTGAAAG |
| 783 | MGP_1 | ATGTGACTGGCACGGGAGTTGATCCTGGTTTTCACNNNNNNCTGATCCTTCTTG<br>CCATCCTGGCCGCCTTAGCGGTAGTAACTTTGTGTTATGAATCACAT |
| 784 | MGP_2 | ATGTGACTGGCACGGGAGTTGATCCTGGTTTTCACNNNNNNCGAGCTCAATAGG<br>GAAGCCTGTGATGACTACAGACTTTGCGAACGCTACGCCATGGTTT |
| 785 | MGST1_1 | ATGTGACTGGCACGGGAGTTGATCCTGGTTTTCACNNNNNNAAGAAGTATCTTC<br>GAACAGATGACAGAGTAGAACGTGTACGCAGAGCCCACCTGAATGA |
| 786 | MGST1_2 | ATGTGACTGGCACGGGAGTTGATCCTGGTTTTCACNNNNNNTATTCCTTGAGTG<br>GTCCCGACCCCTCTACAGCCATCCTGCACTTCAGACTATTTGTCGG |
| 787 | MYH7_1 | ATGTGACTGGCACGGGAGTTGATCCTGGTTTTCACNNNNNNCAGACCAGGCCTT<br>TTGACCTCAAGAAGGATGTCTTCGTGCCTGATGACAAACAGGAGTTT |
| 788 | MYH7_2 | ATGTGACTGGCACGGGAGTTGATCCTGGTTTTCACNNNNNNAGAGCTCTTCAAA<br>CTCAAGAACGCCTATGAGGAGTCCCTGGAACATCTGGAGACCTTCA |
| 789 | NEBL_1 | ATGTGACTGGCACGGGAGTTGATCCTGGTTTTCACNNNNNNCAGGTCTTCTATA<br>AGCCTGTTATTGAAGACTTAAGCATGGAATTGGCCAGAAAATGCACG |
| 790 | NEBL_2 | ATGTGACTGGCACGGGAGTTGATCCTGGTTTTCACNNNNNNAAAGAGCAAAACT<br>ACAAGGCCACTCCGGTAAGCATGACCCCGGAGATAGAGAGAGTGAG |
| 791 | PDE4DIP_1 | ATGTGACTGGCACGGGAGTTGATCCTGGTTTTCACNNNNNNGGATATCGCACTC<br>TGTCCCAGCACCTCAATGACCTGAAGAAGGAGAACTTCAGCCTCAAG |
| 792 | PDE4DIP_2 | ATGTGACTGGCACGGGAGTTGATCCTGGTTTTCACNNNNNNGAAAGCCAAGCTG<br>CTGCAGAGAAGTTGGTGCAAGCCTTAATGGAAAGAAATTCAGAATT |
| 793 | PDIA4_1 | ATGTGACTGGCACGGGAGTTGATCCTGGTTTTCACNNNNNNCCGGACGAGGATT<br>CTTCTAACAGAGAAAATGCCATTGAGGATGAAGAGGAGGAGGAGGAG |
| 794 | PDIA4_2 | ATGTGACTGGCACGGGAGTTGATCCTGGTTTTCACNNNNNNCGTCAAGGTCGTG<br>GTGGGAAAGACCTTTGACTCCATTGTGATGGACCCCAAGAAGGACG |
| 795 | RP9P_1 | ATGTGACTGGCACGGGAGTTGATCCTGGTTTTCACNNNNNNAGATCACGAGTTA<br>TGAAAAACCTCCTCCTGGGCTTATCAAGGTTGGCATTGCAAATGGT |
| 796 | RP9P_2 | ATGTGACTGGCACGGGAGTTGATCCTGGTTTTCACNNNNNNAAAGTTTCTTCAT<br>CGTTGTCCTCCCTGCTGGTCACATGAGTTTACGATTCCTTAGAAGTG |
| 797 | SERPINF2_1 | ATGTGACTGGCACGGGAGTTGATCCTGGTTTTCACNNNNNNCCCGGCGCGTTCC<br>GACTGGCTGCCAGGATGTACCTGCAGAAAGGATTTCCCATCAAAGA |
| 798 | SERPINF2_2 | ATGTGACTGGCACGGGAGTTGATCCTGGTTTTCACNNNNNNGCCTGAAAGGCTT<br>CCCCGCGGAGACAAGCTTTTCGGCCCTGACTTAAAACTTGTGCCC |
| 799 | SOD2_1 | ATGTGACTGGCACGGGAGTTGATCCTGGTTTTCACNNNNNNAACAACCTGAACG<br>TCACCGAGGAGAAGTACCAGGAGGCGTTGGCCAAGGGAGATGTTAC |
| 800 | SOD2_2 | ATGTGACTGGCACGGGAGTTGATCCTGGTTTTCACNNNNNNAGGAGAAGCTGAC<br>GGCTGCATCTGTTGGTGTCCAAGGCTCAGGTTGGGGTTGGCTTGGT |
| 801 | STARD10_1 | ATGTGACTGGCACGGGAGTTGATCCTGGTTTTCACNNNNNNGACCAAGACTTTC<br>GCAGCTTCCGGTCAGAGTGTGAGGCTGAGGTGGGCTGGAACCTGACC |

APPENDIX-continued

PROBE SEQUENCES USED FOR RNA-SEQ ANALYSIS.

| SEQ ID NO: | Name | Sequence |
|---|---|---|
| 802 | STARD10_2 | ATGTGACTGGCACGGGAGTTGATCCTGGTTTTCACNNNNNNAGATGTACAAGGC GTGCCTCAAGTACCCCGAGTGGAAACAGAAGCACCTGCCTCACTTCA |
| 803 | TAF1A_1 | ATGTGACTGGCACGGGAGTTGATCCTGGTTTTCACNNNNNNTTCAGTGAAGAAT TAAAAGGGCCTGTGACAGATGATGAAGAAGTGGAAACATCTGTGCTC |
| 804 | TAF1A_2 | ATGTGACTGGCACGGGAGTTGATCCTGGTTTTCACNNNNNNGAAACCACCTTGC GTGGGTTCAAGAAGAGTGGAACTCCAGGAAAAACTGGTGGCCAGGC |
| 805 | TFR2_1 | ATGTGACTGGCACGGGAGTTGATCCTGGTTTTCACNNNNNNCTTTGGGGTCTAT TCCAGAGAGCGCAACAACTGTCCCCAAGATCCTCTCAGACCGTCTAC |
| 806 | TFR2_2 | ATGTGACTGGCACGGGAGTTGATCCTGGTTTTCACNNNNNNAGGCCTACCCATT CCTGCACACAAAGGAGGACACTTATGAGAACCTGCATAAGGTGCTG |
| 807 | TMEM14A_1 | ATGTGACTGGCACGGGAGTTGATCCTGGTTTTCACNNNNNNATCGGTTTTGGTT ATGCAGCCCTCGTGACATTTGGAAGCATTTTTGGATATAAGCGGAGA |
| 808 | TMEM14A_2 | ATGTGACTGGCACGGGAGTTGATCCTGGTTTTCACNNNNNNGCTTTCTTCCTGG CTACCATAATGGGTGTGAGATTTAAGAGGTCCAAGAAAATAATGCC |
| 809 | TRAPPC1_1 | ATGTGACTGGCACGGGAGTTGATCCTGGTTTTCACNNNNNNCACAACCTGTACC TGTTTGACCGGAATGGAGTGTGTCTGCACTACAGCGAATGGCACCGC |
| 810 | TRAPPC1_2 | ATGTGACTGGCACGGGAGTTGATCCTGGTTTTCACNNNNNNATCCGAGATGTGC TGCACCACATCTACAGTGCGCTGTATGTGGAGCTGGTGGTGAAGAA |

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A composition comprising:
   (1) a tagged genomic library comprising a plurality of DNA fragments, wherein each end of each DNA fragment is ligated to a multifunctional adaptor module comprising:
      (i) a first region comprising a random nucleic acid tag sequence;
      (ii) a second region comprising a sample code sequence; and
      (iii) a third region comprising a primer sequence; and
   (2) a multifunctional capture probe module comprising:
      (i) a first region capable of hybridizing to a partner oligonucleotide; and
      (ii) a second region capable of hybridizing to a specific target region in the tagged genomic library.

2. The composition of claim 1, wherein the partner oligonucleotide comprises a primer binding site.

3. The composition of claim 1, wherein the multifunctional capture probe module comprises a third region comprising a tail sequence, wherein the tail sequence comprises a polymerase chain reaction (PCR) primer binding site.

4. The composition of claim 1, wherein the multifunctional capture probe module is hybridized to a target region of the tagged genomic library.

5. The composition of claim 1, comprising a plurality of multifunctional capture probes, wherein each probe is capable of hybridizing to a different target region in the tagged genomic library.

6. The composition of claim 1, wherein the DNA fragments are end repaired.

7. The composition of claim 1, wherein the DNA fragments comprise a 5'-overhang or a 3'-overhang, and the multifunctional adaptor module comprises an overhang that is complementary to the 5'-overhang or the 3'-overhang.

8. The composition of claim 1, wherein the composition comprises a plurality of multifunctional adaptor modules and each multifunctional adaptor molecule of said plurality of multifunctional adaptor molecules comprises a random nucleic acid tag sequence.

9. The composition of claim 1, wherein each DNA fragment of the plurality of DNA fragments is identified using the random nucleic acid tag and an end sequence of the DNA fragment.

10. The composition of claim 1, wherein the primer sequence of each multifunctional adaptor module of the plurality of multifunctional adaptor modules is the same.

11. A complex comprising:
(1) a single stranded tagged DNA molecule comprising a DNA fragment, wherein each end of the DNA fragment is ligated to a multifunctional adaptor module; and wherein the multifunctional adaptor module comprises:
(i) a first region comprising a random nucleic acid tag sequence;
(ii) a second region comprising a sample code sequence; and
(iii) a third region comprising a primer sequence; and
(2) a multifunctional capture probe module comprising:
(i) a first region capable of hybridizing to a partner oligonucleotide; and
(iii) a second region capable of hybridizing to a specific target region in the DNA fragment
wherein the tagged DNA molecule is hybridized to the multifunctional capture probe module.

12. The complex of claim 11, wherein the partner oligonucleotide comprises a primer binding site.

13. The complex of claim 11, wherein the multifunctional capture probe module comprises a third region comprising a tail sequence, wherein the tail sequence comprises a PCR primer binding site.

14. The complex of claim 11, wherein the DNA fragment is end repaired.

15. The complex of claim 11, wherein the DNA fragment comprises a 5'-overhang or a 3'-overhang, and the multifunctional adaptor module comprises an overhang that is complementary to the 5'-overhang or the 3'-overhang.

16. The complex of claim 11, wherein the multifunctional adaptor module is selected from a plurality of multifunctional adaptor modules and each multifunctional adaptor molecule of said plurality of multifunctional adaptor molecules comprises a random nucleic acid tag sequence.

17. The complex of claim 11, wherein the DNA fragment is identified using the random nucleic acid tag and an end sequence of the DNA fragment.

18. The complex of claim 11, wherein the primer sequence of each multifunctional adaptor module of the plurality of multifunctional adaptor modules is the same.

19. A method of generating a hybrid nucleic acid molecule, the method comprising performing 5' to 3' DNA polymerase extension of the complex of claim 11 using the single stranded tagged DNA molecule as a template to generate a hybrid nucleic acid molecule.

20. The method of claim 19, wherein the hybrid nucleic acid molecule comprises the multifunctional capture probe module and the complement of a region of the tagged DNA molecule sequence located in the 3' direction from the location where the multifunctional capture probe module hybridizes to the target region.

21. The method of claim 19, wherein the DNA fragment comprises a 5'-overhang or a 3'-overhang, and the multifunctional adaptor module comprises an overhang that is complementary to the 5'-overhang or the 3'-overhang.

22. The method of claim 21, further comprising ligating the multifunctional adaptor module to the DNA fragment by hybridizing the complementary overhangs.

23. A method of generating a hybrid nucleic acid molecule, the method comprising:
(1) performing 3'-5' exonuclease enzymatic processing on the complex of claim 13 using an enzyme with 3'-5' exonuclease activity to remove the single stranded 3' ends of the DNA molecule; and
(2) performing PCR on the enzymatically processed complex from (1), wherein the tail portion of the multifunctional capture probe molecule is copied to generate a hybrid nucleic acid molecule.

24. The method of claim 23, wherein the hybrid nucleic acid molecule comprises the target region and the complement of the multifunctional capture probe module tail sequence.

25. The method of claim 23, wherein the DNA fragment comprises a 5'-overhang or a 3'-overhang, and the multifunctional adaptor module comprises an overhang that is complementary to the 5'-overhang or the 3'-overhang.

26. The method of claim 25, further comprising ligating the multifunctional adaptor module to the DNA fragment by hybridizing the complementary overhangs.

27. A hybrid nucleic acid molecule generated by the method of claim 19.

28. A hybrid nucleic acid molecule generated by the method of claim 23.

* * * * *